United States Patent
Barbas, III et al.

(10) Patent No.: US 7,151,201 B2
(45) Date of Patent: Dec. 19, 2006

(54) METHODS AND COMPOSITIONS TO MODULATE EXPRESSION IN PLANTS

(75) Inventors: Carlos F. Barbas, III, Solana Beach, CA (US); Justin T. Stege, San Diego, CA (US); Xueni Guan, San Diego, CA (US); Bipin Dalmia, San Diego, CA (US)

(73) Assignees: The Scripps Research Institute, La Jolla, CA (US); Syngenta Participations AG, Basel (CH)

( * ) Notice: Subject to any disclaimer, the term of this patent is extended or adjusted under 35 U.S.C. 154(b) by 349 days.

(21) Appl. No.: 09/765,555

(22) Filed: Jan. 19, 2001

(65) Prior Publication Data
US 2003/0037355 A1 Feb. 20, 2003

Related U.S. Application Data

(60) Provisional application No. 60/327,552, filed on Jul. 21, 2000, provisional application No. 60/177,468, filed on Jan. 21, 2000.

(51) Int. Cl.
C12N 15/09 (2006.01)
C12N 15/82 (2006.01)
A01H 5/00 (2006.01)

(52) U.S. Cl. .................. 800/278; 800/298; 800/295; 435/468; 435/320.1

(58) Field of Classification Search .............. 800/278, 800/287, 298, 295, 320, 320.1, 320.2, 320.3, 800/317, 317.2, 317.3, 312, 317.4, 279; 435/419, 435/468, 320.1, 430; 536/23.1, 23.2, 24.1, 536/23.6, 24.2, 23.4
See application file for complete search history.

(56) References Cited

U.S. PATENT DOCUMENTS
6,534,261 B1 * 3/2003 Cox et al. .................. 435/6

FOREIGN PATENT DOCUMENTS
WO  WO 98/54311  12/1998
WO  WO 00/41566  7/2000
WO  WO 01/00815  1/2001

OTHER PUBLICATIONS

Guan et al. Heritable endogenous gene regulation in plants with designed polydactyl zinc finger transcription factors. PNAS (2002), 99(20):13296-13301.*
Ordiz et al. Regulation of transgene expression in plants with polydactyl zinc finger transcription factors. PNAS (2002)99(20):13290-13295.*
Choo et al. Advances in zinc fingers engineering. Current Opinion Structural Opinion in Structural Biology (2000), 10:411-416.*
Beerli et al., Proc. Natl. Acad. Sci. USA, 95:14628-14633 (1998).
De Pater et al., Nucleic Acids Reserach (1996) 24(23):4624-4631.
Eulgem et al., EMBO Journal (1999) 18(17):4689-4699.
Klug, J. Mol. Biol. (1999) 293(2):215-218.

(Continued)

Primary Examiner—Medina A. Ibrahim
(74) Attorney, Agent, or Firm—Morrison & Foerster LLP

(57) ABSTRACT

The invention relates to the field of plant and agricultural technology. More specifically, the invention relates to the use of zinc finger proteins and fusions of said proteins to regulate gene expression and metabolic pathways in plants.

54 Claims, 42 Drawing Sheets

OTHER PUBLICATIONS

Liu et al., *Proc. Natl. Acad. Sci. USA*, 94:5525-5530 (1997).
Mena et al., *Plant Journal* (1998) 16(1):53-62.
Raventos et al., Journal of Biological Chemistry (1998) 273(36):23313-23320.
Takatsuji, Cell Mol. Life Sci. (1998) 54(6):582-596.
Takatsuji, *Plant. Mol. Biol.*, 39(6): 1073-8 (1999).
Wu et al., *Proc. Natl. Acad. Sci. USA* (1995) 92:344-348.
Yanagisawa et al., *Plant Cell* (1998) 10(1):75-89.
Database EMBL, EBI accession No. EM_PRO:AF056326 (1998).
European Search Report for EP 01942508.1, mailed on Mar. 31, 2006, 6 pages.
Irish et al., Plant Cell (1995) 7(10):1635-1644.
Segal et al., PNAS USA (1999) 96(6):2758-2763.
Shi et al., Chemistry & Biology (1995) 2(2):83-89.

* cited by examiner

```
  1  AQAALEPGEKPYACPECGKSFSDPGHLVRHQRTHTGEKPYKCPECGKSFS                    50
     AQAALEPGEKPYACPECGKSFSQSSHLVRHQRTHTGEKPYKCPECGKSFS
     AQAALEPGEKPYACPECGKSFSDPGHLVRHQRTHTGEKPYKCPECGKSFS
     AQAALEPGEKPYACPECGKSFSQSSSLVRHQRTHTGEKPYKCPECGKSFS
     AQAALEPGEKPYACPECGKSFSQSSSLVRHQRTHTGEKPYKCPECGKSFS
     AQAALEPGEKPYACPECGKSFSQSSSLVRHQRTHTGEKPYKCPECGKSFS
                            F1

51  QRAHLERHQRTHTGEKPYKCPECGKSFSQSSNLVRHQRTHTGEKPYACPE                   100
     QSSNLVRHQRTHTGEKPYKCPECGKSFSRSDNLVRHQRTHTGEKPYACPE
     TSGSLVRHQRTHTGEKPYKCPECGKSFSQSSSLVRHQRTHTGEKPYACPE
     QSSSLVRHQRTHTGEKPYKCPECGKSFSDCRDLARHQRTHTGEKPYACPE
     QSSNLVRHQRTHTGEKPYKCPECGKSFSQSSNLVRHQRTHTGEKPYACPE
     QSSNLVRHQRTHTGEKPYKCPECGKSFSQSSNLVRHQRTHTGEKPYACPE
          F2                                  F3

101  CGKSFSRSDNLVRHQRTHTGEKPYKCPECGKSFSRSDNLVRHQRTHTGEK                   150
     CGKSFSRSDNLVRHQRTHTGEKPYKCPECGKSFSQAGHLASHQRTHTGEK
     CGKSFSQSSSLVRHQRTHTGEKPYKCPECGKSFSDCRDLARHQRTHTGEK
     CGKSFSQSSSLVRHQRTHTGEKPYKCPECGKSFSRSDNLVRHQRTHTGEK
     CGKSFSTSGSLVRHQRTHTGEKPYKCPECGKSFSQSSHLVRHQRTHTGEK
     CGKSFSQSSNLVRHQRTHTGEKPYKCPECGKSFSQSSNLVRHQRTHTGEK
                   F4                                 F5

151  PYKCPECGKSFSQAGHLASHQRTHTGKKTSGQAG  ZFPm1 (SEQ ID NO:38)              184
     PYKCPECGKSFSRSDNLVRHQRTHTGKKTSGQAG  ZFPm2 (SEQ ID NO:39)
     PYKCPECGKSFSQSSHLVRHQRTHTGKKTSGQAG  ZFPm3 (SEQ ID NO:40)
     PYKCPECGKSFSTSGHLVRHQRTHTGKKTSGQAG  ZFPm4 (SEQ ID NO:41)
     PYKCPECGKSFSTSGNLVRHQRTHTGKKTSGQAG  ZFPAp3 (SEQ ID NO:42)
                   F6

(1)     Sequence of promoter CsVMV (Example 1A) (SEQ ID NO:1):

tctagaaactagcttccagaaggtaattatccaagatgtagcatcaagaatccaatgtttacgggaaaaactatggaag
tattatgtgagctcagcaagaagcagatcaatatgcggcacatatgcaacctatgttcaaaaatgaagaatgtacagatacaagat
cctatactgccagaatacgaagaagaatacgtagaaattgaaaaagaagaaccaggcgaagaaaagaatcttgaagacgtaag
cactgacgacaacaatgaaaagaagaagataaggtcggtgattgtgaaagagacatagaggacacatgtaaggtggaaaatgt
aagggcggaaagtaaccttatcacaaaggaatcttatcccccactacttatccttttatattttccgtgtcattttgcccttgagttttc
ctatataaggaaccaagttcggcatttgtgaaaacaagaaaaaatttggtgtaagctattttctttgaagtactgaggatacaacttca
gagaaatttgtaagtttgta Total 532 bp (2)     Sequence of zinc finger protein 2C7 binding site (Example 1A) (SEQ ID NO:2):

GCG TGG GCG GCG TGG GCG

Total 18 bp.

(3)     Sequence of promoter pc7rbTATA (Example 1A) (SEQ ID NO:3):

cccgggtatataataagcttggcattccggtactgttggtaaagccaccat

Total 51 bp.

(4)     Sequence of pND3008 coding region (Example1B) (SEQ ID NO:4):

agcgtgacccggtcgtgcccctctctagagataatgagcattgcatgtctaagttataaaaaattaccacatatttttttg
tcacacttgtttgaagtgcagtttatctatctttatacatatatttaaactttactctacgaataatataatctatagtactacaataatatca
gtgttttagagaatcatataaatgaacagttagacatggtctaaaggacaattgagtattttgacaacaggactctacagttttatcttt
ttagtgtgcatgtgttctccttttttttttgcaaatagcttcacctatataatacttcatccattttattagtacatccatttagggtttagggtt
aatggtttttatagactaattttttagtacatctattttattctattttagcctctaaattaagaaaactaaaactctatttagtttttttattta
ataatttagatataaaatagaataaaataaagtgactaaaaattaaacaaataccctttaagaaattaaaaaaactaaggaaacatttt
tcttgtttcgagtagataatgccagcctgttaaacgccgtcgacgagtctaacggacaccaaccagcgaaccagcagcgtcgcg
tcgggccaagcgaagcagacggcacggcatctctgtcgctgcctctggaccccctcgagagttccgctccaccgttggacttg
ctccgctgtcggcatccagaaattgcgtggcggagcggcagacgtgagccggcacggcaggcggcctcctcctcctctcacg
gcacggcagctacggggggattccttccaccgctccttcgctttcccttcctcgcccgccgtaataaatagacacccctccaca ccctctttccccaacctcgtgttgttcggagcgcacacacacacaaccagatctcccccaaatccaccgtcggcacctccgctt
caaggtacgccgctcgtcctccccccccccccctctctaccttctctagatcggcgttccggtccatggttagggcccggtagttc
tacttctgttcatgtttgtgttagatccgtgtttgtgttagatccgtgctgctagcgttcgtacacggatgcgacctgtacgtcagacac
gttctgattgctaacttgccagtgtttctctttggggaatcctgggatggctctagccgttccgcagacgggatcgatttcatgattttt
tttgtttcgttgcatagggtttggtttgcccttttcctttatttcaatatatgccgtgcacttgtttgtcgggtcatcttttcatgcttttttttgt
cttggttgtgatgatgtggtctggttgggcggtcgttctagatcggagtagaattctgtttcaaactacctggtggatttattaattttgg
atctgtatgtgtgtgccatacatattcatagttacgaattgaagatgatggatggaaatatcgatctaggataggtatacatgttgatg
cgggttttactgatgcatatacagagatgcttttgttcgcttggttgtgatgatgtggtgtggttgggcggtcgttcattcgttctagat
cggagtagaatactgtttcaaactacctggtgtatttattaattttggaactgtatgtgtgtgtcatacatcttcatagttacgagtttaag
atggatggaaatatcgatctaggataggtatacatgttgatgtgggttttactgatgcatatacatgatggcatatgcagcatctattc
atatgctctaaccttgagtacctatctattataataaacaagtatgttttataattattttgatcttgatatacttggatgatggcatatgca
gcagctatatgtggattttttagccctgccttcatacgctatttatttgcttggtactgtttcttttgtcgatgctcaccctgttgtttggtgt
tacttctgcaggtcgactctagaggatctatggcccaggcggccctcgagctcccctatgcttgccctgtcgagtcctgcgatcgc
cgcttttctaagtcggctgatctgaagcgccatatccgcatccacacaggccagaagcccttccagtgtcgaatatgcatgcgtaa
cttcagtcgtagtgaccaccttaccacccacatccgcacccacacaggcgagaagccttttgcctgtgacatttgtggggaggaag
tttgccaggagtgatgaacgcaagaggcataccaaaatccataccggtgagaagccctatgcttgccctgtcgagtcctgcgatc
gccgcttttctaagtcggctgatctgaagcgccatatccgcatccacacaggccagaagcccttccagtgtcgaatatgcatgcgt
aacttcagtcgtagtgaccaccttaccacccacatccgcacccacacaggcgagaagccttttgcctgtgacatttgtggggagga
agtttgccaggagtgatgaacgcaagaggcataccaaaatccatttaagacagaaggactctagaactagtggccaggccggc
caggctagccccgaaaaagaaacgcaaagttgggcgcgccgacgcgctggacgatttcgatctcgacatgctgggttctgatgc
cctcgatgactttgacctggatatgttgggaagcgacgcattggatgactttgatctggacatgctcggctccgatgctctggacg
atttcgatctcgatatgttaattaactacccgtacgacgttccggactacgcttcttgagaattcgcggccgcgggcccgagcctag
ggaggagctcaagatcccccgaatttccccgatcgttcaaacatttggcaataaagtttcttaagattgaatcctgttgccggtcttg
cgatgattatcatctaatttctgttgaattacgttaagcatgtaataattaacatgtaatgcatgacgttatttatgagatgggtttttatga
ttagagtcccgcaattatacatttaatacgcgatagaaaacaaaatatagcgcgcaaactaggataaattatcgcgcgcggtgtca
tctatgttactagatccgggaattgggtac

| | |
|---|---|
| Total: | 3121 bp |
| ZmUbi promoter: | 44 bp to 2026 bp |
| Six finger ZFP2C7: | 2060 bp to 2588 bp |
| Nuclear localization signal: | 2620 bp to 2641 bp |
| VP64 activation domain: | 2641 bp to 2805 bp |

HA eptitope tag: 2805 bp to 2836 bp

Nos terminator: 2884 bp to 3164 bp (5) Sequence of pND3018 coding region (Example 1B) (SEQ ID NO:5):

agcgtgacccggtcgtgcccctctctagagataatgagcattgcatgtctaagttataaaaaattaccacatattttttg tcacacttgtttgaagtgcagtttatctatctttatacatatatttaaactttactctacgaataatataatctatagtactacaataatatca gtgttttagagaatcatataaatgaacagttagacatggtctaaaggacaattgagtattttgacaacaggactctacagttttatcttt ttagtgtgcatgtgttctccttttttttttgcaaatagcttcacctatataatacttcatccattttattagtacatccatttagggtttagggtt aatggtttttatagactaatttttttagtacatctattttattctattttagcctctaaattaagaaaactaaaactctattttagtttttttattta ataatttagatataaaatagaataaaataaagtgactaaaaattaaacaaatacccttaagaaattaaaaaaactaaggaaacatttt tcttgtttcgagtagataatgccagcctgttaaacgccgtcgacgagtctaacggacaccaaccagcgaaccagcagcgtcgcg tcgggccaagcgaagcagacggcacggcatctctgtcgctgcctctggaccctctcgagagttccgctccaccgttggacttg ctccgctgtcggcatccagaaattgcgtggcggagcggcagacgtgagccggcacggcaggcggcctcctcctcctctcacg gcacggcagctacggggattcctttcccaccgctccttcgctttcccttcctcgcccgccgtaataaatagacaccccctccaca ccctctttccccaacctcgtgttgttcggagcgcacacacacacaaccagatctcccccaaatccaccgtcggcacctccgctt caaggtacgccgctcgtcctcccccccccccctctctaccttctctagatcggcgttccggtccatggttagggcccggtagttc tacttctgttcatgtttgtgttagatccgtgtttgtgttagatccgtgctgctagcgttcgtacacggatgcgacctgtacgtcagacac gttctgattgctaacttgccagtgtttctctttggggaatcctgggatggctctagccgttccgcagacgggatcgatttcatgatttt tttgtttcgttgcatagggtttggtttgcccttttccttatttcaatatatgccgtgcacttgtttgtcgggtcatcttttcatgcttttttttgt cttggttgtgatgatgtggtctggttgggcggtcgttctagatcggagtagaattctgtttcaaactacctggtggatttattaattttgg atctgtatgtgtgtgccatacatattcatagttacgaattgaagatgatggatggaaatatcgatctaggataggtatacatgttgatg cgggttttactgatgcatatacagagatgcttttgttcgcttggttgtgatgatgtggtgtggttgggcggtcgttcattcgttctagat cggagtagaatactgtttcaaactacctggtgtatttattaattttggaactgtatgtgtgtgtcatacatcttcatagttacgagtttaag atggatggaaatatcgatctaggataggtatacatgttgatgtgggttttactgatgcatatacatgatggcatatgcagcatctattc atatgctctaaccttgagtacctatctattataataaacaagtatgttttataattattttgatcttgatatacttggatgatggcatatgca gcagctatatgtggattttttttagccctgccttcatacgctatttatttgcttggtactgtttcttttgtcgatgctcaccctgttgtttggtgt tacttctgcaggtcgactctagaggatccactagtgagccatgggctagcatggccgctgccgtgcgcatgaacatccagatgct gctcgaagccgctgattatctggaacgccgggagcgcgaagccgagcacggctacgccagcatgctgccatatccgaaaaag aaacgcaaggtggcccaggcggccctcgagctcccctatgcttgccctgtcgagtcctgcgatcgccgcttttctaagtcggctg atctgaagcgccatatccgcatccacacaggccagaagcccttccagtgtcgaatatgcatgcgtaacttcagtcgtagtgacca ccttaccacccacatccgcacccacacaggcgagaagccttttgcctgtgacatttgtgggaggaagtttgccaggagtgatgaa cgcaagaggcataccaaaatccataccggtgagaagccctatgcttgccctgtcgagtcctgcgatcgccgcttttctaagtcgg
ctgatctgaagcgccatatccgcatccacacaggccagaagcccttccagtgtcgaatatgcatgcgtaacttcagtcgtagtga
ccaccttaccacccacatccgcacccacacaggcgagaagccttttgcctgtgacatttgtgggaggaagtttgccaggagtgat
gaacgcaagaggcataccaaaatccatttaagacagaaggactctagaactagtggccaggccggccagtacccgtacgacg
ttccggactacgcttcttgaaagcttggtaccgagctcggatcccccgaatttccccgatcgttcaaacatttggcaataaagtttctt
aagattgaatcctgttgccggtcttgcgatgattatcatctaatttctgttgaattacgttaagcatgtaataattaacatgtaatgcatg
acgttatttatgagatgggtttttatgattagagtcccgcaattatacatttaatacgcgatagaaaacaaaatatagcgcgcaaacta
ggataaattatcgcgcgcggtgtcatctatgttactagatccgggaattccggaccggtaccagcggcc

| | |
|---|---|
| Total: | 3068 bp |
| ZmUbi promoter: | 44 bp to 2026 bp |
| SID repression domain: | 2066 bp to 2173 bp |
| Nuclear localization signal: | 2174 bp to 2194 bp |
| Six finger ZFP2C7: | 2207 bp to 2735 bp |
| HA epitope tag: | 2762 bp to 2791 bp |
| Nos terminator: | 2820 bp to 3112 bp |

(6)  Sequence of 6X2C7 binding site (SEQ ID NO:6):

cgtgctagcgcgtgggcggcgtgggcgaacaagcgtgggcggcgtgggcgaacaagcgtgggcggcgtgggc
gactagtgctagcgcgtgggcggcgtgggcgaacaagcgtgggcggcgtgggcgaacaagcgtgggcggcgtgggcgac
tagtg Total: 156 bp (7)  Sequence of 3 finger protein C7 (SEQ ID NO:73):

atggcccaggcggccctcgagccctatgcttgccctgtcgagtcctgcgatcgccgcttttctaagtcggctgatctga
agcgccatatccgcatccacacaggccagaagcccttccagtgtcgaatatgcatgcgtaacttcagtcgtagtgaccaccttac
cacccacatccgcacccacacaggcgagaagccttttgcctgtgacatttgtgggaggaagtttgccaggagtgatgaacgcaa
gaggcataccaaaatccatttaagacagaaggactctagaactagtggccaggccggccaggctagc Total: 314 bp (8) Amino acid sequence of 3 finger protein C7 (SEQ ID NO:74):

MAQAALEPYACPVESCDRRFSKSADLKRHIRIHTGQKPFQCRICMRNFSRSDHLTTHIRTHTGEKPFACDICGRKFARSDERKRHTKIHLRQKDSRTSGQAGQAS

Total: 105 aa (9) Sequence of zinc finger protein ZFPAp3 binding site (SEQ ID NO:7):

GAT GGA GTT GAA GAA GTA

Total: 18 bp

(10) Sequence of zinc finger protein ZFPm1 and ZFPm2 binding site m12: (SEQ ID NO:76): GCC TCC TTC CTC CTC TCA CTC Total: 21 bp ZFPm1 binding site: compliment strand of 1 to 18

ZFPm2 binding site: compliment strand of 4 to 21

(11) Sequence of zinc finger protein ZFPm3 and ZFPm4 binding site m34 (SEQ ID NO:77):

GCC AAC TAC TAC GGC TCC CTC ACC

Total: 24 bp

ZFPm3 binding site: compliment strand of 1 to 18

ZFPm4 binding site: compliment strand of 7 to 24

(12) Partial sequence of pMal-m1 (1-3300 bp) and zinc finger protein ZFPm1 (2719-3270 bp) (SEQ ID NO:14):

ccgacaccatcgaatggtgcaaaacctttcgcggtatggcatgatagcgcccggaagagagtcaattcagggtggt
gaatgtgaaaccagtaacgttatacgatgtcgcagagtatgccggtgtctcttatcagaccgtttcccgcgtggtgaaccaggcca
gccacgtttctgcgaaaacgcgggaaaaagtggaagcggcgatggcggagctgaattacattcccaaccgcgtggcacaaca
actggcgggcaaacagtcgttgctgattggcgttgccacctccagtctggccctgcacgcgccgtcgcaaattgtcgcggcgat
taaatctcgcgccgatcaactgggtgccagcgtggtggtgtcgatggtagaacgaagcggcgtcgaagcctgtaaagcggcg
gtgcacaatcttctcgcgcaacgcgtcagtgggctgatcattaactatccgctggatgaccaggatgccattgctgtggaagctg
cctgcactaatgttccggcgttatttcttgatgtctctgaccagacacccatcaacagtattattttctcccatgaagacggtacgcga ctgggcgtggagcatctggtcgcattgggtcaccagcaaatcgcgctgttagcgggcccattaagttctgtctcggcgcgtctgc gtctggctggctggcataaatatctcactcgcaatcaaattcagccgatagcggaacgggaaggcgactggagtgccatgtccg gttttcaacaaaccatgcaaatgctgaatgagggcatcgttcccactgcgatgctggttgccaacgatcagatggcgctgggcgc aatgcgcgccattaccgagtccgggctgcgcgttggtgcggatatctcggtagtgggatacgacgataccgaagacagctcat gttatatcccgccgttaaccaccatcaaacaggattttcgcctgctggggcaaaccagcgtggaccgcttgctgcaactctctcag ggccaggcggtgaagggcaatcagctgttgcccgtctcactggtgaaaagaaaaaccaccctggcgcccaatacgcaaaccg cctctccccgcgcgttggccgattcattaatgcagctggcacgacaggtttcccgactggaaagcgggcagtgagcgcaacgc aattaatgtgagttagctcactcattaggcacaattctcatgtttgacagcttatcatcgactgcacggtgcaccaatgcttctggcgt caggcagccatcggaagctgtggtatggctgtgcaggtcgtaaatcactgcataattcgtgtcgctcaaggcgcactcccgttct ggataatgttttttgcgccgacatcataacggttctggcaaatattctgaaatgagctgttgacaattaatcatcggctcgtataatgt gtggaattgtgagcggataacaatttcacacaggaaacagccagtccgtttaggtgttttcacgagcacttcaccaacaaggacc atagattatgaaaactgaagaaggtaaactggtaatctggattaacggcgataaaggctataacggtctcgctgaagtcggtaag aaattcgagaaagataccggaattaaagtcaccgttgagcatccggataaactggaagagaaattcccacaggttgcggcaact ggcgatggccctgacattatcttctgggcacacgaccgctttggtggctacgctcaatctggcctgttggctgaaatcaccccgg acaaagcgttccaggacaagctgtatccgtttacctgggatgccgtacgttacaacggcaagctgattgcttacccgatcgctgtt gaagcgttatcgctgatttataacaaagatctgctgccgaacccgccaaaaacctgggaagagatcccggcgctggataaagaa ctgaaagcgaaaggtaagagcgcgctgatgttcaacctgcaagaaccgtacttcacctggccgctgattgctgctgacgggggt tatgcgttcaagtatgaaaacggcaagtacgacattaaagacgtgggcgtggataacgctggcgcgaaagcgggtctgaccttc ctggttgacctgattaaaaacaaacacatgaatgcagacaccgattactccatcgcagaagctgcctttaataaaggcgaaacag cgatgaccatcaacggcccgtgggcatggtccaacatcgacaccagcaaagtgaattatggtgtaacggtactgccgaccttca agggtcaaccatccaaaccgttcgttggcgtgctgagcgcaggtattaacgccgccagtccgaacaaagagctggcaaaaga gttcctcgaaaactatctgctgactgatgaaggtctggaagcggttaataaagacaaaccgctgggtgccgtagcgctgaagtct tacgaggaagagttggcgaaagatccacgtattgccgccaccatggaaaacgcccagaaaggtgaaatcatgccgaacatcc cgcagatgtccgctttctggtatgccgtgcgtactgcggtgatcaacgccgccagcggtcgtcagactgtcgatgaagccctga agacgcgcagactaattcgagctcgaacaacaacaacaataacaataacaacaacctcgggatcgagggaaggatttcagaa ttcggatcctcttcctctgtggcccaggcggccctcgagcccggggagaagccctatgcttgtccggaatgtggtaagtccttctc tcagagctctcacctggtgcgccaccagcgtacccacacgggtgaaaaaccgtataaatgcccagagtgcggcaaatcttttag ccagtccagcaacctggtgcgccatcaacgcactcatactggcgagaagccatacaaatgtccagaatgtggcaagtctttctct cggtctgacaatctcgtccggcaccaacgtactcacaccggggagaagccctatgcttgtccggaatgtggtaagtccttcagcc gcagcgataacctggtgcgccaccagcgtacccacacgggtgaaaaaccgtataaatgcccagagtgcggcaaatcttttagc caggccggccacctggccagccatcaacgcactcatactggcgagaagccatacaaatgtccagaatgtggcaagtctttctct cggtctgacaatctcgtccggcaccaacgtactcacaccggtaaaaaaactagtggccaggccggccagtacccgtacgacgt
tccggactacgct Total: 514 bp Primer F1-f1 of ZFPm1: 2770 bp to 2850 bp Primer F1-f2 of ZFPm1: 2740 bp to 2790 bp Primer F2-f of ZFPm1: 2867 bp to 2940 bp Primer F2-b of ZFPm1: 2824 bp to 2889 bp Primer F3-b1 ZFPm1: 2916 bp to 2973 bp Primer F3-b2 ZFPm1: 2953 bp to 3021 bp Primer F4-f1 of ZFPm1: 3022 bp to 3102 bp Primer F4-f2 of ZFPm1: 2992 bp to 3042 bp Primer F5-f of ZFPm1: 3119 bp to 3192 bp Primer F5-b of ZFPm1: 3076 bp to 3141 bp Primer F6-b1 of ZFPm1: 3168 bp to 3225 bp Primer F6-b2 of ZFPm1: 3205 bp to 3273 bp

(13) Sequence of zinc finger protein ZFPm1
(Translated from pMal-m1: 2719-3270 bp) (SEQ ID NO:75):

AQAALEPGEKPYACPECGKSFSDPGHLVRHQRTHTGEKPYKCPECGKSFS
QRAHLERHQRTHTGEKPYKCPECGKSFSQSSNLVRHQRTHTGEKPYACPECGKS
FSRSDNLVRHQRTHTGEKPYKCPECGKSFSRSDNLVRHQRTHTGEKPYKCPECG
KSFSQAGHLASHQRTHTGKKTSGQAG

(14) Partial sequence of pMal-m2 (1-3300 bp) and zinc finger protein ZFPm2
(2719-3270 bp) (SEQ ID NO:15):

ccgacaccatcgaatggtgcaaaacctttcgcggtatggcatgatagcgcccggaagagagtcaattcagggtggt
gaatgtgaaaccagtaacgttatacgatgtcgcagagtatgccggtgtctcttatcagaccgtttcccgcgtggtgaaccaggcca
gccacgtttctgcgaaaacgcgggaaaaagtggaagcggcgatggcggagctgaattacattcccaaccgcgtggcacaaca
actggcgggcaaacagtcgttgctgattggcgttgccacctccagtctggccctgcacgcgccgtcgcaaattgtcgcggcgat
taaatctcgcgccgatcaactgggtgccagcgtggtggtgtcgatggtagaacgaagcggcgtcgaagcctgtaaagcggcg gtgcacaatcttctcgcgcaacgcgtcagtgggctgatcattaactatccgctggatgaccaggatgccattgctgtggaagctg cctgcactaatgttccggcgttatttcttgatgtctctgaccagacacccatcaacagtattattttctcccatgaagacggtacgcga ctgggcgtggagcatctggtcgcattgggtcaccagcaaatcgcgctgttagcgggcccattaagttctgtctcggcgcgtctgc gtctggctggctggcataaatatctcactcgcaatcaaattcagccgatagcggaacgggaaggcgactggagtgccatgtccg gttttcaacaaaccatgcaaatgctgaatgagggcatcgttcccactgcgatgctggttgccaacgatcagatggcgctgggcgc aatgcgcgccattaccgagtccgggctgcgcgttggtgcggatatctcggtagtgggatacgacgataccgaagacagctcat gttatatcccgccgttaaccaccatcaaacaggattttcgcctgctggggcaaaccagcgtggaccgcttgctgcaactctctcag ggccaggcggtgaagggcaatcagctgttgcccgtctcactggtgaaaagaaaaaccaccctggcgcccaatacgcaaaccg cctctccccgcgcgttggccgattcattaatgcagctggcacgacaggtttcccgactggaaagcgggcagtgagcgcaacgc aattaatgtgagttagctcactcattaggcacaattctcatgtttgacagcttatcatcgactgcacggtgcaccaatgcttctggcgt caggcagccatcggaagctgtggtatggctgtgcaggtcgtaaatcactgcataattcgtgtcgctcaaggcgcactcccgttct ggataatgttttttgcgccgacatcataacggttctggcaaatattctgaaatgagctgttgacaattaatcatcggctcgtataatgt gtggaattgtgagcggataacaatttcacacaggaaacagccagtccgtttaggtgttttcacgagcacttcaccaacaaggacc atagattatgaaaactgaagaaggtaaactggtaatctggattaacggcgataaaggctataacggtctcgctgaagtcggtaag aaattcgagaaagataccggaattaaagtcaccgttgagcatccggataaactggaagagaaattcccacaggttgcggcaact ggcgatggccctgacattatcttctgggcacacgaccgctttggtggctacgctcaatctggcctgttggctgaaatcaccccgg acaaagcgttccaggacaagctgtatccgtttacctgggatgccgtacgttacaacggcaagctgattgcttacccgatcgctgtt gaagcgttatcgctgatttataacaaagatctgctgccgaacccgccaaaaacctgggaagagatcccggcgctggataaagaa ctgaaagcgaaaggtaagagcgcgctgatgttcaacctgcaagaaccgtacttcacctggccgctgattgctgctgacggggt tatgcgttcaagtatgaaaacggcaagtacgacattaaagacgtgggcgtggataacgctggcgcgaaagcgggtctgaccttc ctggttgacctgattaaaaacaaacacatgaatgcagacaccgattactccatcgcagaagctgcctttaataaaggcgaaacag cgatgaccatcaacggcccgtgggcatggtccaacatcgacaccagcaaagtgaattatggtgtaacggtactgccgaccttca agggtcaaccatccaaaccgttcgttggcgtgctgagcgcaggtattaacgccgccagtccgaacaaagagctggcaaaaga gttcctcgaaaactatctgctgactgatgaaggtctggaagcggttaataaagacaaaccgctgggtgccgtagcgctgaagtct tacgaggaagagttggcgaaagatccacgtattgccgccaccatggaaaacgcccagaaaggtgaaatcatgccgaacatcc cgcagatgtccgctttctggtatgccgtgcgtactgcggtgatcaacgccgccagcggtcgtcagactgtcgatgaagccctga aagacgcgcagactaattcgagctcgaacaacaacaacaataacaataacaacaacctcgggatcgagggaaggatttcagaa ttcggatcctcttcctctgtggcccaggcggccctcgagcccggggagaagccctatgcttgtccggaatgtggtaagtccttctc tcagagctctcacctggtgcgccaccagcgtacccacacgggtgaaaaaccgtataaatgcccagagtgcggcaaatcttttag ccagtccagcaacctggtgcgccatcaacgcactcatactggcgagaagccatacaaatgtccagaatgtggcaagtctttctct cggtctgacaatctcgtccggcaccaacgtactcacaccggggagaagcccatgcttgtccggaatgtggtaagtccttcagcc gcagcgataacctggtgcgccaccagcgtacccacacgggtgaaaaaccgtataaatgcccagagtgcggcaaatcttttagc
caggccggccacctggccagccatcaacgcactcatactggcgagaagccatacaaatgtccagaatgtggcaagtctttctct
cggtctgacaatctcgtccggcaccaacgtactcacaccggtaaaaaaactagtggccaggccggccagtacccgtacgacgt
tccggactacgct Total: 514 bp Primer F1-f1 of ZFPm2: 2770 bp to 2850 bp Primer F1-f2 of ZFP m2: 2740 bp to 2790 bp Primer F2-f of ZFP m2: 2867 bp to 2940 bp Primer F2-b of ZFPm2: 2824 bp to 2889 bp Primer F3-b1 ZFPm2: 2916 bp to 2973 bp Primer F3-b2 ZFPm2: 2953 bp to 3021 bp Primer F4-f1 of ZFPm2: 3022 bp to 3102 bp Primer F4-f2 of ZFPm2: 2992 bp to 3042 bp Primer F5-f of ZFPm2: 3119 bp to 3192 bp Primer F5-b of ZFPm2: 3076 bp to 3141 bp Primer F6-b1 of ZFPm2: 3168 bp to 3225 bp Primer F6-b2 of ZFPm2: 3205 bp to 3273 bp

(15)    Partial sequence of pMal-m3 (1-3300 bp) and zinc finger protein ZFPm3
    <u>(2719-3270 bp) (SEQ ID NO:16):</u> ccgacaccatcgaatggtgcaaaacctttcgcggtatggcatgatagcgcccggaagagagtcaattcagggtggt
gaatgtgaaaccagtaacgttatacgatgtcgcagagtatgccggtgtctcttatcagaccgtttcccgcgtggtgaaccaggcca
gccacgtttctgcgaaaacgcgggaaaaagtggaagcggcgatggcggagctgaattacattcccaaccgcgtggcacaaca
actggcgggcaaacagtcgttgctgattggcgttgccacctccagtctggccctgcacgcgccgtcgcaaattgtcgcggcgat
taaatctcgcgccgatcaactgggtgccagcgtggtggtgtcgatggtagaacgaagcggcgtcgaagcctgtaaagcggcg
gtgcacaatcttctcgcgcaacgcgtcagtgggctgatcattaactatccgctggatgaccaggatgccattgctgtggaagctg
cctgcactaatgttccggcgttatttcttgatgtctctgaccagacacccatcaacagtattattttctcccatgaagacggtacgcga
ctgggcgtggagcatctggtcgcattgggtcaccagcaaatcgcgctgttagcgggcccattaagttctgtctcggcgcgtctgc
gtctggctggctggcataaatatctcactcgcaatcaaattcagccgatagcggaacgggaaggcgactggagtgccatgtccg
gttttcaacaaaccatgcaaatgctgaatgagggcatcgttcccactgcgatgctggttgccaacgatcagatggcgctgggcgc aatgcgcgccattaccgagtccgggctgcgcgttggtgcggatatctcggtagtgggatacgacgataccgaagacagctcat
gttatatcccgccgttaaccaccatcaaacaggattttcgcctgctggggcaaaccagcgtggaccgcttgctgcaactctctcag
ggccaggcggtgaagggcaatcagctgttgcccgtctcactggtgaaaagaaaaaccaccctggcgcccaatacgcaaaccg
cctctccccgcgcgttggccgattcattaatgcagctggcacgacaggtttcccgactggaaagcgggcagtgagcgcaacgc
aattaatgtgagttagctcactcattaggcacaattctcatgtttgacagcttatcatcgactgcacggtgcaccaatgcttctggcgt
caggcagccatcggaagctgtggtatggctgtgcaggtcgtaaatcactgcataattcgtgtcgctcaaggcgcactcccgttct
ggataatgttttttgcgccgacatcataacggttctggcaaatattctgaaatgagctgttgacaattaatcatcggctcgtataatgt
gtggaattgtgagcggataacaatttcacacaggaaacagccagtccgtttaggtgttttcacgagcacttcaccaacaaggacc
atagattatgaaaactgaagaaggtaaactggtaatctggattaacggcgataaaggctataacggtctcgctgaagtcggtaag
aaattcgagaaagataccggaattaaagtcaccgttgagcatccggataaactggaagagaaattcccacaggttgcggcaact
ggcgatggccctgacattatcttctgggcacacgaccgctttggtggctacgctcaatctggcctgttggctgaaatcaccccgg
acaaagcgttccaggacaagctgtatccgtttacctgggatgccgtacgttacaacggcaagctgattgcttacccgatcgctgtt
gaagcgttatcgctgatttataacaaagatctgctgccgaacccgccaaaaacctgggaagagatcccggcgctggataaagaa
ctgaaagcgaaaggtaagagcgcgctgatgttcaacctgcaagaaccgtacttcacctggccgctgattgctgctgacggggt
tatgcgttcaagtatgaaaacggcaagtacgacattaaagacgtgggcgtggataacgctggcgcgaaagcgggtctgaccttc
ctggttgacctgattaaaaacaaacacatgaatgcagacaccgattactccatcgcagaagctgcctttaataaaggcgaaacag
cgatgaccatcaacggcccgtgggcatggtccaacatcgacaccagcaaagtgaattatggtgtaacggtactgccgaccttca
agggtcaaccatccaaaccgttcgttggcgtgctgagcgcaggtattaacgccgccagtccgaacaaagagctggcaaaaga
gttcctcgaaaactatctgctgactgatgaaggtctggaagcggttaataaagacaaaccgctgggtgccgtagcgctgaagtct
tacgaggaagagttggcgaaagatccacgtattgccgccaccatggaaaacgcccagaaaggtgaaatcatgccgaacatcc
cgcagatgtccgctttctggtatgccgtgcgtactgcggtgatcaacgccgccagcggtcgtcagactgtcgatgaagccctga
aagacgcgcagactaattcgagctcgaacaacaacaacaataacaataacaacaacctcgggatcgagggaaggatttcagaa
ttcggatcctcttcctctgtggcccaggcggccctcgagcccggggagaagccctatgcttgtccggaatgtggtaagtccttca
gcgatcctggccacctggttcgccaccagcgtacccacacgggtgaaaaaccgtataaatgcccagagtgcggcaaatctttta
gcaccagcggctcccctggtgcgccatcaacgcactcatactggcgagaagccatacaaatgtccagaatgtggcaagtctttca
gccagagctccagcctggtgcgccaccaacgtactcacaccggggagaagccctatgcttgtccggaatgtggtaagtccttca
gccagagcagctccctggtgcgccaccagcgtacccacacgggtgaaaaaccgtataaatgcccagagtgcggcaaatctttt
agtgactgccgcgaccttgctcgccatcaacgcactcatactggcgagaagccatacaaatgtccagaatgtggcaagtctttct
cccaatccagccatctcgtccggcaccaacgtactcacaccggtaaaaaaactagtggccaggccggccagtacccgtacgac
gttccggactacgct Total: 514 bp Primer F1-f1 of ZFPm3: 2770 bp to 2850 bp Primer F1-f2 of ZFP m3: 2740 bp to 2790 bp Primer F2-f of ZFP m3: 2867 bp to 2940 bp Primer F2-b of ZFPm3: 2824 bp to 2889 bp Primer F3-b1 ZFPm3: 2916 bp to 2973 bp Primer F3-b2 ZFPm3: 2953 bp to 3021 bp Primer F4-f1 of ZFPm3: 3022 bp to 3102 bp Primer F4-f2 of ZFPm3: 2992 bp to 3042 bp Primer F5-f of ZFPm3: 3119 bp to 3192 bp Primer F5-b of ZFPm3: 3076 bp to 3141 bp Primer F6-b1 of ZFPm3: 3168 bp to 3225 bp Primer F6-b2 of ZFPm3: 3205 bp to 3273 bp

(16)  Partial sequence of pMal-m4 (1-3300 bp) and zinc finger protein ZFPm4 (2719-3270 bp) (SEQ ID NO:17):

ccgacaccatcgaatggtgcaaaaccttttcgcggtatggcatgatagcgcccggaagagagtcaattcagggtggt
gaatgtgaaaccagtaacgttatacgatgtcgcagagtatgccggtgtctcttatcagaccgtttcccgcgtggtgaaccaggcca
gccacgtttctgcgaaaacgcggggaaaaagtggaagcggcgatggcggagctgaattacattcccaaccgcgtggcacaaca
actggcgggcaaacagtcgttgctgattggcgttgccacctccagtctggccctgcacgcgccgtcgcaaattgtcgcggcgat
taaatctcgcgccgatcaactgggtgccagcgtggtggtgtcgatggtagaacgaagcggcgtcgaagcctgtaaagcggcg
gtgcacaatcttctcgcgcaacgcgtcagtgggctgatcattaactatccgctggatgaccaggatgccattgctgtggaagctg
cctgcactaatgttccggcgttatttcttgatgtctctgaccagacacccatcaacagtattattttctcccatgaagacggtacgcga
ctgggcgtggagcatctggtcgcattgggtcaccagcaaatcgcgctgttagcgggcccattaagttctgtctcggcgcgtctgc
gtctggctggctggcataaatatctcactcgcaatcaaattcagccgatagcggaacgggaaggcgactggagtgccatgtccg
gttttcaacaaaccatgcaaatgctgaatgagggcatcgttcccactgcgatgctggttgccaacgatcagatggcgctgggcgc
aatgcgcgccattaccgagtccgggctgcgcgttggtgcggatatctcggtagtgggatacgacgataccgaagacagctcat
gttatatcccgccgttaaccaccatcaaacaggattttcgcctgctggggcaaaccagcgtggaccgcttgctgcaactctctcag
ggccaggcggtgaagggcaatcagctgttgcccgtctcactggtgaaaagaaaaaccaccctggcgcccaatacgcaaaccg
cctctccccgcgcgttggccgattcattaatgcagctggcacgacaggtttccc gactggaaagcgggcagtgagcgcaacgc
aattaatgtgagttagctcactcattaggcacaattctcatgtttacagcttatcatcgactgcacggtgcaccaatgcttctggcgt caggcagccatcggaagctgtggtatggctgtgcaggtcgtaaatcactgcataattcgtgtcgctcaaggcgcactcccgttct
ggataatgttttttgcgccgacatcataacggttctggcaaatattctgaaatgagctgttgacaattaatcatcggctcgtataatgt
gtggaattgtgagcggataacaatttcacacaggaaacagccagtccgtttaggtgttttcacgagcacttcaccaacaaggacc
atagattatgaaaactgaagaaggtaaactggtaatctggattaacggcgataaaggctataacggtctcgctgaagtcggtaag
aaattcgagaaagataccggaattaaagtcaccgttgagcatccggataaactggaagagaaattcccacaggttgcggcaact
ggcgatggccctgacattatcttctgggcacacgaccgctttggtggctacgctcaatctggcctgttggctgaaatcaccccgg
acaaagcgttccaggacaagctgtatccgtttacctgggatgccgtacgttacaacggcaagctgattgcttacccgatcgctgtt
gaagcgttatcgctgatttataacaaagatctgctgccgaacccgccaaaaacctgggaagagatcccggcgctggataaagaa
ctgaaagcgaaaggtaagagcgcgctgatgttcaacctgcaagaaccgtacttcacctggccgctgattgctgctgacgggggt
tatgcgttcaagtatgaaaacggcaagtacgacattaaagacgtgggcgtggataacgctggcgcgaaagcgggtctgaccttc
ctggttgacctgattaaaaacaaacacatgaatgcagacaccgattactccatcgcagaagctgcctttaataaaggcgaaacag
cgatgaccatcaacggcccgtgggcatggtccaacatcgacaccagcaaagtgaattatggtgtaacggtactgccgaccttca
agggtcaaccatccaaaccgttcgttggcgtgctgagcgcaggtattaacgccgccagtccgaacaaagagctggcaaaaga
gttcctcgaaaactatctgctgactgatgaaggtctggaagcggttaataaagacaaaccgctgggtgccgtagcgctgaagtct
tacgaggaagagttggcgaaagatccacgtattgccgccaccatggaaaacgcccagaaaggtgaaatcatgccgaacatcc
cgcagatgtccgctttctggtatgccgtgcgtactgcggtgatcaacgccgccagcggtcgtcagactgtcgatgaagccctga
aagacgcgcagactaattcgagctcgaacaacaacaacaataacaataacaacaacctcgggatcgagggaaggatttcagaa
ttcggatcctcttcctctgtggcccaggcggccctcgagcccggggagaagccctatgcttgtccggaatgtggtaagtccttca
gccagagcagctccctggtgcgccaccagcgtacccacacgggtgaaaaaccgtataaatgcccagagtgcggcaaatctttt
agccagagcagcagcctggtgcgccatcaacgcactcatactggcgagaagccatacaaatgtccagaatgtggcaagtctttc
agtgattgtcgtgatcttgcgaggcaccaacgtactcacaccggggagaagccctatgcttgtccggaatgtggtaagtccttctc
tcagagctctcacctggtgcgccaccagcgtacccacacgggtgaaaaaccgtataaatgcccagagtgcggcaaatcttttag
ccgcagcgataacctggtgcgccatcaacgcactcatactggcgagaagccatacaaatgtccagaatgtggcaagtctttctca
acttcaggccatttggtccgtcaccaacgtactcacaccggtaaaaaaactagtggccaggccggccagtacccgtacgacgtt
ccggactacgct Total: 514 bp
Primer F1-f1 of ZFPm4: 2770 bp to 2850 bp
Primer F1-f2 of ZFPm4: 2740 bp to 2790 bp
Primer F2-f of ZFPm4: 2867 bp to 2940 bp
Primer F2-b of ZFPm4: 2824 bp to 2889 bp
Primer F3-b1 ZFPm4: 2916 bp to 2973 bp Primer F3-b2 ZFPm4: 2953 bp to 3021 bp Primer F4-f1 of ZFPm4: 3022 bp to 3102 bp
Primer F4-f2 of ZFPm4: 2992 bp to 3042 bp
Primer F5-f of ZFPm4: 3119 bp to 3192 bp
Primer F5-b of ZFPm4: 3076 bp to 3141 bp
Primer F6-b1 of ZFPm4: 3168 bp to 3225 bp
Primer F6-b2 of ZFPm4: 3205 bp to 3273 bp

(17) Partial sequence of pMal-Ap3 (1-3300 bp) and zinc finger protein ZFPAp3 (2719-3270 bp) (SEQ ID NO:18):

ccgacaccatcgaatggtgcaaaaccttcgcggtatggcatgatagcgcccggaagagagtcaattcagggtggt
gaatgtgaaaccagtaacgttatacgatgtcgcagagtatgccggtgtctcttatcagaccgtttcccgcgtggtgaaccaggcca
gccacgtttctgcgaaaacgcgggaaaaagtggaagcggcgatggcggagctgaattacattcccaaccgcgtggcacaaca
actggcgggcaaacagtcgttgctgattggcgttgccacctccagtctggccctgcacgcgccgtcgcaaattgtcgcggcgat
taaatctcgcgccgatcaactgggtgccagcgtggtggtgtcgatggtagaacgaagcggcgtcgaagcctgtaaagcggcg
gtgcacaatcttctcgcgcaacgcgtcagtgggctgatcattaactatccgctggatgaccaggatgccattgctgtggaagctg
cctgcactaatgttccggcgttatttcttgatgtctctgaccagacacccatcaacagtattattttctcccatgaagacggtacgcga
ctgggcgtggagcatctggtcgcattgggtcaccagcaaatcgcgctgttagcgggcccattaagttctgtctcggcgcgtctgc
gtctggctggctggcataaatatctcactcgcaatcaaattcagccgatagcggaacgggaaggcgactggagtgccatgtccg
gttttcaacaaaccatgcaaatgctgaatgagggcatcgttcccactgcgatgctggttgccaacgatcagatggcgctgggcgc
aatgcgcgccattaccgagtccgggctgcgcgttggtgcggatatctcggtagtgggatacgacgataccgaagacagctcat
gttatatcccgccgttaaccaccatcaaacaggattttcgcctgctggggcaaaccagcgtggaccgcttgctgcaactctctcag
ggccaggcggtgaagggcaatcagctgttgcccgtctcactggtgaaaagaaaaaccaccctggcgcccaatacgcaaaccg
cctctccccgcgcgttggccgattcattaatgcagctggcacgacaggtttcccgactggaaagcgggcagtgagcgcaacgc
aattaatgtgagttagctcactcattaggcacaattctcatgtttgacagcttatcatcgactgcacggtgcaccaatgcttctggcgt
caggcagccatcggaagctgtggtatggctgtgcaggtcgtaaatcactgcataattcgtgtcgctcaaggcgcactcccgttct
ggataatgttttttgcgccgacatcataacggttctggcaaatattctgaaatgagctgttgacaattaatcatcggctcgtataatgt
gtggaattgtgagcggataacaatttcacacaggaaacagccagtccgtttaggtgttttcacgagcacttcaccaacaaggacc
atagattatgaaaactgaagaaggtaaactggtaatctggattaacggcgataaaggctataacggtctcgctgaagtcggtaag
aaattcgagaaagataccggaattaaagtcaccgttgagcatccggataaactggaagagaaattcccacaggttgcggcaact ggcgatggccctgacattatcttctgggcacacgaccgctttggtggctacgctcaatctggcctgttggctgaaatcaccccgg
acaaagcgttccaggacaagctgtatccgtttacctgggatgccgtacgttacaacggcaagctgattgcttacccgatcgctgtt
gaagcgttatcgctgatttataacaaagatctgctgccgaacccgccaaaaacctgggaagagatcccggcgctggataaagaa
ctgaaagcgaaaggtaagagcgcgctgatgttcaacctgcaagaaccgtacttcacctggccgctgattgctgctgacggggt
tatgcgttcaagtatgaaaacggcaagtacgacattaaagacgtgggcgtggataacgctggcgcgaaagcgggtctgaccttc
ctggttgacctgattaaaaacaaacacatgaatgcagacaccgattactccatcgcagaagctgcctttaataaaggcgaaacag
cgatgaccatcaacggcccgtgggcatggtccaacatcgacaccagcaaagtgaattatggtgtaacggtactgccgaccttca
agggtcaaccatccaaaccgttcgttggcgtgctgagcgcaggtattaacgccgccagtccgaacaaagagctggcaaaaga
gttcctcgaaaactatctgctgactgatgaaggtctggaagcggttaataaagacaaaccgctgggtgccgtagcgctgaagtct
tacgaggaagagttggcgaaagatccacgtattgccgccaccatggaaaacgcccagaaaggtgaaatcatgccgaacatcc
cgcagatgtccgctttctggtatgccgtgcgtactgcggtgatcaacgccgccagcggtcgtcagactgtcgatgaagccctga
aagacgcgcagactaattcgagctcgaacaacaacaacaataacaataacaacaacctcgggatcgagggaaggatttcagaa
ttcggatcctcttcctctgtggcccaggcggccctcgagcccggggagaagccctatgcttgtccggaatgtggtaagtccttca
gccagagcagctccctggtgcgccaccagcgtacccacacgggtgaaaaaccgtataaatgcccagagtgcggcaaatcttt
agccagtccagcaacctggtgcgccatcaacgcactcatactggcgagaagccatacaaatgtccagaatgtggcaagtcttc
agccagtccagcaacctggtgcgccaccaacgtactcacaccggggagaagccctatgcttgtccggaatgtggtaagtccttc
agcaccagtggctccttggttagacaccagcgtacccacacgggtgaaaaaccgtataaatgcccagagtgcggcaaatctttt
agccagcgcgcccacctggaacgccatcaacgcactcatactggcgagaagccatacaaatgtccagaatgtggcaagtcttt
ctcaacttcaggcaacttggtccgtcaccaacgtactcacaccggtaaaaaaactagtggccaggccggccagtacccgtacga
cgttccggactacgct Total: 514 bp Primer F1-f1 of ZFPAp3: 2770 bp to 2850 bp Primer F1-f2 of ZFPAp3: 2740 bp to 2790 bp Primer F2-f of ZFPAp3: 2867 bp to 2940 bp Primer F2-b of ZFPAp3: 2824 bp to 2889 bp Primer F3-b1 ZFPAp3: 2916 bp to 2973 bp Primer F3-b2 ZFPAp3: 2953 bp to 3021 bp Primer F4-f1 of ZFPAp3: 3022 bp to 3102 bp Primer F4-f2 of ZFPAp3: 2992 bp to 3042 bp Primer F5-f of ZFPAp3: 3119 bp to 3192 bp Primer F5-b of ZFPAp3: 3076 bp to 3141 bp Primer F6-b1 of ZFPAp3: 3168 bp to 3225 bp Primer F6-b2 of ZFPAp3: 3205 bp to 3273 bp

(18) Sequence of oligo m12 (SEQ ID NO:19):

Biotin-GGa gcc tcc ttc ctc ctc tca ctc GGG TTTT CCC gag tga gag gag gaa gga ggc tCC Total: 58 bp Lower case sequence: ZFPm1 and ZFPm2 binding site m12

(19) Sequence of oligo m34 (SEQ ID NO:20):

Biotin-GGa gcc aac tac tac ggc tcc ctc acc GGG TTTT CCC ggt gag gga gcc gta gta gtt ggc tCC Total: 58 bp Lower case sequence: ZFPm3 and ZFPm4 binding site m34

(20) Sequence of oligo Ap3 (SEQ ID NO:21):

Biotin-GGt tac ttc ttc aac tcc atc GGG TTTT CCC gat gga gtt gaa gaa gta aCC

Total: 52 bp

Lower case sequence: ZFPAp3 binding site

(21) Sequence of oligo NRI-1 (SEQ ID NO:22):

Biotin-GG ttc tac ccc tcc cac cgc GGG TTTT CCC gcg gtg gga ggg gta gaa CC

Total: 51 bp

(22) Sequence of oligo NRI-2 (SEQ ID NO:23):

Biotin-GG tgc ggc gac tgc agc agc GGG TTTT CCC gct gct gca gtc gcc gca CC

Total: 51 bp

(23) Sequence of oligo hHD-I (SEQ ID NO:24):

Biotin-GG ggc ccc gcc tcc gcc ggc GGG TTTT CCC gcc ggc gga ggc ggg gcc CC

Total: 51 bp

(24) Sequence of oligo hHD-II (SEQ ID NO:25):

Biotin-GG ggc agc ccc cac ggc gcc GGG TTTT CCC ggc gcc gtg ggg gct gcc CC

Total: 51 bp

(25) Sequence of oligo c5p1-g (SEQ ID NO:26):

Biotin-GG gac acc ccc aac ccc gcc GGG TTTT CCC ggc ggg gtt ggg ggt gtc CC

Total: 51 bp

(26) Sequence of oligo c5p3-g (SEQ ID NO:27):

Biotin-GG ctc tgc tca tcc cac tac GGG TTTT CCC gta gtg gga tga gca gag CC

Total: 51 bp

(27) Sequence of oligo B3c2 (SEQ ID NO:28):

Biotin-GG acc cac cgc gtc ccc tcc GGG TTTT CCC gga ggg gac gcg gtg ggt CC

Total: 51 bp

(28) Sequence of oligo e2c-g (SEQ ID NO:29):

Biotin-GG cac tgc ggc tcc ggc ccc GGG TTTT CCC ggg gcc gga gcc gca gtg CC

Total: 51 bp

(29) Sequence of primer Ap3-F (SEQ ID NO:30):

GGCGAGAGGGAAGATCCAG

Total: 19 bp

(30) Sequence of primer NZlib5' (SEQ ID NO:31):

GGCCCAGGCGGCCCTCGAGC

Total: 20 bp

(31) Sequence of primer Ap3f4-R (SEQ ID NO:32):

CTCCTCTAATACGACTCACTATAGGGACACTCACCTAGCCTCTG

Total: 44 bp

(32) Sequence of primer m4f3-R (SEQ ID NO:33):

CCTCGCAAGATCACGACAATC

Total: 21 bp

(33) Sequence of quantitative PCR probe for AP3 (SEQ ID NO:34):

CCATTTCATCCTCAAGACGACGCAGCT

Total: 27 bp

(34) Sequence of quantitative PCR primer for AP3 (Forward) (SEQ ID NO:35):

TTTGGACGAGCTTGACATTCAG

Total: 22 bp

(35) Sequence of quantitative PCR primer for AP3 (Reverse) (SEQ ID NO:36):

CGCGAACGAGTTTGAAAGTG

Total: 20 bp

(36) Sequence of 2C7-SID (Figure 3) (SEQ ID NO:66):

gacggatcgggagatctcccgatcccctatggtcgactctcagtacaatctgctctgatgccgcatagttaagccagta
tctgctccctgcttgtgtgttggaggtcgctgagtagtgcgcgagcaaaatttaagctacaacaaggcaaggcttgaccgacaatt
gcatgaagaatctgcttagggttaggcgttttgcgctgcttcgcgatgtacgggccagatatacgcgttgacattgattattgacta
gttattaatagtaatcaattacggggtcattagttcatagcccatatatggagttccgcgttacataacttacggtaaatggcccgcct
ggctgaccgcccaacgaccccgcccattgacgtcaataatgacgtatgttcccatagtaacgccaatagggactttccattgac
gtcaatgggtggactatttacggtaaactgcccacttggcagtacatcaagtgtatcatatgccaagtacgccccctattgacgtca
atgacggtaaatggcccgcctggcattatgcccagtacatgaccttatgggactttcctacttggcagtacatctacgtattagtcat
cgctattaccatggtgatgcggttttggcagtacatcaatgggcgtggatagcggtttgactcacggggatttccaagtctccacc
ccattgacgtcaatgggagtttgttttggcaccaaaatcaacgggactttccaaaatgtcgtaacaactccgccccattgacgcaa
atgggcggtaggcgtgtacggtgggaggtctatataagcagagctctctggctaactagagaacccactgcttactggcttatcg
aaattaatacgactcactatagggagacccaagctggctagcatggccgctgccgtgcgcatgaacatccagatgctgctcgaa
gccgctgattatctggaacgccgggagcgcgaagccgagcacggctacgccagcatgctgccatatccgaaaaagaaacgc
aaggtggcccaggcggccctcgagccctatgcttgccctgtcgagtcctgcgatcgccgcttttctaagtcggctgatctgaagc
gccatatccgcatccacacaggccagaagcccttccagtgtcgaatatgcatgcgtaacttcagtcgtagtgaccaccttaccac
ccacatccgcacccacacaggcgagaagccttttgcctgtgacatttgtgggaggaagtttgccaggagtgatgaacgcaaga
ggcataccaaaatccataccggtgagaagccctatgcttgccctgtcgagtcctgcgatcgccgcttttctaagtcggctgatctg
aagcgccatatccgcatccacacaggccagaagcccttccagtgtcgaatatgcatgcgtaacttcagtcgtagtgaccaccta ccacccacatccgcacccacacaggcgagaagccttttgcctgtgacatttgtgggaggaagtttgccaggagtgatgaacgca
agaggcataccaaaatccatttaagacagaaggactctagaactagtggccaggccggccagtacccgtacgacgttccggac
tacgcttcttgaaagcttggtaccgagctcggatccactagtccagtgtggtggaattctgcagatatccagcacagtggcggcc
gctcgagtctagagggcccgtttaaacccgctgatcagcctcgactgtgccttctagttgccagccatctgttgtttgcccctcccc
cgtgccttccttgaccctggaaggtgccactcccactgtcctttcctaataaaatgaggaaattgcatcgcattgtctgagtaggtgt
cattctattctgggggtggggtggggcaggacagcaaggggaggattgggaagacaatagcaggcatgctggggatgcg
gtgggctctatggcttctgaggcggaaagaaccagctggggctctaggggtatccccacgcgccctgtagcggcgcattaag
cgcggcggtgtggtggttacgcgcagcgtgaccgctacacttgccagcgccctagcgcccgctcctttcgctttcttcccttcct
ttctcgccacgttcgccggctttccccgtcaagctctaaatcggggcatcccctttagggttccgatttagtgctttacggcacctcga
ccccaaaaaacttgattagggtgatggttcacgtagtgggccatcgccctgatagacggttttcgccctttgacgttggagtccac
gttctttaatagtggactcttgttccaaactggaacaacactcaaccctatctcggtctattctttgatttataagggatttgggattt
cggcctattggttaaaaaatgagctgatttaacaaaaatttaacgcgaattaattctgtggaatgtgtgtcagttagggtgtggaaag
tccccaggctccccaggcaggcagaagtatgcaaagcatgcatctcaattagtcagcaaccaggtgtggaaagtccccaggct
ccccagcaggcagaagtatgcaaagcatgcatctcaattagtcagcaaccatagtcccgcccctaactccgcccatcccgcccc
taactccgcccagttccgcccattctccgccccatggctgactaattttttttatttatgcagaggccgaggccgcctctgcctctga
gctattccagaagtagtgaggaggcttttttggaggcctaggcttttgcaaaaagctcccgggagcttgtatatccattttcggatct
gatcagcacgtgttgacaattaatcatcggcatagtatatcggcatagtataatacgacaaggtgaggaactaaaccatggccaa
gttgaccagtgccgttccggtgctcaccgcgcgcgacgtcgccggagcggtcgagttctggaccgaccggctcgggttctccc
gggacttcgtggaggacgacttcgccggtgtggtccgggacgacgtgaccctgttcatcagcgcggtccaggaccaggtggt
gccggacaacacccctggcctgggtgtgggtgcgcggcctggacgagctgtacgccgagtggtcggaggtcgtgtccacgaa
cttccgggacgcctccgggccggccatgaccgagatcggcgagcagccgtgggggcgggagttcgccctgcgcgacccgg
ccggcaactgcgtgcacttcgtggccgaggagcaggactgacacgtgctacgagatttcgattccaccgccgccttctatgaaa
ggttgggcttcggaatcgttttccgggacgccggctggatgatcctccagcgcggggatctcatgctggagttcttcgcccaccc
caacttgtttattgcagcttataatggttacaaataaagcaatagcatcacaaatttcacaaataaagcattttttcactgcattctagtt
gtggtttgtccaaactcatcaatgtatcttatcatgtctgtataccgtcgacctctagctagagcttggcgtaatcatggtcatagctgt
ttcctgtgtgaaattgttatccgctcacaattccacacaacatacgagccggaagcataaagtgtaaagcctggggtgcctaatga
gtgagctaactcacattaattgcgttgcgctcactgcccgctttccagtcgggaaacctgtcgtgccagctgcattaatgaatcggc
caacgcgcggggagaggcggtttgcgtattggcgctcttccgcttcctcgctcactgactcgctgcgctcggtcgttcggctgc
ggcgagcggtatcagctcactcaaaggcggtaatacggttatccacagaatcaggggataacgcaggaaagaacatgtgagc
aaaaggccagcaaaaggccaggaaccgtaaaaaggccgcgttgctggcgtttttccataggctccgcccccctgacgagcatc
acaaaaatcgacgctcaagtcagaggtggcgaaacccgacaggactataaagataccaggcgtttccccctggaagctccctc
gtgcgctctcctgttccgaccctgccgcttaccggatacctgtccgcctttctcccttcgggaagcgtggcgctttctcaatgctca
cgctgtaggtatctcagttcggtgtaggtcgttcgctccaagctgggctgtgtgcacgaaccccccgttcagcccgaccgctgcg
ccttatccggtaactatcgtcttgagtccaacccggtaagacacgacttatcgccactggcagcagccactggtaacaggattag
cagagcgaggtatgtaggcggtgctacagagttcttgaagtggtggcctaactacggctacactagaaggacagtatttggtatc
tgcgctctgctgaagccagttaccttcggaaaaagagttggtagctcttgatccggcaaacaaaccaccgctggtagcggtggtt
tttttgtttgcaagcagcagattacgcgcagaaaaaaaggatctcaagaagatcctttgatcttttctacggggtctgacgctcagtg
gaacgaaaactcacgttaagggattttggtcatgagattatcaaaaaggatcttcacctagatccttttaaattaaaaatgaagtttta
aatcaatctaaagtatatatgagtaaacttggtctgacagttaccaatgcttaatcagtgaggcacctatctcagcgatctgtctatttc
gttcatccatagttgcctgactccccgtcgtgtagataactacgatacgggagggcttaccatctggccccagtgctgcaatgata
ccgcgagacccacgctcaccggctccagatttatcagcaataaaccagccagccggaagggccgagcgcagaagtggtcct
gcaactttatccgcctccatccagtctattaattgttgccgggaagctagagtaagtagttcgccagttaatagtttgcgcaacgttgt
tgccattgctacaggcatcgtggtgtcacgctcgtcgtttggtatggcttcattcagctccggttcccaacgatcaaggcgagttac
atgatcccccatgttgtgcaaaaaagcggttagctccttcggtcctccgatcgttgtcagaagtaagttggccgcagtgttatcact
catggttatggcagcactgcataattctcttactgtcatgccatccgtaagatgcttttctgtgactggtgagtactcaaccaagtcatt
ctgagaatagtgtatgcggcgaccgagttgctcttgcccggcgtcaatacgggataataccgcgccacatagcagaactttaaaa gtgctcatcattggaaaacgttcttcggggcgaaaactctcaaggatcttaccgctgttgagatccagttcgatgtaacccactcgt
gcacccaactgatcttcagcatcttttactttcaccagcgtttctgggtgagcaaaaacaggaaggcaaaatgccgcaaaaaagg
gaataagggcgacacggaaatgttgaatactcatactcttccttttcaatattattgaagcatttatcagggttattgtctcatgagcg
gatacatatttgaatgtatttagaaaaataaacaatagggggttccgcgcacatttccccgaaaagtgccacctgacgtc

METHODS AND COMPOSITIONS TO MODULATE EXPRESSION IN PLANTS

RELATED APPLICATIONS

This application claims priority, under 35 U.S.C. § 119(e), of the U.S. Provisional Application Ser. No. 60/327,552, filed Jul. 21, 2000 and U.S. Provisional Patent Application Ser. No. 60/177,468, filed Jan. 21, 2000. The disclosure of the above referenced applications are incorporated by reference in their entirety.

This invention was made with U.S. government support under Contract No. GM53910 by the National Institutes of Health. The U.S. government has certain rights in the invention.

TECHNICAL FIELD

The invention relates to the field of plant and agricultural technology. More specifically, the invention relates to the use of zinc finger proteins and fusions of said proteins to regulate gene expression and metabolic pathways in plants.

BACKGROUND ART

Genetic expression in general, and in plants in particular, is controlled at both transcription and translation levels. Regulation of transcription often involves regulatory factors which contain zinc finger domains of a particular family—e.g., domains which comprise approximately 30 amino acids containing two cysteine and two histidine residues folded around a zinc ion and providing an alpha helical recognition sequence specific at the "fingertip" for a particular 3-nucleotide sequence. The nature of such zinc fingers is set forth, for example, in WO 98/54311, the contents of which are incorporated herein by reference. As there are 64 possible three nucleotide targets for binding by zinc fingers, it is theoretically possible to design 64 individual zinc fingers, each of which would bind specifically to only one of the 64 possible triplets. By combining multiple zinc finger motifs, a larger target sequence could be bound specifically.

It has been calculated that a nucleotide sequence containing only 18 nucleotides would serve as an unique address within even a 68 billion pair genome; thus, an 18 nucleotide sequence would clearly serve as an unique target within the human genome (3.5 billion bp) or maize (2 billion bp). Thus, a hexadactyl zinc finger protein, properly designed, could target any arbitrary unique sequence within the human or maize genome. Considering the complexity of human and maize genome, this specially designed zinc finger protein could target any unique sequence within these and other organisms.

In the context of regulatory transcription factors, zinc finger domains which are responsible for specifically targeting a particular nucleotide sequence within a gene are generally coupled to additional amino acid sequences which serve to modulate expression either by activating (amplifying) or repressing it. Thus, typical transcription regulatory factors comprise both a zinc finger domain responsible for targeting the appropriate position of the genome and a functional portion which controls transcription of the gene once the fusion protein is bound.

Synthetic zinc finger proteins have been synthesized and found to have binding affinity similar to those found in native transcription factors. Further, zinc finger proteins have been designed which are specific for TGA or for one of the triplets of the formula GNN. Thus, zinc finger proteins can be designed to target unique sequences of the formula $(GNN)_6$ or sequences containing 18 nucleotides wherein some of the GNN triplets have been substituted by TGA. As the design of zinc finger proteins progresses, appropriate zinc finger domains can be designed for any desired target sequence.

There is evidence to show that specific synthetic zinc finger proteins can transiently regulate reporter gene, e.g., luciferase, expression in cultured mammalian cells when fused with a transcriptional activation or repression domain (Liu et al., *Proc. Natl. Acad. Sci. USA*, 94:5525–5530 (1997); Wu et al., *Proc. Natl. Acad. Sci. USA*, 92:344–348 (1995); and Beerli et al., *Proc. Natl. Acad. Sci. USA*, 95:14628–14633 (1998)). However, there has been no data showing: (1) if these synthetic zinc finger proteins can be used to manipulate endogenous gene expression; and (2) if such transient regulation can be stabilized. There has also been no scientific evidence predicting if this technology will perform well in a whole living organism as it may in tissue culture system.

In addition to all these unknown factors, a plant cell is considered different than a mammalian cell in numerous aspects even though they share most of the basic features of living organisms. First, plant cells have different subcellular biological structures, such as cell walls, which make the mechanism and procedure of transformation of foreign gene into plant cells significantly different from mammalian cells. Second, the genetic recombination mechanism and frequency in plant cells differ from that in mammalian cells as well. For any given transgene to be expressed and functional in any living cell, the very critical step is integration into host genome, the mechanism of which differs between plant and mammalian cells. Generally, plant cells have much lower integration frequency. Third, most plant cells have specialized metabolic pathway and enzymes catalyzing these pathways so that a gene functioning in a mammalian cell is not necessarily functional in a plant cell. Fourth, the preference of genetic codon usage is different amongst plant, mammalian, and other biological systems.

It is highly desirable to control expression of target genes in plants whether these genes are native to the plant or constitute modifications of the native plant genetic complement. The present invention provides such means, and is exemplified by the control of expression of three genes in plants: (1) the reporter gene luciferase in tobacco and maize cells; (2) the APETALA3 (AP3) gene in *Arabidopsis* plant, and (3) the gene encoding myo inositol 1-phosphate synthase (MIPS) in maize, all of which are representatives of economically valuable genes.

Thus, there remains a need for methods and compositions to control, at will, gene expression and other functions and activities in plants, plant tissues, and plant cells. The present invention address these and other related needs in the art.

SUMMARY OF THE INVENTION

The invention relates to the field of plant and agricultural technology. In one aspect, the present invention is directed to a method to modulate the expression of a target gene in plant cells, which method comprises providing plant cells with a zinc finger protein, said zinc finger protein being capable of binding, and preferably, specifically binding, to a target nucleotide sequence, or a complementary strand thereof, within a target gene, and allowing said zinc finger protein binding to said target nucleotide sequence, whereby the expression of said target gene in said plant cells is modulated.

The zinc finger protein can be provided to the plant cells via any suitable methods known in the art. For example, the zinc finger protein can be exogenously added to the plant cells and the plant cells are maintained under conditions such that the zinc finger protein binds to the target nucleotide sequence and regulates the expression of the target gene in the plant cells. Alternatively, a nucleotide sequence, e.g., DNA or RNA, encoding the zinc finger protein can be expressed in the plant cells and the plant cells are maintained under conditions such that the expressed zinc finger protein binds to the target nucleotide sequence and regulates the expression of the target gene in the plant cells.

A preferred method to modulate the expression of a target gene in plant cells comprises the following steps: a) providing plant cells with an expression system for a zinc finger protein, said zinc finger protein being capable of binding, and preferably specifically binding, to a target nucleotide sequence, or a complementary strand thereof, within a target gene; and b) culturing said plant cells under conditions wherein said zinc finger protein is produced and binds to said target nucleotide sequence, whereby expression of said target gene in said plant cells is modulated.

Any target nucleotide sequence can be modulated by the present method. For example, the target nucleotide sequence can be endogenous or exogenous to the target gene. In a specific embodiment, the target nucleotide sequence is endogenous to the plant but is in a non-naturally-occurring location. The target nucleotide sequence can be located in any suitable place in relation to the target gene. For example, the target nucleotide sequence can be upstream or downstream of the coding region of the target gene. Alternatively, the target nucleotide sequence is within the coding region of the target gene. Preferably, the target nucleotide sequence is a promoter of a regulatory protein. Also preferably, the target nucleotide sequence comprises 3, 6, 9, 12, 15 or 18 nucleotides. More preferably, the target nucleotide sequence comprises 18 nucleotides and wherein the zinc finger protein is a hexadactyl zinc finger protein. Further preferably, the targeted nucleotide sequence is of the formula $(GNN)_n$, and wherein N is any one of the A, T, C or G and n is an integer from 1 to 6. More preferably, the targeted nucleotide sequence is of the formula $(GNN)_6$, and wherein N is any one of the A, T, C or G.

Plant cells containing any copy number of the target nucleotide sequence can be used in the present methods. For example, the plant cells comprising at least two copies of the same or different target nucleotide sequence can be used. Alternatively, each target nucleotide sequence can be located within a different target gene so that more than one different target genes can be modulated.

Any target gene can be modulated by the present method. For example, the target gene can encode a product that affects biosynthesis, modification, cellular trafficking, metabolism and degradation of a peptide, a protein, an oligonucleotide, a nucleic acid, a vitamin, an oligosaccharide, a carbohydrate, a lipid, or a small molecule. Exemplary proteins or peptides include enzymes, transport proteins such as ion channels and pumps, nutrient or storage proteins, contractile or motile proteins such as actins and myosins, structural proteins, defense proteins or regulatory proteins such as antibodies, hormones and growth factors. Exemplary nucleic acids include DNA, such as A-, B- or Z-form DNA, and RNA such as mRNA, tRNA and rRNA. The nucleic acids can be single-, double- and triple-stranded nucleic acids. Exemplary vitamins include water-soluble vitamins such as thiamine, riboflavin, nicotinic acid, pantothenic acid, pyridoxine, biotin, folate, vitamin $B_{12}$ and ascorbic acid, and fat-soluble vitamins such as vitamin A, vitamin D, vitamin E, and vitamin K. Exemplary lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid. In a specific embodiment, the target gene encodes a protein or an RNA. In another specific embodiment, the target gene is a reporter gene, e.g., luciferase, the AP3 gene or the myo inositol 1-phosphate synthase gene. In still another specific embodiment, the present method is used for treating a disorder in the plant cells, wherein the disorder is associated with abnormal expression of the target gene.

When the target gene encodes a target protein, the present method can be used to modulate the expression of said encoded target protein. Expression of any target protein can be modulated by the present method in plant cells. The protein whose expression being modulated can be endogenous or exogenous to the plant cell. The modulation can be activation or inhibition.

In a specific embodiment, the protein whose expression being modulated is an antibody. In another specific embodiment, the protein whose expression being modulated participates in a metabolic pathway or controls a metabolic pathway, e.g., an anabolic or a catabolic pathway. The present method can be used for modulating metabolic pathways of any desirable molecules such as vitamins, taste molecules, e.g., bad taste molecules, anti-oxidants, sugars and flavanoids. The metabolic pathway being modulated can be endogenous or exogenous to the plant cell. In still another specific embodiment, target gene encodes a structural protein, e.g., an enzyme or a co-factor in a metabolic pathway, or a regulatory protein. In yet another specific embodiment, the metabolic pathway being modulated enhances an input or output trait in a plant or seed.

Although in some cases, a zinc finger protein itself is sufficient for modulating gene expression, the zinc finger protein is preferably fused to a protein which activates or represses gene expression, e.g., an activator domain of a regulatory protein or an active domain of a nucleic acid modifying protein.

For modulating the expression of the target gene, the zinc finger protein can bind to the target nucleotide sequence within the target gene. Alternatively, the zinc finger protein can bind to the complementary strand of the target nucleotide sequence. Additionally, the zinc finger protein can specifically bind to an effector domain of the target sequence and whereby the expression of the target gene is modulated by competitive inhibition of said effector domain. In such case, the zinc finger protein preferably does not comprise an effector domain.

The zinc finger protein used in the present methods can comprise a plurality of finger regions. The zinc finger protein can comprise linker regions among the plurality of finger regions. For example, the zinc finger protein used in the present method can contain any number of the 3-finger region. Preferably, the zinc finger protein can comprise at least two 3-finger regions that are separated and linked together with a linker region. The linker region can be any suitable length, e.g., from about 2 to about 10 amino acid residues in length. Preferably, the linker region between any said two 3-finger region is about 5 amino acid residues in length.

In addition to the typical zinc finger domains, the zinc finger protein can further comprise other desirable domains such as effector domains active in the host plant cells. Any types of zinc finger protein can be used in the present method. But preferably, the zinc finger protein comprising a framework from a plant zinc finger protein can be used. Alternatively, synthetic zinc finger proteins or non-naturally-occurring zinc finger proteins can be used.

In a specific embodiment, the zinc finger protein used in the present methods is ZFPm1, ZFPm2, ZFPm3, ZFPm4 or ZFPAp3, alone or fused to an effector domain.

In another specific embodiment, the zinc finger protein used in the present methods is not any zinc finger protein that is disclosed in U.S. Pat. No. 6,140,466 or WO 98/54311, e.g., a zinc finger-nucleotide binding polypeptide variant comprising at least three zinc finger modules that bind to a target cellular nucleotide sequence and modulate the transcriptional function of the cellular nucleotide sequence, wherein the amino acid sequence of each zinc finger module that binds a target cellular nucleotide comprises two cysteines and two histidines whereby both cysteines are amino proximal to both histidines and wherein each of three modules of said variant has at least one amino acid sequence modification.

The present methods can be used to modulate gene expression in any plant cells, e.g., monocot or dicot plant cells. The plant cells can be in any suitable forms. For example, the plant cells can be included within an intact plant, and preferably the plant cells constitute all the cells of an intact plant. Alternatively, the plant cells can be contained in an in vitro culture, and preferably be cultured in planta. The plant cells can also be in the form of protoplasts or spheroplasts.

The present method can be used to achieve any desirable degree of the modulation of a target gene expression. Preferably, the modulation of the gene expression is at least two fold, e.g., at least five fold repression or at least two fold activation. Also preferably, the modulation changes the phenotype of the plant cells, the tissue(s) of the plant or the whole plant.

When the zinc finger protein is provided to plant cells with an expression system for a zinc finger protein, any suitable promoters can be used in directing expression of the zinc finger protein. The expression system can comprise a constitutive promoter or an inducible promoter. In addition, the zinc finger protein can be expressed transiently or stably.

Preferably, the expression system can comprise a tissue-specific promoter. Also preferably, the expression of the zinc finger protein is controlled by a tissue-specific promoter and whereby tissue-specific modulation of the target gene expression is obtained. In this way, the zinc finger protein can be expressed in any desirable plant tissue, such as calli, meristem, leave, root or organ explant in tissue culture.

Also preferably, the zinc finger protein can be expressed in a specific organelle, such as a mitochondria, a nucleus, a plastid or a vacuole. Exemplary plastids include chloroplast, leucoplast, aravloplast and chromoplast.

When the zinc finger protein is provided to plant cells with an expression system for a zinc finger protein, the nucleotide sequence encoding the zinc finger protein can be targeted to or stably integrated in a specific organelle. Such nucleotide sequence can be targeted to a specific organelle by any methods known in the art. For example, the zinc finger protein can be targeted to plastid via a plastid transit peptide, to chloroplast via a chloroplast transit peptide, to mitochondrial via a mitochondrial target peptide or to nucleus via a nuclear targeting peptide.

When the zinc finger protein is provided to plant cells with an expression system for a zinc finger protein, the nucleotide sequence encoding the zinc finger protein can comprise preferred codons of the host plant, e.g., preferred translational start codon of the host plant.

In another aspect, the present invention is directed to a method of modulating a level of a compound in a plant cell, which method comprises expressing in a plant cell a zinc finger protein that binds or specifically binds to a target nucleotide sequence within a target gene to modulate expression of said target gene which is involved in a compound's metabolism in said plant cell, whereby the level of said compound in said plant cell is modulated. The level of any compound, e.g., phytic acid, or target gene, e.g. AP3, can be modulated by the present method in plant cells. Preferably, the zinc finger protein used in the present methods is not any zinc finger protein that is disclosed in U.S. Pat. No. 6,140,466 or WO 98/54311, e.g., a zinc finger-nucleotide binding polypeptide variant comprising at least three zinc finger modules that bind to a target cellular nucleotide sequence and modulate the transcriptional function of the cellular nucleotide sequence, wherein the amino acid sequence of each zinc finger module that binds a target cellular nucleotide comprises two cysteines and two histidines whereby both cysteines are amino proximal to both histidines and wherein each of three modules of said variant has at least one amino acid sequence modification.

In still another aspect, the present invention is directed to an expression vector comprising a nucleotide sequence encoding a zinc finger protein, said zinc finger protein is capable of binding or specifically binding to a target nucleotide sequence, or a complementary strand thereof, within a target gene whose expression is to be modulated by said zinc finger protein. A plant that is regenerated from a plant transformed with the above expression vector is also provided. Preferably, the zinc finger protein used in the present expression vectors is not any zinc finger protein that is disclosed in U.S. Pat. No. 6,140,466 or WO 98/54311, e.g., a zinc finger-nucleotide binding polypeptide variant comprising at least three zinc finger modules that bind to a target cellular nucleotide sequence and modulate the transcriptional function of the cellular nucleotide sequence, wherein the amino acid sequence of each zinc finger module that binds a target cellular nucleotide comprises two cysteines and two histidines whereby both cysteines are amino proximal to both histidines and wherein each of three modules of said variant has at least one amino acid sequence modification.

In yet another aspect, the present invention is directed to a genetically modified plant cell, which cell comprises an expression system for a zinc finger protein, said zinc finger protein is capable of binding, preferably specifically binding, to a target nucleotide sequence, or a complementary strand thereof, within a target gene whose expression is to be modulated by said zinc finger protein.

In yet another aspect, the present invention is directed to a zinc finger protein that is ZFPm1, ZFPm2, ZFPm3, ZFPm4, or ZFPAp3, preferably in combination with positive and negative regulating domains, or a fusion protein comprises a zinc finger of 2C7 and an effector domain of SID (2C7-SID fusion protein).

In yet another aspect, the present invention is directed to an isolated nucleic acid fragment comprising a sequence of nucleotides encoding ZFPm1, ZFPm2, ZFPm3, ZFPm4, ZFPAp3 or a 2C7-SID fusion protein. Plasmids and cells containing the nucleic acid fragments and methods for producing ZFPm1, ZFPm2, ZFPm3, ZFPm4, ZFPAp3 proteins or 2C7-SID fusion proteins using the plasmids and cells are also provided.

In yet another aspect, the present invention is directed to an antibody that specifically binds to the above-described zinc finger protein.

In yet another aspect, the present invention is directed to a zinc finger protein comprising a zinc finger nucleic acid binding domain and an effector domain, wherein said effector domain comprises an active domain of a restriction enzyme, an active domain of a nucleic acid modifying protein, e.g., a nucleic acid methylase, a label or a modification.

In yet another aspect, the present invention is directed to an assay method for determining a suitable position in a gene for regulation of expression in plant cells, which method comprises: a) providing a target gene which contains a nucleotide sequence encoding a reporter protein within the coding region of said target gene and a target nucleotide sequence at a predetermined location within said target gene; b) contacting said target gene with a regulatory factor comprising a zinc finger protein specific for said target nucleotide sequence; and c) assessing the level of expression of said reporter gene in the presence and absence of said contacting; wherein a change in the level of expression of said reporter gene in the presence as opposed to the absence of said contacting identifies said position of said target nucleotide sequence as a position suitable for controlling expression of said target gene in plant cells.

Preferably, the zinc finger protein used in the present assay methods is not any zinc finger protein that is disclosed in U.S. Pat. No. 6,140,466 or WO 98/54311, e.g. a zinc finger-nucleotide binding polypeptide variant comprising at least three zinc finger modules that bind to a target cellular nucleotide sequence and modulate the transcriptional function of the cellular nucleotide sequence, wherein the amino acid sequence of each zinc finger module that binds a target cellular nucleotide comprises two cysteines and two histidines whereby both cysteines are amino proximal to both histidines and wherein each of three modules of said variant has at least one amino acid sequence modification.

BRIEF DESCRIPTION OF THE DRAWINGS

FIG. 6 DNA recognition helix sequences of ZFPm1, ZFPm2, ZFPm3, ZFPm4, and ZFPAp3.

FIG. 24 Nucleotide sequences of various nucleic acids and oligonucleotides disclosed in the present application.

MODES FOR CARRYING OUT THE INVENTION

A. Definitions

Figure 1:
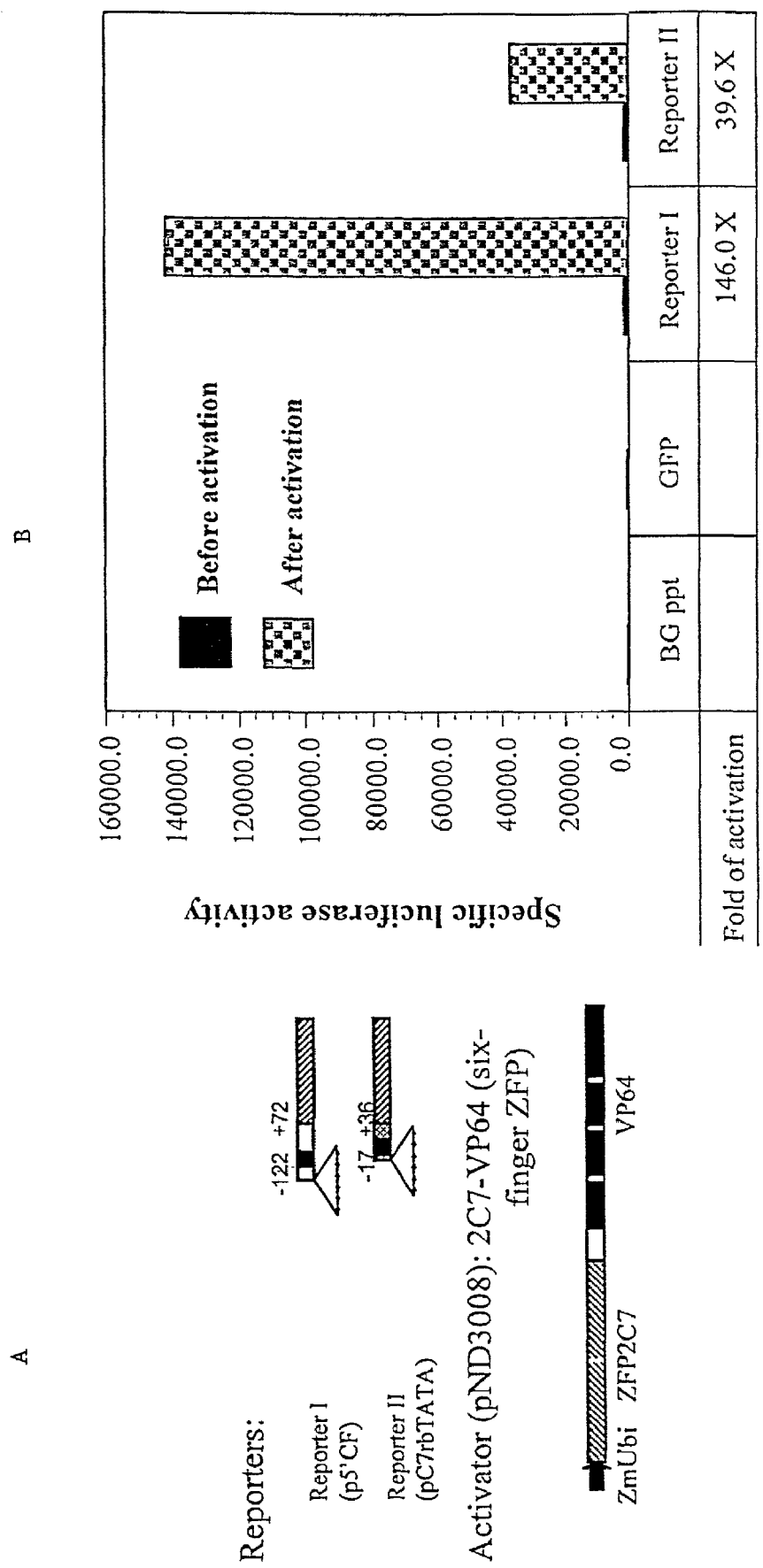
FIG. 1A Constructs for analyzing activation of reporter gene in maize HE89 (F19556) cells.
FIG. 1B Activation of reporter gene in maize HE89 (F19556) cells. Maize Ubiquitin promoter was used to drive the expression of 2C7-VP64 fusion protein (activator). Reporter I (p5'C7F) is generally activated 150 to 250 fold. Reporter II activation is between 40 to 70 fold.

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, "zinc finger protein, (zinc finger polypeptide, or ZFP)" refers to a polypeptide having nucleic acid, e.g., DNA, binding domains that are stabilized by zinc. The individual DNA binding domains are typically referred to as "fingers," such that a zinc finger protein or polypeptide has at least one finger, more typically two fingers, more preferably three fingers, or even more preferably four or five fingers, to at least six or more fingers. Each finger binds from two to four base pairs of DNA, typically three or four base pairs of DNA. A ZFP binds to a nucleic acid sequence called a target nucleic acid sequence. Each finger usually comprises an approximately 30 amino acids, zinc-chelating, DNA-binding subdomain. An exemplary motif of one class, the Cys2-His2 class (C2H2 motif), is -CYS-(X)2-4-CYS-(X)12-HiS-(X)3-5-His, where X is any amino acid, and a single zinc finger of this class consists of an alpha helix containing the two invariant histidine residues and the two cysteine residues of a single beta turn that binds a zinc cation (see, e.g., Berg et al., *Science,* 271:1081–1085 (1996)). A zinc finger protein can have at least two DNA-binding domains, one of which is a zinc finger polypeptide, linked to the other domain via a flexible linker. The two domains can be identical or different. Both domains can be zinc finger proteins, either identical or different zinc finger proteins. Alternatively, one domain can be a non-zinc finger DNA-binding protein, such as one from a transcription factor.

As used herein, "framework (or backbone) derived from a naturally occurring zinc finger protein" means that the protein or peptide sequence within the naturally occurring zinc finger protein that is involved in non-sequence specific binding with a target nucleotide sequence is not substantially changed from its natural sequence. For example, such framework (or backbone) derived from the naturally occurring zinc finger protein maintains at least 50%, and preferably, 60%, 70%, 80%, 90%, 95%, 99% or 100% identity compared to its natural sequence in the non-sequence specific binding region. Alternatively, the nucleic acid encoding such framework (or backbone) derived from the naturally occurring zinc finger protein can be hybridizable with the nucleic acid encoding the naturally occurring zinc finger protein, either entirely or within the non-sequence specific binding region, under low, medium or high stringency condition. Preferably, the nucleic acid encoding such framework (or backbone) derived from the naturally occurring zinc finger protein is hybridizable with the nucleic acid encoding the naturally occurring zinc finger protein, either entirely or within the non-sequence specific binding region, under high stringency condition.

As used herein, "gene" refers to a nucleic acid molecule or portion thereof which comprises a coding sequence, optionally containing introns, and control regions which regulate the expression of the coding sequence and the transcription of untranslated portions of the transcript. Thus, the term "gene" includes, besides coding sequence, regulatory sequence such as the promoter, enhancer, 5' untranslated regions, 3' untranslated region, termination signals, poly adenylation region and the like. Regulatory sequence of a gene may be located proximal to, within, or distal to the coding region.

As used herein, "target gene" refers to a gene whose expression is to be modulated by a zinc finger protein in plant cells.

As used herein, "plant" refers to any of various photosynthetic, eukaryotic multi-cellular organisms of the kingdom Plantae, characteristically producing embryos, containing chloroplasts, having cellulose cell walls and lacking locomotion. As used herein, "plant" includes any plant or part of a plant at any stage of development, including seeds, suspension cultures, embryos, meristematic regions, callus tissue, leaves, roots, shoots, gametophytes, sporophytes, pollen, microspores, and progeny thereof. Also included are cuttings, and cell or tissue cultures. As used in conjunction with the present invention, the term "plant tissue" includes, but is not limited to, whole plants, plant cells, plant organs, e.g., leafs, stems, roots, meristems, plant seeds, protoplasts, callus, cell cultures, and any groups of plant cells organized into structural and/or functional units.

As used herein, "modulate the expression of a target gene in plant cells" refers to increasing (activation) or decreasing (repression) the expression of the target gene in plant cells with a zinc finger protein, alone or in combination with other transcription and/or translational regulatory factors, or nucleic acids encoding such zinc finger protein, in plant cells.

As used herein, "providing plant cells with a zinc finger protein" refers to the provisional to the plant cells, whether in culture or in whole plant, functional zinc finger protein that is capable of modulating a target gene in the plant cells. The functional zinc finger protein can be provided, i.e., delivered, to the plant cells by any means. For example, the zinc finger protein can be delivered directly into the plant cells. Alternatively and preferably, nucleic acids, e.g., DNA or mRNA, encoding such zinc finger protein can be delivered into the plant cells and the plant cells are maintained under the conditions that functional zinc finger protein can be produced within the plant cells.

As used herein, a "target nucleotide sequence" refers to a portion of double-stranded polynucleotide acid, e.g., RNA, DNA, PNA (peptide nucleic acid) or combinations thereof, to which it is advantageous to bind a protein. In one embodiment, a "target nucleotide sequence" is all or part of a transcriptional control element for a gene for which a desired phenotypic result can be attained by altering the degree of its expression. A transcriptional control element includes positive and negative control elements such as a promoter, an enhancer, other response elements, e.g., steroid response element, heat shock response element, metal response element, a repressor binding site, operator, and/or a silencer. The transcriptional control element can be viral, eukaryotic, or prokaryotic. A "target nucleotide sequence" also includes a downstream or an upstream sequence which can bind a protein and thereby modulate, typically prevent transcription.

As used herein, "specifically binds to a target nucleotide sequence" means that the binding affinity of a zinc finger protein to a specified target nucleic acid sequence is statistically higher than the binding affinity of the same zinc finger protein to a generally comparable, but non-target nucleic acid sequence, e.g., a GNN sequence without matching code sequence for the particular zinc finger protein. Normally, the binding affinity of a zinc finger protein to a specified target nucleic acid sequence is at least 1.5 fold, and preferably 2 fold or 5 fold, of the binding affinity of the same zinc finger protein to a non-target nucleic acid sequence. It also refers to binding of a zinc-finger-protein-nucleic-acid-binding domain to a specified nucleic acid target sequence to a detectably greater degree, e.g., at least 1.5-fold over background, than its binding to non-target nucleic acid sequences and to the substantial exclusion of non-target nucleic acids. The zinc finger protein's Kd to each nucleotide sequence can be compared to assess the binding specificity of the zinc finger protein to a particular target nucleotide sequence.

As used herein, a "target nucleotide sequence within a target gene" refers to a functional relationship between the target nucleotide sequence and the target gene in that binding of a zinc-finger-protein to the target nucleotide sequence will modulate the expression of the target gene. The target nucleotide sequence can be physically located anywhere inside the boundaries of the target gene, e.g., 5' ends, coding region, 3' ends, upstream and downstream regions outside of cDNA encoded region, or inside enhancer or other regulatory region, and can be proximal or distal to the target gene.

As used herein, "culturing plant cells" refers to the cultivation or growth of the plant cells. Such cultivation or growth can be in vitro, e.g., in culture medium, or in vivo, e.g., in planta.

As used herein, "endogenous" refers to nucleic acid or protein sequence naturally associated with a target gene or a host cell into which it is introduced.

As used herein, "exogenous" refers to nucleic acid or protein sequence not naturally associated with a target gene or a host cell into which it is introduced, including non-naturally occurring multiple copies of a naturally occurring nucleic acid, e.g., DNA sequence, or naturally occurring nucleic acid sequence located in a non-naturally occurring genome location.

As used herein, "effector (or effector protein)" refer to constructs or their encoded products which are able to regulate gene expression either by activation or repression or which exert other effects on a target nucleic acid. The effector protein may include a zinc finger binding region only, but more commonly also includes a "functional domain" such as a "regulatory domain."

As used herein, "regulatory domain" refer to the portion of the effector protein or effector which enhances or represses gene expression.

As used herein, "compound" refer to any substance that is metabolized in plant cells and its metabolism can be modulated by a zinc-finger-protein in plant cells.

As used herein, "genetically modified plant (or transgenic plant)" refers to a plant which comprises within its genome an exogenous polynucleotide. Generally, and preferably, the exogenous polynucleotide is stably integrated within the genome such that the polynucleotide is passed on to successive generations. The exogenous polynucleotide may be integrated into the genome alone or as part of a recombinant expression cassette. "Transgenic" is used herein to include any cell, cell line, callus, tissue, plant part or plant, the genotype of which has been altered by the presence of exogenous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "essential gene" refers to a gene encoding a protein that is essential to the growth or survival of the plant, e.g., a biosynthetic enzyme, receptor, signal transduction protein, structural gene product, or transport protein.

As used herein, "expression cassette" refers to a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The zinc finger-effector fusions of the present invention are chimeric. The expression cassette may also be one which is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue or organ or stage of development. In the case of a plastid expression cassette, for expression of the nucleotide sequence from a plastid genome, additional elements, i.e., ribosome binding sites, may be required.

As used herein, "minimal promoter" refers to a promoter element, particularly a TATA element, that is inactive or that has greatly reduced promoter activity in the absence of upstream activation. In the presence of a suitable transcription factor, the minimal promoter functions to permit transcription.

As used herein, "significant increase" refer to an increase in gene expression, enzymatic or other biological activity, specificity or affinity, or effector or phenotypic activity, that is larger than the margin of error inherent in the measurement technique, preferably an increase by about 2-fold or greater of the activity without the ZFP or ligand inducer, more preferably an increase by about 5-fold or greater, and most preferably an increase by about 10-fold or greater.

As used herein, "repressor protein" refer to a protein that binds to operator of DNA or to RNA to prevent transcription or translation, respectively.

As used herein, "repression" refer to inhibition of transcription or translation by binding of repressor protein to specific site on DNA or mRNA. Preferably, repression includes a significant change in transcription or translation level of at least 1.5 fold, more preferably at least two fold, and even more preferably at least five fold.

As used herein, "activator protein" refer to a protein that binds to operator of DNA or to RNA to enhance transcription or translation, respectively.

As used herein, "activation" refer to enhancement of transcription or translation by binding of activator protein to specific site on DNA or mRNA. Preferably, activation includes a significant change in transcription or translation level of at least 1.5 fold, more preferably at least two fold, and even more preferably at least five fold.

As used herein, "conservatively modified variant" refer to amino acid and nucleic acid sequences containing individual substitutions, deletions or additions that alter, add or delete a single amino acid or nucleotide or a small percentage of amino acids or nucleotides in the sequence, where the alteration results in the substitution of an amino acid with a chemically similar amino acid. Conservative substitution tables providing functionally similar amino acids are well known in the art. Such conservatively modified variants are in addition to and do not exclude polymorphic variants and alleles of the invention. The following groups each contain amino acids that are conservative substitutions for one another: 1) Alanine (A), Glycine (G); 2) Serine (S), Threonine (T); 3) Aspartic acid (D), Glutamic acid (E); 4) Asparagine (N), Glutamine (Q); 5) Cysteine (C), Methionine (M); 6) Arginine (R), Lysine (K), Histidine (H); 7) Isoleucine (I), Leucine (L), Valine (V); and 8) Phenylalanine (F), Tyrosine (Y), Tryptophan (W). (see, e.g., Creighton, Proteins (1984) for a discussion of amino acid properties).

As used herein, a combination refers to any association between two or among more items.

As used herein, a composition refers to any mixture. It may be a solution, a suspension, liquid, powder, paste, aqueous, non-aqueous or any combination thereof.

As used herein, derivative or analog of a molecule refers to a portion derived from or a modified version of the molecule.

As used herein, operably linked, operatively linked or operationally associated refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. To optimize expression and/or in vitro transcription, it may be helpful to remove, add or alter 5' untranslated portions of the clones to eliminate extra, potentially inappropriate alternative translation initiation (i.e., start) codons or other sequences that may interfere with or reduce expression, either at the level of transcription or translation. Alternatively, consensus ribosome binding sites (see, e.g., Kozak, *J. Biol. Chem.*, 266:19867–19870 (1991)) can be inserted immediately 5' of the start codon and may enhance expression. The desirability of (or need for) such modification may be empirically determined.

As used herein, a promoter region or promoter element refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated.

As used herein: stringency of hybridization in determining percentage mismatch is as follows: (1) high stringency: 0.1×SSPE, 0.1% SDS, 65° C.; (2) medium stringency: 0.2×SSPE, 0.1% SDS, 50° C.; and (3) low stringency: 1.0×SSPE, 0.1% SDS, 50° C. Equivalent stringencies may be achieved using alternative buffers, salts and temperatures.

The term substantially identical or homologous or similar varies with the context as understood by those skilled in the relevant art and generally means at least 70%, preferably means at least 80%, more preferably at least 90%, and most preferably at least 95% identity.

As used herein, substantially identical to a product means sufficiently similar so that the property of interest is sufficiently unchanged so that the substantially identical product can be used in place of the product.

As used herein, isolated means that a substance is either present in a preparation at a concentration higher than that substance is found in nature or in its naturally occurring state or that the substance is present in a preparation that contains other materials with which the substance is not associated with in nature.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, vector or plasmid refers to discrete elements that are used to introduce heterologous DNA into cells for either expression or replication thereof. Selection and use of such vehicles are well known within the skill of the artisan. An expression vector includes vectors capable of expressing DNAs that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "macromolecule" refers to a molecule that, without attaching to another molecule, is capable of generating an antibody that specifically binds to the macromolecule.

As used herein, "small molecule" refers to a molecule that, without forming homo-aggregates or without attaching to a macromolecule or adjuvant, is incapable of generating an antibody that specifically binds to the small molecule. Preferably, the small molecule has a molecular weight that is about or less than 10,000 daltons. More preferably, the small molecule has a molecular weight that is about or less than 5,000 dalton.

As used herein, "vitamin" refers to a trace organic substance required in certain biological species. Most vitamins function as components of certain coenzymes.

As used herein, "lipid" refers to water-insoluble, oily or greasy organic substances that are extractable from cells and tissues by nonpolar solvents, such as chloroform or ether.

As used herein, a "receptor" refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants such as on viruses, cells, or other materials, drugs, polynucleotides, nucleic acids, peptides, cofactors, lectins, sugars, polysaccharides, cells, cellular membranes, and organelles.

As used herein, "nutrient or storage protein" refers to a protein that is used by the cell as the nutrient source or storage form for such nutrient. Non-limiting examples of nutrient or storage proteins include gliadin, ovalbumin, casein, and ferritin.

As used herein, "contractile or motile protein" refers to a protein that endows cells and organisms with the ability to contract, to change shape, or to move about. Non-limiting examples of contractile or motile proteins include actin, myosin, tubulin and dynein.

As used herein, "structural protein" refers to a protein that serves as supporting filaments, cables, or sheets to give biological structures strength or protection. Non-limiting examples of structural proteins include keratin, fibroin, collagen, elastin and proteoglycans.

As used herein, "defense protein" refers to a protein that defends organisms against invasion by other species or protect them from injury. Non-limiting examples of defense proteins include antibodies, fibrinogen, thrombin, botulinus toxin, diphtheria toxin, snake venoms and ricin.

As used herein, "regulatory protein" refers to a protein that helps regulate cellular or physiological activity. Non-limiting examples of regulatory proteins include insulin, growth hormones, corticotropin and repressors.

For clarity of disclosure, and not by way of limitation, the detailed description of the invention is divided into the subsections that follow.

B. Methods for Modulating Gene Expression in Plant

In one aspect, the present invention is directed to a method to modulate the expression of a target gene in plant cells, which method comprises providing plant cells with a zinc finger protein, said zinc finger protein being capable of binding or specifically binding to a target nucleotide sequence, or a complementary strand thereof, within a target gene, and allowing said zinc finger protein binding to said target nucleotide sequence, whereby the expression of said target gene in said plant cells is modulated.

Plant

The present invention can be used over a broad range of plant types, preferably the class of higher plants amenable to transformation techniques, particularly monocots and dicots. Particularly preferred are monocots such as the species of the Family Gramineae including *Sorghum bicolor* and *Zea mays*. The present method can also be used in species from the following genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale,* and *Triticum.*

Preferred plant cells include those from corn (*Zea mays*), canola (*Brassica napus, Brassica rapa* ssp.), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), duckweed (Lemna) soybean (*Glycine max*), tobacco (*Nicotiana tabacum*), potato (*Solanum tuberosum*), peanut (*Arachis hypogaea*), cotton (*Gossypium barbadense, Gossypium hirsutum*), sweet potato (*Qpomoea batatus*), cassava (*Manihot esculenta*), coffee (*Cqfea* spp.), coconut (*Cocos nucijra*), pineapple (*Ananas comosus*), citrus tree (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integr~fblia*), almond (*Prunus amygdalus*), sugar beet (*Beta vulgaris*), sugarcane (*Saccharum* spp.), oats, barley, vegetables, ornamentals, and conifers.

Preferred vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C cantalupensis*), and musk melon (*C. melo*).

Preferred ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbiapulcherrima*), and chrysanthemum.

Conifers that may be employed in practicing the present method include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Isuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Leguminous plants include beans and peas. Beans include guar, locust bean, fenugreek, soybean, garden bean, cowpea, mungbean, lima bean, fava bean, lentils, chickpea, etc. Legumes include, but are not limited to, *Arachis*, e.g., peanuts, *Vicia*, e.g., crown vetch, hairy vetch, adzuki bean, mung bean, and chickpea, *Lupinus*, e.g., lupine, trifolium, *Phaseolus*, e.g., common bean and lima bean, *Pisum*, e.g., field bean, *Melilotus*, e.g., clover, *Medicago*, e.g., alfalfa, *Lotus*, e.g., trefoil, lens, e.g., lentil, and false indigo. Preferred forage and turf grass for use in the methods of the invention include alfalfa, orchard grass, tall fescue, perennial ryegrass, creeping bent grass, and redtop.

More preferably, plants that can be modulated by the present method are crop plants and model plant, e.g., corn, rice, alfalfa, sunflower, canola, soybean, cotton, peanut, sorghum, wheat, tobacco, rice, lemna, etc. Most preferably, gene expression in corn, rice, lemna, and soybean plants are modulated by the present method.

Zinc Finger Proteins used in the Present Method

Any zinc finger proteins can be used in the present method. In addition, zinc finger proteins disclosed or designed and predicted according to the procedures in WO 98/54311 can be used. WO 98/54311 discloses technology which allows the design of zinc finger protein domains which bind specific nucleotide sequences which are unique to a target gene. It has been calculated that a sequence comprising 18 nucleotides is sufficient to specify an unique location in the genome of higher organisms. Typically, therefore, the zinc finger protein domains are hexadactyl, i.e., contain 6 zinc fingers, each with its specifically designed alpha helix for interaction with a particular triplet. However, in some instances, a shorter or longer nucleotide target sequence may be desirable. Thus, the zinc finger domains in the proteins may contain from 2–12 fingers, preferably, 3–8 fingers, more preferably 5–7 fingers, and most preferably 6 fingers.

When a multi-finger protein binds to a polynucleotide duplex, e.g., DNA, RNA, PNA or any hybrids thereof, its fingers typically line up along the polynucleotide duplex with a periodicity of about one finger per 3 bases of nucleotide sequence. The binding sites of individual zinc fingers (or subsites) typically span three to four bases, and subsites of adjacent fingers usually overlap by one base. Accordingly, a three-finger zinc finger protein XYZ binds to the 10 base pair site abcdefghij (where these letters indicate one of the duplex DNA) with the subsite of finger X being ghij, finger Y being defg and finger Z being abcd. For example, as known in the art, to design a three-finger zinc finger protein to bind to the targeted 10 base site abcdefXXXX (wherein each "X" represents a base that would be specified in a particular application), zinc fingers Y and Z would have the same polypeptide sequence as found in the original zinc finger discussed above (perhaps a wild type zinc fingers which bind defg and abcd, respectively). Finger X would have a mutated polypeptide sequence. Preferably, finger X would have mutations at one or more of the base-contacting positions, i.e., finger X would have the same polypeptide sequence as a wild type zinc finger except that at least one of the four amino residues at the primary positions would differ. Similarly, to design a three-finger zinc protein that would bind to a 10 base sequence abcXXXXhij (wherein each "X" is base that would be specified in a particular application), fingers X and Z have the same sequence as the wild type zinc fingers which bind ghij and abcd, respectively, while finger Y would have residues at one or more base-coating positions which differ from those in a wild type finger. The present method can employ multi-fingered proteins in which more than one finger differs from a wild type zinc finger. The present method can also employ multi-fingered protein in which the amino acid sequence in all the fingers have been changed, including those designed by combinatorial chemistry or other protein design and binding assays.

It is also possible to design or select a zinc finger protein to bind to a targeted polynucleotide in which more than four bases have been altered. In this case, more than one finger of the binding protein must be altered. For example, in the 10 base sequence XXXdefgXXX, a three-finger binding protein could be designed in which fingers X and Z differ from the corresponding fingers in a wild type zinc finger, while finger Y will have the same polypeptide sequence as the corresponding finger in the wild type fingers which binds to the subsite defg. Binding proteins having more than three fingers can also be designed for base sequences of longer length. For example, a four finger-protein will optimally bind to a 13 base sequence, while a five-finger protein will optimally bind to a 16 base sequence. A multi-finger protein can also be designed in which some of the fingers are not involved in binding to the selected DNA. Slight variations are also possible in the spacing of the fingers and framework.

While the present method can employ any valid recognition code, the zing finger protein nucleic acid binding domain/nucleoside binding partner pairs disclosed in U.S. Pat. No. 5,789,538, WO 96/06166, and WO 00/23464 can also be used.

Methods for designing and identifying a zinc finger protein with desired nucleic acid binding characteristics also include those described in WO98/53060, which reports a method for preparing a nucleic acid binding protein of the Cys2-His2 zinc finger class capable of binding to a nucleic acid quadruplet in a target nucleic acid sequence.

Zinc finger proteins useful in the present method can comprise at least one zinc finger polypeptide linked via a linker, preferably a flexible linker, to at least a second DNA binding domain, which optionally is a second zinc finger polypeptide. The zinc finger protein may contain more than two DNA-binding domains, as well as one or more regulator domains. The zinc finger polypeptides used in the present method can be engineered to recognize a selected target site in the gene of choice. Typically, a backbone from any suitable C2H2-ZFP, such as SPA, SPIC, or ZIF268, is used as the scaffold for the engineered zinc finger polypeptides (see, e.g., Jacobs, *EMBO J.* (1992) 11:4507; and Desjarlais & Berg, *Proc. Natl. Acad. Sci. USA* (1993) 90:2256–2260). A number of methods can then be used to design and select a zinc finger polypeptide with high affinity for its target. A zinc finger polypeptide can be designed or selected to bind to any suitable target site in the target gene, with high affinity.

Any suitable method known in the art can be used to design and construct nucleic acids encoding zinc finger polypeptides, e.g., phage display, random mutagenesis, combinatorial libraries, computer/rational design, affinity selection, PCR, cloning from cDNA or genomic libraries, synthetic construction and the like. (see, e.g., U.S. Pat. No. 5,786,538; Wu et al., *Proc. Natl. Acad. Sci. USA* (1995) 92:344–348; Jamieson et al., *BiochemistI.* (1994) 33:5689–5695; Rebar & Pabo, *Science* (1994) 263:671–673; Choo & Klug, *Proc. Natl. Acad. Sci. USA* (1994) 91: 11168–11172; Pomerantz et al., *Science,* 267:93–96 (1995); Pomerantz et al., *Proc. Natl. Acad. Sci. USA* (1995) 92:9752–9756; Liu et al., *Proc. Natl. Acad. Sci. USA* (1997) 94:5525–5530; and Desjarlais & Berg,(1994) *Proc. Natl. Acad. Sci. USA* 91:11–99–11103).

Zinc finger proteins useful in the method can be made by any recombinant DNA technology method for gene construction. For example, PCR based construction can be used. Ligation of desired fragments can also be performed, using linkers or appropriately complementary restriction sites. One can also synthesize entire finger domain or parts thereof by any protein synthesis method. Preferred for cost and flexibility is the use of PCR primers that encode a finger sequence or part thereof with known base pair specificity, and that can be reused or recombined to create new combinations of fingers and ZFP sequences.

The amino acid linker should be flexible, a beta turn structure is preferred, to allow each three finger domain to independently bind to its target sequence and avoid steric hindrance of each other's binding. Linkers can be designed and empirically tested.

If recognition code is incomplete, or if desired, in one embodiment, the ZFP can be designed to bind to non-contiguous target sequences. For example, a target sequence for a six-finger ZFP can be a nine base pair sequence (recognized by three fingers) with intervening bases (that do not contact the zinc finger nucleic acid binding domain) between a second nine base pair sequence (recognized by a second set of three fingers). The number of intervening bases can vary, such that one can compensate for this intervening distance with an appropriately designed amino acid linker between the two three-finger parts of ZFP. A range of intervening nucleic acid bases in a target binding site is preferably 20 or less bases, more preferably 10 or less, and even more preferably 6 or less bases. It is of course recognized that the linker must maintain the reading frame between the linked parts of ZFP protein.

A minimum length of a linker is the length that would allow the two zinc finger domains to be connected without providing steric hindrance to the domains or the linker. A linker that provides more than the minimum length is a "flexible linker." Determining the length of minimum linkers and flexible linkers can be performed using physical or computer models of DNA-binding proteins bound to their respective target sites as are known in the art.

The six-finger zinc finger peptides can use a conventional "TGEKP" (SEQ ID NO:78) linker to connect two three-finger zinc finger peptides or to add additional fingers to a three-finger protein. Other zinc finger peptide linkers, both natural and synthetic, are also suitable.

A useful zinc finger framework is that of ZIF268 (see WO00/23464 and references cited therein), however, others are suitable. Examples of known zinc finger nucleotide binding polypeptides that can be truncated, expanded, and/or mutagenized in order to change the function of a nucleotide sequence containing a zinc finger nucleotide binding motif includes TFIIIA and zif268. Other zinc finger nucleotide binding proteins are known to those of skill in the art. The murine CYS2-HiS2 zinc finger protein Zif268 is structurally well characterized of the zinc finger proteins (Pavletich and Pabo, *Science* (1991) 252:809–817; Elrod-Erickson et al., *Structure (London)* (1996) 4:1171–1180; and Swirnoff et al., *Mol. Cell. Biol.* (1995) 15:2275–2287). DNA recognition in each of the three zinc finger domains of this protein is mediated by residues in the N-terminus of the alpha helix contacting primarily three nucleotides on a single strand of the DNA. The operator binding site for this three finger protein is 5'-GCGTGGGCG-'3. Structural studies of Zif268 and other related zinc finger-DNA complexes (Elrod-Erickson et al., *Structure (London)* (1998) 6:451–464; Kim and Berg, *Nature Structural Biology* (1996) 3:940–945; Pavletich and Pabo, *Science* (1993) 261:1701–1707; Houbaviy et al., *Proc. Natl. Acad. Sci. USA* (1996) 93:13577–13582; Fairall et al., *Nature (London)* (1993) 366:483–487; Wuttke et al., *J. Mol. Biol.* (1997) 273:183–206; Nolte et al., *Proc. Natl. Acad. Sci. USA* (1998) 95:2938–2943; and Narayan et al., *J. Biol. Chem.* (1997) 272:7801–7809) have shown that residues from primarily three positions on the α-helix, −1, 3, and 6, are involved in specific base contacts. Typically, the residue at position −1 of the α-helix contacts the 3' base of that finger's subsite while positions 3 and 6 contact the middle base and the 5' base, respectively.

However, it should be noted that at least in some cases, zinc finger domains appear to specify overlapping 4 bp sites rather than individual 3 bp sites. In Zif268, residues in addition to those found at helix positions −1, 3, and 6 are involved in contacting DNA (Elrod-Erickson et al., *Structure* (1996) 4:1171–1180). Specifically, an aspartate in helix position 2 of the middle finger plays several roles in recognition and makes a variety of contacts. The carboxylate of the aspartate side chain hydrogen bonds with arginine at position −1, stabilizing its interaction with the 3'-guanine of its target site. This aspartate may also participate in water-mediated contacts with the guanine's complementary cytosine. In addition, this carboxylate is observed to make a direct contact to the N4 of the cytosine base on the opposite strand of the 5'-guanine base of the finger 1 binding site. It is this interaction which is the chemical basis for target site overlap.

Any suitable method of protein purification known to those of skill in the art can be used to purify the zinc finger proteins of the invention (see Sambrook et al., *Molecular Cloning: A Laboratory Manual* (2d ed., Cold Spring Harbor Laboratory Press, Plainview, N.Y.) (1989)). In addition, any suitable host can be used, e.g., bacterial cells, insect cells, yeast cells, mammalian cells, and the like.

In one embodiment, expression of the zinc finger protein fused to a maltose binding protein (MBP-zinc finger protein) in bacterial strain JM 109 allows for purification through an amylose column (NEB). High expression levels of the zinc finger protein can be obtained by induction with IPTG since the MBP-zinc finger protein fusion in the pMal-c2 expression plasmid is under the control of the IPTG inducible tac promoter (NEB). Bacteria containing the MBP-zinc finger protein fusion plasmids are inoculated in to 2×YT medium containing 10~LM ZnC12, 0.02% glucose, plus 50 ptg/ml ampicillin and shaken at 37° C. At mid-exponential growth IPTG is added to 0.3 mM and the cultures are allowed to shake. After 3 hours the bacteria are harvested by centrifugation, disrupted by sonication, and then insoluble material is removed by centrifugation. The MBP-zinc finger proteins are captured on an amylose-bound resin, washed extensively with buffer containing 20 mM Tris-HCl (pH 7–5), 200 mM NaCl, 5 mM DTT and 50~tM ZnC12, then eluted with maltose in essentially the same buffer (purification is based on a standard protocol from NEB). Purified proteins are quantitated and stored for biochemical analysis.

The biochemical properties of the purified proteins, e.g., Kd, can be characterized by any suitable assay. In one embodiment, Kd is characterized via electrophoretic mobility shift assays ("EMSA") (Buratowski & Chodosh, in Current Protocols in Molecular Biology pp. 12.2.1–12.2.7 (Ausubel ed., 1996)). By "Kd" is meant the dissociation constant for the compound, i.e., the concentration of a compound (e.g., a zinc finger protein) that gives half maximal binding of the compound to its target (i.e., half of the compound molecules are bound to the target) under given conditions (i.e., when [target]<<Kd), as measured using a given assay system. Any assay system can be used, as long as it gives an accurate measurement of the actual Kd of the zinc finger protein. In one embodiment, the Kd for the zinc finger proteins of the invention is measured using an electrophoretic mobility shift assay as described herein.

As described in the Example Section below, the observed affinities of 6-finger proteins tested were determined to be: ZFPm1=2.0 nM, ZFPm2=7.5 nM, ZFPm3=0.18 nM, ZFPm4=0.25 nM and ZFPAp3=2.3 nM (FIG. 12–16). Most of these affinities compare favorably with existing 6 finger proteins. The 2C7 derivative of the Sp1 zinc finger was reported to have a specificity of 0.46 nM and the e2c zinc finger was reported to have an affinity of 0.5 nM. Consequently, zinc fingers used in the invention typically have affinity 0.1 to 1.0 nanomolar range, more typically 0.18 to 0.75 nanomolar, and to picomoloar range and even to femtomolar range. Typically, naturally occurring zinc fingers have Kd in the nanomolar range. Zinc finger proteins useful in the invention may even have an affinity for the target site that is in the femtamolar range, e.g., 100 femtamoles, 10 femtamoles, or less, in some cases as low as one femtamole.

In a specific embodiment, the zinc finger protein used in the present methods comprises a framework (or backbone) derived from a naturally occurring zinc finger protein. Framework (or backbone) derived from any naturally occurring zinc finger protein can be used. For example, the zinc finger protein comprises a framework (or backbone) derived from a zinc finger protein comprising a C2H2 motif can be used. Preferably, the protein or peptide sequence within the β sheet of the C2H2 motif is not substantially changed, or not changed, from its natural sequence.

In another specific embodiment, the zinc finger protein used in the present methods comprises a framework (or backbone) derived from a zinc finger protein that is naturally functional in plant cells. For example, the zinc finger protein used in the present methods can comprise a C3H zinc finger (Terol et al., *Gene*, 260(1–2):45–53 (2000)), a QALGGH motif (Takatsuji, *Plant. Mol. Biol.*, 39(6):1073–8 (1999)), a RING-H2 zinc finger motif (Jensen et al., *FEBS Lett.*, 436(2):283–7 (1998)), a 9 amino acid C2H2 motif (Chou et al., *Proc. Natl. Acad. Sci. USA*, 95(9):5293–8 (1998)), a zinc finger motif of *Arabidopsis* LSD1 (Dietrich et al., *Cell*, 88(5):685–94 (1997)) and a zinc finger motif of BBF/Dof domain proteins (De Paolis et al., *Plant J.*, 10(2):215–23 (1996)).

In another specific embodiment, the zinc finger protein used in the present methods comprises a framework (or backbone) derived from a zinc finger protein that is known in the art as of Jan. 19, 2001.

For example, the zinc finger protein used in the present methods can comprise a framework (or backbone) derived from the zinc finger protein disclosed in the following U.S. patents and PCT patent publications: U.S. Pat. Nos. 6,160, 091, 6,140,466, 6,140,081, 5,831,008, 5,811,304 and 5,789, 538 and WO 00/42219, WO 00/41566, WO 00/27878, WO 00/23464, WO 00/20622, WO 00/20556, WO 99/62952, WO 99/48909, WO 99/46293, WO 99/45132, WO 99/42474, WO 99/21991, WO 98/54311, WO 98/53061, WO 98/45326, WO 96/11267, WO 96/06168 and WO 95/19431.

The zinc finger protein used in the present methods can also comprise a framework (or backbone) derived from the zinc finger protein disclosed in the following references: 1) Cousins R J, Lanningham-Foster L., "Regulation of cysteine-rich intestinal protein, a zinc finger protein, by mediators of the immune response." J Infect Dis. 2000 Sep;182 Suppl 1:S81–4; 2) Bouhouche N, Syvanen M, Kado C L., "The origin of prokaryotic C2H2 zinc finger regulators." Trends Microbiol. 2000 February;8(2):77–81; 3: Klug A., "Zinc finger peptides for the regulation of gene expression." J Mol Biol. 1999 Oct. 22;293(2):215–8; 4) Cook T, Gebelein B, Urrutia R., "Sp1 and its likes: biochemical and functional predictions for a growing family of zinc finger transcription factors." Ann N Y Acad Sci. 1999 Jun 30;880:94–102; 5) Takatsuji H., "Zinc-finger proteins: the classical zinc finger emerges in contemporary plant science." Plant Mol Biol. 1999 April;39(6):1073–8; 6) Huang S., "The retinoblastoma protein-interacting zinc finger gene RIZ in 1p36-linked cancers." Front Biosci. 1999 Jun 15;4:D528–32; 7: Krempler A, Brenig B., "Zinc finger proteins: watchdogs in muscle development." Mol Gen Genet. 1999 March;261(2): 209–15; 8) Hoffmann A, Ciani E, Houssami S, Brabet P, Journot L, Spengler D., "Induction of type I PACAP receptor expression by the new zinc finger protein Zac1 and p53." Ann N Y Acad Sci. 1998 Dec 11;865:49–58; 9) Kroncke K D, Kolb-Bachofen V., "Measurement of nitric oxide-mediated effects on zinc homeostasis and zinc finger transcription factors." Methods Enzymol. 1999;301:126–35; 10) Tseng H., "Basonuclin, a zinc finger protein associated with epithelial expansion and proliferation." Front Biosci. 1998 Sep 1;3:D985–8; 11) Takatsuji H., "Zinc-finger transcription factors in plants." Cell Mol Life Sci. 1998 June;54(6): 582–96; 12) Chilton B S, Hewetson A., "Zinc finger proteins RUSH in where others fear to tread." Biol Reprod. 1998 February;58(2):285–94; 13) Urrutia R., "Exploring the role of homeobox and zinc finger proteins in pancreatic cell proliferation, differentiation, and apoptosis." Int J Pancreatol. 1997 Aug.;22(1):1–14; 14) Mizuno K Higu O., "LIM domains: double zinc finger motifs involved in protein-protein interaction Tanpakushitsu Kakusan Koso. 1997 October;42(13):2061–71; 15: Losson R., "KRAB zinc finger proteins and nuclear receptors: a possible cross-talk. " Biol Chem. July;378(7):579–81;16) Eis PS., "Fluorescnce studies of zinc finger peptides and proteins." Methods Enzymol. 1997;278:330–43; 17) Tamaoki T, Hashimoto T., "ZFH/ ATBF1 gene family: transcription factors containing both homeo- and zinc finger-domains" Tanpakushitsu Kakusan Koso. 1996 September;41(11):1550–9; 18: Hollemann T, Bellefroid E, Stick R, Pieler T., "Zinc finger proteins in early Xenopus development." Int J Dev Biol. 1996 February;40 (1):291–5; 19) Kroncke K D, Kolb-Bachofen V., "Detection of nitric oxide interaction with zinc finger proteins." Methods Enzymol. 1996;269:279–84; 20) Lopingco M C, Perkins A S., "Molecular analysis of Evi1, a zinc finger oncogene involved in myeloid leukemia." Curr Top Microbiol Immunol. 1996;211:211–22: 21) Hromas R, Davis B, Rauscher F J 3rd, Klemsz M, Tenen D, Hoffman S, Xu D, Morris J F., "Hematopoietic transcriptional regulation by the myeloid zinc finger gene, MZF-1." Curr Top Microbiol Immunol. 1996;211:159–64; 22) Nagaoka M, Sugiura Y., Conversion of zinc finger protein to artificial site-specific nuclease: application to chromosome mapping and sequencing" Nippon Rinsho. 1995 Oct;53(10):2589–96; 23) Sarkar B. "Metal replacement in DNA-binding zinc finger proteins and its relevance to mutagenicity and carcinogenicity through free radical generation." Nutrition. 1995 Sep–Oct; 11(5 Suppl):646–9; 24) Gashler A, Sukhatme V P., "Early growth response protein 1 (Egr-1): prototype of a zinc-finger family of transcription factors." Prog Nucleic Acid Res Mol Biol. 1995;50:191–224; 25) Knegtel R M, van Tilborg M A, Boelens R, Kaptein R., "NMR structural studies on the zinc finger domains of nuclear hormone receptors." EXS. 1995; 73:279–95; 26) Sanchez-Garcia I, Rabbitts T H., "The LIM domain: a new structural motif found in zinc-finger-like proteins." Trends Genet. 1994 Sep;10(9):315–20; 27) Pieler T, Bellefroid E., "Perspectives on zinc finger protein function and evolution—an update." Mol Biol Rep. 1994 Jul;20 (1):1–8; 28) Madden S L, Rauscher F J 3d., "Positive and negative regulation of transcription and cell growth mediated by the EGR family of zinc-finger gene products." Ann N Y Acad Sci. 1993 Jun 11;684:75–84; 29) Thiesen H J, Bach C., "DNA recognition of C2H2 zinc-finger proteins. Evidence for a zinc-finger-specific DNA recognition code." Ann N Y Acad Sci. 1993 Jun 11;684:246–9; 30) Freemont P S., "The RING finger. A novel protein sequence motif related to the zinc finger." Ann N Y Acad Sci. 1993 Jun 11;684:174–92; 31) Werner H, Roberts C T Jr, LeRoith D., "The regulation of IGF-I receptor gene expression by positive and negative zinc-finger transcription factors." Adv Exp Med Biol. 1993;343:91–103; 32) Berg J M., "Sp1 and the subfamily of zinc finger proteins with guanine-rich binding sites." Proc Natl Acad Sci U S A. 1992 Dec 1;89(23): 11109–10; 33) Reddy B A, Etkin L D, Freemont P S., "A novel zinc finger coiled-coil domain in a family of nuclear proteins." Trends Biochem Sci. 1992 Sep;17(9):344–5; 34) Freedman L P., "Anatomy of the steroid receptor zinc finger region." Endocr Rev. 1992 May;13(2):129–45; 35) el-Baradi T, Pieler T., "Zinc finger proteins: what we know and what we would like to know." Mech Dev. 1991 Nov; 35(3):155–69; 36) Schule R, Evans R M., "Cross-coupling of signal transduction pathways: zinc finger meets leucine zipper." Trends Genet. 1991 Nov-Dec;7(11–12):377–81; 37) Summers M F., Zinc finger motif for single-stranded nucleic acids? Investigations by nuclear magnetic resonance." J Cell Biochem. 1991 Jan;45(1):41–8; 38) Ashworth A, Denny P., "Zinc finger protein genes in the mouse genome." Mamm Genome. 1991;1(3):196–200; 39) South T L, Kim B, Hare D R, Summers M F., "Zinc fingers and molecular recognition. Structure and nucleic acid binding studies of an HIV zinc finger-like domain." Biochem Pharmacol. 1990 Jul 1;40(1):123–9; 40) Berg J M., "Zinc finger domains: hypotheses and current knowledge." Annu Rev Biophys Biophys Chem. 1990;19:405–21; 41) Copeland N G, Jenkins N A., "Retroviral integration in murine myeloid tumors to identify Evi-1, a novel locus encoding a zinc-finger protein." Adv Cancer Res. 1990;54:141–57; 42) Erickson R P, Verga V., "Is zinc-finger Y the sex-determining gene?" Am J Hum Genet. 1989 Nov;45(5):671–4; and 43) Struhl K., "Helix-turn-helix, zinc-finger, and leucine-zipper motifs for eukaryotic transcriptional regulatory proteins." Trends Biochem Sci. 1989 Apr;14(4):137–40.

Effector Domains

Although in some cases, a zinc finger protein itself is sufficient for modulating gene expression, the zinc finger protein is preferably fused to an effector domain (or regulatory domain or functional domain), i.e., a protein domain which activates or represses gene expression, e.g., an activator domain of a regulatory protein or an active domain of a nucleic acid modifying protein. The foregoing terms—i.e., "effector domain (or effector)," "regulatory domain," and "functional domain" may refer to the materials on either the nucleic acid or protein level as will be clear from the context.

The effector domain can have an activity such as transcriptional modulation activity, DNA modifying activity, protein modifying activity and the like when tethered to a DNA binding domain, i.e., a zinc finger protein. Examples of regulatory domains include proteins or effector domains of proteins such as transcription factors and co-factors, e.g., KRAB, MAD, ERD, SID, nuclear factor kappa B subunit p65, early growth response factor 1, and nuclear hormone receptors, VP16 and VP64, endonucleases, integrases, recombinases, methyltransferases, histone acetyltransferases, histone deacetylases, mutases, restriction enzymes, etc.

Activators and repressors include co-activators and co-repressors (see, e.g., Utley et al., *Nature* (1998) 394:498–502; and WO 00/03026). Effector domains can include DNA-binding domains from a protein that is not a zinc finger protein, such as a restriction enzyme, a nuclear hormone receptor, a homeodomain protein such as engrailed or antenopedia, a bacterial helix-turn-helix motif protein such as lambda repressor and tet repressor, Gal4, TATA binding protein, helix-loop-helix motif proteins such as myc and myo D, leucine zipper type proteins such as fos and jun, and beta sheet motif proteins such as met, arc, and mnt repressors. Particularly preferred activator is the C1 activator domain of maize (Goff et al., *Genes Dev.* (1991) 5(2): 298–309).

In a specific embodiment, the zinc finger protein having an effector domain is one that is responsive to a ligand. The effector domain can effect such a response. Use of ligand inducible binding domain-effector fusions is generally known as a gene switch. Therefore, the ZFP domains discussed here can be used as part of the ligand-binding domain in gene switches. Example of such ligand-responsive domains include hormone receptor ligand binding domains, e.g., estrogen receptor domain, ecydysone receptor system, glucocorticosteroid (Parker, *Curr. Opin. Cell Biol.* (1993) 5:499–504; Beato et al., *Cell* (1995) 83:851–857; Mangelsdorf et al., *Cell* (1995) 83:835–839; and Yamamoto, *Annu. Rev. Genet.* (1985) 19:209–252), inducible promoters of trehalose biosynthetic genes (WO 99/46370), chemically lucible arabidopsis PR-1 promoter (WO 98/03536; and U.S. Pat. No. 5,689,044) and chemically inducible promoter of a cucumber chitinase/lysozyme gene (U.S. Pat. No. 5,654,414). Preferred inducers are small, inorganic, biodegradable, molecules.

The zinc finger protein can covalently or non-covalently associated with one or more regulatory domains. Alternatively, two or more regulatory domains, whether identical or different ones, can be linked together. The regulatory domains can be covalently linked to the zinc finger protein nucleic acid binding domain, e.g. via an amino acid linker, as part of a fusion protein. The zinc finger proteins can also be associated with a regulatory domain via a non-covalent dimerization domain, e.g., a leucine zipper, a STAT protein N terminal domain, or an FK506 binding protein (see, e.g., O'Shea, *Science* (1991) 254:539; Barahmand-Pour et al., *Curr. Top. Microbiol. Immunol.* (1996) 211:121–128; Klemnm et al., *Annu. Rev. Immunol.* (1998) 16:569–592; Klemm et al., *Annu. Rev. Immunol.* (1998) 16:569–592; Ho et al., *Nature* (1996) 382:822–826; and Pomeranz et al., *Biochem.* (1998) 37:965). The regulatory domain can be associated with the zinc finger protein domain at any suitable position, including the C- or N-terminus of the zinc finger protein.

Common regulatory domains for addition to the zinc finger protein made using the methods of the invention include, e.g., DNA-binding domains from transcription factors, effector domains from transcription factors (activators, repressors, co-activators, co-repressors), silencers, nuclear hormone receptors, and chromatin associated proteins and their modifiers, e.g., methylases, kinases, acetylases and deacetylases.

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., *Cell* (1996) 84:825–830) for a review of proteins and nucleic acid elements involved in transcription. Transcription factors in general are reviewed in Bames and Adcock, *Clin. Exp. Allerg* v 25 Suppl. 2:46–49 (1995) and Roeder, *Methods Enz.* (1996) 273:165–171. Databases dedicated to transcription factors are also known (see, e.g., Williams, *Science* (1995) 269:630). Nuclear hon-none receptor transcription factors are described in, for example, Rosen et al., *J. Med. Chem.* (1995) 38:4855–4874. The C/EBP family of transcription factors are reviewed in Wedel et al., *Immunobiology* (1995) 193:171–185. Coactivators and co-repressors that mediate transcription regulation by nuclear hormone receptors are reviewed in, for example, Meier, *Eur. J. Endocrinol.* (1996) 134(2):158–9; Kaiser et al., *Trends Biochem. Sci.* (1996) 21:342–345; and Utley et al., *Nature* (1998) 394:498–502. GATA transcription factors, which are involved in regulation of hematopoiesis, are described in, for example, Simon, *Nat. Genet.* (1995) 11:9–11; and Weiss et al., *Exp. Hematol.* 23:99–107. TATA box binding protein (T13P) and its associated TAF polypeptides (which include TAF30, TAF55, TAF80, TAF1 10, TAFI 50, and TAF250) are described in Goodrich & Tjian, *Curr. Opin. Cell Biol.* (1994) 6:403–409 and Hurley, *Curr. Opin. Struct. Biol.* (1996) 6:69–75. The STAT family of transcription factors are reviewed in, for example, Barahmand-Pour et al., *Curr. Top. Microbiol. Immunol.* (1996) 211:121–128. Transcription factors involved in disease are reviewed in Aso et al., *J Clin. Invest.* (1996) 97:1561–1569.

In one embodiment, the KRAB repression domain from the human KOX-I protein is used as a transcriptional repressor (Thiesen et al., *New Biologist* (1990) 2:363–374; Margolin et al., *Proc. Natl. Acad. Sci. USA* (1994) 91:4509–4513; Pengue et al., *Nuc. Acids Res.* (1994) 22:2908–2914; and Witzgall et al., *Proc. Natl. Acad. Sci. USA* (1994) 91:4514–4518). In another embodiment, KAP-1, a KRAB co-repressor, is used with KRAB (Friedman et al., *Genes Dev.* (1996) 10:2067–2078). Alternatively, KAP-I can be used alone with a zinc finger protein. Other preferred transcription factors and transcription factor domains that act as transcriptional repressors include MAD (see, e.g., Sommer et al., *J Biol. Chem.* (1998) 273:6632–6642; Gupta et al., *Oncogene* (1998) 16:1149–1159; Queva et al., *Oncogene* (1998) 16:967–977; Larsson et al., *Oncogene* (1997) :737–748; Laherty et al., *Cell* (1997) 89:349–356; and Cultraro et al., *Mol Cell. Biol.* (1997) 17:2353–2359); FKHR (forkhead in rhapdosarcoma gene ) (Ginsberg et al., *Cancer Res.* (1998) 15:3542–3546; and Epstein et al., *Mol. Cell. Biol.* (1998) 18:4118–4130); EGR-I (early growth response gene product-1) (Yan et al., *Proc. Natl. Acad. Sci. USA* (1998) 95:8298–8303; and Liu et al., *Cancer Gene Ther.* (1998) 5:3–28); the ets2 repressor factor repressor domain (ERD) (Sgouras et al., *EMBO J* (1995) 14:4781–4793); and the MAD smSIN3 interaction domain (SID) (Ayer et al., *Mol. Cell. Biol.* (1996) 16:5772–5781).

In another embodiment, the HSV VP 16 activation domain is used as a transcriptional activator (see, e.g., Hagmann et al., *J Virol.* (1997) 71:5952–5962). Other preferred transcription factors that could supply activation domains include the VP64 activation domain (Selpel et al., *EMBO J* (1996) 11:4961–4968); nuclear hormone receptors (see, e.g., Torchia et al., *Curr. Opin. Cell. Biol.* (1998) 10:373–383); the p65 subunit of nuclear factor kappa B (Bitko & Barik, *J Virol.* (1998) 72:5610–5618 and Doyle & Hunt, *Neuroreport* (1997) 8:2937–2942); and EGR-I (early growth response gene product-1) (Yan et al., *Proc. Nad. Acad. Sci. USA* (1998) 95:8298–8303; and Liu et al., *Cancer Gene Ther.* (1998) 5:3–28).

Kinases, phosphatases, and other proteins that modify polypeptides involved in gene regulation are also useful as regulatory domains for zinc finger proteins. Such modifiers are often involved in switching on or off transcription mediated by, for example, hormones. Kinases involved in transcription regulation are reviewed in Davis, *Mol. Reprod. Dev.* (1995) 42:459–467, Jackson et al., *Adv. Second Messenger Phosphoprotein Res.* (1993) 28:279–286, and Boulikas, *Crit. Rev. Eukaryot. Gene Expr.* (1995) 5:1–77, while phosphatases are reviewed in, for example, Schonthal & Semin, *Cancer Biol.* (1995) 6:239–248. Nuclear tyrosine kinases are described in Wang, *Trends Biochem. Sci.* (1994) 19:373–376.

Useful domains can also be obtained from the gene products of oncogenes (e.g., myc, jun, fos, myb, max, mad, rel, ets, bcl, myb, mos family members) and their associated factors and modifiers. Oncogenes are described in, for example, Cooper, Oncogenes, 2nd ed., The Jones and Bartlett Series in Biology, Boston, Mass., Jones and Bartlett Publishers, 1995. The ets transcription factors are reviewed in Waslyk et al., *Eur. J Biochem.* (1993) 211:7–18. Myc oncogenes are reviewed in, for example, Ryan et al., *Biochem. J.* (1996) 314:713–721. The Jun and fos transcription factors are described in, for example, The Fos and Jun Families of Transcription Factors, Angel & Henlich, eds. (1994). The max oncogene is reviewed in Hurlin et al., *Cold Spring Harb. Symp. Quant. Biol.* 59:109–116. The myb gene family is reviewed in Kanei-Ishii et al., *Curr. Top. Microbiol. Immunol.* (1996) 211:89–98. The mos family is reviewed in Yew et al., *Curr. Opin. Genet. Dev.* (1993) 3:19–25.

In still another embodiment, histone acetyltransferase is used as a transcriptional activator (see, e.g., Jin & Scotto, *Mol. Cell. Biol.* (1998) 18:4377–4384; Wolffle, *Science* (1996) 272:371–372; Taunton et al., *Science* (1996) 272:408–411; and Hassig et al., *Proc. Natl. Acad. Sci. USA* (1998) 95:3519–3524). In another embodiment, histone deacetylase is used as a transcriptional repressor (see, e.g., Jin & Scotto, *Mol. Cell. Biol.* (1998) 18:4377–4384; Syntichaki & Thireos, *J Biol. Chem.* (1998) 273:24414–24419; Sakaguchi et al., *Genes Dev.* (1998) 12:2831–2841; and Martinez et al., *J Biol. Chem.* (1998) 273:23781–23785).

In a preferred embodiment, the plant effectors listed in the following Table 1 can be used:

TABLE 1

Exemplary plant effectors.

| Gene | Organism | Activator | Repressor | Region Cloned (aa) | GenBank Accession | Plasmid | Reference |
|---|---|---|---|---|---|---|---|
| APETALA (AP1) | Arabidopsis | yes | | 194–255 | S27109 | AP1 Effector | Plant Molecular Biology 40:419–429 (1999) |
| DNA binding with one finger (Dof1) | Maize | yes | | 135–238 | X66076 | Dof1 Effector | The Plant Cell 10:75–89 (1998) |
| Dof2 | Maize | | yes | 112–221 | S59852 | mDof2 Effector | The Plant Cell 10:75–89 (1998) |
| Dof2 | Arabidopsis | | | 115–204 | BAA33197 | AtDof2 Effector | Blast Search |
| Viral Protein 16 (VP16) | Herpes Virus | yes | | | | VP16 Effector | |
| C1 | maize | yes | | | | C1 Effector | |
| G-box binding factor (GBF-1) | Arabidopsis | yes | | 1–110 | P42774 | GBF1 Effector | EMBO 11(4):1275–1289(1992) |
| Mybst1 | Potato | | | 173–358 | | Mybst1Effector | EMBO 13(22): 5383–5392 (1994) |

TABLE 1-continued

Exemplary plant effectors.

| Gene | Organism | Activator | Repressor | Region Cloned (aa) | GenBank Accession | Plasmid | Reference |
|---|---|---|---|---|---|---|---|
| PCP1 | Potato | | | 206–496 | X82328 | PCP1 Effector | Mol. Gen. Genet. 247: 759–763 (1995) |
| PWRKY1 | Parsley | yes | | 1–187 | U48831 | Pwrky1 Effector | EMBO 18(17): 4689–4699 (1999) |
| PWRKY3 | Parsley | | | 1–237 | | Pwrky3 Effector | EMBO 18(17): 4689–4699 (1999) |
| AFT1 (14-3-3 protein) | Arabidopsis | yes | | 1–248 | U02565 | AFT1 Effector | FEBS Letters 443: 282–284 (1999) |
| ZAP1 | Arabidopsis | yes | | 168–282 | X92976 | Zap1 Effector | Nucleic Acids Research 24(23): 4624–4631 (1996) |

Target Genes and Target Nucleotide Sequences

Expression of any target genes in plant can be modulated by the present method. For example, the expression of the APETALA3 (AP3) gene of *Arabidopsis* can be modulated. The APETALA3 (AP3) gene of *Arabidopsis* is a member of the ADS domain proteins that are required to specify the flower organ types and are involved in regulation of floral development. The success illustrated below in targeting this gene for endogenous gene regulation is important for several reasons. First, *Arabidopsis* is a well-studied model organism in which genetic studies are easily and rapidly performed and is considered a typical case. Second, AP3 has been well studied in its role during flower development to specify floral organ identity (see, Yanofsky, *Annu. Rev. Plant Physiol. Plant Mol. Biol.* (1995) 46:167–188; and Irish, *Developmental Biology* (1999) 209:211–220) and detailed analysis of the AP3 promoter and its transcription have already been published (Irish et al., *The Plant Cell* (1995) 7:1635–1644) so that the approach is illustrative for other plants as well. Finally, both ap3 mutants and AP3 overexpressors have previously been shown to have visible flower phenotypic changes (Jack et al, *Cell* (1992) 68:683–687; and Jack et al., *Cell* 1994) 76:703–716), which makes success verifiable. Thus, the AP3 gene is an llent target for demonstrating this technology as a tool for controlling gene expression plants in general.

In another example, the expression of the maize MIPS gene can be modulated. The maize MIPS protein catalyses the inversion of glucose-6-phosphate to myoinositol 1-phosphate which is an early step in synthesis of phytic acid. Low phytic acid content in feed for many species of a als is considered to have a great advantage from environmental and nutritional standpoints since phytic acid metabolism in plant plays a role in the regulation of phosphate are mineral concentration. Controlling the expression of the MIPS gene would therefore provide a means to assure plants with low phytic acid content and act as a dominant trait. The present invention permits such control, as well as control of genetic expression generally in plants.

The target nucleotide sequence is any location within the target gene whose expression is to be regulated which provides a suitable location for controlling expression. The target nucleotide sequence may be within the coding region or upstream or downstream thereof. For activation, upstream from ATG translation start codon is preferred, most preferably upstream of TATTA box but not exceeding 1000 bp from the start of transcription. For repression upstream from the ATG translation start codon is also preferred, but preferably downstream from TATTA box.

The targeted nucleotide sequence can also be a short portion of duplex nucleic acid, e.g., RNA, DNA, PNA or any hybrids thereof, having from about 8 to about 40 base pairs and having a defined sequence for which there is some desirable purpose in determining its presence or absence within a larger polynucleotide. For example, it may be desirable to determine whether a particular promoter or control region is found within the genome of a particular origin. A labeled protein, e.g., bound with a radioactive or fluorescent label, containing zinc fingers which binds to a polynucleotide having this particular sequence can be used to determine whether the genetic material of the organism contains this particular sequence.

The target sequence may reside endogenously in the target gene, e.g., MIPS in maize and AP3 in *Arabidopsis* as shown in the Example Section below, or may be inserted into the gene, e.g., heterologous, as is illustrated below for luciferase in tobacco, for example, using techniques such as homologous recombination.

Where a gene contains a suitable target nucleotide sequence in a region which is appropriate for controlling expression, the regulatory factors employed in the methods of the invention can target the endogenous nucleotide sequence. However, if the target gene lacks an appropriate unique nucleotide sequence or contains such a sequence only in a position where binding to a regulatory factor would be ineffective in controlling expression, it may be necessary to provide a "heterologous" targeted nucleotide sequence. By "heterologous" targeted nucleotide sequence is meant either a sequence completely foreign to the gene to be targeted or a sequence which resides in the gene itself, but in a different position from that wherein it is inserted as a target. Thus, it is possible to completely control the nature and position of the targeted nucleotide sequence.

The target sequence may be any given sequence of interest for which a complementary zinc finger protein is designed. Target genes include both structural and regulatory genes. When the target gene is a regulatory gene, the expression of the gene that is regulated by the target regulatory gene can also be regulated by the zinc finger protein, albeit indirectly. Therefore, expression of single genes or gene families can be controlled by the present methods.

The target gene may, as is the case for the MIPS gene and AP3 gene, be endogenous to the plant cells or plant wherein expression is regulated or may be a transgene which has been inserted into the cells or plants in order to provide a production system for a desired protein or which has been added to the genetic compliment in order to modulate the metabolism of the plant or plant cells, for example as illustrated below for the C7 binding site inserted into tobacco genome.

Selection of ZFP, Effector and Target Nucleotide Sequence

The assay system exemplified in Example 1 (see Example Section below) can be used in selecting desirable ZFP, effector or target nucleotide sequence. The assay system used in the Example 1 generally contains two constructs. One construct contains a reporter gene, e.g., P-glucuronidase (GUS), chloramphenicol acetyl transferase (CAT), or green fluorescent protein (GFP), operably linked to a promoter having a ZFP target nucleotide sequence so that the expression of the reporter gene is amenable to regulation by the ZFP. The other construct contains ZFP gene, and optionally fused to an effector domain. Upon introduction into and expression within plant or plant cells, whether transiently or stably, the ZFP, and optionally the ZFP-effector fusion protein, will regulate the expression of the reporter gene, provided that the ZFP and the target nucleotide sequence have matching "code" sequence, e.g., the pairs listed in Table 2. In such a system, if only one component of the system is changed and the rest of the components are kept constant with the known operative ones, the assay system can be used to screen or select for new ZFP, effector or target nucleotide sequence with desirable specificity or binding affinity.

For example, if a system is started with a ZFP, optionally with an effector and a target nucleotide sequence that are compatible and substitute the ZFP with a new amino acid sequence, it will be possible to determine whether the new amino acid sequence can function as a ZFP with the desired specificity and affinity to the particular target nucleotide sequence by comparing the assay readout with the known ZFP and the new amino acid sequence. New effector and target nucleotide sequence can be identified using similar procedure. If desired, the assay can be conducted quantitatively to identify ZFP, effector or target nucleotide sequence with particular specificity and binding affinity.

Since ZFPs can tolerate changes in the finger region, one can start with a preferred pairs of ZFP and target nucleotide sequence, e.g., the pairs listed in Table 2, and mutagenize the finger region of the ZFP to identify those variants that can still function as a ZFP, but with different specificity to binding affinity. It is often necessary to select ZFP finger sequence by testing against actual DNA sequence, since the juxtaposition of triplets may affect optimal ZFP finger sequence. In addition, particular positions in the finger region, e.g., −1, 3, 6, should be the focused in the mutagenesis analysis because these positions are thought to be critical for the binding between a ZFP and its target nucleotide sequence. Accordingly, ZFPs with different level of specificities and binding affinities can be obtained and these ZFPs can be used in fine-tuned control of a target gene expression in plant.

C. Expression of Zinc Finger Protein in Plant and uses Thereof

The zinc finger protein can be provided to the plant cells via any suitable methods known in the art. For example, the zinc finger protein can be exogenously added to the plant cells and the plant cells are maintained under conditions such that the zinc finger protein binds to the target nucleotide sequence and regulates the expression of the target gene in the plant cells. Alternatively, a nucleotide sequence encoding the zinc finger protein can be expressed in the plant cells and the plant cells are maintained under conditions such that the expressed zinc finger protein binds to the target nucleotide sequence and regulates the expression of the target gene in the plant cells.

The zinc finger gene can be expressed in plant with any suitable plant expression vectors. Typical vectors useful for expression of genes in higher plants are well known in the art and include vectors derived from the tumor-inducing (Ti) plasmid of *Agrobacterium tumefaciens* described by Rogers et al., *Meth. in Enzymol.* (1987) 153:253–277. These vectors are plant integrating vectors in that upon transformation, the vectors integrate a portion of vector DNA into the genome of the host plant. Exemplary *A. tumefaciens* vectors useful herein are plasmids pKYLX6 and pKYLX7 of Schardl et al., *Gene* (1987) 61:1–11 and Berger et al., *Proc. Natl. Acad. Sci. USA* (1989) 86:8402–8406. Another useful vector herein is plasmid pBI 101.2 that is available from Clontech Laboratories, Inc. (Palo Alto, Calif.).

In addition to regulatory domains, often the zinc finger protein can be expressed as a fusion protein such as maltose binding protein ("MBP"), glutathione S transferase (GST), hexahistidine, c-myc, and the FLAG epitope, for ease of purification, monitoring expression, or monitoring cellular and subcellular localization.

The nucleic acid sequence encoding a ZFP can be modified to improve expression of the ZFP in plants by using codon preference. When the nucleic acid is prepared or altered synthetically, advantage can be taken of known codon preferences of the intended plant host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al., *Nucl. Acids Res.* (1989) 17: 477–498). Thus, the maize preferred codon for a particular amino acid may be derived from known gene sequences from maize. Maize codon usage for 28 genes from maize plants are listed in Table 4 of Murray et al., supra.

In one embodiment, the transgene may include a reporter protein such as luciferase, which can be helpful in providing an assay system for determining the position in a target gene in which the targeted nucleotide sequence should reside. Thus, the invention also includes an assay system for determination of a suitable region for targeting by regulatory factors, wherein said assay method comprises providing a chimeric gene comprising a nucleotide sequence encoding a reporter protein optionally fused to coding regions of said gene; said nucleotide sequence operably linked to control sequences endogenous to said gene. The chimeric gene is then provided a targeted nucleotide sequence at various locations within the endogenous portions and the effect on production of the reporter protein of contact with the appropriate zinc finger containing regulatory protein is determined.

It may be desirable in some instances to modify plant cells or plants with families of transgenes representing, for example, a metabolic pathway. In those instances, it may be desirable to design the constructs so that the family can be regulated as a whole, e.g., by designing the control regions of the members of the family with similar or identical targets for the zinc finger protein portion of the effector protein. Such sharing of target sequences in gene families may occur naturally in endogenously produced metabolic sequences.

In most instances, it is desirable to provide the expression system for the effector protein with control sequences that are tissue specific so that the desired gene regulation can occur selectively in the desired portion of the plant. For example, to repress MIPS expression, it is desirable to provide the effector protein with control sequences that are selectively effective in seeds. With respect to the AP3 gene, effector proteins for regulation of expression would be designed for selective expression in flowering portions of the plant. However, in some instances, it may be desirable to have the genetic control expressible in all tissues in instances where an insect resistance gene is the target. In such cases, it may be desirable to place the expression system for the effector protein under control of an inducible promoter so that inducer can be supplied to the plant only when the need arises, for example, activation of an insect resistance gene.

In another embodiment, ZFPs can be used to create functional "gene knockouts" and "gain of function" mutations in a host cell or plant by repression or activation of the target gene expression. Repression or activation may be of a structural gene, e.g., one encoding a protein having for example enzymatic activity, or of a regulatory gene, e.g., one encoding a protein that in turn regulates expression of a structural gene. Expression of a negative regulatory protein can cause a functional gene knockout of one or more genes, under its control. Conversely, a zinc finger having a negative regulatory domain can repress a positive regulatory protein to knockout or prevent expression of one or more genes under control of the positive regulatory protein.

The present invention further provides recombinant expression cassettes comprising a ZFP-encoding nucleic acid. A nucleic acid sequence coding for the desired polynucleotide of the present invention can be used to construct a recombinant expression cassette which can be introduced into the desired host cell. A recombinant expression cassette will typically comprise a polynucleotide encoding creation zinc finger proteins, e.g., ZFPm1, ZFPm2, ZFPm3, ZFPm4 and ZFPAp3, operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the rice actin 1 promoter (U.S. Pat. No. 5,641,876), the cauliflower mosaic virus (CaMV) 35S transcription initiation region (Odell et al., *Nature* (1985) 313: 810–812), the P- or 2'-promoter derived from T-DNA of *Agrobacterium tumefaciens*, the ubiquitin I promoter, the Smas promoter, the cinnamyl alcohol dehydrogenase promoter (U.S. Pat. No. 5,683,439), the Nos promoter, the pEmu promoter, the rubisco promoter, the GRP 1-8 promoter, and other transcription initiation regions from various plant genes known to those of skilled artisans.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the AdhI promoter which is inducible by hypoxia or cold stress, the Hsp70 promoter which is inducible by heat stress, and the PPDK promoter which is inducible by light. Examples of promoters under developmental control include promoters that initiate transcription only, or preferentially, in certain tissues, such as leaves, roots, fruit, seeds, or flowers. An exemplary promoter is the anther specific promoter 5126 (U.S. Pat. Nos. 5,689,049 and 5,689,051). The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; WO 93/22443), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell.

The selection of the promoter used in expression cassettes will determine the spatial and temporal expression pattern of the transgene in the transgenic plant, i.e., the ZFP gene is only expressed in the desired tissue or at a certain time in plant development or growth. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Additionally, the zinc finger encoding gene can be under control of and activated by a promoter responsive to the presence of a pathogen or to plant stress, e.g., cold stress, salt stress, etc., so that the induced ZFP can modulate a gene that counteracts the pathogen, stress, etc. Promoters vary in their strength, i.e., ability to promote transcription. Depending upon the host cell system utilized, any one of a number of suitable promoters can be used, including the gene's native promoter.

A variety of promoters will be useful in the invention, particularly to control the expression of the ZFP and ZFP-effector fusions, the choice of which will depend in part upon the desired level of protein expression and desired tissue-specific, temporal specific, or environmental cue-specific control, if any in a plant cell. Constitutive and tissue specific promoters are of particular interest. Such constitutive promoters include, for example, the core promoter of the Rsyn7, the core CaMV 35S promoter (Odell et al., *Nature* (1985) 313:810–812), CaMV 19S (Gmunder and Kohli, *Mol Gen Genet* 1989 December; 220(1):95–101), rice actin (Wang et al., *Mol. Cell. Biol.*, 12, 3399–3406 (1992); U.S. Pat. No. 5,641,876; and McElroy et al., *Plant Cell* (1985) 2:163–171); ubiquitin (Christensen et al., *Plant Mol. Biol.* (1989)12:619–632 and Christensen et al., *Plant Mol. Biol.* (1992) 18:675–689), pEMU (Last et al., *Theor. Appl. Genet.* (1991) 81:581–588), MAS (Veltenet al, *EMBO J.* (1984) 3:2723–2730), nos (Ebert et al., Proc. Natl. Acad. Sci. U.S.A. 84, 5745–5749 (1987)) Adh (Dennis and Berg, *Nucleic Acids Res.*, 13:7945–7957 (1985)), and constitutive promoters described in, for example, U.S. Pat. Nos. 5,608,149; 5,608,144; 5,604,121; 5,569,597; 5,466,785; 5,399,680; 5,268,463; and 5,608,142.

Ubiquitin is a gene product known to accumulate in many cell types and its promoter has been cloned from several species for use in transgenic plants (e.g. sunflower—Binet et al., *Plant Science* (1991) 79:87–94; maize—Christensen et al., *Plant Molec. Biol.* (1989) 12: 619–632; and *Arabidopsis*—Norris et al., *Plant Mol. Biol.* (1993) 21:895–906). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (*Plant Cell Rep.* (1993) 12:491–495) describe a vector (pAHC25) that comprises the maize ubiquitin promoter and first intron and its high activity in cell suspensions of numerous monocotyledons when introduced via microprojectile bombardment. The *Arabidopsis* ubiquitin promoter is also ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

Several isoforms of actin are known to be expressed in most cell types and consequently the actin promoter is a good choice for a constitutive promoter. In particular, the promoter from the rice ActI gene has been cloned and characterized (McElroy et al., *Plant Cell* (1990) 2:163–171). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al., *Mol. Gen. Genet.* (1991) 231:150–160). These incorporate the ActI-intron 1, AdhI5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (*Mol. Gen. Genet.* (1991) 231:150–160) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al., *Plant Cell Rep.* (1993) 12:506–509).

Tissue-specific promoters can be utilized to target enhanced expression within a particular plant tissue (See generally, copending U.S. Provisional Patent Application entitled "Promoters for Regulation of Plant Gene Expression, Attorney Docket No. 1360.002PRV (Schwegman, Lundberg, Woessner & Kluth), filed Jun. 23, 2000, the content of which is herein incorporated by reference in its entirety. Examples of tissue specific promoters which have been described include the lectin (Vodkin, *Prog. Clinc. Biol. Res.*, 138:87–98 (1983); and Lindstrom et al., *Dev. Genet.*, 11:160–167 (1990)), corn alcohol dehydrogenase 1 (Dennis et al., *Nucleic Acids Res.*, 12:3983–4000 (1984)), corn light harvesting complex (Becker, *Plant Mol Biol.*, 20(1): 49–60

(1992); and Bansal et al., *Proc. Natl. Acad. Sci. U.S.A.*, 89:3654–3658 (1992)), corn heat shock protein (Odell et al., *Nature* (1985) 313:810–812; and Marrs et al., *Dev. Genet.*, 14(1):27–41 (1993)), small subunit RuBP carboxylase (Waksman et al., *Nucleic Acids Res.*, 15(17):7181 (1987); and Berry-Lowe et al., *J. Mol. Appl. Genet.*, 1(6):483–498 (1982)), Ti plasmid mannopine synthase (Ni et al., *Plant Mol. Biol.*, 30(1):77–96 (1996)), Ti plasmid nopaline synthase (Bevan, *Nucleic Acids Res.*, 11(2):369–385 (1983)), petunia chalcone isomerase (Van Tunen et al., *EMBO J.*, 7:1257–1263 (1988)), bean glycine rich protein 1 (Keller et al., *Genes Dev.*, 3:1639–1646 (1989)), truncated CaMV 35s (Odell et al., *Nature* (1985) 313:810–812), potato patatin (Wenzler et al., *Plant Mol. Biol.*, 13:347–354 (1989)), root cell (Yamamoto et al., *Nucleic Acids Res.*, 18:7449 (1990)), maize zein (Reina et al., *Nucleic Acids Res.*, 18:6425 (1990); Kriz et al., *Mol. Gen. Genet.*, 207:90–98 1987; Wandelt and Feix, *Nucleic Acids Res.*, 17:2354 (1989); Langridge and Feix, *Cell*, 34:1015–1022 (1983); and Reina et al., *Nucleic Acids Res.*, 18:7449 (1990)), globulin-1 (Belanger et al., *Genetics*, 129:863–872 (1991)), α-tubulin, cab (Sullivan et al., *Mol. Gen. Genet.*, 215:431–440 (1989)), PEPCase (Cushman et al., *Plant Cell*, 1(7):715–25 (1989)), R gene complex-associated promoters (Chandler et al., *Plant Cell*, 1:1175–1183 (1989)), and chalcone synthase promoters (Franken et al., *EMBO J.*, 10:2605–2612, 1991)).

Tissue-specific promoters disclosed in the following references may also be used: Yamamoto et al., *Plant J* (1997) 12(2):255–265; Kawamata et al., *Plant Cell Physiol.* (1997) 38(7):792–803; Hansen et al., *Mol. Gen Genet.* (1997) 254(3):337; Russell et al., *Transgenic Res.* (1997) 6(2):15 7–168; Rinehart et al., *Plant Physiol.* (1996) 112(3):1331; Van Camp et al., *Plant Physiol.* (1996) 112(2):525–535; Canevascini et al., *Plant Physiol.* (1996) 112(2):513–524; Yamamoto et al., *Plant Cell Pkysiol* (1994) 35(5):773–778; Lam, *Results Probl. Cell Differ.* (1994) 20:181–196; Orozco et al., *Plant Mol. Biol.* (1993) 23(6):1129–1138; Matsuoka et al., *Proc Natl. Acad. Sci. USA* (1993) 90(20):9586–9590; and Guevara-Garcia et al., *Plant J.* (1993) 4(3):495–505. Such promoters can be modified, if necessary, for weak expression.

A maize gene encoding phosphoenol carboxylase (PEPC) has been described by Hudspeth & Grula (*Plant Molec Biol* 12: 579–589 (1989)). Using standard molecular biological techniques the promoter for this gene can be used to drive the expression of any gene in a leaf specific manner in transgenic plants. Other leaf-specific promoters are known in the art, and include those described in, for example, Yamamoto et al., *Plant J.* (1997) 12(2):255–265; Kwon et al., *Plant Physiol.* (1994) 105:357–367; Yamamoto et al., *Plant Cell Physiol.* (1994) 35(5):773–778; Gotor et al., *Plant J.* (1993) 3:509–518; Orozco et al., *Plant Mol. Biol.* (1993) 23(6):1129–1138; and Matsuoka et al., *Proc. Natl. Acad. Sci. USA* (1993) 90(20):9586–9590.

Another pattern of gene expression is root expression. A suitable root promoter is the promoter of the maize metallothionein-like (MTL) gene described by de Framond (*FEBS* (1991) 290:103–106) and also in U.S. Pat. No. 5,466,785, incorporated herein by reference. This "MTL" promoter is transferred to a suitable vector such as pCGN1761ENX for the insertion of a selected gene and subsequent transfer of the entire promoter-gene-terminator cassette to a transformation vector of interest. Other examples of root-specific promoters which have been described include the RB7 promoter from *Nicotiana tabacum* (U.S. Pat. Nos. 5,459,252 and 5,750,386).

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

Inducible promoters and other types of regulated promoters can also be used. For example, PR-1 promoters, ethanol-inducible promoters, glucocorticoid-inducible promoters, wound-inducible promoters, promoters for pith-preferred expression and promoters for receptor mediated transactivation in the presence of a chemical ligand can be used.

The double 35S promoter in pCGN1761ENX may be replaced with any other promoter of choice that will result in suitably high expression levels. By way of example, one of the chemically regulatable promoters described in U.S. Pat. No. 5,614,395, such as the tobacco PR-1a promoter, may replace the double 35S promoter. Alternately, the *Arabidopsis* PR-1 promoter described in Lebel et al., *Plant J.* (1998) 16:223–233 may be used. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (U.S. Pat. No.5,639,949). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al., (1998) *Nat. Biotechnol* 16:177–180). In *A. nidulans*, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al., *Nat. Biotechnol* (1998) 16:177–180) are replaced by a coding sequence of the present invention to form an expression cassette having the coding sequence under the control of the alca gene promoter. This is carried out using methods well known in the art.

Induction of expression of a nucleic acid sequence of the present invention using systems based on steroid hormones is also contemplated. For example, a glucocorticoid-mediated induction system is used (Aoyama and Chua, *The Plant Journal* (1997) 11:605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al., *Science* (1986) 231:699–704) fused to the transactivating domain of the herpes viral protein VP16 (Triezenberg et al., *Genes Devel.* (1988) 2:718–729) fused to the hormone-binding domain of the rat glucocorticoid receptor (Picard et al., (1988) *Cell* 54:1073–1080). The expression of the fusion protein is controlled by any promoter suitable for expression in plants known in the art or described here. This expression cassette is also comprised in the plant comprising a nucleic acid sequence of the invention fused to the 6xGAL4/minimal promoter. Thus, tissue- or organ-specificity of the fusion protein is achieved leading to inducible tissue- or organ-specificity of the insecticidal toxin.

Wound inducible promoters may also be suitable for gene expression. Numerous such promoters have been described (e.g. Xu et al., *Plant Molec. Biol.* (1993) 22:573–588; Logemann et al., *Plant Cell* (1989) 1:151–158; Rohrmeier & Lehle, *Plant Molec. Biol.* (1993) 22:783–792; Firek et al., *Plant Molec. Biol.* (1993) 22:129–142; and Warner et al., *Plant J.* (1993) 3:191–201) and all are suitable for use with the instant invention. Logemann et al. describe the 5′ upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

U.S. Pat. No. 5,880,333 describes a system whereby class II hormone receptors such as Ecdysone Receptor (EcR) and Ultraspiracle (USP), which function together as a heterodimer, regulate the expression of a target polypeptide in a plant cell in the presence of an appropriate chemical ligand, e.g., tebufenozide.

Particularly preferred are the inducible PR1 promoter, maize ubiquitin promoter, and rice actin promoter.

Any combination of constitutive or inducible and non-tissue specific or tissue specific may be used to control ZFP expression.

The desired control may be temporal, developmental or environmentally controlled using the appropriate promoter. Environmentally controlled promoters are those that respond to assault by pathogen, pathogen toxin, or other external compound (e.g., intentionally applied small molecule inducer). An example of a temporal or developmental promoter is a fruit ripening-dependent promoter.

Thus, the present invention provides compositions, and methods for making, heterologous promoters and/or enhancers operably linked to a ZFP and ZFP-effector fusion encoding polynucleotide of the present invention.

By selection of different strength of promoter to express ZFP-effector fusion protein, one can control the effect of ZFP in gene expression regulation in many levels. Generally, The stronger the promoter is, the stronger the effect of ZFP-effector protein is. However, moderate level of gene expression activation or repression is desirable since overexpression of certain foreign protein or over-activation of certain endogenous gene in certain cell type may cause toxicity effect. As in the example of AP3 gene activation, the Ubiquitin promoter (strong promoter) was originally used to express ZFPAp3-VP64 activation fusion protein. We have switched to a weaker promoter AP3 endogenous promoter to express the same constructs to achieve even clear phenotype changes.

Methods for identifying promoters with a particular expression pattern, in terms of, e.g., tissue type, cell type, stage of development, and/or environmental conditions, are well known in the art. See, e.g., The Maize Handbook, Chapters 114–115, Freeling and Walbot, Eds., Springer, N.Y. (1994); Corn and Corn Improvement, Pedition, Chapter 6, Sprague and Dudley, Eds., American Society of Agronomy, Madison, Wis. (1988).

A typical step in promoter isolation is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5′ end of the transcript of the indicated gene. For differential hybridization, subtractive hybridization and differential display, the nucleic acid sequence identified as enriched in the target tissue is used to identify the sequence at the 5′ end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that do not have activity in any other common tissue.

To identify the promoter sequence, the 5' portions of the clones can be analyzed for sequences characteristic of promoter sequences. For instance, promoter sequence elements include the TATA box consensus sequence (TATAAT), which is usually an AT-rich stretch of 5–10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S I analysis, and/or RNase protection. To confirm the presence of the AT-rich sequence, a structure-function analysis can be performed involving mutagenesis of the putative region and quantification-of the mutation's effect on expression of a linked downstream reporter gene. See, e.g., The Maize Handbook, Chapter 114, Freeling and Walbot, Eds., Springer, New York (1994).

In plants, further upstream from the TATA box, at positions −80 to −100, there is typically a promoter element (i.e., the CAAT box) with a series of adenines surrounding the trinucleotide G (or T) N G (Messing et al., in Genetic Engineering in Plants, Kosage, Meredith and Hollaender, Eds., pp. 221–227 1983). In maize, there is no well conserved CAAT box but there are several short, conserved protein-binding motifs upstream of the TATA box. These include motifs for the trans-acting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1,000-fold (Buchman and Berg, *Mol. Cell Biol.* (1988) 8:4395–4405; and Callis et al., *Genes Dev.* (1987) 1:1183–1200). Such intron enhancement of gene expression is typically greatest when placed near the 5' end of the transcription unit. Use of maize introns Adh1-S intron 1, 2, and 6, the Bronze-I intron are known in the art (See generally, The Maize Handbook, Chapter 116, Freeling and Walbot, Eds, Springer, New York (1994))

Plant transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al., *Biotechniques* (1986) 4:320–334), electroporation (Riggs et al., *Proc. Natl. Acad Sci. USA* (1986) 83:5602–5606), *Agrobacterium*-mediated transformation (Townsend et al., U.S. Pat. No. 5,563,055), direct gene transfer (Paszkowski et al., *EMBO J.* (1984) 3:2717–2722), and ballistic particle acceleration (see, for example, Sanford et al., U.S. Pat. No. 4,945,050; Tomes et al. (1995). "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al., *Biotechnology* (1988) 6:923–926). Also see Weissingeretal., *Ann. Rev. Genet.* (1988) 22:421–477; Sanford et al., *Particulate Science and Technology* (1987) 5:27–37 (onion); Christou et al., *Plant Physiol.* (1988) 87:671–674 (soybean); McCabe et al., *BiolTechnology* (1988) 6:923–926 (soybean); Finer and McMullen, *In Vitro Cell Dev. Biol.* (1991) 27P: 175–182 (soybean); Singh et al., *Theor. Appl. Genet.* (1998) 96:319–324 (soybean); Datta et al., *Biotechnology* (1990) 8:736–740 (rice); Klein et al., *Proc. Natl. Acad Sci. USA* (1988) 85:4305–4309 (maize); Klein et al., *Biotechnology* (1988) 6:559–563 (maize); Tomes, U.S. Pat. No. 5,240,855; Buising et al., U.S. Pat. Nos. 5,322, 783 and 5,324,646; Tomes et al. (1995). "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al., *Plant Physiol.* (1988) 91:440–444 (maize); Fromm et al., *Biotechnology* (1990) 8:833–839 (maize); Hooykaas-Van Slogteren et al., *Nature (London)* (1984) 311:763–764; Bowen et al., U.S. Pat. No. 5,736,369 (cereals); Bytebier et al., *Proc. Natl. Acad Sci. USA* (1987) 84:5345–5349 (Liliaceae). In The Experimental Manipulation of Ovule Tissues, ed. Chapman et al. (Longman, N.Y.), pp. 197–209 (pollen); Kaeppler et al., *Plant Cell Reports* (1990) 9:415–418 and Kaeppler et al., *Theor. Appl. Genet.* (1992) 84:560–566 (whisker-mediated transformation); D'Halluin et al., *Plant Cell* (1992) 4:1495–1505 (electroporation); Li et al., *Plant Cell Reports* (1993) 12:250–255 and Christou and Ford, *Annals qfBotany* (1995) 75:407–413 (rice); Osjoda et al., *Nature Biotechnology* (1996) 14:745–750 (maize via *Agrobacterium tumefaciens*); all of which are herein incorporated by reference.

The zinc finger protein with optional effector domain can be targeted to a specific organelle within the plant cell. Targeting can be achieved with providing the ZFP an appropriate targeting peptide sequence, such as a secretory signal peptide (for secretion or cell wall or membrane targeting, a plastid transit peptide, a chloroplast transit peptide, a mitochondrial target peptide, a vacuole targeting peptide, or a nuclear targeting peptide, and the like (Reiss et al., *Mol. Gen. Genet.* (1987) 209(1):116–121; Settles and Martienssen, *Trends Cell Biol* (1998) 12:494–501; Scott et al., *J Biol Chem* (2000) 10:1074; and Luque and Correas, *J Cell Sci* (2000) 113:2485–2495).

For examples, certain plastid organelle targeting sequences are disclosed in WO 00/12732 (see also de Castro Silva Filho et al., *Plant Mol. Biol.* (1996) 30:769–1780; Schnell, D. J. et al., *J Biol. Chem.* (1991) 266(5):3335–3342; and Lamppa et al., *J Biol. Chem.* (1988) 263:14996–14999). Plastids are a class of plant organelles derived from proplastids and include chloroplasts, leucoplasts, aravloplasts, and chromoplasts. The plastids are major sites of biosynthesis in plants. In addition to photosynthesis in the chloroplast, plastids are also sites of lipid biosynthesis, nitrate reduction to ammonium, and starch storage. And while plastids contain their own circular genome, most of the proteins localized to the plastids are encoded by the nuclear genome and are imported into the organelle from the cytoplasm.

As described in the Example Section below, a nuclear localization peptide (see FIG. 3) was used to target the ZFP-effector fusions to the nucleus.

The modified plant may be grown into plants in accordance with conventional ways (See, e.g., McCormick et al., *Plant Cell. Reports* (1986) 81–84). These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The method of the invention is particularly appealing to the plant breeder because it has the effect of providing a dominant trait, which minimizes the level of crossbreeding necessary to develop a phenotypically desirable species which is also commercially valuable. Typically, modification of the plant genome by conventional methods creates heterozygotes where the modified gene is phenotypically recessive. Crossbreeding is required to obtain homozygous forms where the recessive characteristic is found in the phenotype. This crossbreeding is laborious and time consuming. The need for such crossbreeding is eliminated in the case of the present invention which provides an immediate phenotypic effect.

When the target gene encodes a target protein, the present method can be used to modulate the expression of said encoded target protein. Expression of any target protein can be modulated by the present method in plant cells. The protein whose expression being modulated can be endogenous or exogenous to the plant cell. The modulation can be activation or inhibition.

In a specific embodiment, the protein whose expression being modulated is an antibody. In another specific embodiment, the protein whose expression being modulated participates in a metabolic pathway or controls a metabolic pathway, e.g., an anabolic or a catabolic pathway. The present method can be used for modulating metabolic pathways of any desirable molecules such as vitamins, taste molecules, e.g., bad taste molecules, anti-oxidants, sugars and flavanoids. The metabolic pathway being modulated can be endogenous or exogenous to the plant cell. In still another specific embodiment, target gene encodes a structural protein, e.g., an enzyme or a co-factor in a metabolic pathway, or a regulatory protein. In yet another specific embodiment, The metabolic pathway being modulated enhances an input or output trait in a plant or seed.

Enzyme activity means herein the ability of an enzyme to catalyze the conversion of a substrate into a product. A substrate for the enzyme comprises the natural substrate of the enzyme but also comprises analogues of the natural substrate, which can also be converted, by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g., ATP, phosphoenolpyruvate, acetyl phosphate or phosphocreatine) remaining in the reaction mixture after a certain period of time or by determining the amount of a used donor of free energy or energy-rich molecule (e.g., ADP, pyruvate, acetate or creatine) in the reaction mixture after a certain period of time.

Co-factor is a natural reactant, such as an organic molecule or a metal ion, required in an enzyme-catalyzed reaction. A co-factor can be regenerated and reused. Exemplary co-factors include NAD(P), riboflavin (including FAD and FMN), folate, molybdopterin, thiamin, biotin, lipoic acid, pantothenic acid and coenzyme A, S-adenosylmethionine, pyridoxal phosphate, ubiquitinone, menaquinone.

D. Genetically Modified Plant Cells, Tissues and Seeds

In yet another aspect, the present invention is directed to a genetically modified plant cell, which cell comprises an expression system for a zinc finger protein, said zinc finger protein is capable of binding, and preferably specifically binding, to a target nucleotide sequence, or a complementary strand thereof, within a target gene whose expression is to be modulated by said zinc finger protein.

The genetically modified plant cell can comprise any desirable target nucleotide sequence and target gene. Within the genetically modified plant cell, the target nucleotide sequence can be endogenous or exogenous to the targeted gene. The target gene can be endogenous or exogenous to the plant cells. The genetically modified plant cell can exist in culture or can be contained in an intact plant.

Within the genetically modified plant cell, the zinc finger protein can be used to control the expression of any target genes. In a specific embodiment, the zinc finger protein controls its own expression by binding to a target sequence within the zinc finger protein gene. In another specific embodiment, the zinc finger protein controls its own expression by binding to a first target sequence within the zinc finger protein gene and controls the expression of the target gene by binding to a second target sequence within the target gene. Preferably, the first target sequence within the zinc finger protein gene is different from the second target sequence within the target gene. The expression of the zinc finger protein gene can be further controlled by second promoter, e.g., an inducible promoter. The zinc finger protein contained in the genetically modified plant cell can contain any number of zinc finger sequence. Preferably, the zinc finger protein comprises at least two zinc finger sequences, e.g., from about 2 to about 6 zinc finger sequences or from about 3 to about 6 zinc finger sequences.

Any plant cell can be genetically modified to comprise an expression system for a zinc finger protein, so that the expression of a target gene is modulated by said zinc finger protein. Exemplary plants include tobacco, tomato, potato, banana, soybean, pepper, wheat, rye, rice, spinach, carrot, maize and corn.

A method to modulate expression in a plant cell is provided, which method comprises culturing the genetically modified plant cell(s). Preferably, such genetically modified plant cell(s) is cultured in planta.

In a specific embodiment, a transgenic plant cell is provided, which plant cell is transformed with a nucleic acid comprising a functional geminiviral replicase gene operably linked to a fruit ripening-dependent promoter. In another specific embodiment, a genetically modified plant cell is provided, which cell comprises a heterologous zinc finger protein that specifically binds to a target nucleotide sequence in said plant cell wherein said heterologous zinc finger protein is constitutively or inducibly expressed.

A genetically modified plant tissue is also provided herein, which tissue comprises the above-described genetically modified plant cell(s).

A genetically modified plant seed, e.g., a tobacco, tomato, potato, banana, soybean, pepper, wheat, rye, rice, spinach, carrot, maize and corn seed, is further provide herein, which seed comprises the above-described genetically modified plant cell(s).

A transgenic plant seed is further provide herein, which seed is transformed with a nucleic acid comprising a functional geminiviral replicase gene operably linked to a fruit ripening-dependent promoter.

In a specific embodiment, the genetically modified plant cell, tissue, seed and whole plant does not contain a zinc finger protein that is disclosed in U.S. Pat. No. 6,140,466 or WO 98/54311, e.g., a zinc finger-nucleotide binding polypeptide variant comprising at least three zinc finger modules that bind to a target cellular nucleotide sequence and modulate the transcriptional function of the cellular nucleotide sequence, wherein the amino acid sequence of each zinc finger module that binds a target cellular nucleotide comprises two cysteines at two histidines whereby both cysteines are amino proximal to both histidines and where each of three modules of said variant has at least one amino acid sequence modification.

E. Nucleic Acids Encoding ZFPm1, ZFPm2, ZFPm3, ZFPm4 and ZFPAp3

In yet another aspect, the present invention is directed to an isolated nucleic acid fragment, comprising a sequence of nucleotides encoding ZFPm1 (SEQ ID NO:14), ZFPm2 (SEQ ID NO:15), ZFPm3 (SEQ ID NO:16), ZFPm4 (SEQ ID NO:17) or ZFPAp3 (SEQ ID NO:18). The isolated nucleic acid fragment can be DNA or RNA. An isolated nucleic acid fragment, which is hybridizable to the nucleic acid fragment encoding ZFPm1, ZFPm2, ZFPm3, ZFPm4 or ZFPAp3 under low, medium and high stringency condition is also provided. Preferably, the isolated nucleic acid fragment hybridizes to the nucleic acid fragment encoding ZFPm1, ZFPm2, ZFPm3, ZFPm4 or ZFPAp3 under high stringency condition. Plasmids comprising the nucleic acid fragment encoding ZFPm1, ZFPm2, ZFPm3, ZFPm4 or ZFPAp3 and cells comprising such plasmids are further provided. Any suitable cells can be used and preferably, bacterial cells, yeast cells, fungal cells, plant cells, insect cells and animal cells are used.

The nucleic acid fragment encoding ZFPm1, ZFPm2, ZFPm3, ZFPm4 or ZFPAp3 can be prepared by any methods known in the art, e.g., recombinant production, chemical synthesis or a combination thereof (See generally, *Current Protocols in Molecular Biology* (1998) § 20, John Wiley & Sons, Inc; Knorre, *Design and Targeted Reactions of Oligonucleotide Derivative*, CRC Press, 1994; and Staut (Ed.), *Nucleic Acid Chemstry: Improved and New Synthetic Procedures, Methods and Techniques*, John Wiley & Sons, Inc., 1978). In a specific embodiment, a method for producing a ZFPm1, ZFPm2, ZFPm3, ZFPm4 or ZFPAp3 protein is provided, which method comprises growing the cells harboring plasmids containing the nucleic acid fragment encoding ZFPm1, ZFPm2, ZFPm3, ZFPm4 or ZFPAp3 under conditions whereby these zinc finger proteins are expressed by the cell; and recovering the expressed zinc finger protein.

The isolated nucleic acids encoding ZFPm1, ZFPm2, ZFPm3, ZFPm4 or ZFPAp3 typically consists of at least 25 (continuous) nucleotides, 50 nucleotides, 100 nucleotides, 150 nucleotides, or 200 nucleotides, or a full-length coding sequence. In another embodiment, the nucleic acids are smaller than 35, 200, or 500 nucleotides in length. Nucleic acids can be single or double stranded. Nucleic acids that hybridize to or are complementary to the foregoing sequences, in particular the inverse complement to nucleic acids that hybridize to the foregoing sequences (i.e., the inverse complement of a nucleic acid strand has the complementary sequence running in reverse orientation to the strand so that the inverse complement would hybridize without mismatches to the nucleic acid strand) are also provided. In specific aspects, nucleic acids are provided which comprise a sequence complementary to (specifically are the inverse complement of) at least 10, 25, 50, 100, or 200 nucleotides or the entire coding region of a ZFPm1, ZFPm2, ZFPm3, ZFPm4 or ZFPAp3 coding sequence.

The nucleic acids encoding ZFPm1, ZFPm2, ZFPm3, ZFPm4 or ZFPAp3 provided herein include those with nucleotide sequences encoding substantially the same amino acid sequences as found in FIG. 6, and those encoding amino acid sequences with functionally equivalent amino acids.

F. ZFPm1, ZFPm2, ZFPm3, ZFPm4 and ZFPAp3 Proteins

In yet another aspect, the present invention is directed to a zinc finger protein that is ZFPm1 (SEQ ID NO:38), ZFPm2 (SEQ ID NO:39), ZFPm3 (SEQ ID NO:40), ZFPm4 (SEQ ID NO:41) or ZFPAp3 (SEQ ID NO:42), preferably in combination with positive and negative regulating domains. The ZFPm1, ZFPm2, ZFPm3, and ZFPm4 zinc fingers are specific for the MIPS gene, meaning they can specifically and strongly bind to nucleotide sequence within the MIPS gene. ZFPAp3 is designed to bind to AP3 in *Arabidopsis* . The positive regulatory domain VP64 (Beerli et al., *Proc. Natl. Acad. Sci. USA* (1998) 95:14628–14633) is fused to the C-terminal of each zinc finger domain. The negative regulatory domains SID (mSin3 interaction domain) (Ayer et al., *Mol. Cell. Biol.* (1996) 16:5772–5781) or SKD (a modified Kruppel-associated box) (Margolin et al., *Proc. Natl. Acad. Sci. USA* (1994) 91:4509–4513) are fused to the N-terminal of each zinc finger domain.

In yet another aspect, the present invention is directed to a zinc finger protein comprising a zinc finger nucleic acid binding domain and an effector domain, wherein said effector domain comprises an active domain of a restriction enzyme, an active domain of a nucleic acid modifying protein, e.g., a nucleic acid methylase, a label or a modification.

The zinc finger proteins can be made by any methods known in the art. The zinc finger proteins can be produced by chemical synthesis (see e.g., *Fmoc Solid Phase Peptide*

Synthesis: A Practical Approach, Chan and White (Ed.), Oxford University Press, 2000; Peptide Synthesis Protocols, Vol. 35, Pennington and Dunn (Ed.), Humana Press, 1995; and Chemical Approaches to the Synthesis of Peptides and Proteins, Lloyd-Williams et al. (Ed.), CRC Press, Inc., 1997), recombinant production (See generally, Current Protocols in Molecular Biology (1998) § 20, John Wiley & Sons, Inc.), or a combination thereof. Preferably, the zinc finger proteins are produced by recombinant production.

Functional fragments, analogs or derivatives of the ZFPm1, ZFPm2, ZFPm3, ZFPm4 or ZFPAp3 polypeptides are also provided. Preferably, such fragments, analogs or derivatives can be recognized an antibody raised against a ZFPm1, ZFPm2, ZFPm3, ZFPm4 or ZFPAp3 polypeptide. Also preferably, such fragments, analogs or derivatives comprise an amino acid sequence that has at least 60% identity, more preferably at least 90% identity to the ZFPm1 (SEQ ID NO:38), ZFPm2 (SEQ ID NO:39), ZFPm3 (SEQ ID NO:40), ZFPm4 (SEQ ID NO:41) or ZFPAp3 (SEQ ID NO:42) polypeptide (See FIG. 6).

G. Antibodies Recognizing ZFPm1, ZFPm2, ZFPm3, ZFPm4 and ZFPAp3 Proteins

An antibody that specifically binds to the ZFPm1, ZFPm2, ZFPm3, ZFPm4 or ZFPAp3 proteins is also provided. Antibodies, whether polyclonal or monoclonal antibodies, can be raised against the zinc finger proteins by any methods known in the art (see e.g., *Antibody Production: Essential Techniques*, Delves, Wiley, John & Sons, Inc., 1997; *Basic Methods in Antibody Production and Characterization*, Howard and Bethell, CRC Press, Inc., 1999; and *Monoclonal Antibody Production Techniques and Applications*: Hybridoma Techniques, Schook, Marcel Dekker, 1987). These antibodies can be used to assess the expression level and localization of ZFP protein in cells, e.g., plant cells.

For production of the antibody, various host animals can be immunized by injection with the ZFPm1, ZFPm2, ZFPm3, ZFPm4 or ZFPAp3 proteins, or a derivative of the foregoing, such as a cross-linked zinc finger protein. Such host animals include but are not limited to rabbits, mice, rats, and the like. Various adjuvants can be used to increase the immunological response, depending on the host species, and include but are not limited to Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and corynebacterium parvum.

For preparation of monoclonal antibodies directed towards ZFPm1, ZFPm2, ZFPm3, ZFPm4 or ZFPAp3 proteins or domains, derivatives, fragments or analogs thereof, any technique that provides for the production of antibody molecules by continuous cell lines in culture may be used. Such techniques include but are not restricted to the hybridoma technique originally developed by Kohler and Milstein (*Nature* 256:495–497 (1975)), the trioma technique, the human B-cell hybridoma technique (Kozbor et al., *Immunology Today* 4:72 (1983)), and the EBV hybridoma technique to produce human monoclonal antibodies (Cole et al., in *Monoclonal Antibodies and Cancer Therapy*, Alan R. Liss, Inc., pp. 77–96 (1985)). In an additional embodiment, monoclonal antibodies can be produced in germ-free animals (WO89/12690). Human antibodies may be used and can be obtained by using human hybridomas (Cote et al., *Proc. Natl. Acad. Sci. USA* 80:2026–2030 (1983)) or by transforming human B cells with EBV virus in vitro (Cole et al., in *Monoclonal Antibodies and Cancer Therapy*, Alan R. Liss, Inc., pp. 77–96 (1985)). Techniques developed for the production of "chimeric antibodies" (Morrison et al., *Proc. Natl. Acad. Sci. USA* 81:6851–6855 (1984); Neuberger et al., *Nature* 312:604–608 (1984); and Takeda et al., *Nature* 314:452–454 (1985)) by splicing the genes from a mouse antibody molecule specific for the ZFPm1, ZFPm2, ZFPm3, ZFPm4 or ZFPAp3 protein together with genes from a human antibody molecule of appropriate biological activity can be used; such antibodies are within the scope of this invention.

Techniques described for the production of single chain antibodies (U.S. Pat. No. 4,946,778) can be adapted to produce ZFPm1, ZFPm2, ZFPm3, ZFPm4 or ZFPAp3 protein-specific single chain antibodies. An additional embodiment utilizes the techniques described for the construction of Fab expression libraries (Huse et al., *Science* 246:1275–1281 (1989)) to allow rapid and easy identification of monoclonal Fab fragments with the desired specificity for ZFPm1, ZFPm2, ZFPm3, ZFPm4 or ZFPAp3 proteins, or domains, derivatives, or analogs thereof. Non-human antibodies can be "humanized" by known methods (see, e.g., U.S. Pat. No. 5,225,539).

Antibody fragments that contain the idiotypes of ZFPm1, ZFPm2, ZFPm3, ZFPm4 or ZFPAp3 proteins can be generated by techniques known in the art in accordance with the methods of the present invention. For example, such fragments include but are not limited to: the F(ab')2 fragment which can be produced by pepsin digestion of the antibody molecule; the Fab' fragments that can be generated by reducing the disulfide bridges of the F(ab')2 fragment, the Fab fragments that can be generated by treating the antibody molecular with papain and a reducing agent, and Fv fragments.

In the production of antibodies, screening for the desired antibody can be accomplished by techniques known in the art in accordance with the methods of the present invention, e.g., ELISA (enzyme-linked immunosorbent assay). To select antibodies specific to a particular domain of the ZFPm1, ZFPm2, ZFPm3, ZFPm4 or ZFPAp3 proteins, one may assay generated hybridomas for a product that binds to the fragment of a ZFPm1, ZFPm2, ZFPm3, ZFPm4 or ZFPAp3 proteins that contain such a domain.

H. Nucleic Acids Encoding ZFP-SID Fusion Proteins

In yet another aspect, the present invention is directed to an isolated nucleic acid fragment, comprising a sequence of nucleotides encoding a fusion protein comprises a zinc finger domain, e.g., 2C7 and an effector domain of SID (mSin3A Interaction Domain). A fusion protein comprising the 2C7 and the SID domains is termed as a 2C7-SID fusion protein. The isolated nucleic acid fragment can be DNA or RNA. An isolated nucleic acid fragment, which is hybridizable to the nucleic acid fragment encoding the 2C7-SID fusion protein under low, medium and high stringency condition is also provided. Preferably, the isolated nucleic acid fragment hybridizes to the nucleic acid fragment encoding the 2C7-SID fusion protein under high stringency condition. Also preferably, the isolated nucleic acid fragment has the nucleotide sequence set forth in SEQ ID NO:5 or SEQ ID NO:66. Plasmids comprising the nucleic acid fragment encoding the 2C7-SID fusion protein and cells comprising such plasmids are further provided. Any suitable cells can be used and preferably, bacterial cells, yeast cells, fungal cells, plant cells, insect cells and animal cells are used.

The nucleic acid fragment encoding the 2C7-SID fusion protein can be prepared by any methods known in the art, e.g., recombinant production, chemical synthesis or a combination thereof (See generally, *Current Protocols in Molecular Biology* (1998) § 20, John Wiley & Sons, Inc; Knorre, *Design and Targeted Reactions of Oligonucleotide Derivative*, CRC Press, 1994; and Staut (Ed.), *Nucleic Acid Chemstry: Improved and New Synthetic Procedures, Methods and Techniques*, John Wiley & Sons, Inc., 1978). In a specific embodiment, a method for producing a 2C7-SID fusion protein is provided, which method comprises growing the cells harboring plasmids containing the nucleic acid fragment encoding the 2C7-SID fusion protein under conditions whereby these zinc finger proteins are expressed by the cell; and recovering the expressed 2C7-SID fusion protein.

The isolated nucleic acids encoding the 2C7-SID fusion protein typically consists of at least 25 (continuous) nucleotides, 50 nucleotides, 100 nucleotides, 150 nucleotides, or 200 nucleotides, or a full-length coding sequence. In another embodiment, the nucleic acids are smaller than 35, 200, or 500 nucleotides in length. Nucleic acids can be single or double stranded. Nucleic acids that hybridize to or are complementary to the foregoing sequences, in particular the inverse complement to nucleic acids that hybridize to the foregoing sequences (i.e., the inverse complement of a nucleic acid strand has the complementary sequence running in reverse orientation to the strand so that the inverse complement would hybridize without mismatches to the nucleic acid strand) are also provided. In specific aspects, nucleic acids are provided which comprise a sequence complementary to (specifically are the inverse complement of) at least 10, 25, 50, 100, or 200 nucleotides or the entire coding region of the 2C7-SID fusion protein coding sequence.

The nucleic acids encoding the 2C7-SID fusion protein provided herein include those with nucleotide sequences encoding substantially the same amino acid sequences as found in FIGS. 6 and 24, and those encoding amino acid sequences with functionally equivalent amino acids.

Any suitable SID domains can be used. Preferably, the SID domain is derived from a SID domain of the MAD 1 protein.

I. ZFP-SID Fusion Proteins

In yet another aspect, the present invention is directed to a ZFP-SID, e.g., 2C7-SID, fusion protein comprising a zinc finger of 2C7 and an effector domain of SID. The negative regulatory domains SID (mSin3 interaction domain) (Ayer et al., *Mol. Cell. Biol.* (1996) 16:5772–5781) or SKD (a modified Kruppel-associated box) (Margolin et al., *Proc. Natl. Acad. Sci. USA* (1994) 91:4509–4513) can be fused to the C- or N-terminal of the 2C7 zinc finger domain. Preferably, the SID domain is fused to the N-terminal of the 2C7 zinc finger domain. Also preferably, the 2C7-SID fusion protein comprises a nuclear localization signal.

The 2C7-SID fusion protein can be made by any methods known in the art. It can be produced by chemical synthesis (see e.g., *Fmoc Solid Phase Peptide Synthesis: A Practical Approach*, Chan and White (Ed.), Oxford University Press, 2000; *Peptide Synthesis Protocols*, Vol. 35, Pennington and Dunn (Ed.), Humana Press, 1995; and *Chemical Approaches to the Synthesis of Peptides and Proteins*, Lloyd-Williams et al. (Ed.), CRC Press, Inc., 1997), recombinant production (See generally, *Current Protocols in Molecular Biology* (1998) § 20, John Wiley & Sons, Inc.), or a combination thereof. Preferably, the 2C7-SID fusion proteins are produced by recombinant production. Functional fragments, analogs or derivatives of the 2C7-SID fusion proteins or polypeptides are also provided. Preferably, such fragments, analogs or derivatives can be recognized an antibody raised against a 2C7-SID fusion protein or polypeptide. Also preferably, such fragments, analogs or derivatives comprise an amino acid sequence that has at least 60% identity, more preferably at least 90% identity to the 2C7-SID fusion protein encoded by the nucleotide sequence set forth in SEQ ID NO:5 or SEQ ID NO:66.

J. Antibodies Recognizing ZFP-SID Fusion Protein

An antibody that specifically binds to a ZFP-SID, e.g., 2C7-SID, fusion proteins is also provided. Antibodies, whether polyclonal or monoclonal antibodies, can be raised against the 2C7-SID fusion proteins by any methods known in the art (see e.g., *Antibody Production: Essential Techniques*, Delves, Wiley, John & Sons, Inc., 1997; *Basic Methods in Antibody Production and Characterization*, Howard and Bethell, CRC Press, Inc., 1999; *and Monoclonal Antibody Production Techniques and Applications*: Hybridoma Techniques, Schook, Marcel Dekker, 1987). These antibodies can be used to assess the expression level and localization of ZFP protein in cells, e.g., plant cells.

For production of the antibody, various host animals can be immunized by injection with the 2C7-SID fusion proteins, or a derivative of the foregoing, such as a cross-linked fusion protein. Such host animals include but are not limited to rabbits, mice, rats, and the like. Various adjuvants can be used to increase the immunological response, depending on the host species, and include but are not limited to Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette Guerin (BCG) and corynebacterium parvum.

For preparation of monoclonal antibodies directed towards 2C7-SID fusion proteins or domains, derivatives, fragments or analogs thereof, any technique that provides for the production of antibody molecules by continuous cell lines in culture may be used. Such techniques include but are not restricted to the hybridoma technique originally developed by Kohler and Milstein (*Nature* 256:495–497 (1975)), the trioma technique, the human B-cell hybridoma technique (Kozbor et al., *Immunology Today* 4:72 (1983)), and the EBV hybridoma technique to produce human monoclonal antibodies (Cole et al., in *Monoclonal Antibodies and Cancer Therapy*, Alan R. Liss, Inc., pp. 77–96 (1985)). In an additional embodiment, monoclonal antibodies can be produced in germ-free animals (WO89/12690). Human antibodies may be used and can be obtained by using human hybridomas (Cote et al., *Proc. Natl. Acad. Sci. USA* 80:2026–2030 (1983)) or by transforming human B cells with EBV virus in vitro (Cole et al., in *Monoclonal Antibodies and Cancer Therapy*, Alan R. Liss, Inc., pp. 77–96 (1985)). Techniques developed for the production of "chimeric antibodies" (Morrison et al., *Proc. Natl. Acad. Sci. USA* 81:6851–6855 (1984); Neuberger et al., *Nature* 312: 604–608 (1984); and Takeda et al., *Nature* 314:452–454 (1985)) by splicing the genes from a mouse antibody molecule specific for the 2C7-SID fusion proteins together with genes from a human antibody molecule of appropriate biological activity can be used; such antibodies are within the scope of this invention.

Techniques described for the production of single chain antibodies (U.S. Pat. No. 4,946,778) can be adapted to produce 2C7-SID fusion protein-specific single chain antibodies. An additional embodiment utilizes the techniques described for the construction of Fab expression libraries (Huse et al., Science 246:1275–1281 (1989)) to allow rapid and easy identification of monoclonal Fab fragments with the desired specificity for 2C7-SID fusion proteins, or domains, derivatives, or analogs thereof. Non-human antibodies can be "humanized" by known methods (see, e.g., U.S. Pat. No. 5,225,539).

Antibody fragments that contain the idiotypes of 2C7-SID fusion proteins can be generated by techniques known in the art in accordance with the methods of the present invention. For example, such fragments include but are not limited to: the F(ab')2 fragment which can be produced by pepsin digestion of the antibody molecule; the Fab' fragments that can be generated by reducing the disulfide bridges of the F(ab')2 fragment, the Fab fragments that can be generated by treating the antibody molecular with papain and a reducing agent, and Fv fragments.

In the production of antibodies, screening for the desired antibody can be accomplished by techniques known in the art in accordance with the methods of the present invention, e.g., ELISA (enzyme-linked immunosorbent assay). To select antibodies specific to a particular domain of the 2C7-SID fusion proteins, one may assay generated hybridomas for a product that binds to the fragment of a 2C7-SID fusion protein that contains such a domain.

Literature Cited

Ayer, D. E., Laherty, C. D., Lawrence, Q. A., Armstrong, A. P. and Eisenman, R. N. (1996) *Mol Cell. Biol.* 16, 5772–5781

Barbas, C. F., Gottesfeld, J. M., and Wright, P. E. WO 95/19431 Zinc finger protein derivatives and methods therefor Beato, M., Herrlich, P., and G. Schutz Steroid hormone receptors: Many actors In search of a plot *Cell* 1995 83: 851–857

Beerli, R., Segal, D., Dreier B., and Barbas, C. F. (1998) *Proc. Natl. Acad. Sci. USA* 95, 14628–14633

Byzova, M., Franken, J., Aarts, M., Almeida-Engler, J., Engler, G., Mariani, C., Campagne, M., and Angenent, G. (1999) *Arabidopsis STERILE APETALA*, a multifunctional gene regulating inflorescence, flower, and ovule development *Gene and Development* 13, 1002–1014

Callis, J., Raasch, J. A., and Vierstra, R. D. (1990) Ubiquitin extension proteins of *Arabidopsis thaliana J Biol. Chem.* 265, 12486–12493

Calvert, L. A. Ospina, M. D., and Shepherd, R. J. (1995) Characterization of cassava vein mosaic virus: a distinct plant papraretrovirus *J. Gen. Virol.* 76, 1271–1278

Chourey, P. S. and Zurawski, D. B. (1981) Callus formation from protoplasts of a maize cell culture *Theor. Appl. Genet.* 59, 341–344 1981

Cornejo, M. J., Luth, D., Blankenship, K. M., Anderson, O. D., and Blechl, A. E. (1993) Activity of a maize ubiquitin promoter in transgenic rice *Plant Mol Biol* 23 (3), 567–81

Gibbs, A. J., (1977) *CMI/AAB Descriptions of plant viruses* 184

Irish, V., and Yamamoto, Y. (1995) Conservation of floral homeotic gene function between *Arabidopsis and Antirrhinum The Plant Cell* 7, 1635–1644

Irish, V. F. (1999) Patterning the flower *Developmental Biology* 209, 211–220

Jack, T., Brockman, L., and Meyerowitz, E. (1992) The homeotic gene APETALA3 of *Arabidopsis thaliana* encodes a ADS box and is expressed in petals and stamens *Cell* 68, 683–687

Jack, T., Fox, G., and Meyerowitz, E. (1994) *Arabidopsis* homeotic gene APETALA3 ectopic expression: transcriptional and post-transcriptional regulation determine floral organ identity *Cell* 76, 703–716

Kim, J. and Pabo, C. O. (1998) Getting a handhold on DNA: Design of poly-zinc finger proteins with femtomolar dissociation constants *Proc. Natl. Acad. Sci. USA* 95, 2812–2817

Liu, Q., Segal, D., Ghiara, J., and Barbas, C. F. (1997) Design of polydactyl zinc-finger proteins for unique addressing within complex genomes *Proc. Natl. Acad. Sci. USA* 94, 5525–5530

Luque, C. M. and Correas, I. (2000) A constitutive region is responsible for nuclear targeting of 4.1R: modulation by alternative sequences results in differential intracellular localization *J Cell Sci* 113, 2485–2495

Mangelsdorf, D. J., Thummel, C., Beato, M., Herrlich, P., Schutz, G., Umesono, K., Blumberg, B., Kastner, P., Mark, M., and Chambon, P (1995) The Nuclear Receptor Superfamily: the Second Decade Cell 1995 83: 835–839

Margolin, J. F., Friedman, J. R., Meyer, W. K. Vassing, H., Thiesen, H. and Rauscher, F. J. (1994) *Proc. Natl. Acad. Sci. USA* 91, 4509–4513

Norris, S. R., Meyer, S. E. and Callis, J. (1993) The intron of *Arabidopsis thaliana* polyubiquitin genes is conserved in location and is a quantitative determinant of chimeric gene expression *Plant Mole. Biol.* 21, 895–906

Parker, M. G. (1993) Curr. Opin. Cell Biol. 5, 499–504

Pineiro, M., and Coupland, G. (1998) The control of flowering time and floral identity in *Arabidopsis Plant Physiol.* 117, 1–8

Reiss, B., Wasmann, C. C., and Bohnert, H. J. (1987) Regions in the transit peptide of SSU essential for transport into chloroplasts Mol. Gen. Genet. 209(1), 116–21

Scott, S. V., Nice, D. C. 3rd, Nau, J. J., Weisman, L. S., Kamada, Y., Keizer-Gunnink, I,. Funakoshi, T., Veenhuis, M., Ohsumi, Y., Klionsky, D. J. (2000) Apg13p and Vac8p are part of a complex of phosphoproteins that are required for cytoplasm to vacuole targeting *J Biol Chem* 10, 1074

Segal, D., Dreier, B., Beerli, R. R., and Barbas, C. F. (1999) Toward controlling gene expression at will: Selection and design of zinc finger domains recognizing each of the 5'-GNN-3' DNA target sequences *Proc. Natl. Acad. Sci. USA* 96, 2758–2763

Settles, A. M. and Martienssen, R. (1998) Old and new pathways of protein export in chloroplasts and bacteria *Trends Cell Biol* 12, 494–501

Talamond, P., Gallon, G., and Treche, S. (1998) Rapid and sensitive liquid chromatographic method using a conductivity detector for the determination of phytic acid in food *J. of Chromatography* 805, 143–147

Verdaguer, B. (1996) Isolation and expression in transgenic tobacco and rice plants, of the Casseva Vein Mosaic Virus (CsVMV) promoter *Plant Mol. Biol.* 31, 1129–1139

Verdaguer, B. (1998) Functional organization of the Casseva Vein Mosaic Virus (CsVMV) promoter *Plant Mol. Biol.* 37, 1055–1067

Weigel, D. (19950 The genetics of flower development: From floral induction to ovule morphogenesis *Annu Rev. Genetics* 29, 19–39

Wu, H., Yang, W., and Barbas, C. F. (1995) Building zinc fingers by selection: Toward a therapeutic application *Proc. Natl. Acad. Sci. USA* 92, 344–348

Yamamoto, K. R. (1985) Steroid Receptor Regulated Transcription of Specific Genes and Gene Networks *Annu. Rev. Genet.* 19: 209–252.

Yanofsky, M. (1995) *Annu. Rev. Plant Physiol. Plant Mol. Biol.* 46, 167–188

All references cited herein are incorporated by reference as if each were specifically incorporated by reference.

The following examples are intended to illustrate but not to limit the invention.

K. EXAMPLES

The invention is illustrated by materials and methods for controlling genetic expression in plants, e.g., the luciferase transgene, *Arabidopsis* AP3 gene, and the maize MIPS gene. "Providing" herein means maintaining a plant cell, either in planta or ex planta, either in a plant or in cell or tissue culture, under conditions in which expression and production of a desired zinc finger protein is produced in the plant cell. The regulatory factor, or "effector protein," will at least comprise a zinc finger component which binds specifically to a nucleotide sequence contained within the target gene such that the binding of the zinc finger protein modulates expression of the target gene (See generally Kim and Pabo, *Proc. Natl. Acad. Sci. U.S.A.*, 95:2812–2817 (1998)) and may also contain a regulatory domain. Thus, the zinc finger protein can be fused to an additional amino acid sequence which provides regulation, although as stated above, in some instances, binding of the zinc finger portion alone has an effect on expression. This is especially the case when the binding target is in the TATTA box region where transcription is initiated.

Example 1

ZFP-effector Fusion Protein Function on Luciferase Reporter Gene in Maize Cells

To establish this Zinc Finger Protein ("ZFP") technology in plants, we have shown that transient trans-activation and trans-repression of a reporter gene can be achieved in representative plant cells. These transient regulation is mediated by a previously synthesized synthetic zinc finger proteins, 2C7. The binding site of zinc finger protein 2C7 sequence was originally from the type 1 human immune deficiency virus (HIV-1) genome. The synthetic zinc finger protein 2C7 has been show to be able to specifically bind to this site and activate reporter gene's expression in human Hela cell line (Liu et al., *Proc. Natl. Acad. Sci. USA* (1997) 94:5525–5530; and Wu et al., *Proc. Natl. Acad. Sci. USA* (1995) 92:344–348). The claimed method comprises providing plant cells, either in culture or in intact plants, with a functional ZFP, or an expression system for production of a suitable ZFP. However, by "culturing" is meant maintaining a plant cell, either in planta or ex planta, either in a plant or in cell or tissue culture, under conditions in which expression and production of a desired zinc finger protein is produced in the plant cell.

A. Reporter Constructs

Luciferase reporter plasmids were constructed from the Cassava Vein Mosaic Virus promoter (CsVMV) (SEQ ID NO:1) (Calvert et al., *J. Gen. Virol.* (1995) 76:1271–1278; Verdaguer et al., *Plant Mol. Biol.* (1996) 31:1129–1139, Verdaguer et al., *Plant Mol. Biol.* (1998) 37:1055–1067). Six tandem repeats of 2C7 binding sites (6X2C7) (SEQ ID NO:2) was inserted at the upstream of reporter. Reporter I (p5'C7F) is a deleted and thus inactive version of promoter CsVMV which contains nucleotide sequence –112 bp to +72 bp of the full length CsVMV promoter with 6X 2C7 binding site is inserted at the 5' end. Reporter II (pc7rbTATA) contains a minimal promoter (SEQ ID NO:3) with 6X2C7 binding site inserted at the 5' end. Reporter I contains a longer promoter sequence and is stronger than the promoter in reporter I (FIG. 1).

B. Effector Constructs

Maize ubiquitin promoter ZmUbi (Cornejo et al., *Plant Mol Biol* (1993) 23(3):567–81) was used to express the ZFP-effector fusion proteins. The activation construct (pND3008) (SEQ ID NO:4) consists of several functional domains: zinc finger protein domain 2C7, nuclear localization signal, the transcriptional activation domain VP64 which is fused to the relative C-terminal of ZFP2C7 and HA epitope tag sequence (FIG. 1). The function of HA tag is for the detection of zinc finger protein expression through Western procedures. The repression construct (pND3018) (SEQ ID NO:5) consists of repression domain SID, nuclear localization signal, ZFP2C7 domain, and HA epitope tag sequence. The repression domain SID is fused to the relative N-terminal of ZFP2C7 domain.

C. Transient Assay

Maize protoplasts were prepared from maize cell line HE89 (F19556) and transformed using standard procedure (Chourey and Zurawski, *Theor. Appl. Genet.* 59:341–344 (1981)). For each transformation reaction, lug of luciferase reporter constructs and 10 ug activator were co-transformed into one million purified protoplasts. The transformed protoplasts were incubated at 28° C. in dark for 24–48 hrs. Collect cells by centrifugation at 500 g for 5 min. Aspirate off media. Resuspend in 80ul 1.2× Passive Lysis Buffer (Promega). Freeze at –80° C. for >10 min. Thaw completely at room temp. Vortex and spin at 3500 RPM for 5 min at 4° C. Collect supernatant. Assay 20 ul extract for luciferase with the Luciferase Assay Kit (Promega).

The luciferase activity of the target reporter is normalized to the protein contents of each sample to generate the specific activity. This will correct for any variations in transformation efficiency and cell extractions.

D. Function of ZFP-effector Fusion Protein in Maize Protoplasts

The effects of the 2C7-VP64 ZFP-activator fusion was tested on Reporter I and II reporters (FIG. 1). With Reporter I (p5'c7F), 146 to 250 fold of activation is achieved with the 2C7-Vp64 activator. With Reporter II (pc7rbTATA), 40 to 70 fold of activation is achieved with the 2C7-Vp64 activator.

The effect of the 2C7-SID ZFP-repressor fusions on tested on Reporter I. The 2C7-SID effector produces almost 2 fold of repression.

Example 2

Figure 2:
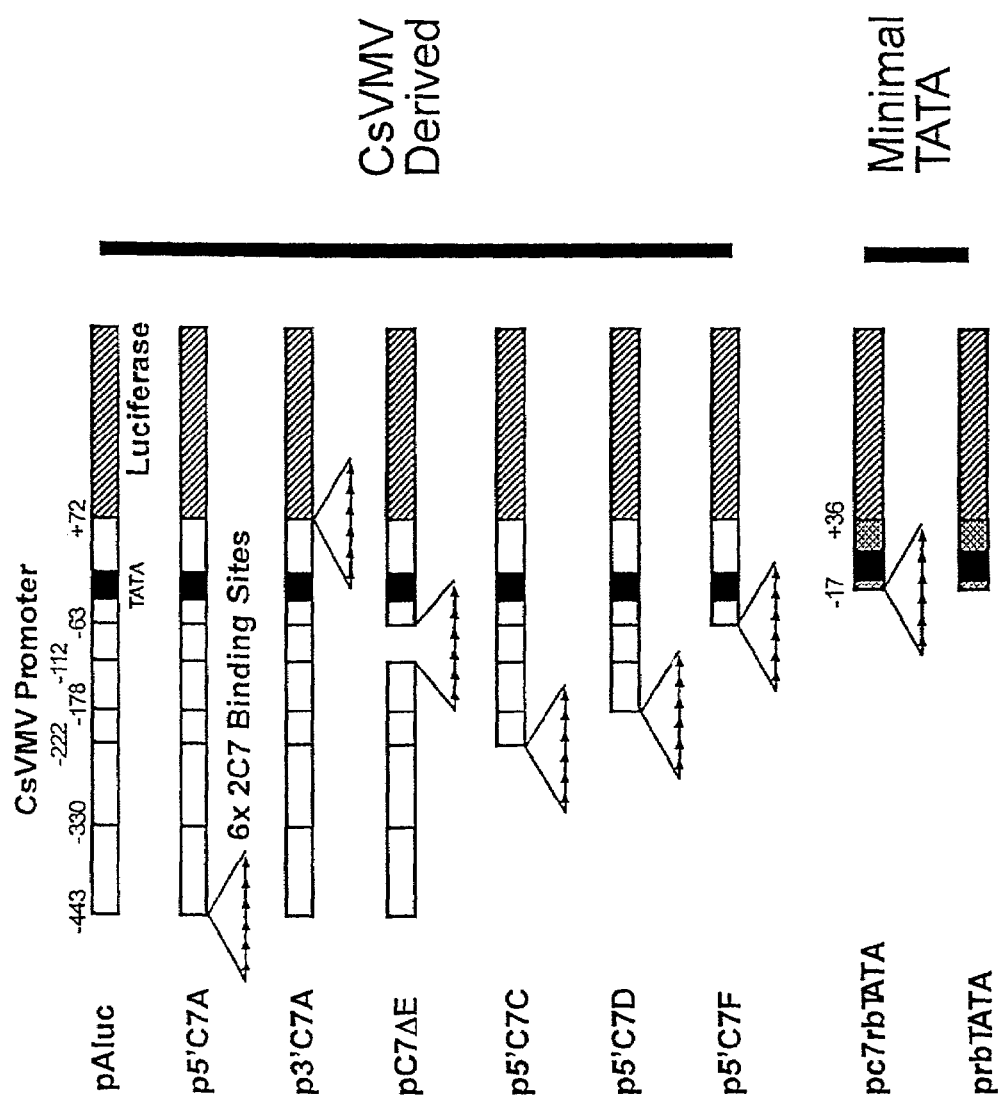
FIG. 2 Reporter plasmids for evaluating different binding site positions. pAluc: Full length CsVMV; p5'C7A: Full length CsVMV with 6×2c7 binding sites at the 5' end; p3'C7A: Full length CsVMV with 6×2c7 binding sites at the 3' end of the 5'UTR; pC7δE: CsVMV with 6×2c7 binding sites replacing −112 to −63; p5'C7C: CsVMV (−222 to +72) with 6×2c7 binding sites at the 5' end; p5'C7D: CsVMV (−178 to +72) with 6×2c7 binding sites at the 5' end; p5'C7F: CsVMV (−112 to +72) with 6×2c7 binding sites at the 5' end; pc7rbTATA: Minimal promoter with a TATA box with 6×2c7 binding sites at the 5' end; prbTATA: Minimal promoter with a TATA box with no ZFP binding sites.

Position Effect of Zinc Finger Protein Binding Site on the Activation of Luciferase Reporter Constructs in Tobacco Cells A. Reporter Constructs A series of luciferase reporter plasmids were constructed from the full length and partial deletion version of Cassava Vein Mosaic Virus promoter (CsVMV promoter with six tandem repeats of 18 bp 2C7 (GCG TGG GCG GCG TGG GCG) (SEQ ID NO:43) binding sites (6X2C7) inserted at different locations within fragments of this promoter (FIG. 2) (Verdaguer et al., *Plant Mol. Biol.* (1998) 37:1055–1067). Plasmid pAluc contains a full-length CsVMV promoter (same as in pND3008, see SEQ ID NO:1) driving the expression of luciferase gene. Plasmid p5'C7A contains the same full-length CsVMV promoter with 6X2C7 inserted at the 5' end using Xba I site. Plasmid p3'C7A is almost identical to p5'C7A except the 6X2C7 was inserted at the 3' end using Xba I site. Plasmid pC7δE contains the deleted CsVMV promoter with 6X2C7 binding site replacing nucleotide sequence −112 to −63 of CsVMV. Plasmid p5'C7C contains a partial deleted CsVMV (−222 to +72) with 6X2C7 inserted at the 5' end. Plasmid p5'C7D contains a partial deleted CsVMV (−178 to +72) with 6X2C7 inserted at the 5' end. Plasmid p5'C7F and pc7rbTATA are the same in example 1A. Plasmid prbTATA is identical to pc7rbTATA except no 6X2C7 binding site. The promoter activity in each construct is further decreased than the previous version as the promoter sequence gets shorter. For example, the activity of p5'C7A is higher than p5'C7C, p5'C7D is higher than p5'C7F, and their activities are all higher than the minimal promoter construct pc7rbTATA.

B. Effector Constructs

Figure 3:
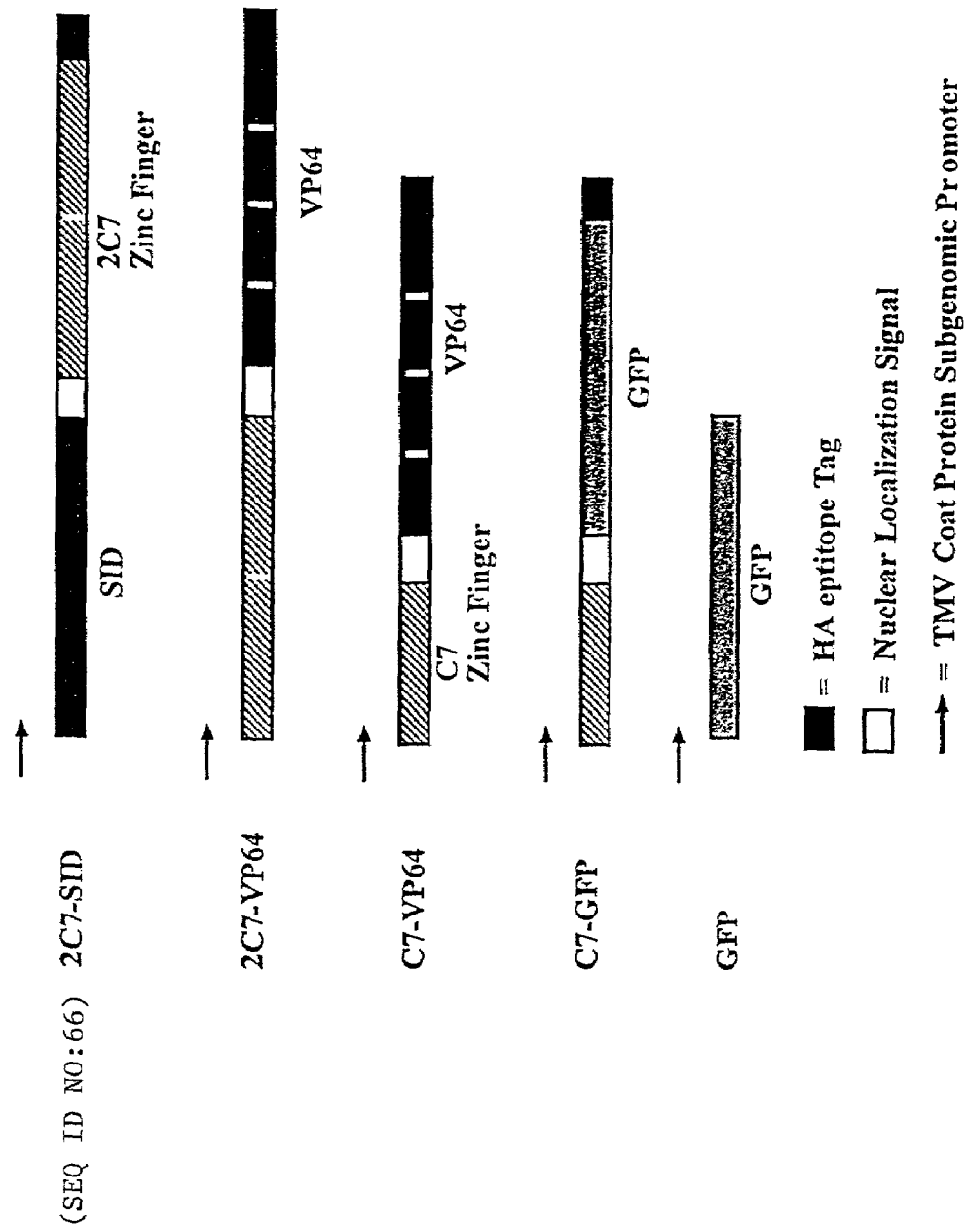
FIG. 3 Zinc finger protein-effector fusion constructs for evaluation of the position effect of ZFP binding site in tobacco cells. 2C7-SID: 6 finger ZFP fused to the Sin3 interaction domain (SID); 2C7-SKD: 6 finger ZFP fused to the super krab domain (SKD); 2C7-VP64: 6 finger ZFP fused to 4 repeats of the minimal VP16 activation domain (VP64); C7-VP64: 3 finger ZFP fused to 4 repeats of the minimal VP16 activation domain (VP64); C7-GFP: 3 finger ZFP fused to the Green Fluorescent Protein (GFP); GFP: Free GFP.

Tobacco mosaic virus (TMV) (Gibbs, *CMI/AAB Descriptions of plant viruses* (1977) 184) was used as an expression vector for the ZFP-effector fusion proteins. The coding region for the coat protein was replaced by the ZFP fusion sequence (FIG. 3). Plasmid p2C7-SID consists of TMV promoter and SID-2C7 repression domain (same as in pND3018). Plasmid p2C7-VP64 consists of TMV promoter and 2C7-VP64 activation domain (same as in pND3008). Plasmid pC7-VP64 is similar to p2C7-VP64 except the 6 finger zinc finger protein 2C7 (in pND3008 and pND3018) is replaced by 3 finger protein C7 (SEQ ID NO:6). Plasmid pC7-GFP consists TMV promoter and GFP fragment (Ref). It was used as background control. *Arabidopsis* ubiquitin promoter UBQ3 was also used to express the ZFP fusion proteins(constructs did not show here and the results are similar).

C. Transient Assay

TMV viral RNA was made from the effector constructs with the T7 Megascript Kit (Ambion). Collect log phase tobacco BY-2 cells in conical tubes. Wash with 0.4M mannitol. Digest cell walls by adding 20 ml Enzyme Solution (1% Cellulase Onezuka RS (Karlan Research USA #2019), 0.1% Pectolyase Y-23 (Karlan Research USA #8006), 0.4M mannitol, pH 5.8). Incubate in deep petri dish (NUNC 4031) at 22–28° C. in dark with continuous or occasional swirling for 2 hrs. Wash 2× with 0.4M mannitol. Collect by centrifugation at 300 g for 2 min. Remove as much supernatant as possible and resuspend in 15–25 ml Electroporation Buffer (0.3M mannitol, 5 mM MES, 70 mM KCl, pH 5.8). Count cells on hemacytometer and adjust concentration to $1.6 \times 10^6$/ml. Add 0.3 ml cells to a 0.4 cm electroporation cuvette. Add 100 ul Electroporation Buffer containing 1 ug reporter plasmid DNA, 0.1 ug/ul Renilla Luciferase (RL) control plasmid with no ZFP binding sites, and 25 ug viral RNA, mix gently with pipette, and immediately electroporate (R=∞, C=125 uF, V=300V). Incubate on ice for 30 min. Incubate at RT for 5 min. Transfer 100 ul eletroporated cells to 3 ml Protoplast Culture Media (2.2 g/l Murashige and Skoog Plant Salt Base-Gibco BRL #11117-074, 0.1 g/l myo-inositol, 1 mg/l thiamin-HCl, 0.2 mg/l 2,4-D, 10 g/l sucrose, 0.4M mannitol, and pH 5.8). Incubate cells in 3 ml media in 15 ml conical tube placed on side or in 1–2 ml media in a small petri dish (Corning #25050-35). Incubate at 28° C. in dark for 48 hrs. Collect cells by centrifugation at 500 g for 5 min. Aspirate off media. Resuspend in 80 ul 1.2×Passive Lysis Buffer (Promega). Freeze at −80° C. for >10 min. Thaw completely at room temp. Vortex and spin at 3500 RPM for 5 min at 4° C. Collect supernatant. Assay 20 ul extract for luciferase and RL activity with the Dual Luciferase Assay Kit (Promega).

In this transient assay, the luciferase activity of the target reporter is normalized to the RL activity of the control reporter by division. This will correct for any variations in transformation efficiency and cell extract concentration. The normalized activity of an effector is presented as the normalized activity of reporter plus effector relative to the activity of the target reporter without effector expression. Thus, a relative activity of 1 means there is no effector function.

Figure 4:
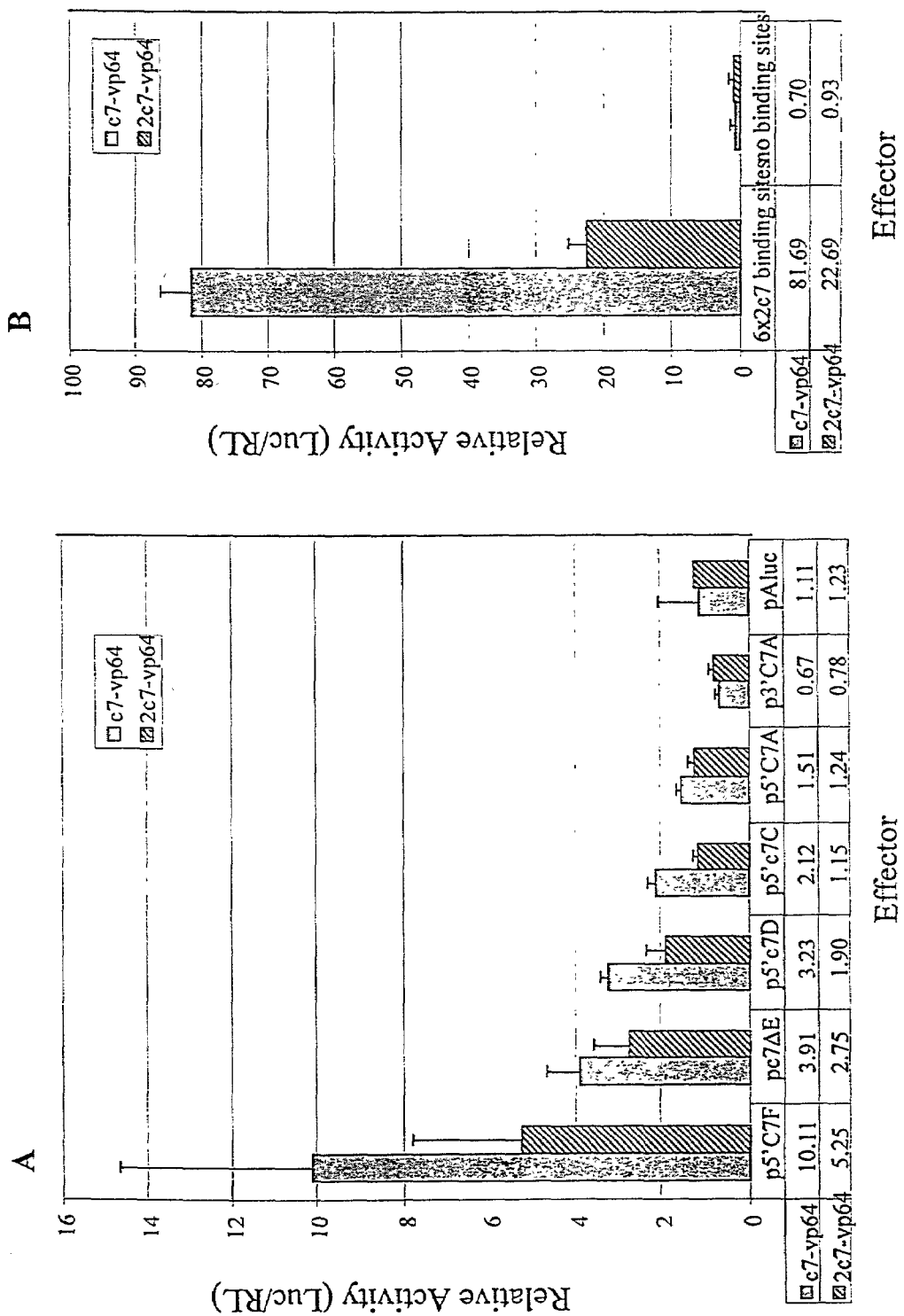
FIG. 4A Effects of zinc finger protein binding site on reporter gene expression levels and activation and activation of reporter gene with 3-( blue) or 6-zinc (cross hatch) finger proteins. A) Effects of different binding site positions on activation by a 3-finger effector (c7-vp64, solid bars) or a 6-finger protein (2c7-vp64, striped bars).
FIG. 4B Activation of a minimal TATA containing reporter.

D. Effect of Binding Site Position and ZFP-activator Fusion Protein Function in Tobacco Protoplasts The effects of the C7-VP64 and 2C7-VP64 ZFP-activator fusions were tested on these reporters (FIG. 4). The results show zinc finger domain 2C7-VP64 fusion protein activated the expression of luciferase reporter gene in both tobacco cells and in maize cells. The activation level was dependent on the position of zinc finger protein binding sites. Generally, the closer of the binding site is to the TATA box, the higher of the activation level. Three-finger zinc finger protein (C7) generally gives higher activation level than the six-finger zinc finger protein (2C7). It is probably due to the fact of doubling the total numbers of activator when a 3-finger protein was used. With a minimal promoter, Reporter II (pc7rbTATA), almost 100-fold of activation is achieved with the C7-Vp64 activator. The 2C7-VP64 activator gives 23-fold of activation. A stronger promoter, p5'c7F (Reporter I), is activated 10 fold by C7-VP64 and 5 fold by 2C7-VP64. From this experiment, it is clear that the zinc finger-binding site is preferred upstream of TATA box.

E. Effect of ZFP-repressors in Tobacco Protoplasts

Figure 5:
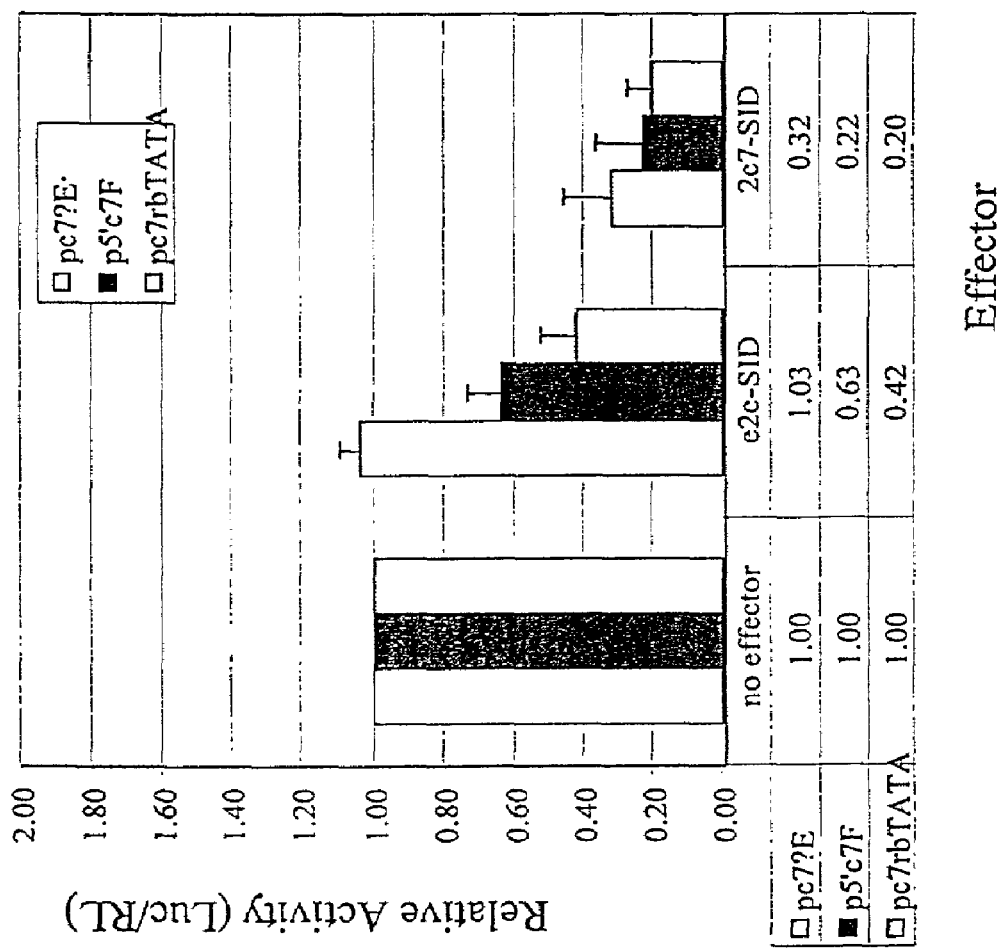
FIG. 5 Repression of reporters with 3- or 6-finger zinc finger fusion proteins.
Figure 7:
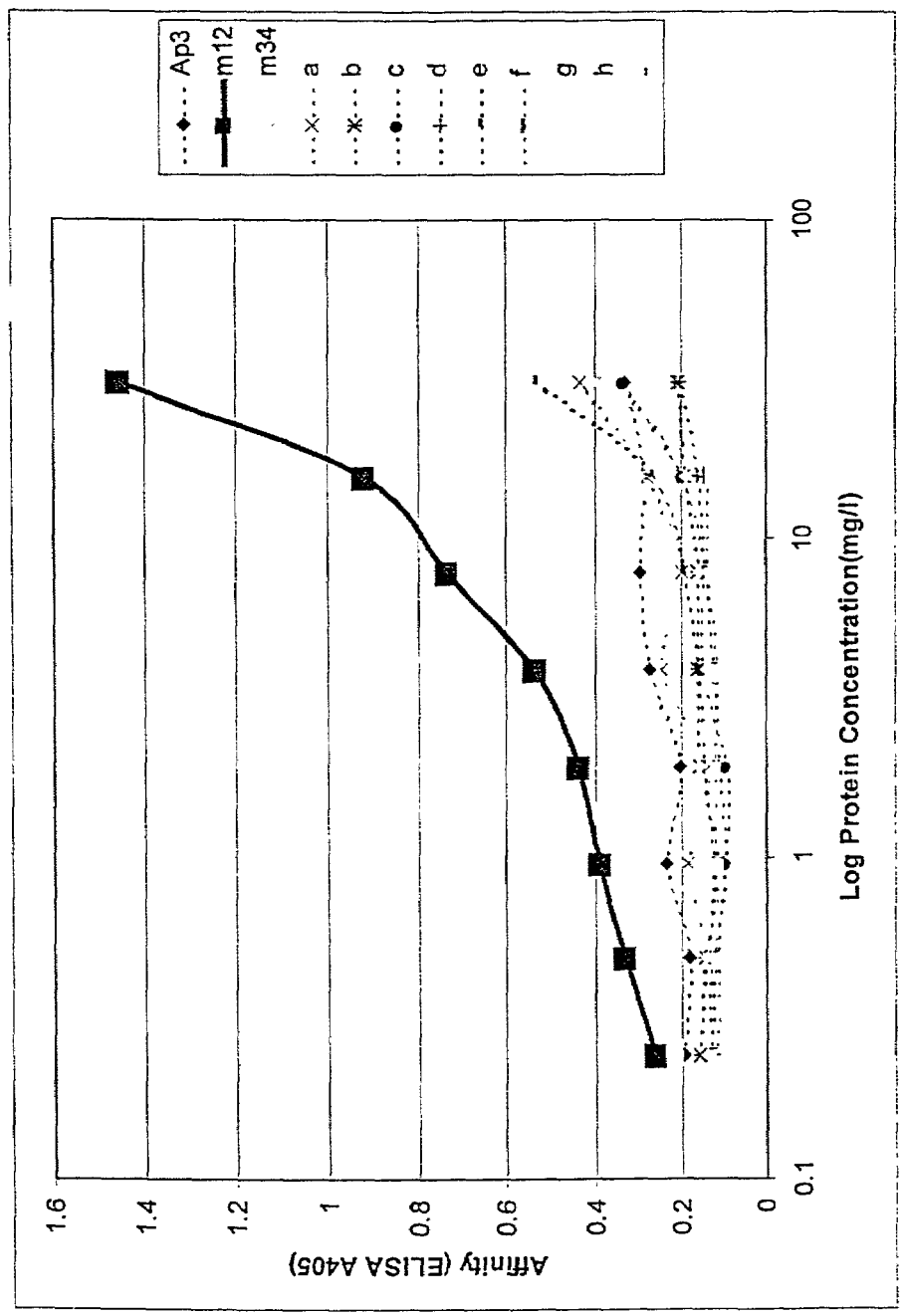
FIG. 7 ELISA analysis of ZFPm1 DNA-binding specificity. Six-finger protein ZFPm1 was purified through affinity column from as MBP fusion protein from *E. coli*. Specificity of binding was analyzed by measuring the binding activity in total lysates to immobilized biotinylated hairpin oligonucleotides containing the indicated 18-bp targets. Assay were performed in duplicate. Binding site tested: Ap3, m12, m34, 8 other non-target oligos (a–h) and no oligo control (−).
Figure 8:
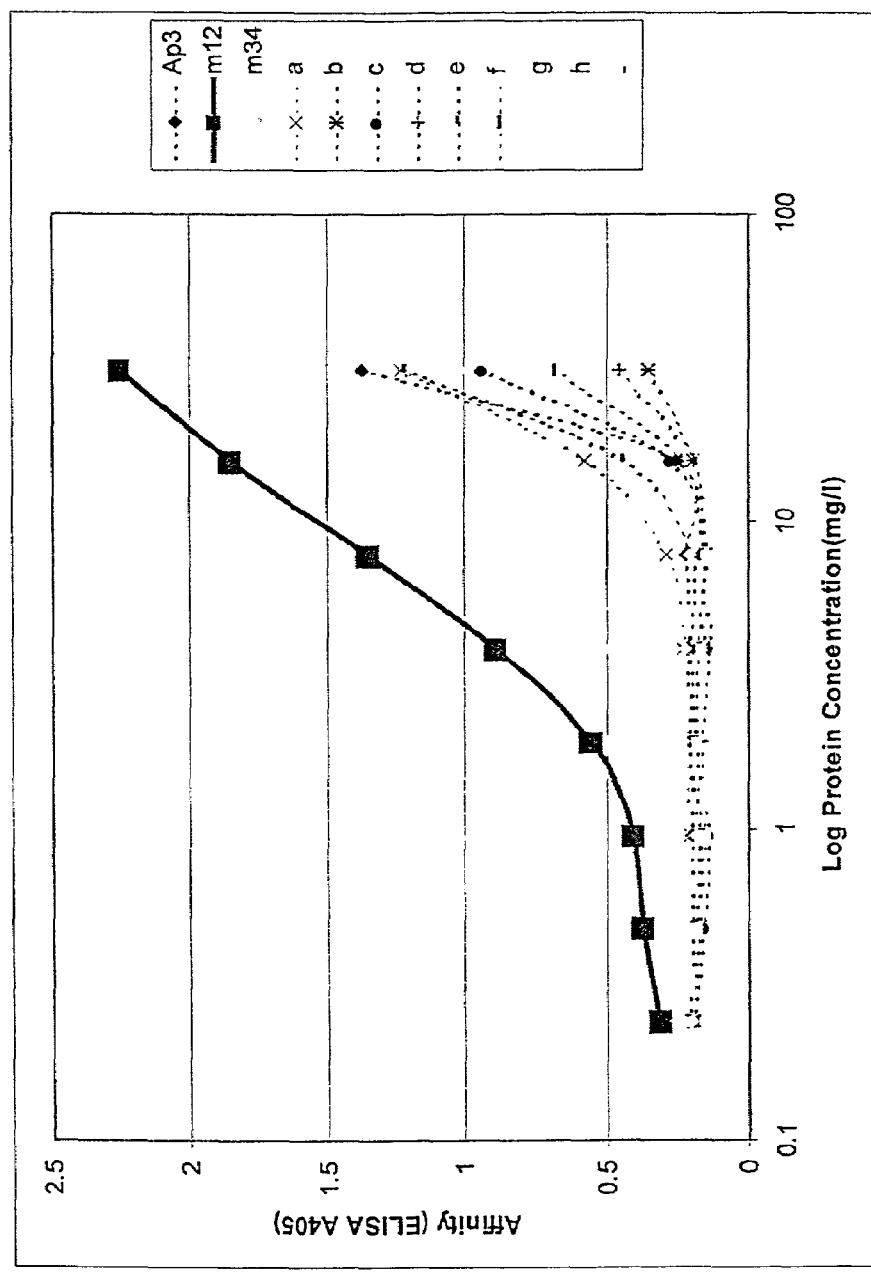
FIG. 8 ELISA analysis of ZFPm2 DNA-binding specificity. Six-finger protein ZFPm2 was purified through affinity column from as MBP fusion protein from *E. coli*. Specificity of binding was analyzed by measuring the binding activity in total lysates to immobilized biotinylated hairpin oligonucleotides containing the indicated 18-bp targets. Assay were performed in duplicate. Binding site tested: Ap3, m12, m34, 8 other non-target oligos (a–h) and no oligo control (−).
Figure 9:
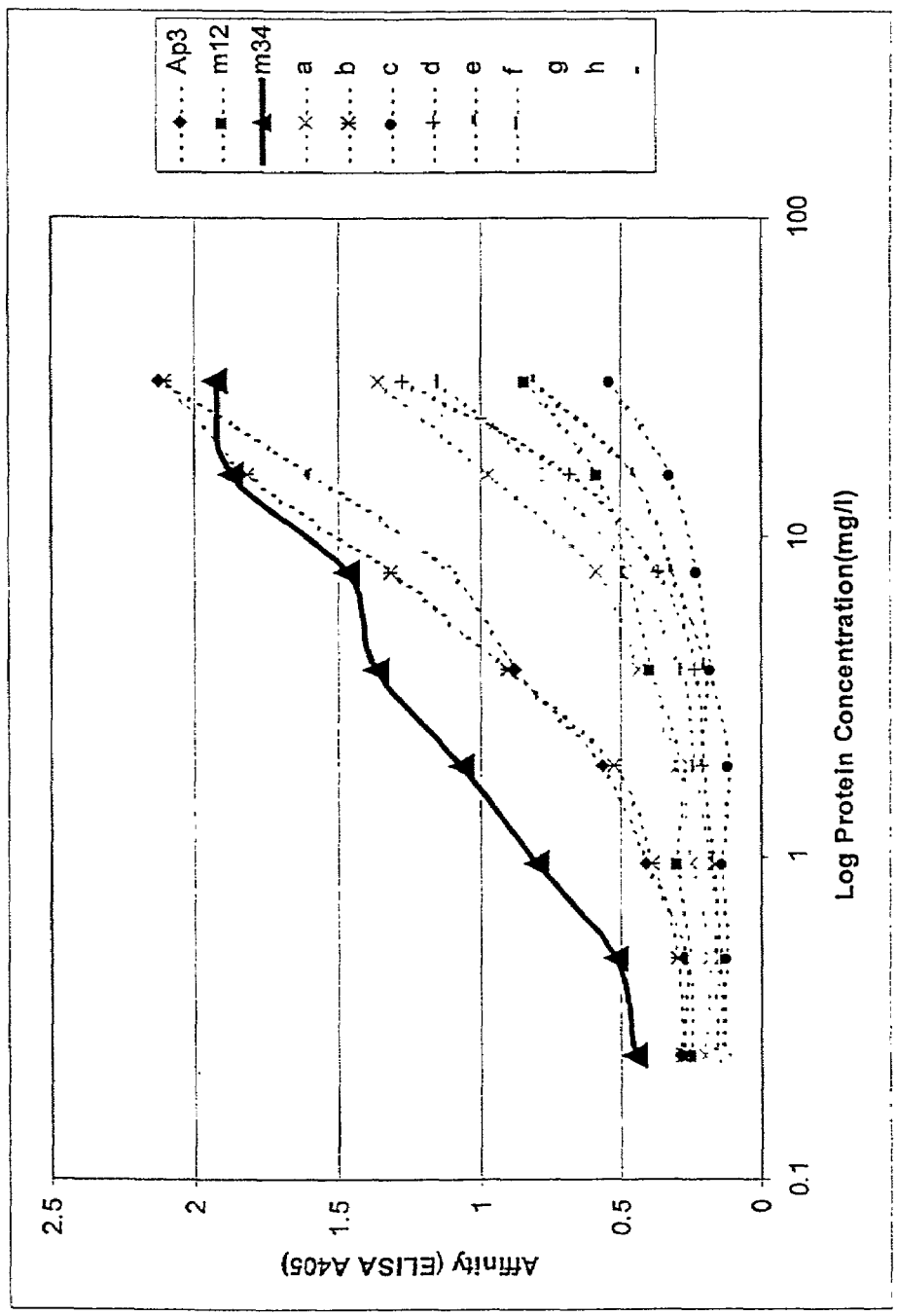
FIG. 9 ELISA analysis of ZFPm3 DNA-binding specificity. Six-finger protein ZFPm3 was purified through affinity column from as MBP fusion protein from *E. coli*. Specificity of binding was analyzed by measuring the binding activity in total lysates to immobilized biotinylated hairpin oligonucleotides containing the indicated 18-bp targets. Assay were performed in duplicate. Binding site tested: Ap3, m12, m34, 8 other non-target oligos (a–h) and no oligo control (−).
Figure 10:
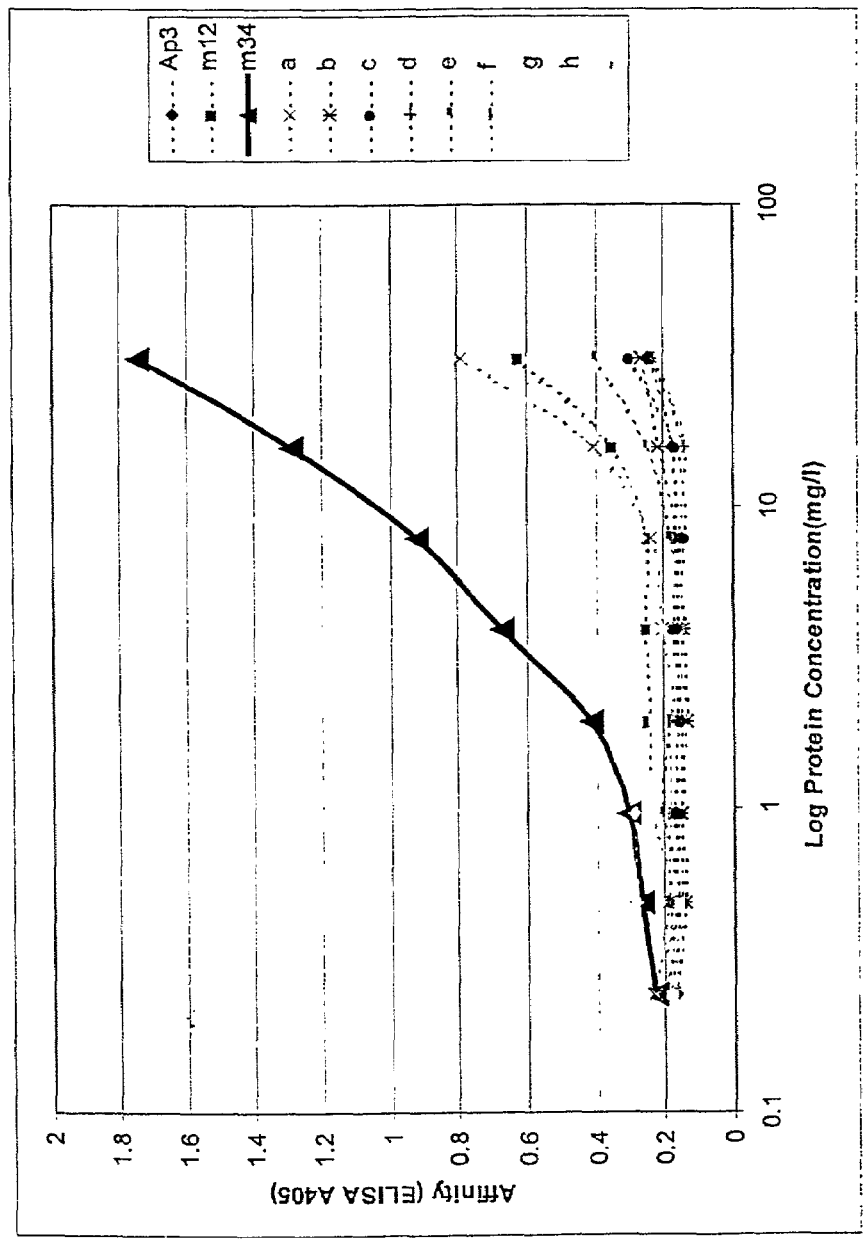
FIG. 10 ELISA analysis of ZFPm4 DNA-binding specificity. Six-finger protein ZFPm4 was purified through affinity column from as MBP fusion protein from *E. coli*. Specificity of binding was analyzed by measuring the binding activity in total lysates to immobilized biotinylated hairpin oligonucleotides containing the indicated 18-bp targets. Assay were performed in duplicate. Binding site tested: Ap3, m12, m34, 8 other non-target oligos (a–h) and no oligo control (−).
Figure 11:
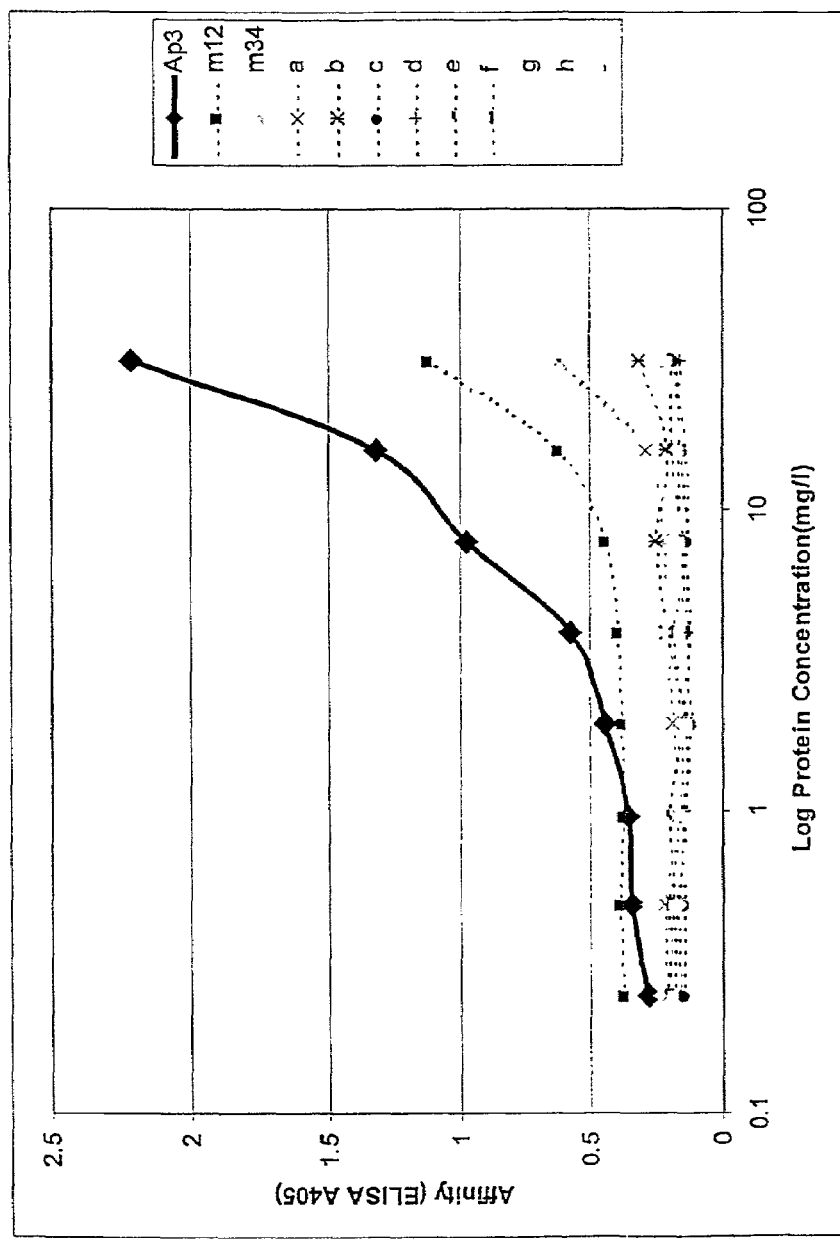
FIG. 11 ELISA analysis of ZFPmAp3 DNA-binding specificity. Six-finger protein ZFPAp3 was purified through affinity column from as MBP fusion protein from *E. coli*. Specificity of binding was analyzed by measuring the binding activity in total lysates to immobilized biotinylated hairpin oligonucleotides containing the indicated 18-bp targets. Assay were performed in duplicate. Binding site tested: Ap3, m12, m34, 8 other non-target oligos (a–h) and no oligo control (−).
Figure 12:
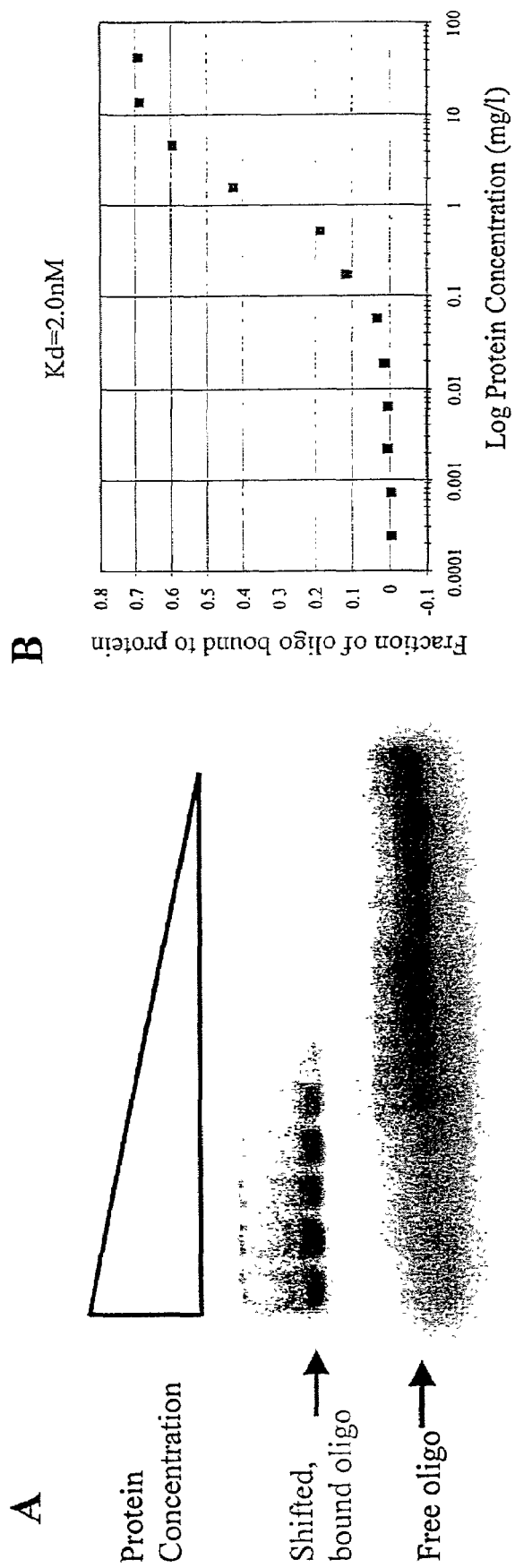
FIG. 12 Gel Shift analysis of ZFPm1 DNA-binding affinity. Six-finger protein ZFPm1 was purified through affinity column from as MBP fusion protein from *E. coli*. A. Affinity of binding was determined from a gel shift analysis of the binding of labeled m12 oligo to decreasing concentrations of the purified ZFPm1 protein. B. The affinity of ZFPm1 was calculated to be approximately 2 nM from the concentration where one half of the labeled oligo is bound to the ZFPm1 protein.
Figure 13:
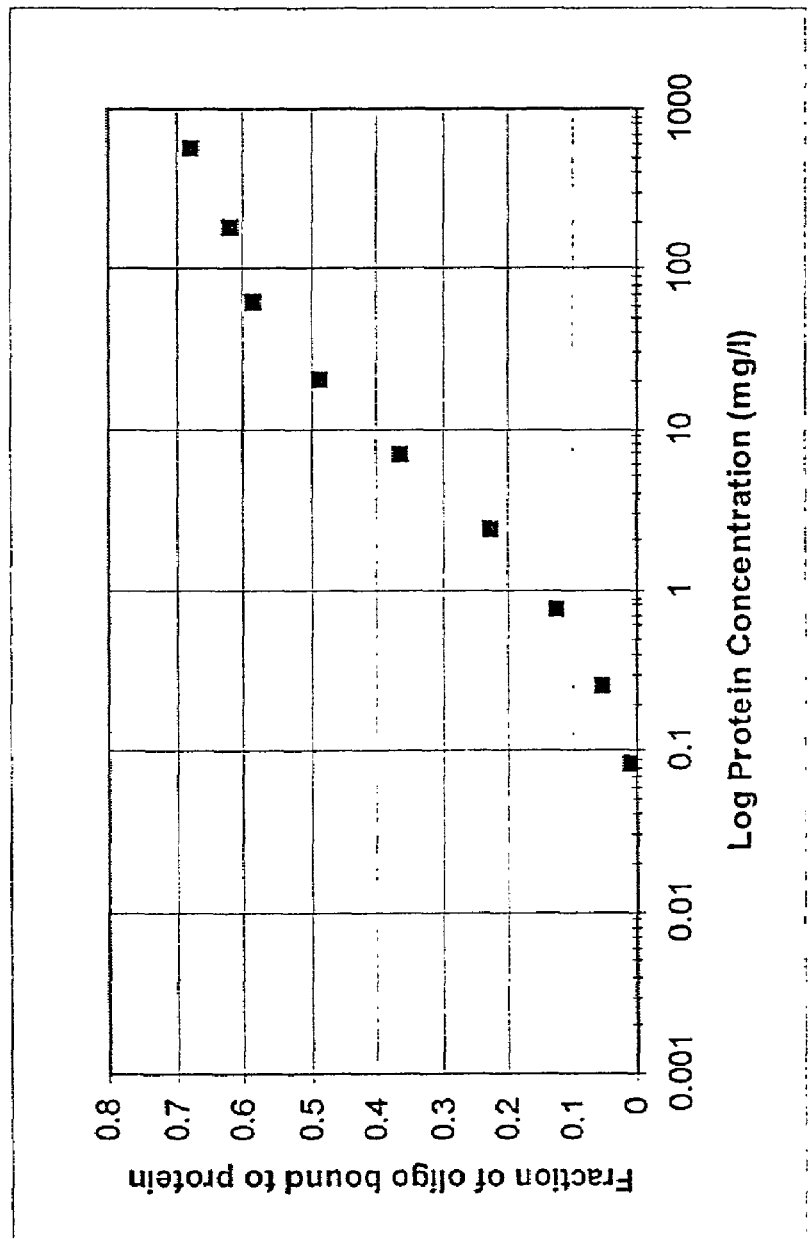
FIG. 13 Gel Shift analysis of ZFPm2 DNA-binding affinity. Six-finger protein ZFPm2 was purified through affinity column from as MBP fusion protein from *E. coli*. Affinity of binding was determined from a gel shift analysis of the binding of labeled m12 oligo to decreasing concentrations of the purified ZFPm2 protein. The affinity of ZFPm2 was calculated to be approximately 7.5 nM from the concentration where one half of the labeled oligo is bound to the ZFPm2 protein.
Figure 14:
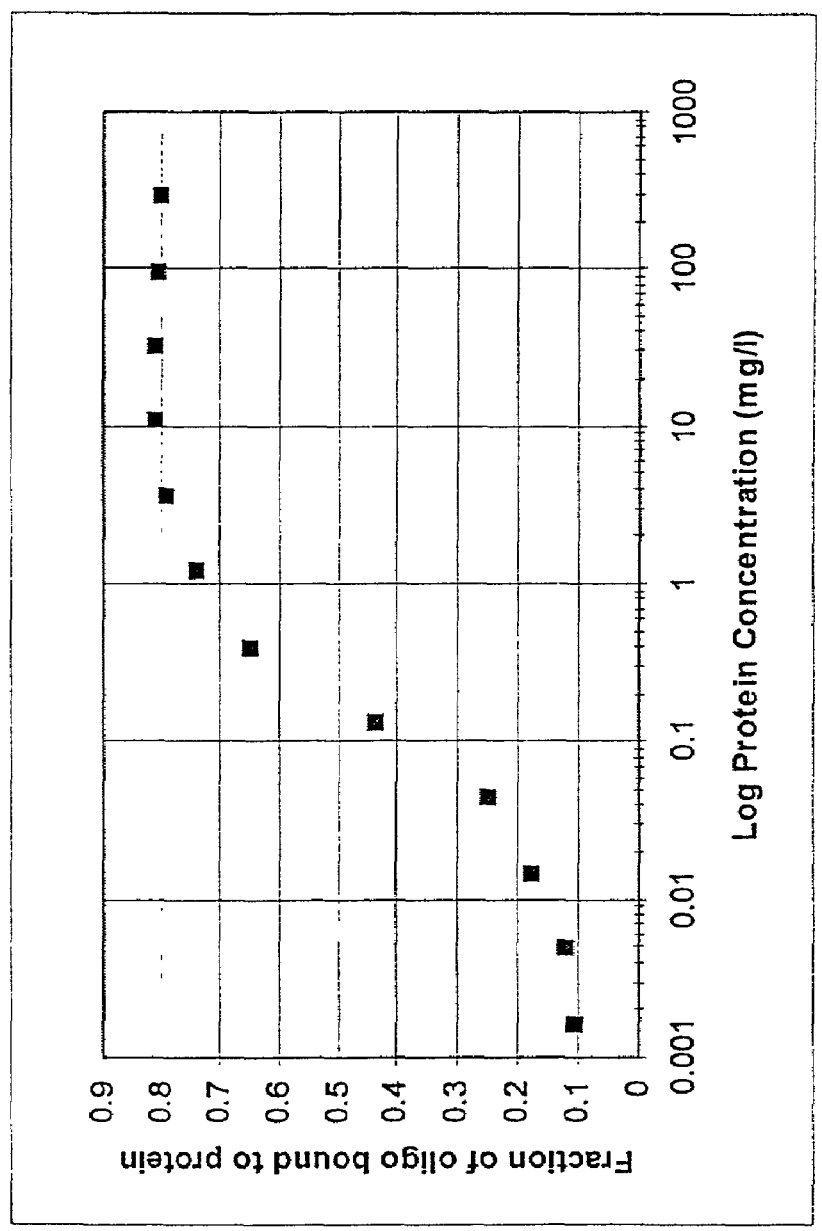
FIG. 14 Gel Shift analysis of ZFPm3 DNA-binding affinity. Six-finger protein ZFPm3 was purified through affinity column from as MBP fusion protein from *E. coli*. Affinity of binding was determined from a gel shift analysis of the binding of labeled m34 oligo to decreasing concentrations of the purified ZFPm3 protein. The affinity of ZFPm3 was calculated to be approximately 0.18 nM from the concentration where one half of the labeled oligo is bound to the ZFPm3 protein.
Figure 15:
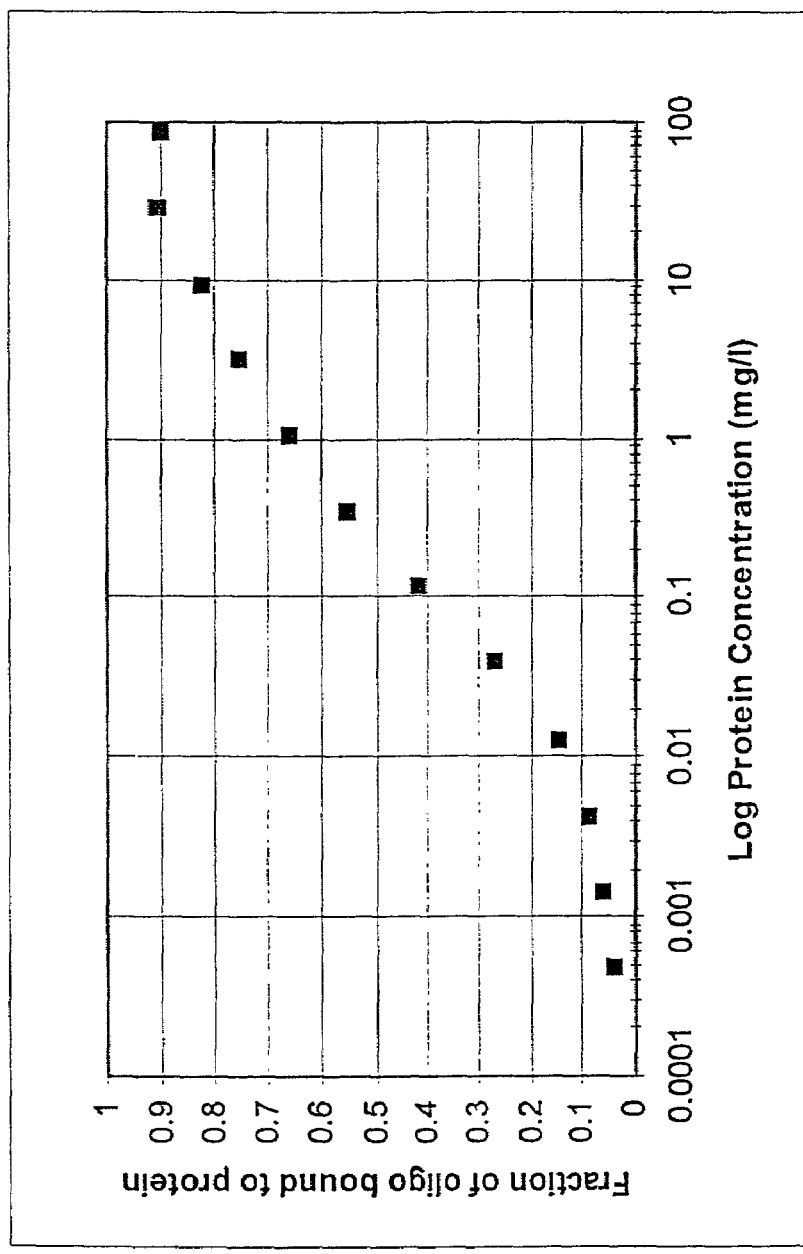
FIG. 15 Gel Shift analysis of ZFPm4 DNA-binding affinity. Six-finger protein ZFPm4 was purified through affinity column from as MBP fusion protein from *E. coli*. Affinity of binding was determined from a gel shift analysis of the binding of labeled m34 oligo to decreasing concentrations of the purified ZFPm4 protein. The affinity of ZFPm4 was calculated to be approximately 0.25 nM from the concentration where one half of the labeled oligo is bound to the ZFPm4 protein.
Figure 16:
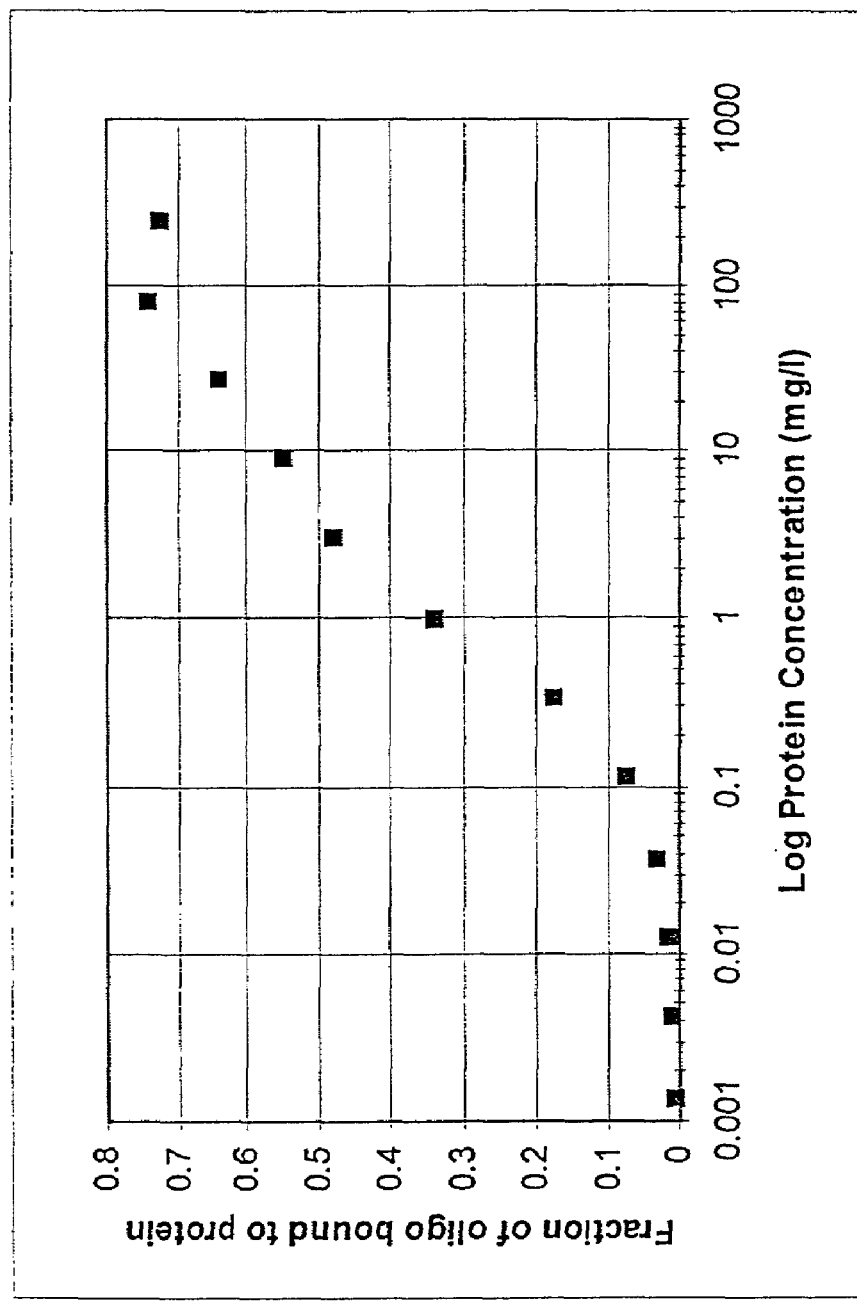
FIG. 16 Gel Shift analysis of ZFPAp3 DNA-binding affinity. Six-finger protein ZFPAp3 was purified through affinity column from as MBP fusion protein from *E. coli*. Affinity of binding was determined from a gel shift analysis of the binding of labeled Ap3 oligo to decreasing concentrations of the purified ZFPAp3 protein. The affinity of ZFPAp3 was calculated to be approximately 2.3 nM from the concentration where one half of the labeled oligo is bound to the ZFPAp3 protein.

To determine whether repression can be achieved, the effects of the 2C7-SID, 2C7-SKD, and e2c-SID ZFP-repressor fusions on three different reporter plasmids: Reporter I (p5'C7F), Reporter II (pc7rbTATA), and pC7δE. Where studied. The 2C7-SID effector produces almost 5-fold repression of all the reporters (FIG. 5). The 2C7-SKD shows no specific repression of any of the reporters. Similarly, the e2c-SID repressor does not cause much repression of the reporters (FIG. 5).

Thus, ZFP fusions to the SID repressor domain provide effective, specific repression of their target genes. However, the repression domain SKD and the e2c zinc finger protein are not functional in plant cells.

Example 3

Selection of Zinc Finger Protein Binding Sites for Endogenous Gene MIPS and AP3

The genes for AP3 (U30729) and MIPS (AF056326) were examined for suitable zinc finger binding sites. At the time of construction, the zinc finger library covered all the GNN triplets and the TGA triplet as shown in the recognition code provided in Table 2) (see also Segal et al., *Proc. Natl. Acad. Sci. USA* (1999) 96:2758–2763. Potential zinc finger-binding sites were selected by searching for 6 triplets (18 consecutive base pairs) with either GNN or TGA.

TABLE 2

GNN triplets and the TGA triplet recognition code

| Target Sequence | ZFP domain | |
|---|---|---|
| GAA | SQSSNLV | (SEQ ID NO:44) |
| GAC | SDPGNLV | (SEQ ID NO:45) |

TABLE 2-continued

GNN triplets and the TGA triplet recognition code

| Target Sequence | ZFP domain | |
|---|---|---|
| GAG | SRSDNLVR | (SEQ ID NO:46) |
| GA | STSGNLV | (SEQ ID NO:47) |
| GCA | SQSGDLRR | (SEQ ID NO:48) |
| GCC | SDCRDLAR | (SEQ ID NO:49) |
| GCG | SRSDDLVR | (SEQ ID NO:50) |
| GCT | STSGELV | (SEQ ID NO:51) |
| GGA | SQSSHLVR | (SEQ ID NO:52)or |
|  | SQRAHLER | (SEQ ID NO:53) |
| GGC | SDPGHLVR | (SEQ ID NO:54) |
| GGG | SRSDKLVR | (SEQ ID NO:55) |
| GGT | STSGHLVR | (SEQ ID NO:56) |
| GTA | SQSSSLVR | (SEQ ID NO:57) |
| GTC | SDPGALVR | (SEQ ID) NO:58) |
| GTG | SRSDVLVR | (SEQ ID NO:59) or |
|  | SRKDSLVR | (SEQ ID NO:60) |
| GTT | STSGSLVR | (SEQ ID NO:61) |
| TGA | SQAGHLAS | (SEQ ID NO:62) |

For the AP3 gene, only one target site was identified as a possible ZFP binding site using the current code. This site (5'-tac ttc ttc aac tcc atc-3') was located from −112 to −95 relative to the start of translation, about 70 base pairs upstream of the start of transcription. ZFPAp3 was selected to bind the compliment of this sequence (5'-GAT GGA GTT GAA GAA GTA-3') (SEQ ID NO:7). Of course, with a complete code falls in place in combo with present leadings, any sequence can be targeted.

For the MIPS gene, there were two possible regions in which ZFP could be targeted using current code. One was at the very 5' end of the cDNA from position −85 to −65 relative to the translational start site (5'-GCC TCC TTC CTC CTC TCA CTC-3') (SEQ ID NO:8). Two possible zinc fingers could be made to this site. ZFPm1 binds the compliment of this sequence from −68 to −85 (5'-TGA GAG GAG GAA GGA GGC-3') (SEQ ID NO:9) and ZFPm2 binds from −65 to −82 (5'-GAG TGA GAG GAG GAA GGA-3') (SEQ ID NO:10) of the compliment. Another location for ZFP binding sites was within the translated region of the gene from 294 to 317 (5'-GCC AAC TAC TAC GGC TCC CTC ACC-3') (SEQ ID NO: 11) after the translational start site. Two ZFPs were selected to bind the compliment of this site. ZFPm3 binds from 311 to 294 (5'-GGA GCC GTA GTA GTT GGC-3') (SEQ ID NO:12) and ZFPm4 binds from 317 to 300 (5'-GGT GAG GGA GCC GTA GTA-3') (SEQ ID NO:13). All four of these zinc finger proteins of the six-finger (hectadactyl) type were constructed. The activity of these different zinc fingers when fused to transcriptional regulatory domains should provide us with more information about the optimal binding position. This information will aid in selecting binding sites for new target genes.

Example 4

Construction of New Zinc Finger Protein ZFPAp3, ZFPm1, ZFPm2, ZFPm3, and ZFPm4

Since the specificity of the ZFP is determined by the DNA binding alpha helix, polydactyl zinc finger proteins with novel DNA specificity can be constructed by modifying the recognition helices of existing zinc finger proteins. A human zinc finger protein Sp1C has been selected to serve as a framework in the present example. It has been demonstrated that the Sp1C protein can provide a good framework for zinc finger domain modification (Beerli et al., Proc. Natl. Acad. Sci. USA (1998) 95:14628–14633).

New zinc finger proteins were constructed in two steps. First, three-finger ZFPs are constructed by PCR from overlapping oligonucleotides. These three-finger ZFPs are then fused together to create a six-finger (polydactyl) zinc finger protein to bind a specific 18 bp sequence. PCR construction of three-finger proteins was carried out in two sequential PCR reactions. In PCR1, the F2-b (finger 2-backward) and F2-f (finger 2-forward) primers were used as a template for PCR extension reaction with the F1-f1 (finger 1-first forward) and F3-b1 (finger 3 first backward) primers.

For example, in a 100 ul reaction, 1 ug F1-f1, 1 ug F3-b1. 0.1 ug F2-f, 0.1 ug F2-b, 8 ul 2.5 mM dNTP mix, 10 ul 10×Taq Buffer with 15 mM MgCl2 (Perkin Elmer), 0.5 ul 5 u/ul AmpliTaq Gold (Perkin Elmer). PCR conditions 1) 94° C. for 30sec; 2) 94° C. for 30sec; 3) 60° C. for 30sec; 4) 72° C. for 30sec; 5) repeat steps 2–4, 25 times; 6) 72° C. for 1 min. In the second reaction, PCR2, 1 ul of the PCR extension product from PCR1 is used as a template for PCR with F1-f2 (finger 1 second forward) and B3-b2 (finger 3 second backward) to extend the construct. In a 100 ul reaction, 1 ug F1-f2, 1 ug F3-b2, 1 ul PCR1 reaction, 8 ul 2.5 mM dNTP mix, 10 ul 10×Taq Buffer with 15 mM MgCl2 (Perkin Elmer), 0.5ul 5u/ul AmpliTaq Gold (Perkin Elmer). Amplify with same conditions used in PCR1. The 320 bp PCR product was digested with SfiI and the 300 bp fragment was isolated and ligated into a derivative of the pMal-C2 vector (New England Biolabs). When transformed into XL1-Blue E. coli, this vector provided IPTG-inducible expression of the zinc finger fused to the Maltose Binding Protein (MBP). The MBP fusion allows easy purification and detection of the zinc finger protein. Similarly, the second half of zinc finger protein domain (also containing three fingers) was synthesized using PCR extension reaction.

The following provides details of a typical construction of a zinc finger, in this case, construction of ZFPm2: The following primers were used to construct the ZFPm2a protein: F1-f1 (ggt aag tcc ttc AGC CGC AGC GAT AAC CTG GTG CGC cac cag cgt acc cac acg ggt gaa aaa ccg tat aaa tgc cca gag) (SEQ ID NO: 67), F1-f2 (gag gag gag gag gtg gcc cag gcg gcc ctc gag ccc ggg gag aag ccc tat gct tgt ccg gaa tgt ggt aag tcc ttc AGC CGC AGC) (SEQ ID NO: 68), F2-f (GC CAG GCC GGC CAC CTG GCC AGC cat caa cgc act cat act ggc gag aag cca tac aaa tgt cca gaa tgt ggc) (SEQ ID NO: 69), F2-b (GCT GGC CAG GTG GCC GGC CTG GCT aaa aga ttt gcc gca ctc tgg gca ttt ata cgg ttt ttc acc) (SEQ ID NO: 70), F3-b1 (CCG GAC GAG ATT GTC AGA CCG AGA gaa aga ctt gcc aca ttc tgg aca ttt gta tgg c) (SEQ ID NO: 71), F3-b2 (gag gag gag gag ctg gcc ggc ctg gcc act agt ttt ttt acc ggt gtg agt acg ttg gtg CCG GAC GAG ATT GTC AGA CCG) (SEQ ID NO: 72). These primers were used as described above to generate the 3-finger protein, ZFPm2a (SEQ ID NO:63):

```
  1 gaggaggagg aggtggccca ggcggccctc gagcccgggg
    agaagccta 50
 51 tgcttgtccg gaatgtggta agtccttcAG CCGCAGCGAT
    AACCTGGTGC 100
101 GCcaccagcg tacccacacg ggtgaaaaac cgtataaatg ccca-
    gagtgc 150
151 ggcaaatctt ttAGCCAGGC CGGCCACCTG
    GCCAGCcatc aacgcactca 200
201 tactggcgag aagccataca aatgtccaga atgtggcaag
    tctttcTCTC 250
251 GGTCTGACAA TCTCGTCCGG caccaacgta ctca-
    caccgg taaaaaaact 300
301 agtggccagg ccggccagct cctcctcctc 330
```

This protein has the framework of the Sp1C zinc finger protein (lower case sequences) with the DNA recognition helices replaced with the appropriate sequences (upper case sequences) to generate a zinc finger with a new binding specificity (5'-GAG TGA GAG). A similar set of primers was used to generate the ZFPm2b (SEQ ID NO:64) protein:

```
  1 gaggaggagg aggtggccca ggcggccctc gagcccgggg
    agaagccta 50
 51 tgcttgtccg gaatgtggta agtccttcTC TCAGAGCTCT
    CACCTGGTGC 100
101 GCcaccagcg tacccacacg ggtgaaaaac cgtataaatg ccca-
    gagtgc 150
151 ggcaaatctt ttAGCCAGTC CAGCAACCTG
    GTGCGCcatc aacgcactca 200
201 tactggcgag aagccataca aatgtccaga atgtggcaag
    tctttcTCTC 250
251 GGTCTGACAA TCTCGTCCGG caccaacgta ctca-
    caccgg taaaaaaact 300
301 agtggccagg ccggccagct cctcctcctc 330
```

This protein also has a Sp1C framework with altered recognition helices to bind (5'-GAG GAA GGA-3'). The first set of three finger protein (ZFPa) was fused to C-terminal to the second set of three finger protein (ZFPb) by ligating the ZFPa SpeIiXmaI 0.3 kb fragment and ZFPb XhoI-BsrFI 0.3 kb fragment into the pMal-C2 vector digested with XhoI and SpeI. The resulting six-finger zinc finger protein should specifically bind the target 18 bp sequence 5'-GAG TGA GAG GAG GAA GGA-3' (SEQ ID NO:65).

Using the same method, three-finger proteins with a Sp1C framework were made to bind the m1, m3, m4, and Ap3 target sites. These three-finger proteins were fused together to create the six-finger zinc finger. Restriction sites were designed in to allow ligation of the fragments. The five constructs that carried the ZFP genes were named as pMAL-m1, pMAL-m2, pMAL-m3, pMAL-m4, and pMAL-Ap3. The coding regions are the 500 bp fragment from Sfi digestion of each pMa1 plasmid and are named ZFPm1 (SEQ ID NO:14), ZFPm2 (SEQ ID NO:15), ZFPm3 (SEQ ID NO:16), ZFPm4 (SEQ ID NO: 17), and ZFPAp3 (SEQ ID NO: 18).

Example 5

Expression and Purification of ZFPA3, ZFPm1, ZFPm2, ZFPm3, and ZFPm4 Proteins in *E. coli*

A. Preparation of Zinc Finger Protein Crude Extracts

Zinc Finger Protein fusions were prepared as follows, primarily to obtain material for use in raising anti-ZFP antibodies and to assess binding affinity and specificity in vitro.

*E. coli* (XL1-Blue and (K12TB1) containing the zinc finger expression plasmid was first collected for each construct. Grow 3 ml culture of bacteria overnight in SB (10 g/l MOPS, 30 g/l Bacto Peptone, 20 g/l Yeast extract)+50 ug/ml Carbenicillin+1% Glucose at 37° C. Start 5 ml culture w/0.25 ml of overnight culture in SB+50 ug/ml Carbenicillin+0.2% Glucose+90 um ZnCl2 at 37° C. for 2 hrs. Add IPTG to a concentration of 0.3 mM. Shake at 37° .C for 2 hrs. Pellet bacteria at 2000 g for 5 min. Resuspend pellet in 0.3 ml Zn Buffer A (10 mM Tris base, 90 mM KCl, 1 mM MgCL2, pH 7.5)+5 mM DTT. Freeze suspension at −80° C. Freeze thaw 6 times between dry ice/ethanol bath and 37° C. water bath. Spin 14K for 5 min at 4° C. The supernatant is then ready for ELISA assay.

B. Purification of ZFPAp3, ZFPm1, ZFPm2, ZFPm3, and ZFPm4

All five zinc-finger proteins were affinity purified using New England Biolab's pMAL protein fusion purification Kit. One hundred ml of *E. coli* (K12TB1) that carried construct pMAL-m1, pMAL-m2, pMAL-m3, pMAL-m4, and pMAL-Ap3 separately was grown at 30° C. for overnight under the selection of Carbenicillin (same condition as above). Cells were collected through centrifugation and lysed through brief sonication on ice. The ZFPm1-MBP fusion protein was purified from this total lysate using New England Biolab's Kit (#800). The purified samples were quantitated and loaded on SDS-PAGE to estimate the quality. All five proteins were shown as single band on SDS-PAGE gel.

C. ZFP Antibody Production

Two antibodies were generated from the purified zinc finger proteins. Antibody I was made against the ZFPm1 antigen. Antibody II was made against an equal mixture of the ZFPm3 and ZFPm4 antigens. Both antibodies were tittered using ELISA procedure and Western Blots of zinc finger protein expressing cells.

Example 6

Characterization of DNA Binding Specificity of ZFPAp3, ZFPm1, ZFPm2, ZFPm3, and ZFPm4

Zinc finger protein can be characterized by any methods known in the art. For example, the zinc finger protein can be characterized by in vitro assay such as ELISA and in vivo assay such as gel shifting assay. ELISA assay can be used to characterized biding specificity of a particular zinc finger protein for a variety of target nucleotide sequences. Gel shifting assay can be sued to characterize binding affinity, i. e., obtaining binding constant, of a particular zinc finger protein for a particular target nucleotide sequence.

In this study, crude extracts of the three-finger and six-finger proteins were used for ELISA assay to evaluate the newly synthesized zinc finger protein's DNA binding specificity. The assay was also repeated with the purified six-finger proteins.

A. ELISA Procedures

Coat ELISA plates (Costar 3690) with streptavidin. Use 25 ul/well of 8 ug/ml streptavidin in PBS. Incubate at 37° C. for 1 hr. Wash 2× with dH2O. Bind wells with 25 ul/well of 4 ng/ul biotinylated target oligonucleotide in PBS. Incubate at 37° C. for 1 hr. Wash 2× with dH2O. Block with 175 ul/well of 3% BSA in Zn Buffer A. Incubate at 37° C. for 1 hr. Tap plates dry. Perform 1:2 serial dilutions of extract in Binding Buffer (1%BSA, 5 mM DTT, .12 ug/ul Salmon Sperm DNA in ZnBA). Usually from 1:4 to 1:512 for multi-target ELISA or 1:4 to 1:32 for screening clones for specific DNA binding activity. Incubate 1 hr at room temperature. Wash 8× with dH2O. Add primary antibody: 25 ul/well of 1:1000 dilution of mouse anti-MBP (Sigma M-6295) in 1% BSA ZnBA (no DTT). Incubate 30 min at room temperature. Wash 8× with dH2O. Add secondary antibody: 25 ul/well of 1:1000 dilution of goat anti-mouse/Alkaline Phosphatase (Pierce 31324) in 1% BSA ZnBA (no DTT). Incubate 30 min at room temperature. Wash 8× with dH2O. Develop with 25 ul developer (1 tablet of Sigma 104 Phosphatase Substrate (Sigma 104–105)/5 ml AP Developing Buffer [100 ml diethanolamine+0.05 g MgCl2+97.5 Sodium Azide, adjust to 500 ml with ddH2O, pH 9.88]). Incubate at room temperature for 5–60 min until color reaction is yellow. Read A405 with a plate reader.

B. ZFP Specificity Evaluation

Hairpin oligonucleotides with a 5' biotin conjugate were synthesized. The oligo m12 (5'-Biotin-GGa gcc tcc ttc ctc ctc tca ctc GGG TTTT CCC gag tga gag gag gaa gga ggc tCC-3') (SEQ ID NO:19) has the target sites for ZFPm1 and ZFPm2. Oligo m34 (5'-Biotin-GGa gcc aac tac tac ggc tcc ctc acc GGG TTTT CCC ggt gag gga gcc gta gta gtt ggc tCC-3') (SEQ ID NO:20) has the target sites for ZFPm3 and ZFPm4. The oligo Ap3 has the target site for the ZFPAp3 protein (5'-Biotin-GGt tac ttc ttc aac tcc atc GGG TTTT CCC gat gga gtt gaa gaa gta aCC-3') (SEQ ID NO:21). The individual three-finger ZFPs were evaluated on ELISA with the m12, m34, and Ap3 target oligos. In every case, the three-finger proteins bound their target oligo with significantly higher affinity than the non-target oligos. The eight non-target oligos are: NRI-1 (SEQ ID NO:22), NRI-2 (SEQ ID NO:23), hHD-I (SEQ ID NO:24), hHD-II (SEQ ID NO:25), c5c1-g (SEQ ID NO:26), c5p3-g (SEQ ID NO:27), B3c2 (SEQ ID NO:28), and e2c-g (SEQ ID NO:29). All five six-finger proteins, ZFPm1, ZFPm2, ZFPm3, ZFPm4, and ZFPAp3 were tested more extensively by ELISA with the m12, m34, Ap3, and the above eight non-target oligos. The six-finger proteins bound their targets better than any of the non-target oligos. ZFPm1, ZFPm4 and ZFPAp3 showed even higher specificity than ZFPm2 and ZFPm3 (FIG. 7–11). M12 site is a sequence that contains overlapping m1 and m2 binding sites. Similarly, m34 contains overlapping m3 and m4 sequences.

To evaluate the specificity of new zinc finger protein, the affinity of each protein was determined for binding to the target sequence and several non-target sequences at appropriate protein concentration. For example, to protein ZFPm1 and ZFPm2, the non-target oligoes are: Oligo m34 (SEQ ID NO:20), Oligo Ap3 (SEQ ID NO:21), NRI-1 (SEQ ID NO:22), NRI-2 (SEQ ID NO:23), hHD-I (SEQ ID NO:24), hHD-II (SEQ ID NO:25), c5c1-g (SEQ ID NO:26), c5p3-g (SEQ ID NO:27), B3c2 (SEQ ID NO:28), and e2c-g (SEQ ID NO:29). Similarly, to protein ZFPm3 and ZFPm4, the non-target oligoes are Oligo m12 (SEQ ID NO:19), oligo Ap3 (SEQ ID NO:21), and the eight other oligoes. To protein ZFPAp3, the non-target oligoes are Oligo m12, oligo m34 (SEQ ID NO:20), and the eight other oligoes. The affinity reading for target oligo was further normalized to the no oligo control which has the least affinity. Table 3 showed the relative affinity of each zinc finger protein to the listed 11 oligo sequences. This relative affinity represents the fold of specificity of each protein to its target (specific or non-specific). The higher number of the fold of specificity means the more specific of this protein to that particular oligo. For ZFPm1, ZFPm2, ZFPm3, ZFPm4, and ZFPAp3, the fold of specificity to its own target oligo are 18, 23, 13, 16, and 27, respectively, the highest number among all 11 oligoes tested. The result indicates that the six-finger protein, as well as the three-finger proteins, bound their target oligo with significantly higher affinity than the non-target oligoes in every case.

TABLE 3

ZFP specificity

| Protein (ug/ml) | Ap3 | m12 | m34 | NRI-1 | NRI-2 | hHD-I | hHD-II | c5c1-g | c5p3-g | B3c2 | e2c-g | no oligo |
|---|---|---|---|---|---|---|---|---|---|---|---|---|
| AFPm1 (31.0) | 4 | 18 | 5 | 5 | 4 | 5 | 4 | 7 | 3 | 4 | 2 | 1 |
| ZEPm2 (15.5) | 3 | 23 | 13 | 7 | 2 | 3 | 2 | 5 | 3 | 4 | 2 | 1 |
| ZFPm3 (1.9) | 7 | 3 | 13 | 4 | 6 | 1 | 3 | 3 | 3 | 3 | 9 | 1 |
| ZFPm4 (15.5) | 2 | 4 | 16 | 5 | 3 | 2 | 2 | 3 | 2 | 5 | 5 | 1 |
| ZFPAp3 (31.0) | 27 | 14 | 10 | 8 | 4 | 2 | 2 | 2 | 2 | 3 | 3 | 1 |

Refinements in binding affinity and specificity can be further obtained by random mutagenesis, as by PCR mutagenesis to introduce mutations in the ZFP to improve ZFP specificity or affinity.

C. DNA Binding Affinity of ZFPm1, ZFPm2, ZFPm3 ZFPm4, and ZFPAp3

The affinity of the purified six-finger proteins was measured using gel shift assay. The target oligos used in the ELISA assays were radioactively labeled using [γ32P]-ddATPk and terminal transferase. Ten serial dilutions of 1:3 with the purified protein (starting with ~1 mg/ml) in binding buffer (1 pM labeled oligo, 10% Glycerol, 0.8% BSA, 0.1 ug/ul salmon sperm DNA in Zn Buffer A) were performed. The ZFP was allowed to bind at room temperature for 1 hr. The samples were then run on 5–6% non-denaturing PAGE gel in TBE. The gel was dried and exposed with Phosphoimager. The affinity (Kd) of the ZFP was calculated from this gel. The Kd value is the concentration of the protein at which half of the labeled oligo is shifted to a higher molecular weight on the gel by binding to the ZFP. The affinities of these 6-finger proteins were determined to be: ZFPm1=2.0 nM, ZFPm2=7.5 nM, ZFPm3=0.18 nM, ZFPm4=0.25 nM and ZFPAp3=2.3 nM (FIG. 12–16). Most of these affinities compare favorably with the existed 6 finger proteins. The 2C7 derivative of the Sp1 zinc finger has a specificity of 0.46 nM and the e2c zinc finger constructed earlier (Beerli et al., *Proc. Natl. Acad. Sci. USA* (1998) 95:14628–14633) has an affinity of 0.5 nM.

D. Evaluation of Zinc Finger Protein ZFPm1, ZFPm2, ZFPm3, and ZFPm4 in Reporter I System (In Vivo Characterization)

To evaluate the in vivo binding ability of the zinc finger proteins, ZFPm1, ZFPm2, ZFPm3, and ZFPm4 were cloned into plasmid reporter I system. Two steps are involved: First step is to modify the reporter construct by replacing 2C7 binding site with MIPS gene specific binding site m12 and m34. The second step is to modify the activators (activation constructs) by replacing the 2C7 fragment with each of these four new zinc finger proteins. To evaluate ZFPm1, the ZFPm1-VP64 activation construct is co-transformed with m12-luciferase reporter construct. The luciferase reading from this activation transformation is compared to the BG luciferase activity (no activator). The ZFPm2, ZFPm3, and ZFPm4 are evaluated using the similar steps.

Figure 17:
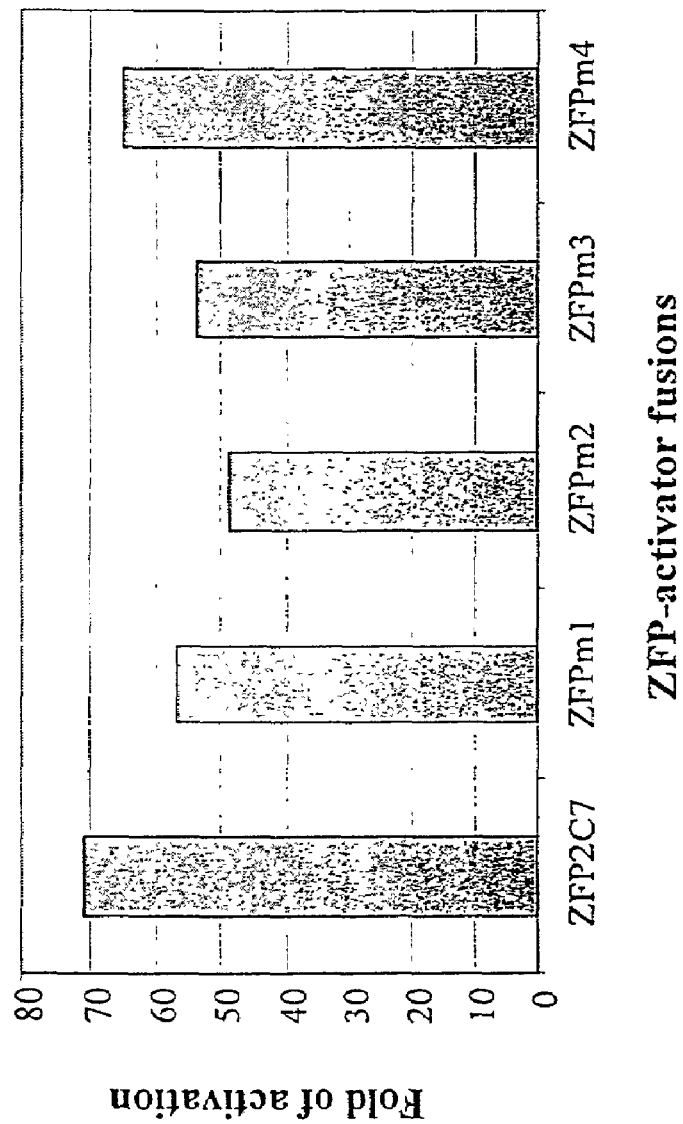
FIG. 17 In vivo characterization of newly synthesized zinc finger protein ZFPm1, ZFPm2, ZFPm3, and ZFPm4 in plant reporter system. The four activation fusion constructs are: ZmUbi::ZFPm1-VP64//nos, ZmUbi::ZFPm2-VP64//nos, ZmUbi::ZFPm3-VP64//nos, and ZmUbi::ZFPm4-VP64//nos. The reporter constructs are similar to reporter I in FIG. 1 except the 2C7 binding site was replaced by MIPS gene specific ZFP binding site m12 for ZFPm1 and ZFPm2 and by the second MIPS gene specific ZFP binding site m34 for ZFPm3 and ZFPm4.

The results show that all four new zinc finger proteins can mediate the activation of reporter gene. In this case, an endogenous target gene sequences were used as a heterologous target gene to activate the protein Luc fusion by piggy backing the VP64 regulator protein activator domain to a ZFP specific for the endogenous target gene sequence. The activation level is comparable to the 2C7 zinc finger protein (FIG. 17).

Example 7

Figure 18:
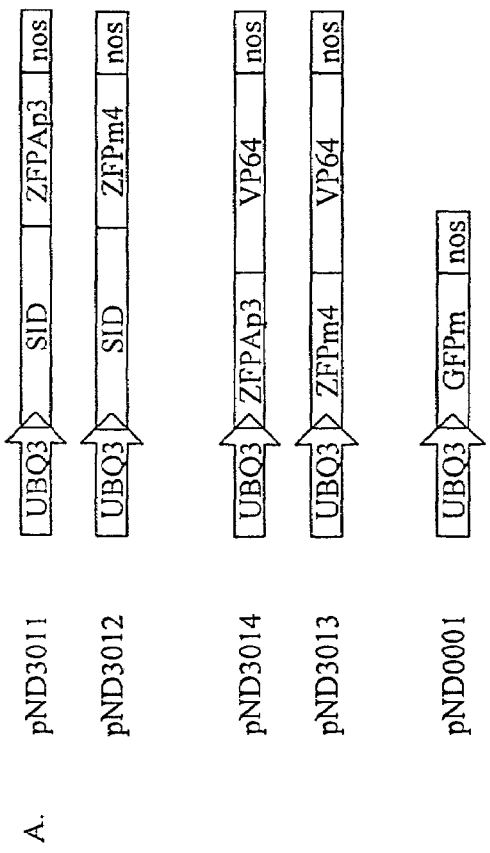
FIG. 18 ZFP-Effector fusion constructs for Arabidopsis transformation. ZFP-Effector constructs for *Arabidopsis* transformation. A. Transient transformation vectors: pND3011 and pND3012 are transcriptional repressors. pND3014 and pND3013 are transcriptional activators. pND0001 is control vector. B. Stable transformation vectors for Agrobacteria mediated plant transformation method.

Evaluation of AP3-specific ZFP-activators with Transient Assays in *Arabidopsis* Leaf Protoplasts A. Transformation of AP3-specific ZFP-activators into *Arabidopsis* Leaf Protoplasts The ZFPAp3 domain was fused to the N terminal of the VP64 activation domain and then cloned into plant expression vector under the control of the UBQ3 promoter (FIG. 18).

For transient expression of AP3 activator in *Arabidopsis* protoplasts, cut 10 fully expanded *Arabidopsis* leaves into 1 mm strips and add to 10 ml enzyme solution (2.5 mg/ml Yakult Macerozyme R10, 15 mg/ml Yakult Cellulase R10, 0.4M Mannitol, 10 mM MES-KOH (pH 5.6), 19 mM CaCl2, 0.35 ul/ml beta-Mercaptoethanol, 0.1% BSA). Incubate 30 min in the dark at room temp under vacuum (run vacuum pump for 3–4 min then hold vacuum and turn off pump). Incubate 1.5 hours on orbital shaker at room temp 40 rpm, in the dark. Incubate 5 min on orbital shaker at room temp 80 rpm, in the dark. Filter protoplasts through 70 um nylon mesh. Dilute with 4 mL 200 mM $CaCl_2$. Spin at 60 g 4° C., 5 min. Remove supernatant. Re-suspend pellet in 3 mL wash solution (333 mM Mannitol, 133 mM $CaCl_2$). Spin at 40 g for 5 minute 4° C. Remove supernatant. Suspend pellet in 2 mL W5 solution (154 mM NaCl, 125 mM $CaCl_2$, 5 mM KCl, 5 mM Glucose, 1.5 mM MES pH 5.6 with KOH). Incubate on ice 30 min. Count cells. Spin in 40 g, 4° C., 5 min. Remove supernatant. Re-suspend to $2 \times 10^6$ cells per mL MMM solution (0.6 M Mannitol, 22.5 mM $MgCl_2$, 7.5 mM-MES-KOH pH 5.6). Add 6 ug of effector plasmid DNA to a 2 ml centrifuge tube. Add 60 uL protoplast solution. Add 69 uL of a 40% PEG, 400 mM Mannitol, 100 mM $Ca(NO_3)_2$ solution. Mix thoroughly but gently by rolling tube. Incubate 30 min. at room temp. Dilute with 200 uL W5 solution, mix gently, and incubate 10 min at room temp. Add 400 uL W5 mix gently, incubate 10 min. room temp. Add 800 uL W5, mix gently. Spin in microcentrifuge at 60×g, room temp. for 5 min. Remove supernatant from all tubes. Re-suspend with 800 uL of 400 mM mannitol/W5 4:1 solution. Spin in microcentrifuge at 60×g, room temp. for 5 min. Remove supernatant. Re-suspend with 600 uL of culture medium (500 mM Mannitol, 10 mM KCl, 4 mM MES-KOH pH 5.6). Plate in 12 well Falcon culture plates. Incubate at room temp under fluorescent light for 24 hrs. Harvest the protoplasts using a large bore pipette Spin in microcentrifuge at 400 g, room temp, 5 min.

B. RT-PCR Analysis of Endogenous Gene AP3 Expression Level

Extract RNA with Qiagen Plant RNeasy kit. RTPCR 200 ng of RNA with Qiagen 1-step RTPCR kit in a 25 ul reaction [5 ul 5× Buffer, 1 ul dNTP's, 0.125 ul 100 uM Ap3-F (SEQ ID NO:30) (5'-GGCGAGAGGGAAGATCCAG-3'), 0.125 ul l 100 uM Ap3-4R (5'-CTCCTCTAATACGACTCACTAT-AGGGACACTCACCTAGCCTCTG-3') (SEQ ID NO:37), 1 ul Enzyme mix). Thermocycler setting: 50° C. 30', 95° C. 15', (94° C. 30", 60° C. 30", 72° C. 1')×39 cycles, 72° C. 10".

C. PCR Analysis of Effector Fusion Protein Expression Level

Using the RNA prepared above, the amount of activator expression can also be determined. AP3-specific effector expression can be detected by RTPCR as described above using a generic zinc finger forward primer, NZlib5' (GGC-CCAGGCGGCCCTCGAGC) (SEQ ID NO:31) and an Ap3-specific reverse primer Ap3f4-R, (CTAACCAAGGAGC-CACTGGTG) (SEQ ID NO:32). Similarly, the m4-specific effector expression can be detected using NZlib5' and a m4-specific reverse primer, m4f3-R (CCTCGCAAGAT-CACGACAATC) (SEQ ID NO:33).

D. Effects of Expressing ZFPAp3-activator Fusion Protein on the Transcriptional Level of Endogenous Gene AP3

Figure 19:
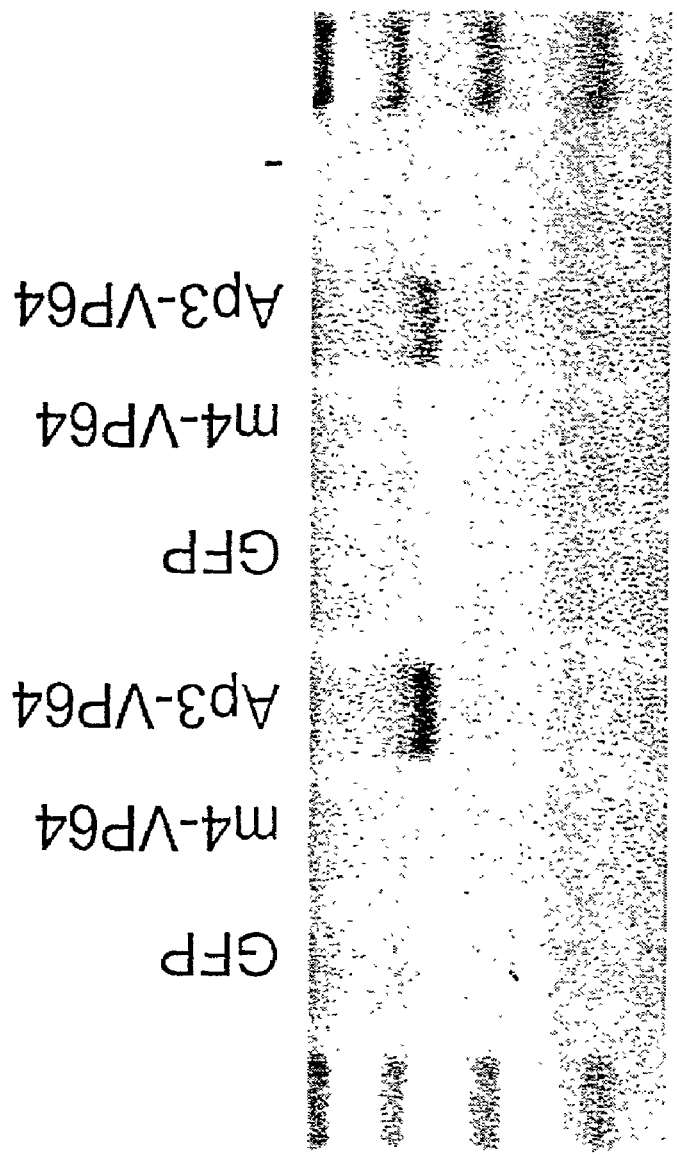
FIG. 19 Transient activation of endogenous AP3 gene in *Arabidopsis* leaf cells. RT-PCR was used to detect AP3 expression in *Arabidopsis* leaf protoplasts transformed with a GFP (pND0001, control), m4-VP64 (pND3013, non-specific activation control), and Ap3-VP64 (pND3014, AP3 specific activation). When no RNA was used in the RT-PCR reaction, no bands were seen (−). Transient transformation of a GFP or m4-VP64 construct have no effect on AP3 expression. The AP3-specific activator Ap3-VP64 causes a clear activation of AP3 expression.

The AP3 gene is expressed exclusively in the developing flower, so no expression was expected in the leaf-derived protoplasts. Three constructs, AP3 activation (pND3014), m4 activation (pND3013) and GFP control (pND0001) were transformed into *Arabidopsis* leaf cells (protoplasts) respectively. The ZFPm4-specific constructs was used as a control in this experiment to show that the gene specific transcription factors generated with this technology affect only their target gene since the ZFPm4-specific activator (ZFPm4-VP64) should have no effect on the endogenous AP3 gene. The result show that only in the cells that are transformed with AP3 activation constructs there are AP3 transcripts detected (FIG. 19). Thus the ZFP domain is able to direct the activation domain (VP64) to the specific endogenous target gene.

Example 8

Stable Repression and Stable Activation of AP3 Gene Expression in Transgenic *Arabidopsis*

A. Transformation of AP3-specific ZFP-repression Construct into *Arabidopsis* Plant An *Agrobacteria* transformation vector that contains expression cassette of UBQ3::SID-ZFPAp3//nos with hygromycin as selection marker was created and named as pND0051. Similarly, expression cassette of UBQ3::ZF-PAp3-VP64//nos (ZFPAp3 activation construct) was cloned into this *Agrobacteria* transformation vector as well and named as pND0052 (FIG. 18). These plasmids were then transformed into *Arabidopsis* plants using *Agrobacteria*-mediated transformation methods. About 20 transgenic plants were generated.

B. PCR Analysis of Effector Fusion Protein Expression Level

The expression of ZFPAp3 gene in each transgenic event was identified by RT-PCR (Example 7, section C).

C. RT-PCR Analysis of Endogenous Gene AP3 Expression Level

The transcriptional level of endogenous AP3 gene in each transgenic event was detected by RT-PCR (Example 7, section B).

D. Quantitative Analysis of AP3 Gene Expression Levels by Quantitative PCR

The TaqMan assay was used for quantifying AP3 gene expression in transformed *Arabidopsis* plant. The quantitative PCR probe for AP3 (SEQ ID NO:34) and two primers (SEQ ID NO:35 and SEQ ID NO:36) were designed using Primer Express (Perkin Elmer). RNA samples were prepared from average of two flower heads using RNAwiz method (Example 7, Section B). TaqMan PCR reaction was done using 250 ng total RNA and TaqMan One-step RT-PCR Master mix reagent. Thermal cycling conditions are: 48° C., 30 min.; 95° C., 10 min.; then followed by 40 cycles of 95° C., 15"; 60° C., 1 min. Data were analyzed using relative quantification of the comparative Ct method. For comparative Ct method, thioredoxin3 gene was used as a relative internal standard at this time.

E. Effects of Expressing ZFPAp3-repressor Fusion Protein on the Transcriptional Level of Endogenous Gene AP3

Both RT-PCR and quantitative PCR with AP3 specific primer was performed on these transgenic events (above example 7A). The endogenous gene AP3 expression level has been changed in several events, especially for three events: ND0052-2e, ND0052-257, and ND0051-1a.

Figure 20:
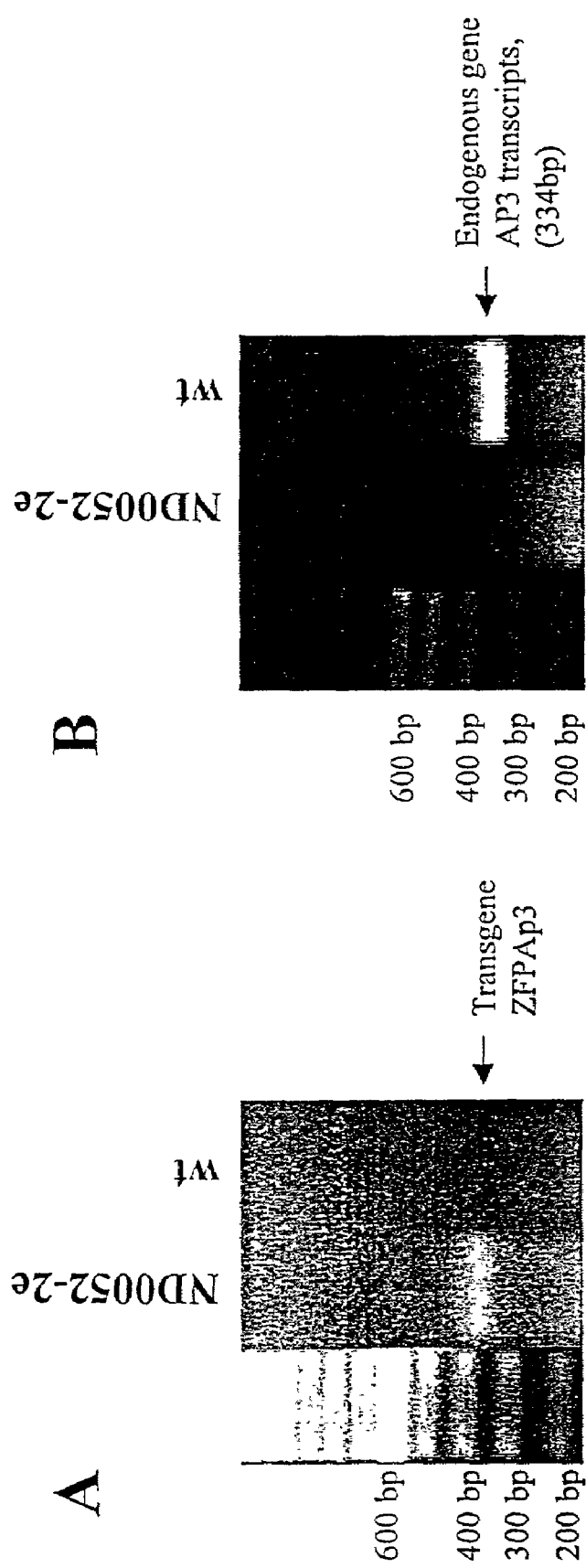
FIG. 20 Endogenous gene AP3 specifically repressed by the expression of ZFPAp3-repressor fusion protein in transgenic plant ND0052-2e. A. PCR identification of transgene ZFPAp3 in transgenic event ND0052-2e and wt plant. B. RT-PCR evaluation of endogenous gene AP3 expression level in transgenic event ND0052-2e and wild-type (wt) plant. In plant ND0052-2e, the expression of AP3 gene is significantly repressed by the expression of ZFPAp3-repressor (ZFPAp3-SID) fusion protein (Quantitative PCR shows a 46 fold of repression). The cDNA used in RT-PCR analysis was isolated from the flowers of each plant.

Plant ND0052-2e contains very high expression level of ZFPAp3-SID transgene (FIG. 20A). The transcriptional level of endogenous AP3 gene has been significantly down regulated (FIG. 20B). Quantitative analysis shows a nearly 50 fold of repression was achieved in this plant (FIG. 21).

Figure 21:
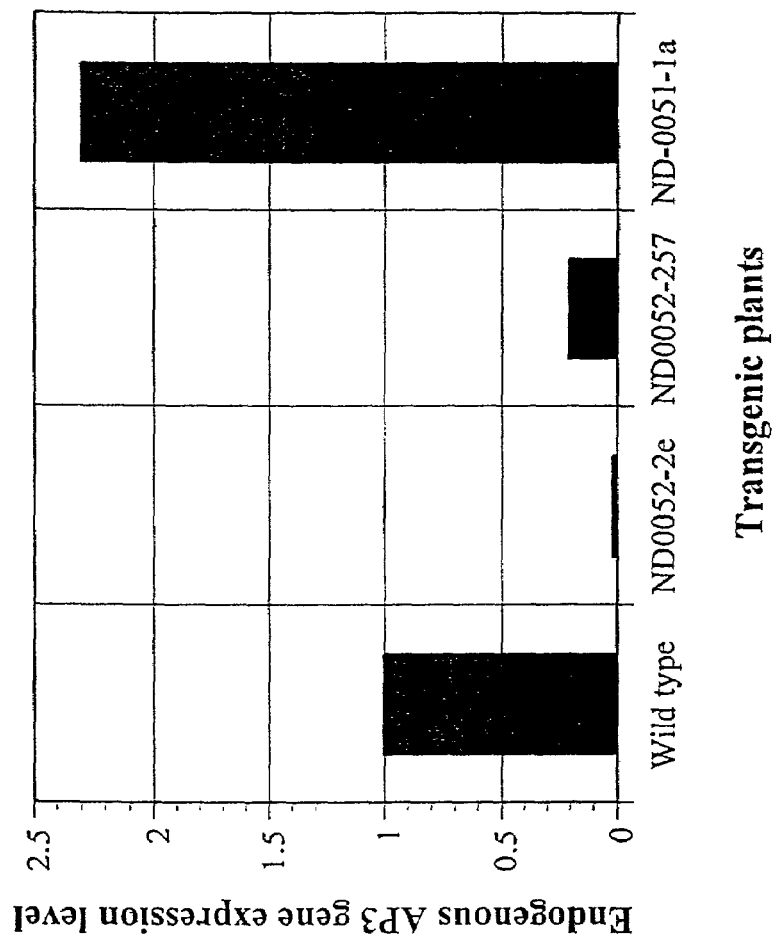
FIG. 21 Quantitative analysis of endogenous gene AP3 gene expression level in transgenic ZFPAp3 plants. The expression level of AP3 gene in transgenic plant is normalized to the wild type plant (defined as scale of 1). Repression event ND0052-2e shows a 46-fold of activation and ND0052 257 shows a 5 fold of repression. Activation event ND0052-1a shows a 2-fold of activation. Each sample was performed on triplicate assays.

The transcriptional level of endogenous AP3 gene in Plant ND0052-257 is less repressed compared to plant ND0052-2e, about 5 fold (FIG. 21).

Only one event containing activation construct was confirmed and designated as ND0051-1a. Curiously, there was a two-fold activation of the endogenous AP3 gene in this plant (FIG. 21). The phenotype of this plant looks normal. We have not been able to detect the protein expression level in this plant. Considering the significantly less number of activation events that were finally identified (ten to twenty times less than the number of repression events, Table I), it is reasonable to assume that over-activation and over-expression of AP3 gene is toxic to the plant. This toxic effect could cause lose of transgenic events during selection and regeneration. Consistent with this notion is that our transient regulation data indicates that activation is much more efficient than repression. Expression of ZFPAp3 VP64 construct with a weaker promoter or with an inducible promoter would or might increase transgenic events.

F. Phenotype Changes Caused by Expressing ZFPAp3-repressor Fusion Protein in Transgenic *Arabidopsis*

Among the repression events, there are three independent events that showed significant phenotype changes: flower structures and fertility. They are named as ND0052-2e, ND0052-2d, and ND0052-257. Molecular analysis has been performed on the ND0052-2e and ND0052-257 (Example 8, section E).

The first event, ND0051-2e, did not have a typical flower formation compared to the wildtype flower: the petals are under developed (short and narrow) and partially converted to sepal-like structure; the stamens are much smaller in size compared to the wildtype plant. However, there may be some pullens on the anther. The carpel appears normal except that the size is significantly bigger and developed much faster than the stamens. Generally, the phenotype of this flower is similar to the flowers from previously characterized mutant ap3 (Jack et al., *Cell* (1992) 68:683–687, Jack et al., *Cell* (1994) 76:703–716) and sap (Byzova et al., *Gene and Development* (1999) 13:1002–1014) but is definitely not identical. This plant is sterile. Comparing with the morphology of this flower with the wild type flower, it appears that the un-proportional development of stamen and stigma is the cause of sterility. More detailed analysis can be carried out in this area.

The second event is named as ND0052-257. This is a sterile plant too. The flower is very similar to flower from ND0052-2e. However, there seems missing one petal in the two flowers that we have dissected.

The third event is named as ND0051-2d. Same as the previous two, it is a sterile plant. There is no silique formation in this plant. The plant died during flowering stage.

Wild type flowers have four organ types (sepal, petal, stamen, carpel) arranged in concentric whorls. The AP3 gene is involved in the determination of organ identity. Misexpression of the AP3 gene results in homeotic mutations where whorl-specific organ identity will be altered. While we expected the phenotypes of the activated and repressed AP3 plants that generated through zinc finger protein technology should mimic the phenotype of previously described AP3 overexpressors, ap3 mutants (Jack et al., *Cell* (1992) 68:683–687, Jack et al., *Cell* (1994) 76:703–716), and sap (Byzova et al., *Gene and Development* (1999) 13:1002–1014), we also think the phenotype can not be identical since the mechanism of repression AP3 gene is different.

The promoter driving the expression of zinc finger protein is ubiquitin3 (UBQ3) promoter. UBQ3 is a constitutive promoter and the expression pattern and strength is very different from the native AP3 promoter.

We are analyzing more transgenic plants (both repression events and activation events) now. We will choose several plants (4 to 5) with different expression level of zinc finger protein through Western analysis. The level of AP3 expression can then be correlated with the floral phenotype and effector expression levels.

AP3 gene is one of the many genes that are involved in floral organ determination (Weigel, *Annu. Rev. Genetics* (1995) 29:19–39; and Pineiro and Coupland, *Plant Physiol* (1998) 117:108). It is very likely that there are other genes, especially the down stream genes, that play a role in this very complex process as well. We plan to conduct gene chip assay (Affymetrix) on the final selected AP3 events. This assay should provide us with more insight into the floral development and regulation process.

More sterile plants have been identified other than the three events mentioned above. It is estimated that the chance of getting sterile phenotype with our repression construct is about 5 to 10%.

Example 9

Stable Activation of AP3 Gene Expression in Transgenic *Arabidopsis* with Floral Specific Promoter AP3

*Arabidopsis* AP3 promoter region (1.9 kb) was isolated by PCR according to Irish and Yamamoto (Plant Cell 7 (10), 1635–1644 (1995)). This fragment was used to replace the UBQ3 fragment in the pND0052 construct. The final construct was named as pND3045 (AraAP3 promoter::ZFPAp3-VP64//nos). pND3045 was transformed into *Arabidopsis* as described in previous section. About 400 plants were generated through selection media. There are several plants that have shown sterile phenotype already. Molecular analysis on these events can be performed as previously described.

High numbers of transgenic plants have been easily selected with this tissue specific activation construct. With our previous activation construct pND0051 (with constitute promoter UBQ3), we only obtained three transgenic plants and none of them shows high level of ZFP expression and none of them shows phenotypic changes. These results support our previous hypothesis that over-activation and over-expression of AP3 gene is toxic to the plant.

Example 10

Evaluation of Regulation of Endogenous Gene Expression using the Zinc Finger Proteins having Less than Six Fingers The Ap3-VP64 6-finger construct appears to work effectively and specifically to activate and repress AP3 expression in *Arabidopsis* protoplasts or even the whole plant. This is a good system to test the activity of zinc finger protein with less than 6 fingers, such as 3-finger effector constructs. The 6-finger ZFPAp3 protein was constructed from two 3-finger proteins (See Example 3). ZPFAp3a is a 3-finger protein with fingers 4–6 of ZFPAp3. Similarly, ZFPAp3b has fingers 1 to 3 of ZFPAp3.

To test these 3-finger constructs, the Ap3-VP64 expression plasmid is digested with SfiI to remove the 6-finger Ap3 coding region. The 300 bp SfiI fragment of the AP3 3-finger proteins is ligated in this digested vector to generate Ap3a-VP64 and Ap3b-VP64 constructs. The activation of AP3 expression in protoplasts is tested with these constructs using the method described in Example 7 and 8. Generally, 3-finger protein is less specific than the 6-finger protein. But, this may not be the case for all the targets (genes). If some of these 3-finger effectors are able to specifically and effectively activate AP3 expression, this will indicate that 6 finger proteins are not required for all targets. This will also demonstrate the versatility of this technology with respect to the number of zinc fingers required.

Example 11

Evaluation of ZFP-activator/Repressor Fusion Protein Function in Maize

MIPS is an endogenous maize enzyme. Its gene expression level can be monitored at three levels after transforming the maize cells with ZFPmips-activator or ZFPmips-repressor. The first level is on the transcriptional level. Quantitative PCR can be used to analyze the abundant of MIPS transcripts. The second level is on the protein expression level. We have generated MIPS specific antibody and can analyze the amount of MIPS protein expressed on Western blot. The third level is on the function level of MIPS enzyme. The activity of MIPS enzyme can be monitored by the concentration of its product, phytic acid through HPLC (Talamond et al., *J. of Chromatography* (1998) 805:143–147) and colorimetric method (Sigma, #670-A).

A. Construction of Maize MIPS-specific ZFP-effectors

Four activation constructs were generated for ZFPm1, ZFPm2, ZFPm3, and ZFPm4 (ZFPmips) by fusing the ZFPmips domain to the N terminal of the VP64 activation domain. Two repression constructs were generated for ZFPm1 and ZFPm4 by fusing the ZFPmips domain to the C terminal of the SID repression domain. Then the ZFPmips-effector cassette was cloned into monocot expression vector under the control of the maize ubiquitin (ZmUbi) promoter (same as in pND3008). A "nos" fragment was placed at the 3' end of this cassette as transcription terminator (same as in pND3008). These six constructs are named as pND3015, pND3023, pND3024, pND3016, pND3019, and pND3017 (FIG. 22).

Our transient regulation result in maize cells indicates that activation is more efficient than repression. So we have transformed all eight constructs into maize cells. A successful activation of MIPS gene in maize is an indication of success of this zinc finger protein technology in regulating another endogenous gene in another plant species. Maize is monocot and considered as crop plant with MIPS as an agronomic trait.

B. Function of ZFPmips-effectors in Maize

Figure 22:
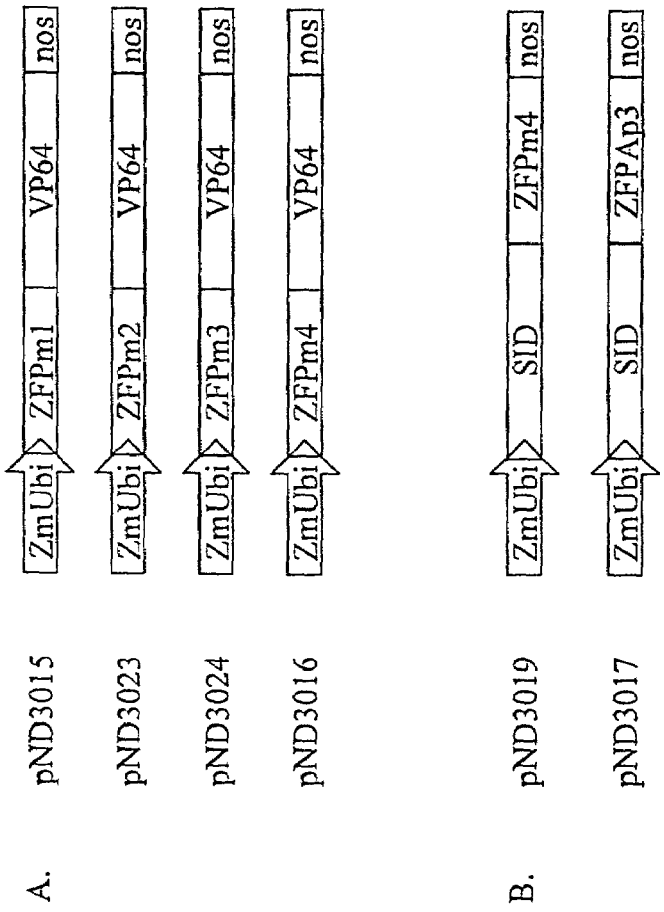
FIG. 22 ZFP-Effector fusion constructs for maize transformation. A. MIPS gene specific activation constructs. B. MIPS gene specific repression constructs.
Figure 23:
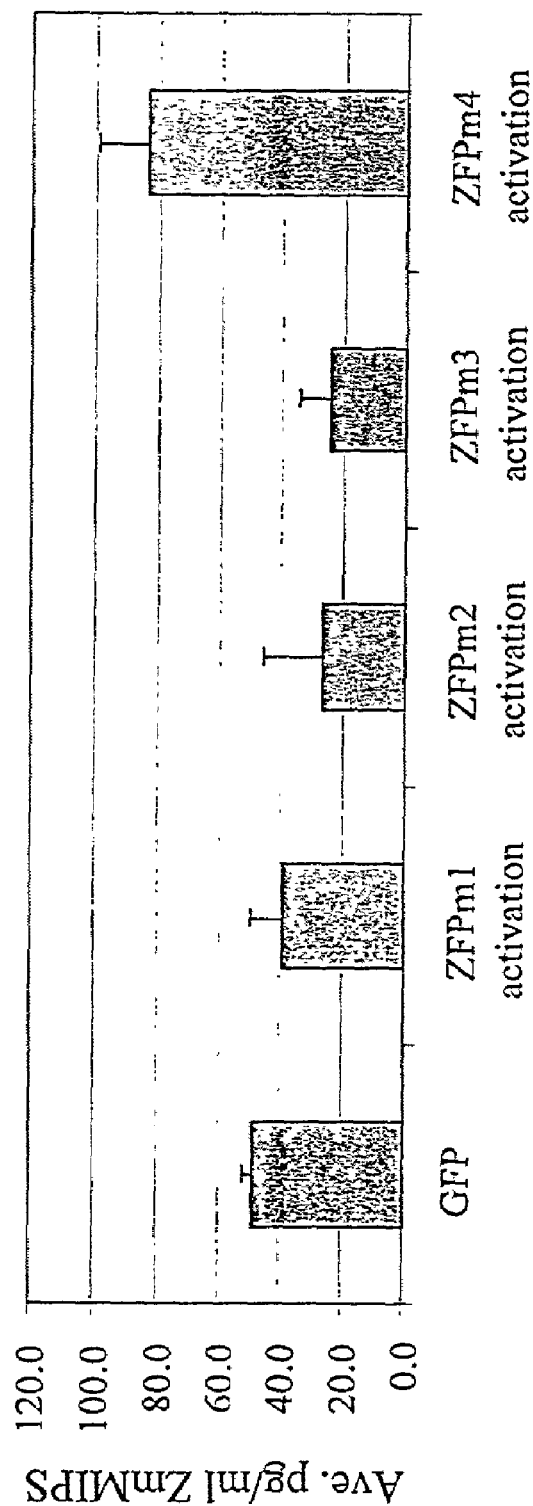
FIG. 23 Transient activation of endogenous MIPS gene in maize cells. Quantitative PCR was used to detect MIPS expression in maize cells transformed with a GFP (control), m1-VP64 (pND3015), m2-VP64 (pND3023), m3-VP64 (pND3024), and m4-VP64 (pND3016). The activator ZFPm4-VP64 causes activation of MIPS expression.

A maize type II cell line HE89 was used to evaluate the ZFPmips-effector fusion constructs function (FIG. 22). Protoplasts from HE89 suspension cells were isolated and transformed using standard procedures (Chourey and Zurawski, 1981). The activation constructs pND3015, pND3023, pND3024, and pND3016 were transformed into freshly prepared protoplasts. The transcription level of MIPS gene was detected through quantitative PCR. With pND3016 (ZFPm4-VP64 activation constructs), at least 2-fold of activation is detected (FIG. 23). We also measured phytic acid concentration in maize tissues that were transformed by the activation construct of pND3016. We found that the phytic acid concentration is increased from 304 pg/ml to 569 pg/ml (detection was carried out with HPLC).

We have demonstrated herein that zinc finger protein approach can be used in both up-regulation (as example of AP3 in *Arabidopsis* , MIPS in maize) and down-regulation (as example of AP3 in *Arabidopsis* ) of endogenous gene expression in plant.

The above examples are included for illustrative purposes only and is not intended to limit the scope of the invention. Since modifications will be apparent to those of skill in this art, it is intended that this invention be limited only by the scope of the appended claims.

SEQUENCE LISTING

<160> NUMBER OF SEQ ID NOS: 79

<210> SEQ ID NO 1
<211> LENGTH: 532
<212> TYPE: DNA
<213> ORGANISM: Artificial Sequence
<220> FEATURE:
<223> OTHER INFORMATION: Promoter CsVMV

<400> SEQUENCE: 1

-continued

```
tctagaaact agcttccaga aggtaattat ccaagatgta gcatcaagaa tccaatgttt      60
acgggaaaaa ctatggaagt attatgtgag ctcagcaaga agcagatcaa tatgcggcac     120
atatgcaacc tatgttcaaa aatgaagaat gtacagatac aagatcctat actgccagaa    180
tacgaagaag aatacgtaga aattgaaaaa gaagaaccag gcgaagaaaa gaatcttgaa    240
gacgtaagca ctgacgacaa caatgaaaag aagaagataa ggtcggtgat tgtgaaagag   300
acatagagga cacatgtaag gtggaaaatg taagggcgga agtaacctt atcacaaagg    360 aatcttatcc cccactactt atcctttat attttccgt gtcatttttg cccttgagtt     420
ttcctatata aggaaccaag ttcggcattt gtgaaaacaa gaaaaaattt ggtgtaagct    480
attttctttg aagtactgag gatacaactt cagagaaatt tgtaagtttg ta           532
```

<210> SEQ ID NO 2
<211> LENGTH: 18
<212> TYPE: DNA
<213> ORGANISM: Artificial Sequence
<220> FEATURE:
<223> OTHER INFORMATION: Zinc finger protein 2C7 binding site

<400> SEQUENCE: 2

```
gcgtgggcgg cgtgggcg                                                   18
```

<210> SEQ ID NO 3
<211> LENGTH: 51
<212> TYPE: DNA
<213> ORGANISM: Artificial Sequence
<220> FEATURE:
<223> OTHER INFORMATION: Promoter pc7rbTATA

<400> SEQUENCE: 3

```
cccgggtata taataagctt ggcattccgg tactgttggt aaagccacca t              51
```

<210> SEQ ID NO 4
<211> LENGTH: 3121
<212> TYPE: DNA
<213> ORGANISM: Artificial Sequence
<220> FEATURE:
<223> OTHER INFORMATION: pND3008 coding region

<400> SEQUENCE: 4

```
agcgtgaccc ggtcgtgccc ctctctagag ataatgagca ttgcatgtct aagttataaa      60
aaattaccac atatttttt tgtcacactt gtttgaagtg cagtttatct atctttatac    120
atatatttaa actttactct acgaataata taatctatag tactacaata atatcagtgt    180
tttagagaat catataaatg aacagttaga catggtctaa aggacaattg agtattttga    240
caacaggact ctacagtttt atcttttag tgtgcatgtg ttctcctttt tttttgcaaa    300
tagcttcacc tatataatac ttcatccatt ttattagtac atccatttag ggtttagggt    360
taatggtttt tatagactaa tttttttagt acatctattt tattctattt tagcctctaa    420
attaagaaaa ctaaaactct attttagttt tttatttaa taatttagat ataaaataga    480
ataaaataaa gtgactaaaa attaaacaaa taccctttaa gaaattaaaa aaactaagga    540 aacattttc ttgtttcgag tagataatgc cagcctgtta acgccgtcg acgagtctaa     600 cggacaccaa ccagcgaacc agcagcgtcg cgtcgggcca agcgaagcag acggcacggc    660
atctctgtcg ctgcctctgg accctctcg agagttccgc tccaccgttg gacttgctcc     720
gctgtcggca tccagaaatt gcgtggcgga gcggcagacg tgagccggca cggcaggcgg    780
```

-continued

```
cctcctcctc ctctcacggc acggcagcta cggggggattc ctttcccacc gctccttcgc    840
tttcccttcc tcgcccgccg taataaatag acaccccctc cacaccctct ttccccaacc    900
tcgtgttgtt cggagcgcac acacacacaa ccagatctcc cccaaatcca cccgtcggca    960
cctccgcttc aaggtacgcc gctcgtcctc ccccccccc cctctctacc ttctctagat    1020
cggcgttccg gtccatggtt agggcccggt agttctactt ctgttcatgt ttgtgttaga    1080
tccgtgtttg tgttagatcc gtgctgctag cgttcgtaca cggatgcgac ctgtacgtca    1140
gacacgttct gattgctaac ttgccagtgt ttctctttgg ggaatcctgg gatggctcta    1200
gccgttccgc agacgggatc gatttcatga ttttttttgt ttcgttgcat agggtttggt    1260
ttgccctttt cctttatttc aatatatgcc gtgcacttgt ttgtcgggtc atcttttcat    1320 gcttttttt gtcttggttg tgatgatgtg gtctggttgg gcggtcgttc tagatcggag    1380
tagaattctg tttcaaacta cctggtggat ttattaattt tggatctgta tgtgtgtgcc    1440
atacatattc atagttacga attgaagatg atggatggaa atatcgatct aggataggta    1500
tacatgttga tgcgggtttt actgatgcat atacagagat gcttttttgtt cgcttggttg    1560 tgatgatgtg gtgtggttgg gcggtcgttc attcgttcta gatcggagta gaatactgtt    1620
tcaaactacc tggtgtattt attaattttg gaactgtatg tgtgtgtcat acatcttcat    1680
agttacgagt ttaagatgga tggaaatatc gatctaggat aggtatacat gttgatgtgg    1740
gttttactga tgcatataca tgatggcata tgcagcatct attcatatgc tctaaccttg    1800
agtacctatc tattataata aacaagtatg ttttataatt attttgatct tgatatactt    1860
ggatgatggc atatgcagca gctatatgtg gatttttta gccctgcctt catacgctat    1920
ttatttgctt ggtactgttt cttttgtcga tgctcaccct gttgtttggt gttacttctg    1980
caggtcgact ctagaggatc tatggcccag gcggccctcg agctccccta tgcttgccct    2040
gtcgagtcct gcgatcgccg cttttctaag tcggctgatc tgaagcgcca tatccgcatc    2100
cacacaggcc agaagcccctt ccagtgtcga atatgcatgc gtaacttcag tcgtagtgac    2160
caccttacca cccacatccg cacccacaca ggcgagaagc cttttgcctg tgacatttgt    2220
gggaggaagt ttgccaggag tgatgaacgc aagaggcata ccaaaatcca taccggtgag    2280
aagccctatg cttgccctgt cgagtcctgc gatcgccgct tttctaagtc ggctgatctg    2340
aagcgccata tccgcatcca cacaggccag aagcccttcc agtgtcgaat atgcatgcgt    2400
aacttcagtc gtagtgacca ccttaccacc cacatccgca cccacacagg cgagaagcct    2460
tttgcctgtg acatttgtgg gaggaagttt gccaggagtg atgaacgcaa gaggcatacc    2520
aaaatccatt taagacagaa ggactctaga actagtggcc aggccggcca ggctagcccg    2580 aaaagaaac gcaaagttgg gcgcgccgac gcgctggacg atttcgatct cgacatgctg    2640
ggttctgatg ccctcgatga ctttgacctg gatatgttgg gaagcgacgc attggatgac    2700
tttgatctgg acatgctcgg ctccgatgct ctggacgatt cgatctcga tatgttaatt    2760 aactacccgt acgacgttcc ggactacgct tcttgagaat cgcggccgc gggcccgagc    2820 ctagggagga gctcaagatc ccccgaattt ccccgatcgt tcaaacattt ggcaataaag    2880
tttcttaaga ttgaatcctg ttgccggtct tgcgatgatt atcatctaat ttctgttgaa    2940
ttacgttaag catgtaataa ttaacatgta atgcatgacg ttatttatga gatgggtttt    3000
tatgattaga gtcccgcaat tatacattta atacgcgata gaaaacaaaa tatagcgcgc    3060
aaactaggat aaattatcgc gcgcggtgtc atctatgtta ctagatccgg gaattgggta    3120
c                                                                    3121
```

<210> SEQ ID NO 5
<211> LENGTH: 3069
<212> TYPE: DNA
<213> ORGANISM: Artificial Sequence
<220> FEATURE:
<223> OTHER INFORMATION: pND3018 coding redion

<400> SEQUENCE: 5

| | | | | | |
|---|---|---|---|---|---|
| agcgtgaccc | ggtcgtgccc | ctctctagag | ataatgagca | ttgcatgtct | aagttataaa | 60 |
| aaattaccac | atatttttt | tgtcacactt | gtttgaagtg | cagtttatct | atctttatac | 120 |
| atatatttaa | actttactct | acgaataata | taatctatag | tactacaata | atatcagtgt | 180 |
| tttagagaat | catataaatg | aacagttaga | catggtctaa | aggacaattg | agtattttga | 240 |
| caacaggact | ctacagtttt | atcttttag | tgtgcatgtg | ttctcctttt | tttttgcaaa | 300 |
| tagcttcacc | tatataatac | ttcatccatt | ttattagtac | atccatttag | ggtttagggt | 360 |
| taatggtttt | tatagactaa | ttttttagt | acatctattt | tattctattt | tagcctctaa | 420 |
| attaagaaaa | ctaaaactct | attttagttt | tttatttaa | taatttagat | ataaaataga | 480 |
| ataaaataaa | gtgactaaaa | attaaacaaa | tacccttaa | gaaattaaaa | aaactaagga | 540 |
| aacatttttc | ttgtttcgag | tagataatgc | cagcctgtta | aacgccgtcg | acgagtctaa | 600 |
| cggacaccaa | ccagcgaacc | agcagcgtcg | cgtcgggcca | agcgaagcag | acggcacggc | 660 |
| atctctgtcg | ctgcctctgg | accccctctcg | agagttccgc | tccaccgttg | gacttgctcc | 720 |
| gctgtcggca | tccagaaatt | gcgtggcgga | gcggcagacg | tgagccggca | cggcaggcgg | 780 |
| cctcctcctc | ctctcacggc | acggcagcta | cggggattc | ctttcccacc | gctccttcgc | 840 |
| tttcccttcc | tcgcccgccg | taataaatag | acacccctc | cacaccctct | tccccaacc | 900 |
| tcgtgttgtt | cggagcgcac | acacacacaa | ccagatctcc | cccaaatcca | cccgtcggca | 960 |
| cctccgcttc | aaggtacgcc | gctcgtcctc | ccccccccc | cctctctacc | ttctctagat | 1020 |
| cggcgttccg | gtccatggtt | agggcccggt | agttctactt | ctgttcatgt | ttgtgttaga | 1080 |
| tccgtgtttg | tgttagatcc | gtgctgctag | cgttcgtaca | cggatgcgac | ctgtacgtca | 1140 |
| gacacgttct | gattgctaac | ttgccagtgt | ttctctttgg | ggaatcctgg | gatggctcta | 1200 |
| gccgttccgc | agacgggatc | gatttcatga | ttttttttgt | ttcgttgcat | agggtttggt | 1260 |
| ttgccctttt | cctttatttc | aatatatgcc | gtgcacttgt | ttgtcgggtc | atcttttcat | 1320 |
| gctttttttt | gtcttggttg | tgatgatgtg | gtctggttgg | gcggtcgttc | tagatcggag | 1380 |
| tagaattctg | tttcaaacta | cctggtggat | ttattaattt | tggatctgta | tgtgtgtgcc | 1440 |
| atacatattc | atagttacga | attgaagatg | atggatggaa | atatcgatct | aggataggta | 1500 |
| tacatgttga | tgcgggtttt | actgatgcat | atacagagat | gcttttgtt | cgcttggttg | 1560 |
| tgatgatgtg | gtgtggttgg | gcggtcgttc | attcgttcta | gatcggagta | gaatactgtt | 1620 |
| tcaaactacc | tggtgtattt | attaatttg | gaactgtatg | tgtgtgtcat | acatcttcat | 1680 |
| agttacgagt | ttaagatgga | tggaaatatc | gatctaggat | aggtatacat | gttgatgtgg | 1740 |
| gttttactga | tgcatataca | tgatggcata | tgcagcatct | attcatatgc | tctaaccttg | 1800 |
| agtacctatc | tattataata | aacaagtatg | tttttataatt | attttgatct | tgatatactt | 1860 |
| ggatgatggc | atatgcagca | gctatatgtg | gattttttta | gccctgcctt | catacgctat | 1920 |
| ttatttgctt | ggtactgttt | cttttgtcga | tgctcaccct | gttgtttggt | gttacttctg | 1980 |
| caggtcgact | ctagaggatc | cactagtgag | ccatgggcta | gcatggccgc | tgccgtgcgc | 2040 |

```
atgaacatcc agatgctgct cgaagccgct gattatctgg aacgccggga gcgcgaagcc    2100
gagcacggct acgccagcat gctgccatat ccgaaaaaga aacgcaaggt ggcccaggcg    2160
gccctcgagc tcccctatgc ttgccctgtc gagtcctgcg atcgccgctt ttctaagtcg    2220
gctgatctga agcgccatat ccgcatccac acaggccaga agcccttcca gtgtcgaata    2280
tgcatgcgta acttcagtcg tagtgaccac cttaccaccc acatccgcac ccacacaggc    2340
gagaagcctt ttgcctgtga catttgtggg aggaagtttg ccaggagtga tgaacgcaag    2400
aggcatacca aaatccatac cggtgagaag ccctatgctt gccctgtcga gtcctgcgat    2460
cgccgctttt ctaagtcggc tgatctgaag cgccatatcc gcatccacac aggccagaag    2520
cccttccagt gtcgaatatg catgcgtaac ttcagtcgta gtgaccacct taccacccac    2580
atccgcaccc acacaggcga gaagcctttt gcctgtgaca tttgtgggag gaagtttgcc    2640
aggagtgatg aacgcaagag gcataccaaa atccatttaa acagaaagga ctctagaact    2700
agtggccagg ccggccagta cccgtacgac gttccggact acgcttcttg aaagcttggt    2760
accgagctcg gatccccgga atttccccga tcgttcaaac atttggcaat aaagtttctt    2820
aagattgaat cctgttgccg gtcttgcgat gattatcatc taatttctgt tgaattacgt    2880
taagcatgta ataattaaca tgtaatgcat gacgttattt atgagatggg ttttttatgat  2940 tagagtcccg caattataca tttaatacgc gatagaaaac aaaatatagc gcgcaaacta    3000
ggataaatta tcgcgcgcgg tgtcatctat gttactagat ccgggaattc cggaccggta    3060
ccagcggcc                                                           3069

<210> SEQ ID NO 6
<211> LENGTH: 156
<212> TYPE: DNA
<213> ORGANISM: Artificial Sequence
<220> FEATURE:
<223> OTHER INFORMATION: 6X2C7 binding site

<400> SEQUENCE: 6
cgtgctagcg cgtgggcggc gtgggcgaac aagcgtgggc ggcgtggcg aacaagcgtg      60 ggcggcgtgg gcgactagtg ctagcgcgtg ggcggcgtgg gcgaacaagc gtgggcggcg   120
tgggcgaaca agcgtgggcg gcgtgggcga ctagtg                             156

<210> SEQ ID NO 7
<211> LENGTH: 18
<212> TYPE: DNA
<213> ORGANISM: Artificial Sequence
<220> FEATURE:
<223> OTHER INFORMATION: ZFPAp3

<400> SEQUENCE: 7
gatggagttg aagaagta                                                   18

<210> SEQ ID NO 8
<211> LENGTH: 21
<212> TYPE: DNA
<213> ORGANISM: Artificial Sequence
<220> FEATURE:
<223> OTHER INFORMATION: ZFP from -85 to -65

<400> SEQUENCE: 8
gcctccttcc tcctctcact c                                               21

<210> SEQ ID NO 9
<211> LENGTH: 18
```

```
<212> TYPE: DNA
<213> ORGANISM: Artificial Sequence
<220> FEATURE:
<223> OTHER INFORMATION: ZFPm1 from -68 to -85

<400> SEQUENCE: 9
tgagaggagg aaggaggc                                                  18

<210> SEQ ID NO 10
<211> LENGTH: 18
<212> TYPE: DNA
<213> ORGANISM: Artificial Sequence
<220> FEATURE:
<223> OTHER INFORMATION: ZFPm2 from -65 to -82

<400> SEQUENCE: 10
gagtgagagg aggaagga                                                  18

<210> SEQ ID NO 11
<211> LENGTH: 24
<212> TYPE: DNA
<213> ORGANISM: Artificial Sequence
<220> FEATURE:
<223> OTHER INFORMATION: ZFP from 294 to 317

<400> SEQUENCE: 11
gccaactact acggctccct cacc                                           24

<210> SEQ ID NO 12
<211> LENGTH: 18
<212> TYPE: DNA
<213> ORGANISM: Artificial Sequence
<220> FEATURE:
<223> OTHER INFORMATION: ZFPm3 from 311 to 294

<400> SEQUENCE: 12
ggagccgtag tagttggc                                                  18

<210> SEQ ID NO 13
<211> LENGTH: 18
<212> TYPE: DNA
<213> ORGANISM: Artificial Sequence
<220> FEATURE:
<223> OTHER INFORMATION: ZFPm4 from 317 to 300

<400> SEQUENCE: 13
ggtgagggag ccgtagta                                                  18

<210> SEQ ID NO 14
<211> LENGTH: 3300
<212> TYPE: DNA
<213> ORGANISM: Artificial Sequence
<220> FEATURE:
<223> OTHER INFORMATION: Partial sequence of pMal-m1 and zinc finger
      protein ZFPm1

<400> SEQUENCE: 14
ccgacaccat cgaatggtgc aaaacctttc gcggtatggc atgatagcgc ccggaagaga     60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta atctcgcgc cgatcaactg ggtgccagcg    360
```

```
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct gctgcaact ctctcagggc caggcggtga    1020 aggcaatca gctgttgccc gtctcactgg tgaaaagaaa accaccctg gcgcccaata    1080 cgcaaaccgc ctctccccgc gcgttggccg attcattaat gcagctggca cgacaggttt    1140
cccgactgga aagcgggcag tgagcgcaac gcaattaatg tgagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt ccgtttaggt gttttcacga    1500
gcacttcacc aacaaggacc atagattatg aaaactgaag aaggtaaaact ggtaatctgg    1560 attaacggcg ataaaggcta taacggtctc gctgaagtcg gtaagaaatt cgagaaagat    1620
accggaatta aagtcaccgt tgagcatccg gataaactgg aagagaaatt cccacaggtt    1680
gcggcaactg gcgatggccc tgacattatc ttctgggcac acgaccgctt ggtggctac    1740 gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta aacaaagat ctgctgccga cccgccaaa aacctgggaa    1920 gagatcccgg cgctggataa agaactgaaa gcgaaggta agagcgcgct gatgttcaac    1980
ctgcaagaac cgtacttcac ctggccgctg attgctgctg acggggtta tgcgttcaag    2040 tatgaaaacg gcaagtacga cattaaagac gtgggcgtgg ataacgctgg cgcgaaagcg    2100
ggtctgacct tcctggttga cctgattaaa aacaaacaca tgaatgcaga caccgattac    2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta ataaagacaa accgctgggt gccgtagcgc tgaagtctta cgaggaagag    2460
ttggcgaaag atccacgtat tgccgccacc atggaaaacg cccagaaagg tgaaatcatg    2520
ccgaacatcc gcagatgtc cgctttctgg tatgccgtgc gtactgcggt gatcaacgcc    2580
gccagcggtc gtcagactgt cgatgaagcc ctgaaagacg cgcagactaa ttcgagctcg    2640
aacaacaaca acaataacaa taacaacaac ctcgggatcg agggaaggat ttcagaattc    2700
```

-continued

```
ggatcctctt cctctgtggc ccaggcggcc ctcgagcccg gggagaagcc ctatgcttgt      2760
ccggaatgtg gtaagtcctt ctctcagagc tctcacctgg tgcgccacca gcgtacccac      2820
acgggtgaaa aaccgtataa atgcccagag tgcggcaaat cttttagcca gtccagcaac      2880
ctggtgcgcc atcaacgcac tcatactggc gagaagccat acaaatgtcc agaatgtggc      2940
aagtctttct ctcggtctga caatctcgtc cggcaccaac gtactcacac cggggagaag      3000
ccctatgctt gtccggaatg tggtaagtcc ttcagccgca gcgataacct ggtgcgccac      3060
cagcgtaccc acacgggtga aaaccgtat aaatgcccag agtgcggcaa atcttttagc      3120
caggccggcc acctggccag ccatcaacgc actcatactg gcgagaagcc atacaaatgt      3180
ccagaatgtg gcaagtcttt ctctcggtct gacaatctcg tccggcacca acgtactcac      3240
accggtaaaa aaactagtgg ccaggccggc cagtacccgt acgacgttcc ggactacgct      3300
```

<210> SEQ ID NO 15
<211> LENGTH: 3300
<212> TYPE: DNA
<213> ORGANISM: Artificial Sequence
<220> FEATURE:
<223> OTHER INFORMATION: Partial sequence of pMal-m2 and zinc finger
      protein ZFPm2

<400> SEQUENCE: 15

```
ccgacaccat cgaatggtgc aaaacctttc gcggtatggc atgatagcgc ccggaagaga       60
gtcaattcag ggtggtgaat gtgaaaccag taacgttata cgatgtcgca gagtatgccg      120
gtgtctctta tcagaccgtt tcccgcgtgg tgaaccaggc cagccacgtt tctgcgaaaa      180
cgcgggaaaa agtggaagcg gcgatggcgg agctgaatta cattcccaac cgcgtggcac      240
aacaactggc gggcaaacag tcgttgctga ttggcgttgc cacctccagt ctggccctgc      300
acgcgccgtc gcaaattgtc gcggcgatta atctcgcgc cgatcaactg ggtgccagcg      360
tggtggtgtc gatggtagaa cgaagcggcg tcgaagcctg taaagcggcg gtgcacaatc      420
ttctcgcgca acgcgtcagt gggctgatca ttaactatcc gctggatgac caggatgcca      480
ttgctgtgga agctgcctgc actaatgttc cggcgttatt tcttgatgtc tctgaccaga      540
cacccatcaa cagtattatt ttctcccatg aagacggtac gcgactgggc gtggagcatc      600
tggtcgcatt gggtcaccag caaatcgcgc tgttagcggg cccattaagt tctgtctcgg      660
cgcgtctgcg tctggctggc tggcataaat atctcactcg caatcaaatt cagccgatag      720
cggaacggga aggcgactgg agtgccatgt ccggttttca acaaaccatg caaatgctga      780
atgagggcat cgttcccact gcgatgctgg ttgccaacga tcagatggcg ctgggcgcaa      840
tgcgcgccat taccgagtcc gggctgcgcg ttggtgcgga tatctcggta gtgggatacg      900
acgataccga agacagctca tgttatatcc gccgttaac caccatcaaa caggattttc      960
gcctgctggg gcaaaccagc gtggaccgct tgctgcaact ctctcagggc caggcggtga     1020
agggcaatca gctgttgccc gtctcactgg tgaaaagaaa aaccaccctg gcgcccaata     1080
cgcaaaccgc ctctccccgc gcgttggccg attcattaat gcagctggca cgacaggttt     1140
cccgactgga aagcgggcag tgagcgcaac gcaattaatg tgagttagct cactcattag     1200
gcacaattct catgtttgac agcttatcat cgactcacg gtgcaccaat gcttctggcg     1260
tcaggcagcc atcggaagct gtggtatggc tgtgcaggtc gtaaatcact gcataattcg     1320
tgtcgctcaa ggcgcactcc cgttctggat aatgtttttt gcgccgacat cataacggtt     1380
ctggcaaata ttctgaaatg agctgttgac aattaatcat cggctcgtat aatgtgtgga     1440
```

-continued

```
attgtgagcg gataacaatt tcacacagga acagccagt  ccgtttaggt gttttcacga    1500
gcacttcacc aacaaggacc atagattatg aaaactgaag aaggtaaact ggtaatctgg    1560
attaacggcg ataaaggcta taacggtctc gctgaagtcg gtaagaaatt cgagaaagat    1620
accggaatta aagtcaccgt tgagcatccg gataaactgg aagagaaatt cccacaggtt    1680
gcggcaactg gcgatggccc tgacattatc ttctgggcac acgaccgctt tggtggctac    1740
gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta aacaaagat  ctgctgccga cccgccaaa  acctgggaa     1920 gagatcccgg cgctggataa agaactgaaa gcgaaggta  agagcgcgct gatgttcaac    1980
ctgcaagaac cgtacttcac ctggccgctg attgctgctg acggggtta  tgcgttcaag    2040 tatgaaaacg gcaagtacga cattaaagac gtgggcgtgg ataacgctgg cgcgaaagcg    2100
ggtctgacct tcctggttga cctgattaaa aacaaacaca tgaatgcaga caccgattac    2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta ataagacaa  accgctgggt gccgtagcgc tgaagtctta cgaggaagag    2460
ttggcgaaaa atccacgtat tgccgccacc atggaaaacg cccagaaagg tgaaatcatg    2520
ccgaacatcc gcagatgtc  cgctttctgg tatgccgtgc gtactgcggt gatcaacgcc    2580
gccagcggtc gtcagactgt cgatgaagcc ctgaaagacg cgcagactaa ttcgagctcg    2640
aacaacaaca acaataacaa taacaacaac ctcgggatcg agggaaggat ttcagaattc    2700
ggatcctctt cctctgtggc ccaggcggcc ctcgagcccg gggagaagcc ctatgcttgt    2760
ccggaatgtg gtaagtcctt ctctcagagc tctcacctgg tgcgccacca gcgtacccac    2820
acgggtgaaa aaccgtataa atgcccagag tgcggcaaat cttttagcca gtccagcaac    2880
ctggtgcgcc atcaacgcac tcatactggc gagaagccat acaaatgtcc agaatgtggc    2940
aagtctttct ctcggtctga caatctcgtc cggcaccaac gtactcacac cggggagaag    3000
ccctatgctt gtccggaatg tggtaagtcc ttcagccgca gcgataacct ggtgcgccac    3060
cagcgtaccc acacgggtga aaaaccgtat aaatgcccag agtgcggcaa atcttttagc    3120
caggccggcc acctggccag ccatcaacgc actcatactg gcgagaagcc atacaaatgt    3180
ccagaatgtg gcaagtcttt ctctcggtct gacaatctcg tccggcacca acgtactcac    3240
accggtaaaa aaactagtgg ccaggccggc cagtacccgt acgacgttcc ggactacgct    3300
```

<210> SEQ ID NO 16
<211> LENGTH: 3300
<212> TYPE: DNA
<213> ORGANISM: Artificial Sequence
<220> FEATURE:
<223> OTHER INFORMATION: PArtial sequence of pMal-m3 and zinc finger
       protein ZFPm3

<400> SEQUENCE: 16

```
ccgacaccat cgaatggtgc aaaacctttc gcggtatggc atgatagcgc ccggaagaga    60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
```

-continued

| | | | | |
|---|---|---|---|---|
| cgcgggaaaa | agtggaagcg | gcgatggcgg | agctgaatta | cattcccaac cgcgtggcac | 240 |
| aacaactggc | gggcaaacag | tcgttgctga | ttggcgttgc | cacctccagt ctggccctgc | 300 |
| acgcgccgtc | gcaaattgtc | gcggcgatta | aatctcgcgc | cgatcaactg ggtgccagcg | 360 |
| tggtggtgtc | gatggtagaa | cgaagcggcg | tcgaagcctg | taaagcggcg gtgcacaatc | 420 |
| ttctcgcgca | acgcgtcagt | gggctgatca | ttaactatcc | gctggatgac caggatgcca | 480 |
| ttgctgtgga | agctgcctgc | actaatgttc | cggcgttatt | tcttgatgtc tctgaccaga | 540 |
| cacccatcaa | cagtattatt | ttctcccatg | aagacggtac | gcgactgggc gtggagcatc | 600 |
| tggtcgcatt | gggtcaccag | caaatcgcgc | tgttagcggg | cccattaagt tctgtctcgg | 660 |
| cgcgtctgcg | tctggctggc | tggcataaat | atctcactcg | caatcaaatt cagccgatag | 720 |
| cggaacggga | aggcgactgg | agtgccatgt | ccggttttca | acaaaccatg caaatgctga | 780 |
| atgagggcat | cgttcccact | gcgatgctgg | ttgccaacga | tcagatggcg ctgggcgcaa | 840 |
| tgcgcgccat | taccgagtcc | gggctgcgcg | ttggtgcgga | tatctcggta gtgggatacg | 900 |
| acgataccga | agacagctca | tgttatatcc | gccgttaac | caccatcaaa caggatttc | 960 |
| gcctgctggg | gcaaaccagc | gtggaccgct | tgctgcaact | ctctcagggc caggcggtga | 1020 |
| agggcaatca | gctgttgccc | gtctcactgg | tgaaagaaa | aaccaccctg gcgcccaata | 1080 |
| cgcaaaccgc | ctctccccgc | gcgttggccg | attcattaat | gcagctggca cgacaggttt | 1140 |
| cccgactgga | aagcgggcag | tgagcgcaac | gcaattaatg | tgagttagct cactcattag | 1200 |
| gcacaattct | catgtttgac | agcttatcat | cgactgcacg | gtgcaccaat gcttctggcg | 1260 |
| tcaggcagcc | atcggaagct | gtggtatggc | tgtgcaggtc | gtaaatcact gcataattcg | 1320 |
| tgtcgctcaa | ggcgcactcc | cgttctggat | aatgtttttt | gcgccgacat cataacggtt | 1380 |
| ctggcaaata | ttctgaaatg | agctgttgac | aattaatcat | cggctcgtat aatgtgtgga | 1440 |
| attgtgagcg | gataacaatt | tcacacagga | aacagccagt | ccgtttaggt gttttcacga | 1500 |
| gcacttcacc | aacaaggacc | atagattatg | aaaactgaag | aaggtaaact ggtaatctgg | 1560 |
| attaacggcg | ataaaggcta | taacggtctc | gctgaagtcg | gtaagaaatt cgagaaagat | 1620 |
| accggaatta | aagtcaccgt | tgagcatccg | gataaactgg | aagagaaatt cccacaggtt | 1680 |
| gcggcaactg | gcgatggccc | tgacattatc | ttctgggcac | acgaccgctt tggtggctac | 1740 |
| gctcaatctg | gcctgttggc | tgaaatcacc | ccggacaaag | cgttccagga caagctgtat | 1800 |
| ccgtttacct | gggatgccgt | acgttacaac | ggcaagctga | ttgcttaccc gatcgctgtt | 1860 |
| gaagcgttat | cgctgattta | taacaaagat | ctgctgccga | acccgccaaa aacctgggaa | 1920 |
| gagatcccgg | cgctggataa | agaactgaaa | gcgaaaggta | agagcgcgct gatgttcaac | 1980 |
| ctgcaagaac | cgtacttcac | ctggccgctg | attgctgctg | acgggggtta tgcgttcaag | 2040 |
| tatgaaaacg | gcaagtacga | cattaaagac | gtgggcgtgg | ataacgctgg cgcgaaagcg | 2100 |
| ggtctgacct | tcctggttga | cctgattaaa | aacaaacaca | tgaatgcaga caccgattac | 2160 |
| tccatcgcag | aagctgcctt | taataaaggc | gaaacagcga | tgaccatcaa cggcccgtgg | 2220 |
| gcatggtcca | acatcgacac | cagcaaagtg | aattatggtg | taacggtact gccgaccttc | 2280 |
| aagggtcaac | catccaaacc | gttcgttggc | gtgctgagcg | caggtattaa cgccgccagt | 2340 |
| ccgaacaaag | agctggcaaa | agagttcctc | gaaaactatc | tgctgactga tgaaggtctg | 2400 |
| gaagcggtta | ataaagacaa | accgctgggt | gccgtagcgc | tgaagtctta cgaggaagag | 2460 |
| ttggcgaaag | atccacgtat | tgccgccacc | atggaaaacg | cccagaaagg tgaaatcatg | 2520 |
| ccgaacatcc | cgcagatgtc | cgctttctgg | tatgccgtgc | gtactgcggt gatcaacgcc | 2580 |

-continued

```
gccagcggtc gtcagactgt cgatgaagcc ctgaaagacg cgcagactaa ttcgagctcg   2640
aacaacaaca acaataacaa taacaacaac ctcgggatcg agggaaggat ttcagaattc   2700
ggatcctctt cctctgtggc ccaggcggcc ctcgagcccg gggagaagcc ctatgcttgt   2760
ccggaatgtg gtaagtcctt cagcgatcct ggccacctgg ttcgccacca gcgtacccac   2820
acgggtgaaa aaccgtataa atgcccagag tgcggcaaat cttttagcac cagcggctcc   2880
ctggtgcgcc atcaacgcac tcatactggc gagaagccat acaaatgtcc agaatgtggc   2940
aagtctttca gccagagctc cagcctggtg cgccaccaac gtactcacac cggggagaag   3000
ccctatgctt gtccggaatg tggtaagtcc ttcagccaga gcagctccct ggtgcgccac   3060
cagcgtaccc acacgggtga aaaccgtat aaatgcccag agtgcggcaa atcttttagt   3120
gactgccgcg accttgctcg ccatcaacgc actcatactg gcgagaagcc atacaaatgt   3180
ccagaatgtg gcaagtcttt ctcccaatcc agccatctcg tccggcacca acgtactcac   3240
accggtaaaa aaactagtgg ccaggccggc cagtacccgt acgacgttcc ggactacgct   3300
```

<210> SEQ ID NO 17
<211> LENGTH: 3300
<212> TYPE: DNA
<213> ORGANISM: Artificial Sequence
<220> FEATURE:
<223> OTHER INFORMATION: Partial sequence of pMal-m4 and zinc finger
      protein ZFPm4

<400> SEQUENCE: 17

```
ccgacaccat cgaatggtgc aaaacctttc gcggtatggc atgatagcgc ccggaagaga     60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta atctcgcgc gatcaactg ggtgccagcg     360 tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc gccgttaac caccatcaaa caggattttc    960
gcctgctggg gcaaaccagc gtggaccgct tgctgcaact ctctcagggc caggcggtga    1020
agggcaatca gctgttgccc gtctcactgg tgaaagaaa accacccctg cgcccaata    1080 cgcaaaccgc ctctccccgc gcgttggccg attcattaat gcagctggca cgacaggttt    1140
cccgactgga aagcgggcag tgagcgcaac gcaattaatg tgagttagct cactcattag    1200
gcacaattct catgtttgac agcttatcat cgactcacg gtgcaccaat gcttctggcg    1260
tcaggcagcc atcggaagct gtggtatggc tgtgcaggtc gtaaatcact gcataattcg    1320
```

```
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt ccgtttaggt gttttcacga     1500
gcacttcacc aacaaggacc atagattatg aaaactgaag aaggtaaact ggtaatctgg    1560
attaacggcg ataaaggcta taacggtctc gctgaagtcg gtaagaaatt cgagaaagat    1620
accggaatta aagtcaccgt tgagcatccg gataaactgg aagagaaatt cccacaggtt    1680
gcggcaactg gcgatggccc tgacattatc ttctgggcac acgaccgctt tggtggctac    1740
gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta aacaaagat ctgctgccga acccgccaaa acctgggaa      1920 gagatcccgg cgctggataa agaactgaaa gcgaaaggta gagcgcgct gatgttcaac     1980 ctgcaagaac cgtacttcac ctggccgctg attgctgctg acggggtta tgcgttcaag    2040 tatgaaaacg gcaagtacga cattaaagac gtgggcgtgg ataacgctgg cgcgaaagcg    2100
ggtctgacct tcctggttga cctgattaaa acaaacaca tgaatgcaga caccgattac     2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta ataaagacaa accgctgggt gccgtagcgc tgaagtctta cgaggaagag    2460
ttggcgaaag atccacgtat tgccgccacc atggaaaacg cccagaaagg tgaaatcatg    2520
ccgaacatcc cgcagatgtc cgctttctgg tatgccgtgc gtactgcggt gatcaacgcc    2580
gccagcggtc gtcagactgt cgatgaagcc ctgaaagacg cgcagactaa ttcgagctcg    2640
aacaacaaca acaataacaa taacaacaac ctcgggatcg agggaaggat ttcagaattc    2700
ggatcctctt cctctgtggc ccaggcggcc ctcgagcccg gggagaagcc ctatgcttgt    2760
ccggaatgtg gtaagtcctt cagccagagc agctccctgg tgcgccacca gcgtacccac    2820
acgggtgaaa aaccgtataa atgcccagag tgcggcaaat cttttagcca gagcagcagc    2880
ctggtgcgcc atcaacgcac tcatactggc gagaagccat acaaatgtcc agaatgtggc    2940
aagtctttca gtgattgtcg tgatcttgcg aggcaccaac gtactcacac cggggagaag    3000
ccctatgctt gtccggaatg tggtaagtcc ttctctcaga gctctcacct ggtgcgccac    3060
cagcgtaccc acacgggtga aaaaccgtat aaatgcccag agtgcggcaa atcttttagc    3120
cgcagcgata acctggtgcg ccatcaacgc actcatactg gcgagaagcc atacaaatgt    3180
ccagaatgtg gcaagtcttt ctcaacttca ggccatttgg tccgtcacca acgtactcac    3240
accggtaaaa aaactagtgg ccaggccggc cagtacccgt acgacgttcc ggactacgct    3300
```

<210> SEQ ID NO 18
<211> LENGTH: 3300
<212> TYPE: DNA
<213> ORGANISM: Artificial Sequence
<220> FEATURE:
<223> OTHER INFORMATION: Parial sequence of pMal-Ap3 and zinc finger
      protein ZFPAp3

<400> SEQUENCE: 18

```
ccgacaccat cgaatggtgc aaaacctttc gcggtatggc atgatagcgc ccggaagaga      60
```

```
gtcaattcag ggtggtgaat gtgaaaccag taacgttata cgatgtcgca gagtatgccg      120
gtgtctctta tcagaccgtt tcccgcgtgg tgaaccaggc cagccacgtt tctgcgaaaa      180
cgcgggaaaa agtggaagcg gcgatggcgg agctgaatta cattcccaac cgcgtggcac      240
aacaactggc gggcaaacag tcgttgctga ttggcgttgc cacctccagt ctggccctgc      300
acgcgccgtc gcaaattgtc gcggcgatta aatctcgcgc cgatcaactg ggtgccagcg      360
tggtggtgtc gatggtagaa cgaagcggcg tcgaagcctg taaagcggcg gtgcacaatc      420
ttctcgcgca acgcgtcagt gggctgatca ttaactatcc gctggatgac caggatgcca      480
ttgctgtgga agctgcctgc actaatgttc cggcgttatt tcttgatgtc tctgaccaga      540
cacccatcaa cagtattatt ttctcccatg aagacggtac gcgactgggc gtggagcatc      600
tggtcgcatt gggtcaccag caaatcgcgc tgttagcggg cccattaagt tctgtctcgg      660
cgcgtctgcg tctggctggc tggcataaat atctcactcg caatcaaatt cagccgatag      720
cggaacggga aggcgactgg agtgccatgt ccggttttca acaaaccatg caaatgctga      780
atgagggcat cgttcccact gcgatgctgg ttgccaacga tcagatgcg ctgggcgcaa      840 tgcgcgccat taccgagtcc gggctgcgcg ttggtgcgga tatctcggta gtgggatacg      900
acgataccga agacagctca tgttatatcc cgccgttaac caccatcaaa caggattttc      960
gcctgctggg gcaaaccagc gtggaccgct tgctgcaact ctctcagggc caggcggtga     1020
agggcaatca gctgttgccc gtctcactgg tgaaaagaaa aaccaccctg gcgcccaata     1080
cgcaaaccgc ctctccccgc gcgttggccg attcattaat gcagctggca cgacaggttt     1140
cccgactgga aagcgggcag tgagcgcaac gcaattaatg tgagttagct cactcattag     1200
gcacaattct catgtttgac agcttatcat cgactgcacg gtgcaccaat gcttctggcg     1260
tcaggcagcc atcggaagct gtggtatggc tgtgcaggtc gtaaatcact gcataattcg     1320
tgtcgctcaa ggcgcactcc cgttctggat aatgtttttt gcgccgacat cataacggtt     1380
ctggcaaata ttctgaaatg agctgttgac aattaatcat cggctcgtat aatgtgtgga     1440
attgtgagcg gataacaatt tcacacagga acagccagt ccgtttaggt gttttcacga     1500
gcacttcacc aacaaggacc atagattatg aaaactgaag aaggtaaact ggtaatctgg     1560
attaacggcg ataaaggcta taacggtctc gctgaagtcg gtaagaaatt cgagaaagat     1620
accggaatta aagtcaccgt tgagcatccg gataaactgg aagagaaatt cccacaggtt     1680
gcggcaactg cgatggcccc tgacattatc ttctgggcac acgaccgctt ggtggctac       1740 gctcaatctg gcctgttggc tgaaatcacc ccggacaaag cgttccagga caagctgtat     1800
ccgtttacct gggatgccgt acgttacaac ggcaagctga ttgcttaccc gatcgctgtt     1860
gaagcgttat cgctgatttta aacaaagat ctgctgccga acccgccaaa aacctgggaa      1920
gagatcccgg cgctggataa agaactgaaa gcgaaaggta gagcgcgct gatgttcaac      1980 ctgcaagaac cgtacttcac ctggccgctg attgctgctg acgggggtta tgcgttcaag     2040
tatgaaaacg gcaagtacga cattaaagac gtgggcgtgg ataacgctgg cgcgaaagcg     2100
ggtctgacct tcctggttga cctgattaaa aacaaacaca tgaatgcaga caccgattac      2160
tccatcgcag aagctgcctt taataaaggc gaaacagcga tgaccatcaa cggcccgtgg     2220
gcatggtcca acatcgacac cagcaaagtg aattatggtg taacggtact gccgaccttc     2280
aagggtcaac catccaaacc gttcgttggc gtgctgagcg caggtattaa cgccgccagt     2340
ccgaacaaag agctggcaaa agagttcctc gaaaactatc tgctgactga tgaaggtctg     2400
```

```
gaagcggtta ataaagacaa accgctgggt gccgtagcgc tgaagtctta cgaggaagag    2460
ttggcgaaag atccacgtat tgccgccacc atggaaaacg cccagaaagg tgaaatcatg    2520
ccgaacatcc cgcagatgtc cgctttctgg tatgccgtgc gtactgcggt gatcaacgcc    2580
gccagcggtc gtcagactgt cgatgaagcc ctgaaagacg cgcagactaa ttcgagctcg    2640
aacaacaaca acaataacaa taacaacaac ctcgggatcg agggaaggat ttcagaattc    2700
ggatcctctt cctctgtggc ccaggcgcc ctcgagcccg gggagaagcc ctatgcttgt    2760
ccggaatgtg gtaagtcctt cagccagagc agctccctgg tgcgccacca gcgtacccac    2820
acgggtgaaa aaccgtataa atgcccagag tgcggcaaat cttttagcca gtccagcaac    2880
ctggtgcgcc atcaacgcac tcatactggc gagaagccat acaaatgtcc agaatgtggc    2940
aagtctttca gccagtccag caacctggtg cgccaccaac gtactcacac cggggagaag    3000
ccctatgctt gtccggaatg tggtaagtcc ttcagcacca gtggctcctt ggttagacac    3060
cagcgtaccc acacgggtga aaaaccgtat aaatgcccag agtgcggcaa atcttttagc    3120
cagcgcgccc acctggaacg ccatcaacgc actcatactg gcgagaagcc atacaaatgt    3180
ccagaatgtg gcaagtcttt ctcaacttca ggcaacttgg tccgtcacca acgtactcac    3240
accggtaaaa aaactagtgg ccaggccggc cagtacccgt acgacgttcc ggactacgct    3300
```

<210> SEQ ID NO 19
<211> LENGTH: 58
<212> TYPE: DNA
<213> ORGANISM: Artificial Sequence
<220> FEATURE:
<223> OTHER INFORMATION: Oligo m12

<400> SEQUENCE: 19

```
ggagcctcct tcctcctctc actcgggttt tcccgagtga gaggaggaag gaggctcc          58
```

<210> SEQ ID NO 20
<211> LENGTH: 64
<212> TYPE: DNA
<213> ORGANISM: Artificial Sequence
<220> FEATURE:
<223> OTHER INFORMATION: Oligo m34

<400> SEQUENCE: 20

```
ggagccaact actacggctc cctcaccggg ttttcccggt gagggagccg tagtagttgg          60
ctcc                                                                      64
```

<210> SEQ ID NO 21
<211> LENGTH: 52
<212> TYPE: DNA
<213> ORGANISM: Artificial Sequence
<220> FEATURE:
<223> OTHER INFORMATION: Oligo Ap3

<400> SEQUENCE: 21

```
ggttacttct tcaactccat cgggttttcc cgatggagtt gaagaagtaa cc                  52
```

<210> SEQ ID NO 22
<211> LENGTH: 50
<212> TYPE: DNA
<213> ORGANISM: Artificial Sequence
<220> FEATURE:
<223> OTHER INFORMATION: Oligo NRI-1

<400> SEQUENCE: 22

```
ggttctaccc ctcccaccgc gggttttccc gcggtgggag gggtagaacc                    50
```

<210> SEQ ID NO 23
<211> LENGTH: 50
<212> TYPE: DNA
<213> ORGANISM: Artificial Sequence
<220> FEATURE:
<223> OTHER INFORMATION: Oligo NRI-2

<400> SEQUENCE: 23
ggtgcggcga ctgcagcagc gggttttccc gctgctgcag tcgccgcacc        50

<210> SEQ ID NO 24
<211> LENGTH: 50
<212> TYPE: DNA
<213> ORGANISM: Artificial Sequence
<220> FEATURE:
<223> OTHER INFORMATION: Oligo hHD-I

<400> SEQUENCE: 24
ggggccccgc ctccgccggc gggttttccc gccggcggag cggggcccc        50

<210> SEQ ID NO 25
<211> LENGTH: 50
<212> TYPE: DNA
<213> ORGANISM: Artificial Sequence
<220> FEATURE:
<223> OTHER INFORMATION: Oligo hHD-II

<400> SEQUENCE: 25
ggggcagccc ccacggcgcc gggttttccc ggcgccgtgg gggctgcccc        50

<210> SEQ ID NO 26
<211> LENGTH: 50
<212> TYPE: DNA
<213> ORGANISM: Artificial Sequence
<220> FEATURE:
<223> OTHER INFORMATION: Oligo c5p1-g

<400> SEQUENCE: 26
gggacacccc caacccccgcc gggttttccc ggcgggttg ggggtgtccc        50

<210> SEQ ID NO 27
<211> LENGTH: 50
<212> TYPE: DNA
<213> ORGANISM: Artificial Sequence
<220> FEATURE:
<223> OTHER INFORMATION: Oligo c5p3-g

<400> SEQUENCE: 27
ggctctgctc atcccactac gggttttccc gtagtgggat gagcagagcc        50

<210> SEQ ID NO 28
<211> LENGTH: 50
<212> TYPE: DNA
<213> ORGANISM: Artificial Sequence
<220> FEATURE:
<223> OTHER INFORMATION: Oligo B3c2

<400> SEQUENCE: 28
ggacccaccg cgtcccctcc gggttttccc ggaggggacg cggtgggtcc        50

<210> SEQ ID NO 29
<211> LENGTH: 50
<212> TYPE: DNA
<213> ORGANISM: Artificial Sequence
<220> FEATURE:

```
<223> OTHER INFORMATION: Oligo e2c-g

<400> SEQUENCE: 29
ggcactgcgg ctccggcccc gggttttccc ggggccggag ccgcagtgcc         50

<210> SEQ ID NO 30
<211> LENGTH: 19
<212> TYPE: DNA
<213> ORGANISM: Artificial Sequence
<220> FEATURE:
<223> OTHER INFORMATION: Primer Ap3-F

<400> SEQUENCE: 30
ggcgagaggg aagatccag                                          19

<210> SEQ ID NO 31
<211> LENGTH: 20
<212> TYPE: DNA
<213> ORGANISM: Artificial Sequence
<220> FEATURE:
<223> OTHER INFORMATION: Primer NZlib5'

<400> SEQUENCE: 31
ggcccaggcg gccctcgagc                                         20

<210> SEQ ID NO 32
<211> LENGTH: 44
<212> TYPE: DNA
<213> ORGANISM: Artificial Sequence
<220> FEATURE:
<223> OTHER INFORMATION: Primer Ap3f4-R

<400> SEQUENCE: 32
ctcctctaat acgactcact atagggacac tcacctagcc tctg              44

<210> SEQ ID NO 33
<211> LENGTH: 21
<212> TYPE: DNA
<213> ORGANISM: Artificial Sequence
<220> FEATURE:
<223> OTHER INFORMATION: Primer m4f3

<400> SEQUENCE: 33
cctcgcaaga tcacgacaat c                                       21

<210> SEQ ID NO 34
<211> LENGTH: 27
<212> TYPE: DNA
<213> ORGANISM: Artificial Sequence
<220> FEATURE:
<223> OTHER INFORMATION: PCR probe for AP3

<400> SEQUENCE: 34
ccatttcatc ctcaagacga cgcagct                                 27

<210> SEQ ID NO 35
<211> LENGTH: 22
<212> TYPE: DNA
<213> ORGANISM: Artificial Sequence
<220> FEATURE:
<223> OTHER INFORMATION: PCR primer for AP3 (forward)

<400> SEQUENCE: 35
tttggacgag cttgacattc ag                                      22
```

```
<210> SEQ ID NO 36
<211> LENGTH: 20
<212> TYPE: DNA
<213> ORGANISM: Artificial Sequence
<220> FEATURE:
<223> OTHER INFORMATION: PCR primer for AP3 (reverse)

<400> SEQUENCE: 36
cgcgaacgag tttgaaagtg                                              20

<210> SEQ ID NO 37
<211> LENGTH: 44
<212> TYPE: DNA
<213> ORGANISM: Artificial Sequence
<220> FEATURE:
<223> OTHER INFORMATION: Oligonucleotide

<400> SEQUENCE: 37
ctcctctaat acgactcact atagggacac tcacctagcc tctg                   44

<210> SEQ ID NO 38
<211> LENGTH: 184
<212> TYPE: PRT
<213> ORGANISM: Artificial Sequence
<220> FEATURE:
<223> OTHER INFORMATION: ZFPm1

<400> SEQUENCE: 38
```

Ala Gln Ala Ala Leu Glu Pro Gly Glu Lys Pro Tyr Ala Cys Pro Glu
 1               5                  10                  15

Cys Gly Lys Ser Phe Ser Asp Pro Gly His Leu Val Arg His Gln Arg
            20                  25                  30

Thr His Thr Gly Glu Lys Pro Tyr Lys Cys Pro Glu Cys Gly Lys Ser
        35                  40                  45

Phe Ser Gln Arg Ala His Leu Glu Arg His Gln Arg Thr His Thr Gly
    50                  55                  60

Glu Lys Pro Tyr Lys Cys Pro Glu Cys Gly Lys Ser Phe Ser Gln Ser
65                  70                  75                  80

Ser Asn Leu Val Arg His Gln Arg Thr His Thr Gly Glu Lys Pro Tyr
                85                  90                  95

Ala Cys Pro Glu Cys Gly Lys Ser Phe Ser Arg Ser Asp Asn Leu Val
            100                 105                 110

Arg His Gln Arg Thr His Thr Gly Glu Lys Pro Tyr Lys Cys Pro Glu
        115                 120                 125

Cys Gly Lys Ser Phe Ser Arg Ser Asp Asn Leu Val Arg His Gln Arg
    130                 135                 140

Thr His Thr Gly Glu Lys Pro Tyr Lys Cys Pro Glu Cys Gly Lys Ser
145                 150                 155                 160

Phe Ser Gln Ala Gly His Leu Ala Ser His Gln Arg Thr His Thr Gly
                165                 170                 175

Lys Lys Thr Ser Gly Gln Ala Gly
            180

```
<210> SEQ ID NO 39
<211> LENGTH: 184
<212> TYPE: PRT
<213> ORGANISM: Artificial Sequence
<220> FEATURE:
<223> OTHER INFORMATION: ZFPm2

<400> SEQUENCE: 39
```

```
Ala Gln Ala Ala Leu Glu Pro Gly Glu Lys Pro Tyr Ala Cys Pro Glu
 1               5                  10                  15

Cys Gly Lys Ser Phe Ser Gln Ser Ser His Leu Val Arg His Gln Arg
             20                  25                  30

Thr His Thr Gly Glu Lys Pro Tyr Lys Cys Pro Glu Cys Gly Lys Ser
         35                  40                  45

Phe Ser Gln Ser Ser Asn Leu Val Arg His Gln Arg Thr His Thr Gly
     50                  55                  60

Glu Lys Pro Tyr Lys Cys Pro Glu Cys Gly Lys Ser Phe Ser Arg Ser
65                  70                  75                  80

Asp Asn Leu Val Arg His Gln Arg Thr His Thr Gly Glu Lys Pro Tyr
                 85                  90                  95

Ala Cys Pro Glu Cys Gly Lys Ser Phe Ser Arg Ser Asp Asn Leu Val
             100                 105                 110

Arg His Gln Arg Thr His Thr Gly Glu Lys Pro Tyr Lys Cys Pro Glu
         115                 120                 125

Cys Gly Lys Ser Phe Ser Gln Ala Gly His Leu Ala Ser His Gln Arg
         130                 135                 140

Thr His Thr Gly Glu Lys Pro Tyr Lys Cys Pro Glu Cys Gly Lys Ser
145                 150                 155                 160

Phe Ser Arg Ser Asp Asn Leu Val Arg His Gln Arg Thr His Thr Gly
             165                 170                 175

Lys Lys Thr Ser Gly Gln Ala Gly
             180

<210> SEQ ID NO 40
<211> LENGTH: 184
<212> TYPE: PRT
<213> ORGANISM: Artificial Sequence
<220> FEATURE:
<223> OTHER INFORMATION: ZFPm3

<400> SEQUENCE: 40

Ala Gln Ala Ala Leu Glu Pro Gly Glu Lys Pro Tyr Ala Cys Pro Glu
 1               5                  10                  15

Cys Gly Lys Ser Phe Ser Asp Pro Gly His Leu Val Arg His Gln Arg
             20                  25                  30

Thr His Thr Gly Glu Lys Pro Tyr Lys Cys Pro Glu Cys Gly Lys Ser
         35                  40                  45

Phe Ser Thr Ser Gly Ser Leu Val Arg His Gln Arg Thr His Thr Gly
     50                  55                  60

Glu Lys Pro Tyr Lys Cys Pro Glu Cys Gly Lys Ser Phe Ser Gln Ser
65                  70                  75                  80

Ser Ser Leu Val Arg His Gln Arg Thr His Thr Gly Glu Lys Pro Tyr
                 85                  90                  95

Ala Cys Pro Glu Cys Gly Lys Ser Phe Ser Gln Ser Ser Ser Leu Val
             100                 105                 110

Arg His Gln Arg Thr His Thr Gly Glu Lys Pro Tyr Lys Cys Pro Glu
         115                 120                 125

Cys Gly Lys Ser Phe Ser Asp Ser Arg Asp Leu Ala Arg His Gln Arg
         130                 135                 140

Thr His Thr Gly Glu Lys Pro Tyr Lys Cys Pro Glu Cys Gly Lys Ser
145                 150                 155                 160

Phe Ser Gln Ser Ser His Leu Val Arg His Gln Arg Thr His Thr Gly
             165                 170                 175
```

```
Lys Lys Thr Ser Gly Gln Ala Gly
            180
```

<210> SEQ ID NO 41
<211> LENGTH: 184
<212> TYPE: PRT
<213> ORGANISM: Artificial Sequence
<220> FEATURE:
<223> OTHER INFORMATION: ZFPm4

<400> SEQUENCE: 41

```
Ala Gln Ala Ala Leu Glu Pro Gly Glu Lys Pro Tyr Ala Cys Pro Glu
 1               5                  10                  15

Cys Gly Lys Ser Phe Ser Gln Ser Ser Leu Val Arg His Gln Arg
            20                  25                  30

Thr His Thr Gly Glu Lys Pro Tyr Lys Cys Pro Glu Cys Gly Lys Ser
        35                  40                  45

Phe Ser Gln Ser Ser Ser Leu Val Arg His Gln Arg Thr His Thr Gly
    50                  55                  60

Glu Lys Pro Tyr Lys Cys Pro Glu Cys Gly Lys Ser Phe Ser Asp Cys
65                  70                  75                  80

Arg Asp Leu Ala Arg His Gln Arg Thr His Thr Gly Glu Lys Pro Tyr
                85                  90                  95

Ala Cys Pro Glu Cys Gly Lys Ser Phe Ser Gln Ser Ser Leu Val
            100                 105                 110

Arg His Gln Arg Thr His Thr Gly Glu Lys Pro Tyr Lys Cys Pro Glu
        115                 120                 125

Cys Gly Lys Ser Phe Ser Arg Ser Asp Asn Leu Val Arg His Gln Arg
    130                 135                 140

Thr His Thr Gly Glu Lys Pro Tyr Lys Cys Pro Glu Cys Gly Lys Ser
145                 150                 155                 160

Phe Ser Thr Ser Gly His Leu Val Arg His Gln Arg Thr His Thr Gly
                165                 170                 175

Lys Lys Thr Ser Gly Gln Ala Gly
            180
```

<210> SEQ ID NO 42
<211> LENGTH: 184
<212> TYPE: PRT
<213> ORGANISM: Artificial Sequence
<220> FEATURE:
<223> OTHER INFORMATION: ZFPAp3

<400> SEQUENCE: 42

```
Ala Gln Ala Ala Leu Glu Pro Gly Glu Lys Pro Tyr Ala Cys Pro Glu
 1               5                  10                  15

Cys Gly Lys Ser Phe Ser Gln Ser Ser Leu Val Arg His Gln Arg
            20                  25                  30

Thr His Thr Gly Glu Lys Pro Tyr Lys Cys Pro Glu Cys Gly Lys Ser
        35                  40                  45

Phe Ser Gln Ser Ser Asn Leu Val Arg His Gln Arg Thr His Thr Gly
    50                  55                  60

Glu Lys Pro Tyr Lys Cys Pro Glu Cys Gly Lys Ser Phe Ser Gln Ser
65                  70                  75                  80

Ser Asn Leu Val Arg His Gln Arg Thr His Thr Gly Glu Lys Pro Tyr
                85                  90                  95

Ala Cys Pro Glu Cys Gly Lys Ser Phe Ser Thr Ser Gly Ser Leu Val
            100                 105                 110
```

```
Arg His Gln Arg Thr His Thr Gly Glu Lys Pro Tyr Lys Cys Pro Glu
            115                 120                 125

Cys Gly Lys Ser Phe Ser Gln Ser Ser His Leu Val Arg His Gln Arg
        130                 135                 140

Thr His Thr Gly Glu Lys Pro Tyr Lys Cys Pro Glu Cys Gly Lys Ser
145                 150                 155                 160

Phe Ser Thr Ser Gly Asn Leu Val Arg His Gln Arg Thr His Thr Gly
                165                 170                 175

Lys Lys Thr Ser Gly Gln Ala Gly
            180

<210> SEQ ID NO 43
<211> LENGTH: 18
<212> TYPE: DNA
<213> ORGANISM: Artificial Sequence
<220> FEATURE:
<223> OTHER INFORMATION: Promoter 18bp 2C7

<400> SEQUENCE: 43
gcgtgggcgg cgtgggcg                                                 18

<210> SEQ ID NO 44
<211> LENGTH: 7
<212> TYPE: PRT
<213> ORGANISM: Artificial Sequence
<220> FEATURE:
<223> OTHER INFORMATION: ZFP domain

<400> SEQUENCE: 44

Ser Gln Ser Ser Asn Leu Val
1               5

<210> SEQ ID NO 45
<211> LENGTH: 7
<212> TYPE: PRT
<213> ORGANISM: Artificial Sequence
<220> FEATURE:
<223> OTHER INFORMATION: ZFP domain

<400> SEQUENCE: 45

Ser Asp Pro Gly Asn Leu Val
1               5

<210> SEQ ID NO 46
<211> LENGTH: 8
<212> TYPE: PRT
<213> ORGANISM: Artificial Sequence
<220> FEATURE:
<223> OTHER INFORMATION: ZFP domain

<400> SEQUENCE: 46

Ser Arg Ser Asp Asn Leu Val Arg
1               5

<210> SEQ ID NO 47
<211> LENGTH: 7
<212> TYPE: PRT
<213> ORGANISM: Artificial Sequence
<220> FEATURE:
<223> OTHER INFORMATION: ZFP domain

<400> SEQUENCE: 47

Ser Thr Ser Gly Asn Leu Val
1               5
```

```
<210> SEQ ID NO 48
<211> LENGTH: 8
<212> TYPE: PRT
<213> ORGANISM: Artificial Sequence
<220> FEATURE:
<223> OTHER INFORMATION: ZFP domain

<400> SEQUENCE: 48

Ser Gln Ser Gly Asp Leu Arg Arg
1               5

<210> SEQ ID NO 49
<211> LENGTH: 8
<212> TYPE: PRT
<213> ORGANISM: Artificial Sequence
<220> FEATURE:
<223> OTHER INFORMATION: ZFP domain

<400> SEQUENCE: 49

Ser Asp Cys Arg Asp Leu Ala Arg
1               5

<210> SEQ ID NO 50
<211> LENGTH: 8
<212> TYPE: PRT
<213> ORGANISM: Artificial Sequence
<220> FEATURE:
<223> OTHER INFORMATION: ZFP domain

<400> SEQUENCE: 50

Ser Arg Ser Asp Asp Leu Val Arg
1               5

<210> SEQ ID NO 51
<211> LENGTH: 7
<212> TYPE: PRT
<213> ORGANISM: Artificial Sequence
<220> FEATURE:
<223> OTHER INFORMATION: ZFP domain

<400> SEQUENCE: 51

Ser Thr Ser Gly Glu Leu Val
1               5

<210> SEQ ID NO 52
<211> LENGTH: 8
<212> TYPE: PRT
<213> ORGANISM: Artificial sequence
<220> FEATURE:
<223> OTHER INFORMATION: ZFP domain

<400> SEQUENCE: 52

Ser Gln Ser Ser His Leu Val Arg
1               5

<210> SEQ ID NO 53
<211> LENGTH: 8
<212> TYPE: PRT
<213> ORGANISM: Artificial Sequence
<220> FEATURE:
<223> OTHER INFORMATION: ZFP domain

<400> SEQUENCE: 53

Ser Gln Arg Ala His Leu Glu Arg
1               5
```

```
<210> SEQ ID NO 54
<211> LENGTH: 8
<212> TYPE: PRT
<213> ORGANISM: Artificial Sequence
<220> FEATURE:
<223> OTHER INFORMATION: ZFP domain

<400> SEQUENCE: 54

Ser Asp Pro Gly His Leu Val Arg
 1               5

<210> SEQ ID NO 55
<211> LENGTH: 8
<212> TYPE: PRT
<213> ORGANISM: Artificial Sequence
<220> FEATURE:
<223> OTHER INFORMATION: ZFP domain

<400> SEQUENCE: 55

Ser Arg Ser Asp Lys Leu Val Arg
 1               5

<210> SEQ ID NO 56
<211> LENGTH: 8
<212> TYPE: PRT
<213> ORGANISM: Artificial Sequence
<220> FEATURE:
<223> OTHER INFORMATION: ZFP domain

<400> SEQUENCE: 56

Ser Thr Ser Gly His Leu Val Arg
 1               5

<210> SEQ ID NO 57
<211> LENGTH: 8
<212> TYPE: PRT
<213> ORGANISM: Artificial Sequence
<220> FEATURE:
<223> OTHER INFORMATION: ZFP domain

<400> SEQUENCE: 57

Ser Gln Ser Ser Ser Leu Val Arg
 1               5

<210> SEQ ID NO 58
<211> LENGTH: 8
<212> TYPE: PRT
<213> ORGANISM: Artificial Sequence
<220> FEATURE:
<223> OTHER INFORMATION: ZFP domain

<400> SEQUENCE: 58

Ser Asp Pro Gly Ala Leu Val Arg
 1               5

<210> SEQ ID NO 59
<211> LENGTH: 8
<212> TYPE: PRT
<213> ORGANISM: Artificial Sequence
<220> FEATURE:
<223> OTHER INFORMATION: ZFP domain

<400> SEQUENCE: 59

Ser Arg Ser Asp Val Leu Val Arg
 1               5
```

<210> SEQ ID NO 60
<211> LENGTH: 8
<212> TYPE: PRT
<213> ORGANISM: Artificial Sequence
<220> FEATURE:
<223> OTHER INFORMATION: ZFP domain

<400> SEQUENCE: 60

Ser Arg Lys Asp Ser Leu Val Arg
1               5

<210> SEQ ID NO 61
<211> LENGTH: 8
<212> TYPE: PRT
<213> ORGANISM: Artificial Sequence
<220> FEATURE:
<223> OTHER INFORMATION: ZFP domain

<400> SEQUENCE: 61

Ser Thr Ser Gly Ser Leu Val Arg
1               5

<210> SEQ ID NO 62
<211> LENGTH: 8
<212> TYPE: PRT
<213> ORGANISM: Artificial Sequence
<220> FEATURE:
<223> OTHER INFORMATION: ZFP domain

<400> SEQUENCE: 62

Ser Gln Ala Gly His Leu Ala Ser
1               5

<210> SEQ ID NO 63
<211> LENGTH: 330
<212> TYPE: DNA
<213> ORGANISM: Artificial sequence
<220> FEATURE:
<223> OTHER INFORMATION: ZFPm2a

<400> SEQUENCE: 63
gaggaggagg aggtggccca ggcggccctc gagcccgggg agaagcccta tgcttgtccg      60
gaatgtggta agtccttcag ccgcagcgat aacctggtgc gccaccagcg tacccacacg     120
ggtgaaaaac cgtataaatg cccagagtgc ggcaaatctt ttagccaggc cggccacctg     180
gccagccatc aacgcactca tactggcgag aagccataca atgtccaga atgtggcaag      240 tctttctctc ggtctgacaa tctcgtccgg caccaacgta ctcacaccgg taaaaaaact    300
agtggccagg ccggccagct cctcctcctc                                     330

<210> SEQ ID NO 64
<211> LENGTH: 330
<212> TYPE: DNA
<213> ORGANISM: Artificial sequence
<220> FEATURE:
<223> OTHER INFORMATION: ZFP2b

<400> SEQUENCE: 64
gaggaggagg aggtggccca ggcggccctc gagcccgggg agaagcccta tgcttgtccg      60
gaatgtggta agtccttctc tcagagctct cacctggtgc gccaccagcg tacccacacg     120
ggtgaaaaac cgtataaatg cccagagtgc ggcaaatctt ttagccagtc cagcaacctg     180
gtgcgccatc aacgcactca tactggcgag aagccataca atgtccaga atgtggcaag      240 tctttctctc ggtctgacaa tctcgtccgg caccaacgta ctcacaccgg taaaaaaact    300

```
agtggccagg ccggccagct cctcctcctc                                   330

<210> SEQ ID NO 65
<211> LENGTH: 18
<212> TYPE: DNA
<213> ORGANISM: Artificial sequence
<220> FEATURE:
<223> OTHER INFORMATION: Oligonucleotide

<400> SEQUENCE: 65
gagtgagagg aggaagga                                                18

<210> SEQ ID NO 66
<211> LENGTH: 5731
<212> TYPE: DNA
<213> ORGANISM: Artificial sequence
<220> FEATURE:
<223> OTHER INFORMATION: 2C7-SID

<400> SEQUENCE: 66
gacggatcgg gagatctccc gatcccctat ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacgggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
atggccgctg ccgtgcgcat gaacatccag atgctgctcg aagccgctga ttatctggaa   960
cgccgggagc gcgaagccga gcacggctac gccagcatgc tgccatatcc gaaaaagaaa  1020
cgcaaggtgg cccaggcggc cctcgagccc tatgcttgcc ctgtcgagtc ctgcgatcgc  1080
cgcttttcta gtcggctga tctgaagcgc catatccgca tccacacagg ccagaagccc  1140
ttccagtgtc gaatatgcat gcgtaacttc agtcgtagtg accacctac cacccacatc  1200 cgcacccaca caggcgagaa gccttttgcc tgtgacattt gtgggaggaa gtttgccagg  1260
agtgatgaac gcaagaggca taccaaaatc cataccggtg agaagcccta tgcttgccct  1320
gtcgagtcct gcgatcgccg cttttctaag tcggctgatc tgaagcgcca tatccgcatc  1380
cacacaggcc agaagccctt ccagtgtcga atatgcatgc gtaacttcag tcgtagtgac  1440
caccttacca cccacatccg cacccacaca ggcgagaagc cttttgcctg tgacatttgt  1500
gggaggaagt ttgccaggag tgatgaacgc aagaggcata ccaaaatcca tttaagacag  1560
aaggactcta gaactagtgg ccaggccggc cagtacccgt acgacgttcc ggactacgct  1620
```

-continued

```
tcttgaaagc ttggtaccga gctcggatcc actagtccag tgtggtggaa ttctgcagat    1680
atccagcaca gtggcggccg ctcgagtcta gagggcccgt ttaaacccgc tgatcagcct    1740
cgactgtgcc ttctagttgc cagccatctg ttgtttgccc ctcccccgtg ccttccttga    1800
ccctggaagg tgccactccc actgtccttt cctaataaaa tgaggaaatt gcatcgcatt    1860
gtctgagtag gtgtcattct attctggggg gtgggtggg gcaggacagc aaggggagg      1920 attgggaaga caatagcagg catgctgggg atgcggtggg ctctatggct tctgaggcgg    1980
aaagaaccag ctgggctct agggggtatc cccacgcgcc ctgtagcggc gcattaagcg     2040
cggcgggtgt ggtggttacg cgcagcgtga ccgctacact tgccagcgcc ctagcgcccg    2100
ctcctttcgc tttcttccct tcctttctcg ccacgttcgc cggctttccc cgtcaagctc    2160
taaatcgggg catcccttta gggttccgat ttagtgcttt acggcacctc gaccccaaaa    2220
aacttgatta gggtgatggt tcacgtagtg ggccatcgcc ctgatagacg gtttttcgcc    2280
ctttgacgtt ggagtccacg ttctttaata gtggactctt gttccaaact ggaacaacac    2340
tcaaccctat ctcggtctat tcttttgatt tataagggat tttggggatt tcggcctatt    2400
ggttaaaaaa tgagctgatt taacaaaaat ttaacgcgaa ttaattctgt ggaatgtgtg    2460
tcagttaggg tgtggaaagt ccccaggctc cccaggcagg cagaagtatg caaagcatgc    2520
atctcaatta gtcagcaacc aggtgtggaa agtcccagg ctccccagca ggcagaagta     2580
tgcaaagcat gcatctcaat tagtcagcaa ccatagtccc gcccctaact ccgcccatcc    2640
cgcccctaac tccgcccagt tccgcccatt ctccgcccca tggctgacta atttttttta    2700
tttatgcaga ggccgaggcc gcctctgcct ctgagctatt ccagaagtag tgaggaggct    2760
tttttggagg cctaggcttt tgcaaaaagc tcccgggagc ttgtatatcc attttcggat    2820
ctgatcagca cgtgttgaca attaatcatc ggcatagtat atcggcatag tataatacga    2880
caaggtgagg aactaaacca tggccaagtt gaccagtgcc gttccggtgc tcaccgcgcg    2940
cgacgtcgcc ggagcggtcg agttctggac cgaccggctc gggttctccc gggacttcgt    3000
ggaggacgac ttcgccggtg tggtccggga cgacgtgacc ctgttcatca gcgcggtcca    3060
ggaccaggtg gtgccggaca cacccctggc ctgggtgtgg gtgcgcggcc tggacgagct    3120
gtacgccgag tggtcggagg tcgtgtccac gaacttccgg gacgcctccg gccggccat    3180 gaccgagatc ggcgagcagc cgtggggcg ggagttcgcc ctgcgcgacc cggccggcaa     3240
ctgcgtgcac ttcgtggccg aggagcagga ctgacacgtg ctacgagatt tcgattccac    3300
cgccgccttc tatgaaaggt tgggcttcgg aatcgttttc cgggacgccg gctggatgat    3360
cctccagcgc gggatctca tgctggagtt cttcgcccac cccaacttgt ttattgcagc     3420
ttataatggt tacaaataaa gcaatagcat cacaaatttc acaaataaag cattttttc     3480 actgcattct agttgtggtt tgtccaaact catcaatgta tcttatcatg tctgtatacc    3540
gtcgacctct agctagagct tggcgtaatc atggtcatag ctgtttcctg tgtgaaattg    3600
ttatccgctc acaattccac acaacatacg agccggaagc ataaagtgta aagcctgggg    3660
tgcctaatga gtgagctaac tcacattaat tgcgttgcgc tcactgcccg ctttccagtc    3720
gggaaacctg tcgtgccagc tgcattaatg aatcggccaa cgcgcgggga gaggcggttt    3780
gcgtattggg cgctcttccg cttcctcgct cactgactcg ctgcgctcgg tcgttcggct    3840
gcggcgagcg gtatcagctc actcaaaggc ggtaatacgg ttatccacag aatcagggga    3900
taacgcagga aagaacatgt gagcaaaagg ccagcaaaag gccaggaacc gtaaaaaggc    3960
cgcgttgctg gcgtttttcc ataggctccg ccccctgac gagcatcaca aaaatcgacg     4020
```

-continued

```
ctcaagtcag aggtggcgaa acccgacagg actataaaga taccaggcgt ttccccctgg    4080
aagctccctc gtgcgctctc ctgttccgac cctgccgctt accggatacc tgtccgcctt    4140
tctcccttcg ggaagcgtgg cgctttctca atgctcacgc tgtaggtatc tcagttcggt    4200
gtaggtcgtt cgctccaagc tgggctgtgt gcacgaaccc cccgttcagc ccgaccgctg    4260
cgccttatcc ggtaactatc gtcttgagtc caacccggta agacacgact tatcgccact    4320
ggcagcagcc actggtaaca ggattagcag agcgaggtat gtaggcggtg ctacagagtt    4380
cttgaagtgg tggcctaact acggctacac tagaaggaca gtatttggta tctgcgctct    4440
gctgaagcca gttaccttcg gaaaaagagt tggtagctct tgatccggca acaaaccac     4500 cgctggtagc ggtggttttt tgtttgcaa gcagcagatt acgcgcagaa aaaaggatc      4560 tcaagaagat cctttgatct tttctacggg gtctgacgct cagtggaacg aaaactcacg    4620 ttagggatt ttggtcatga gattatcaaa aaggatcttc acctagatcc ttttaaatta     4680
aaaatgaagt tttaaatcaa tctaaagtat atatgagtaa acttggtctg acagttacca    4740
atgcttaatc agtgaggcac ctatctcagc gatctgtcta tttcgttcat ccatagttgc    4800
ctgactcccc gtcgtgtaga taactacgat acgggagggc ttaccatctg gccccagtgc    4860
tgcaatgata ccgcgagacc cacgctcacc ggctccagat ttatcagcaa taaaccagcc    4920
agccggaagg gccgagcgca gaagtggtcc tgcaacttta tccgcctcca tccagtctat    4980
taattgttgc cgggaagcta gagtaagtag ttcgccagtt aatagtttgc gcaacgttgt    5040
tgccattgct acaggcatcg tggtgtcacg ctcgtcgttt ggtatggctt cattcagctc    5100
cggttcccaa cgatcaaggc gagttacatg atccccatg ttgtgcaaaa aagcggttag     5160
ctccttcggt cctccgatcg ttgtcagaag taagttggcc gcagtgttat cactcatggt    5220
tatggcagca ctgcataatt ctcttactgt catgccatcc gtaagatgct tttctgtgac    5280
tggtgagtac tcaaccaagt cattctgaga atagtgtatg cggcgaccga gttgctcttg    5340
cccggcgtca atacgggata ataccgcgcc acatagcaga actttaaaag tgctcatcat    5400
tggaaaacgt tcttcggggc gaaaactctc aaggatctta ccgctgttga tccagttc     5460 gatgtaaccc actcgtgcac ccaactgatc ttcagcatct tttactttca ccagcgtttc    5520
tgggtgagca aaaacaggaa ggcaaaatgc cgcaaaaaag gaataagggc gacacggaa     5580 atgttgaata ctcatactct ccttttttca atattattga agcatttatc agggttattg    5640
tctcatgagc ggatacatat ttgaatgtat ttagaaaaat aaacaaatag gggttccgcg    5700
cacatttccc cgaaaagtgc cacctgacgt c                                   5731
```

<210> SEQ ID NO 67
<211> LENGTH: 81
<212> TYPE: DNA
<213> ORGANISM: Artificial sequence
<220> FEATURE:
<223> OTHER INFORMATION: Primer F1-f1

<400> SEQUENCE: 67

```
ggtaagtcct tcagccgcag cgataacctg gtgcgccacc agcgtaccca cacgggtgaa    60
aaaccgtata aatgcccaga g                                              81
```

<210> SEQ ID NO 68
<211> LENGTH: 87
<212> TYPE: DNA
<213> ORGANISM: Artificial sequence
<220> FEATURE:

```
<223> OTHER INFORMATION: Primer F1-f2

<400> SEQUENCE: 68
gaggaggagg aggtggccca ggcggccctc gagcccgggg agaagcccta tgcttgtccg    60
gaatgtggta agtccttcag ccgcagc                                        87

<210> SEQ ID NO 69
<211> LENGTH: 74
<212> TYPE: DNA
<213> ORGANISM: Artificial sequence
<220> FEATURE:
<223> OTHER INFORMATION: Primer F2-f

<400> SEQUENCE: 69
gccaggccgg ccacctggcc agccatcaac gcactcatac tggcgagaag ccatacaaat    60
gtccagaatg tggc                                                      74

<210> SEQ ID NO 70
<211> LENGTH: 66
<212> TYPE: DNA
<213> ORGANISM: Artificial sequence
<220> FEATURE:
<223> OTHER INFORMATION: Primer F2-b

<400> SEQUENCE: 70
gctggccagg tggccggcct ggctaaaaga tttgccgcac tctgggcatt tatacggttt    60
ttcacc                                                               66

<210> SEQ ID NO 71
<211> LENGTH: 58
<212> TYPE: DNA
<213> ORGANISM: Artificial sequence
<220> FEATURE:
<223> OTHER INFORMATION: Primer F3-b1

<400> SEQUENCE: 71
ccggacgaga ttgtcagacc gagagaaaga cttgccacat tctggacatt tgtatggc      58

<210> SEQ ID NO 72
<211> LENGTH: 81
<212> TYPE: DNA
<213> ORGANISM: Artificial sequence
<220> FEATURE:
<223> OTHER INFORMATION: Primer F3-b2

<400> SEQUENCE: 72
gaggaggagg agctggccgg cctggccact agtttttta ccggtgtgag tacgttggtg     60
ccggacgaga ttgtcagacc g                                              81

<210> SEQ ID NO 73
<211> LENGTH: 315
<212> TYPE: DNA
<213> ORGANISM: Artificial sequence
<220> FEATURE:
<223> OTHER INFORMATION: 3 finger protein C7

<400> SEQUENCE: 73
atggcccagg cggccctcga gccctatgct tgccctgtcg agtcctgcga tcgccgcttt    60
tctaagtcgg ctgatctgaa gcgccatatc cgcatccaca caggccagaa gcccttccag   120
tgtcgaatat gcatgcgtaa cttcagtcgt agtgaccacc ttaccaccca catccgcacc   180
cacacaggcg agaagccttt tgcctgtgac atttgtggga ggaagtttgc caggagtgat   240
```
gaacgcaaga ggcataccaa aatccattta agacagaagg actctagaac tagtggccag    300
gccggccagg ctagc                                                      315

<210> SEQ ID NO 74
<211> LENGTH: 105
<212> TYPE: PRT
<213> ORGANISM: Artificial sequence
<220> FEATURE:
<223> OTHER INFORMATION: Amino acid sequence of 3 finger protein C7

<400> SEQUENCE: 74

Met Ala Gln Ala Ala Leu Glu Pro Tyr Ala Cys Pro Val Glu Ser Cys
 1               5                  10                  15

Asp Arg Arg Phe Ser Lys Ser Ala Asp Leu Lys Arg His Ile Arg Ile
            20                  25                  30

His Thr Gly Gln Lys Pro Phe Gln Cys Arg Ile Cys Met Arg Asn Phe
        35                  40                  45

Ser Arg Ser Asp His Leu Thr Thr His Ile Arg Thr His Thr Gly Glu
    50                  55                  60

Lys Pro Phe Ala Cys Asp Ile Cys Gly Arg Lys Phe Ala Arg Ser Asp
65                  70                  75                  80

Glu Arg Lys Arg His Thr Lys Ile His Leu Arg Gln Lys Asp Ser Arg
                85                  90                  95

Thr Ser Gly Gln Ala Gly Gln Ala Ser
            100                 105

<210> SEQ ID NO 75
<211> LENGTH: 184
<212> TYPE: PRT
<213> ORGANISM: Artificial sequence
<220> FEATURE:
<223> OTHER INFORMATION: Zinc finger protein ZFPm1

<400> SEQUENCE: 75

Ala Gln Ala Ala Leu Glu Pro Gly Glu Lys Pro Tyr Ala Cys Pro Glu
 1               5                  10                  15

Cys Gly Lys Ser Phe Ser Asp Pro Gly His Leu Val Arg His Gln Arg
            20                  25                  30

Thr His Thr Gly Glu Lys Pro Tyr Lys Cys Pro Glu Cys Gly Lys Ser
        35                  40                  45

Phe Ser Gln Arg Ala His Leu Glu Arg His Gln Arg Thr His Thr Gly
    50                  55                  60

Glu Lys Pro Tyr Lys Cys Pro Glu Cys Gly Lys Ser Phe Ser Gln Ser
65                  70                  75                  80

Ser Asn Leu Val Arg His Gln Arg Thr His Thr Gly Glu Lys Pro Tyr
                85                  90                  95

Ala Cys Pro Glu Cys Gly Lys Ser Phe Ser Arg Ser Asp Asn Leu Val
            100                 105                 110

Arg His Gln Arg Thr His Thr Gly Glu Lys Pro Tyr Lys Cys Pro Glu
        115                 120                 125

Cys Gly Lys Ser Phe Ser Arg Ser Asp Asn Leu Val Arg His Gln Arg
    130                 135                 140

Thr His Thr Gly Glu Lys Pro Tyr Lys Cys Pro Glu Cys Gly Lys Ser
145                 150                 155                 160

Phe Ser Gln Ala Gly His Leu Ala Ser His Gln Arg Thr His Thr Gly
                165                 170                 175

```
Lys Lys Thr Ser Gly Gln Ala Gly
            180

<210> SEQ ID NO 76
<211> LENGTH: 21
<212> TYPE: DNA
<213> ORGANISM: Artificial Sequence
<220> FEATURE:
<223> OTHER INFORMATION: Zinc finger protein ZFPm1 and ZFPm2 binding
      site m12

<400> SEQUENCE: 76
gcctccttcc tcctctcact c                                              21

<210> SEQ ID NO 77
<211> LENGTH: 24
<212> TYPE: DNA
<213> ORGANISM: Artificial Sequence
<220> FEATURE:
<223> OTHER INFORMATION: Zinc finger protein ZFPm3 and ZFPm4 binding
      site m34

<400> SEQUENCE: 77
gccaactact acggctccct cacc                                           24

<210> SEQ ID NO 78
<211> LENGTH: 5
<212> TYPE: PRT
<213> ORGANISM: Artificial Sequence
<220> FEATURE:
<223> OTHER INFORMATION: Zinc finger peptide linker

<400> SEQUENCE: 78

Thr Gly Glu Lys Pro
1               5

<210> SEQ ID NO 79
<211> LENGTH: 6
<212> TYPE: PRT
<213> ORGANISM: Artificial sequence
<220> FEATURE:
<223> OTHER INFORMATION: DNA binding motif

<400> SEQUENCE: 79

Gln Ala Leu Gly Gly His
1               5
```

We claim:

1. A method to stably modulate the expression level of a target gene in a plant cell comprising:
   a) introducing into a plant cell an expression vector comprising a nucleotide sequence encoding a synthetic zinc finger protein that specifically binds to a target nucleotide sequence, or a complementary strand thereof, within a target gene,
   wherein said target nucleotide sequence comprises 18 consecutive nucleotides of the formula $(GNN)_6$, wherein N is any one of A, T, C or G, and wherein said zinc finger protein is a hexadactyl zinc finger protein; and
   b) culturing said plant cell under conditions such that said finger protein is stably expressed and binds to said target nucleotide sequence, whereby the expression of said target gene in said plant cell is stably modulated.

2. A method to stably modulate the expression level of a target gene in a plant comprising:
   a) introducing into a plant cell an expression vector comprising a nucleotide sequence encoding a synthetic zinc finger protein that specifically binds to a target nucleotide sequence, or a complementary strand thereof, within a target gene,
   wherein said target nucleotide sequence comprises 18 consecutive nucleotides of the formula $(GNN)_6$, wherein N is any one of A, T, C or G and wherein said zinc finger protein is a hexadactyl zinc finger protein;
   b) culturing said plant cell under conditions such that said zinc finger protein is stably expressed and binds to said target nucleotide sequence; and
   c) growing a plant from the plant cell,
   whereby expression of said target gene in said plant is stably modulated.

3. The method of claim 1, Wherein the target nucleotide sequence is endogenous or exogenous to the target gene.

4. The method of claim 1, wherein the target nucleotide sequence is at the 5' regulatory region, 3' regulatory region (upstream of, downstream of], or within the coding region of the target gene.

5. The method of claim 1, wherein the target nucleotide sequence is DNA, RNA, PNA or a combination thereof.

6. The method of claim 4, wherein the target nucleotide sequence is at the 5' regulatory region of the target gene.

7. The method of claim 1, wherein the target nucleotide sequence is endogenous to the plant cell but is in a non-naturally-occurring location.

8. The method of claim 1, wherein the plant cell comprises at least two copies of the same or different target nucleotide sequence(s).

9. The method of claim 8, wherein each target nucleotide sequence is located within a different target gene, whereby more than one different target genes are modulated.

10. The method of claim 1, wherein the target gene encodes a protein or a peptide of interest.

11. The method of claim 1, wherein the target gene is Apetala3 (Ap3).

12. The method of claim 1, wherein the target gene encodes a protein and the expression of said encoded protein is modulated.

13. The method of claim 12, wherein the protein whose expression being modulated is heterologous to the plant cell.

14. The method of claim 13, wherein the protein whose expression being modulated is an antibody.

15. The method of claim 12, wherein the expression of the protein is activated or repressed.

16. The method of claim 1, wherein the target gene encodes a protein that confers a desired trait in said plant cell.

17. The method of claim 12, wherein the target gene encodes an enzyme, a transport protein, a nutrient protein, a storage protein, a defense protein or a regulatory protein.

18. The method of claim 17, wherein the target gene encodes an enzyme.

19. The method of claim 1, wherein the zinc finger protein binds to the complementary strand of the target nucleotide sequence.

20. The method of claim 1, wherein the zinc finger protein comprises two 3-finger regions separated by a linker region, wherein the linker region is from 2 to 10 amino acid residues in length.

21. The method of claim 20, wherein the linker region is about 5 amino acid residues in length.

22. The method of claim 1, wherein the zinc finger protein comprises a framework from a plant zinc finger protein.

23. The method of claim 1, wherein the zinc finger protein is selected from the group consisting of ZFPm1, ZFPm2, ZFPm3, ZFPm4 and ZFPAp3.

24. The method of claim 1, wherein the plant cell is a monocot plant cell or dicot plant cell.

25. The method of claim 1, wherein the plant cell is a protoplast or a spheroplast.

26. The method of claim 15, wherein the expression of the protein is activated at least two fold.

27. The method of claim 15, wherein the expression of the protein is repressed at least five fold.

28. The method of claim 1, wherein the plant cell is contained in an in vitro culture.

29. The method of claim 1, further comprising growing the plant cell into a plant.

30. The method of claim 1, wherein the expression vector further comprises an inducible promoter.

31. The method of claim 1, wherein the expression vector further comprises a tissue specific promoter.

32. The method of claim 1, wherein the zinc finger protein is stably expressed in a specific organelle.

33. The method of claim 32, wherein the organelle is selected from the group consisting of a mitochondria, a nucleus, a plastid and a vacuole.

34. The method of claim 33, wherein the plastid is selected from the group consisting of a chloroplast, a leucoplast, an aravloplast and a chromoplast.

35. The method of claim 32, wherein the zinc finger protein is targeted to a specific organelle via a targeting peptide.

36. The method of claim 35, wherein the zinc finger protein is targeted to plastid via a plastid transit peptide, to chloroplast via a chloroplast transit peptide, to mitochondrial via a mitochondrial target peptide or to nucleus via a nuclear targeting peptide.

37. A method of stably modulating the level of a compound in a plant cell, which method comprises introducing into a plant cell an expression vector comprising a nucleotide sequence encoding a synthetic zinc finger protein that specifically binds to a target nucleote sequence, or a complementary strand thereof, within a target gene encoding an enzyme that catalysis synteses of said compound, wherein said target nucleotide sequence is of the formula $(GNN)_6$, wherein N is any one of A, T, C or G and wherein said zinc finger protein is a hexadactyl zinc finger protein; and culturing said plant cell under conditions wherein said zinc finger protein is stably expressed and binds to said target nucleotide sequence, whereby the level of said compound in said plant cell is stably modulated.

38. The method of claim 37, wherein the compound is phytic acid.

39. The method of claim 37, wherein the target gene encodes a Myoinositol 1-phosphate synthase.

40. An expression vector comprising a nucleotide sequence encoding a synthetic zinc finger protein selected from the group consisting SEQ ID NO: 38, SEQ ID NO: 39, SEQ ID NO: 40, SEQ ID NO: 41, and SEQ ID NO: 42, said zinc finger protein that specifically binds to a target nucleotide sequence, or a complementary strand thereof, within a target gene, wherein said target nucleotide sequence comprises 18 consecutive nucleotides and wherein said zinc finger protein is a hexadactyl zinc finger protein.

41. A stably transformed plant cell comprising the expression vector of claim 40, wherein said synthetic zinc finger protein is expressed under the control of a promoter.

42. The stably transformed plant cell of claim 41, wherein the target nucleotide sequence is endogenous or exogenous to the targeted gene.

43. The stably transformed plant cell of claim 41, wherein the target gene is endogenous or exogenous to the plant cell.

44. The stably transformed plant cell of claim 41, wherein the promoter is an inducible promoter.

45. The stably transformed plant cell of claim 41, which is from a plant selected from the group consisting of a tobacco, tomato, potato, banana, soybean, pepper, wheat, rye, rice, spinach, carrot and corn.

46. The stably transformed plant cell of claim 41, wherein said promoter is a constitutive promoter.

47. The stably transformed plant cell of claim 41, wherein said promoter is an inducible promoter.

48. A stably transformed plant tissue comprising the expression vector of claim 40.

49. A stably transformed plant seed comprising the expression vector of claim 40.

50. The stably transformed plant seed of claim 49, which is from a plant selected from the group consisting of a tobacco, tomato, potato, banana, soybean, pepper, wheat, rye, rice, spinach, carrot and corn seed.

51. A plant stably transformed with the expression vector of claim 40.

52. The method of claim 1, wherein the zinc finger protein comprises a framework (or backbone) obtained from a naturally occurring zinc finger protein.

53. The method of claim 1, wherein the zinc finger protein comprises a framework (or backbone) obtained from a zinc finger protein comprising a C2H2 motif.

54. The method of claim 53, wherein the protein or peptide sequence within the β sheet of the C2H2 motif is not changed from its natural sequence.

* * * * *